US008178107B1

(12) United States Patent
Eaton et al.

(10) Patent No.: US 8,178,107 B1
(45) **Date of Patent: *May 15, 2012**

(54) METHOD OF TREATMENT OF THROMBOCYTOPENIA OR RISK THEREOF USING MPL LIGAND (THROMBOPOIETIN), VARIANTS, AND FRAGMENTS THEREOF

(75) Inventors: Dan L. Eaton, San Rafael, CA (US); Frederic J. De Sauvage, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/425,020

(22) Filed: Apr. 18, 1995

Related U.S. Application Data

(60) Division of application No. 08/249,376, filed on May 25, 1994, which is a continuation-in-part of application No. 08/223,263, filed on Apr. 4, 1994, which is a continuation-in-part of application No. 08/196,689, filed on Feb. 15, 1994, which is a continuation-in-part of application No. 08/185,607, filed on Jan. 21, 1994, now abandoned, which is a continuation-in-part of application No. 08/176,553, filed on Jan. 3, 1994, now abandoned.

(51) Int. Cl.
*C12N 15/12* (2006.01)
*C12N 15/19* (2006.01)
*C07K 14/52* (2006.01)

(52) U.S. Cl. .................. 424/198.1; 435/69.5; 435/71.1; 435/70.1; 435/69.7; 530/351; 530/402; 530/325; 530/326; 424/192.1; 424/178.1

(58) Field of Classification Search ................ 530/331, 530/351; 424/85.1, 198.1; 514/2; 435/69.1, 435/69.5; 935/9
See application file for complete search history.

(56) References Cited

U.S. PATENT DOCUMENTS

| | | | | | |
|---|---|---|---|---|---|
| 4,002,531 | A | * | 1/1977 | Royer | 435/188 |
| 4,847,325 | A | * | 7/1989 | Shadle et al. | 525/54.1 |
| 4,894,440 | A | | 1/1990 | Rosenberg | 530/351 |
| 5,073,627 | A | | 12/1991 | Curtis et al. | 530/351 |
| 5,108,910 | A | | 4/1992 | Curtis et al. | 435/69.7 |
| 5,128,449 | A | | 7/1992 | McDonald et al. | 530/351 |
| 5,223,408 | A | | 6/1993 | Goeddel et al. | 435/69.7 |
| 5,260,417 | A | | 11/1993 | Grant et al. | 530/351 |
| 5,326,558 | A | | 7/1994 | Turner et al. | 424/85.1 |

FOREIGN PATENT DOCUMENTS

| | | |
|---|---|---|
| WO | WO 90/12877 | 11/1990 |
| WO | WO 93/11247 | 6/1993 |
| WO | WO 95/21919 | 8/1995 |
| WO | WO 96/23888 | 8/1996 |
| WO | WO 96/25498 | 8/1996 |

OTHER PUBLICATIONS

Bartley et al., "Identification and Cloning of a Megakaryocyte Growth and Development Factor That is a Ligand for the Cytokine Receptor Mpl" *Cell* 77:1117-1124 (1994).
Bazan, J., "Structural Design and Molecular Evolution of a Cytokine Receptor Superfamily" *Proc. Natl. Acad. Sci. USA* 87:6934-6938 (1990).
Bowie et al., "Deciphering the Message in Protein Sequences: Tolerance to Amino Acid Substitutions" *Science* 247:1306-1310 (1990).
Davis et al., "The Receptor for Ciliary Neurotrophic Factor" *Science* 253:59-63 (1991).
de Sauvage et al., "Stimulation of Megakaryocytopoiesis and Thrombopoiesis by the c-Mpl Ligand" *Nature* 369:533-538 (Jun. 16, 1994).
Foster et al., "Human Thrombopoietin: Gene Structure, cDNA Sequence, Expression, and Chromosomal Localization" *Proc. Natl. Acad. Sci. USA* 91(26):13023-13027 (1994).
Gearing et al., "Expression Cloning of a Receptor for Human Granulocyte-macrophage Colony-stimulating Factor" *EMBO Journal* 8(12):3667-3676 (1989).
Gerard et al., "The Core Polypeptide of Cystic Fibrosis Tracheal Mucin Contains a Tandem Repeat Structure" *J. Clin. Invest.* 86:1921-1927 (1990).
Gurney et al., "Genomic Structure, Chromosomal Localization, and Conserved Alternative Splice Forms of Thrombopoietin" *Blood* 85(4):981-988 (1995).
Hill et al., "Correlation of in vitro and in vivo Biological Activities During the Partial Purification of Thrombopoietin" *Experimental Hematology* 20:354-360 (1992).
Hill et al., "The Effect of Partially Purified Thrombopoietin on Guinea Pig Megakaryocyte Ploidy in vitro" *Experimental Hematology* 17(8):903-907 (1989).
Hoffman, R., "Regulation of Megakaryocytopoiesis" *Blood* 74(4):1196-1212 (1989).
Hunt et al., "Purification and Biologic Characterization of Plasma-derived Megakaryocyte Growth and Development Factor" *Blood* 86(2):540-547 (1995).
Kaushansky et al., "Promotion of Megakaryocyte Progenitor Expansion and Differentiation by the c-Mpl Ligand Thrombopoietin" *Nature* 369:568-571 (Jun. 16, 1994).
Kaushansky, K., "Thrombopoietin: The Primary Regulator of Platelet Production" *Blood* 86(2):419-431 (1995). Kellar et al., "Thrombopoietin-induced Stimulation of Megakaryocyte-enriched Bone Marrow Cultures" *Int. Cong. Throm. Haem.* (Abstract P5-028/0668) 42(1):283 (1979)
Kuter et al., "Appearance of a Megakaryocyte Growth-promoting Activity, Megapoietin, During Acute Thrombocytopenia in the Rabbit" *Blood* 84(5):1464-1472 (1994).
Lok et al., "Cloning and Expression of Murine Thrombopoietin cDNA and Stimulation of Platelet Production in vivo" *Nature* 369:565-568 (Jun. 16, 1994).
Lok et al., "The Structure, Biology and Potential Therapeutic Applications of Recombinant Thrombopoietin" *Stem Cells* 12(6):586-598 (1994).
McDonald et al., "A Four-step Procedure for the Purification of Thrombopoietin" *Experimental Hematology* 17(8):865-871 (1989).

(Continued)

*Primary Examiner* — Lorraine Spector
(74) *Attorney, Agent, or Firm* — Merchant & Gould P.C.

(57) ABSTRACT

Isolated mpl ligand, isolated DNA encoding mpl ligand, and recombinant or synthetic methods of preparing mpl ligand are disclosed. These mpl ligands are shown to influence the replication, differentiation or maturation of blood cells, especially megakaryocytes and megakaryocyte progenitor cells. Accordingly, these compounds may be used for treatment of thrombocytopenia.

27 Claims, 39 Drawing Sheets

OTHER PUBLICATIONS

McDonald et al., "Monoclonal Antibodies to Human Urinary Thrombopoietin" *Proc. Soc. Exp. Biol. Med.* 182:151-158 (1986).
McDonald et al., "Purification and Assay of Thrombopoietin" *Experimental Hematology* 2(6):355-361 (1974).
McDonald et al., "Studies on the Purification of Thrombopoietin from Kidney Cell Culture Medium" *Journal of Laboratory and Clinical Medicine* 106(2):162-174 (1985).
McDonald, T., "Thrombopoietin: Its Biology, Purification, and Characterization" *Experimental Hematology* 16(3):201-205 (1988).
Metcalf, D., "Thrombopoietin—At Last" *Nature* 369:519-520 (1994).
Methia et al., "Oligodeoxynucleotides Antisense to the Proto-oncogene c-Mpl Specifically Inhibit in vitro Megakaryocytopoiesis" *Blood* 82(5):1395-1401 (1993).
Mignotte et al., "Structure and Transcription of the Human c-Mpl Gene (MPL)" *Genomics* 20:5-12 (1994).
Nicola et al., "Subunit Promiscuity Among Hemopoietic Growth Factor Receptors" *Cell* 67:1-4 (1991).
Skoda et al., "Murine c-Mpl: a Member of the Hematopoietic Growth Factor Receptor Superfamily That Transduces a Proliferative Signal" *EMBO Journal* 12(7):2645-2653 (1993).
Sohma et al., "Molecular Cloning and Chromosomal Localization of the Human Thrombopoietin Gene" *FEBS Letters* 353(1):57-61 (1994).
Souyri et al., "A Putative Truncated Cytokine Receptor Gene Transduced by the Myeloproliferative Leukemia Virus Immortalizes Hematopoietic Progenitors" *Cell* 63:1137-1147 (1990).
Vigon et al., "Characterization of the Murine Mpl Proto-oncogene, a Member of the Hematopoietic Cytokine Receptor Family: Molecular Cloning, Chromosomal Location and Evidence for a Function in Cell Growth" *Oncogene* 8:2607-2615 (1993).
Vigon et al., "Expression of the c-Mpl Proto-oncogene in Human Hematologic Malignancies" *Blood* 82(3):877-883 (1993).
Vigon et al., "Molecular Cloning and Characterization of Mpl, the Human Homolog of the v-Mpl Oncogene: Identification of a Member of the Hematopoietic Growth Factor Receptor Superfamily" *Proc. Natl. Acad. Sci. USA* 89:5640-5644 (1992).
Wendling et al., "c-Mpl Ligand is a Humoral Regulator of Megakaryocytopoiesis" *Nature* 369:571-574 (1994).
Withy et al., "Growth Factors Produced by Human Embryonic Kidney Cells that Influence Megakaryopoiesis Include Erythropoietin, Interleukin 6, and Fransforming Growth Factor-Beta" *Journal of Cellular Physiology* 153:362-372 (1992).
McDonald et al., "Thrombopoietin from Human Embryonic Kidney Cells is the Same Factor as c-mpl-Ligand" *Blood* (letter only) 85:292-294 (1995).
McDonald, "Thrombopoietin: Its Biology, Clinical Aspects, and Possibilities" *The American Journal of Pediatric Hematology/Oncology* 14(1):8-21 (1992).

* cited by examiner

FIG. 1A

```
  1 tcttcctacccatctgctccccagagggctgcctgctgtgcacttgggtcctggagcccttctccacccggatagattcctcacccttggcccgcctttg

101 ccccaccctactctgcccagaagtgcaagagcctaagccgcctccatggccccaggaaggattcaggggagaggccccaaacagggagccacgccagcca

                  -20                   -10
                  MetGluLeuThrGluLeuLeuLeuValValMetLeuLeuLeuThrAlaArgLeuThrLeuSerSerProAlaProProAlaCysAsp
201 gacaccccggccagaATGGAGCTGACTGAATTGCTCCTCGTGGTCATGCTTCTCCTAACTGCAAGGCTAACGCTGTCCAGCCCGGCTCCTCCTGCTTGTG

      10                  20                  30                  40
    LeuArgValLeuSerLysLeuLeuArgAspSerHisValLeuHisSerArgLeuSerGlnCysProGluValHisProLeuProThrProValLeuLeu
301 ACCTCCGAGTCCTCAGTAAACTGCTTCGTGACTCCCATGTCCTTCACAGCAGACTGAGCCAGTGCCCAGAGGTTCACCCTTTGCCTACACCTGTCCTGCT

                     50                  60                  70
    ProAlaValAspPheSerLeuGlyGluTrpLysThrGlnMetGluGluThrLysAlaGlnAspIleLeuGlyAlaValThrLeuLeuLeuGluGlyVal
401 GCCTGCTGTGGACTTTAGCTTGGGAGAATGGAAAACCCAGATGGAGGAGACCAAGGCACAGGACATTCTGGGAGCAGTGACCCTTCTGCTGGAGGGAGTG

          80                  90                  100
    MetAlaAlaArgGlyGlnLeuGlyProThrCysLeuSerSerLeuLeuGlyGlnLeuSerGlyGlnValArgLeuLeuLeuGlyAlaLeuGlnSerLeuLeu
501 ATGGCAGCACGGGGACAACTGGGACCCACTTGCCTCTCATCCCTCCTGGGGCAGCTTTCTGGACAGGTCCGTCTCCTCCTTGGGGCCCTGCAGAGCCTCC

      110                 120                 130                 140
    GlyThrGlnLeuProProGlnGlyArgThrThrAlaHisLysAspProAsnAlaIlePheLeuSerPheGlnHisLeuLeuArgGlyLysValArgPhe
601 TTGGAACCCAGCTTCCTCCACAGGGCAGGACCACAGCTCACAAGGATCCCAATGCCATCTTCCTGAGCTTCCAACACCTGCTCCGAGGAAAGGTGCGTTT

                    150                 160                 170
    LeuMetLeuValGlyGlySerThrLeuCysValArgArgAlaProProThrThrAlaValProSerArgThrSerLeuValLeuThrLeuAsnGluLeu
701 CCTGATGCTTGTAGGAGGGTCCACCCTCTGCGTCAGGCGGGCCCCACCCACCACAGCTGTCCCCAGCAGAACCTCTCTAGTCCTCACACTGAACGAGCTC

               180                 190                 200
    ProAsnArgThrSerGlyLeuLeuGluThrAsnPheThrAlaSerAlaArgThrThrGlySerGlyLeuLeuLysTrpGlnGlnGlyPheArgAlaLysIle
801 CCAAACAGGACTTCTGGATTGTTGGAGACAAACTTCACTGCCTCAGCCAGAACTACTGGCTCTGGGCTTCTGAAGTGGCAGCAGGGATTCAGAGCCAAGA
```

FIG. 1B

```
     210                            220                            230                            240
   ProGlyLeuLeuAsnGlnThrSerArgSerLeuAspGlnIleProGlyTyrLeuAsnArgIleHisGluLeuLeuAsnGlyThrArgGlyLeuPhePro
901 TTCCTGGTCTGCTGAACCAAACCTCCAGGTCCCTGGACCAAATCCCCGGATACCTGAACAGGATACACGAACTCTTGAATGGAACTCGTGGACTCTTTCC

                        250                            260                            270
  GlyProSerArgArgThrLeuGlyAlaProAspIleSerSerGlyThrSerAspThrGlySerLeuProProAsnLeuGlnProGlyTyrSerProSer
1001 TGGACCCTCACGCAGGACCCTAGGAGCCCCGGACATTTCCTCAGGAACATCAGACACAGGCTCCCTGCCACCCAACCTCCAGCCTGGATATTCTCCTTCC

              280                            290                            300
 ProThrHisProProThrGlyGlnTyrThrLeuPheProLeuProProThrLeuProThrProValValGlnLeuHisPrcLeuLeuProAspProSerAla
1101 CCAACCCATCCTCCTACTGGACAGTATACGCTCTTCCCTCTTCCACCCACCTTGCCCACCCCTGTGGTCCAGCTCCACCCCCTGCTTCCTGACCCTTCTG

     310                            320                            330
  ProThrProThrProThrSerProLeuLeuAsnThrSerTyrThrHisSerGlnAsnLeuSerGlnGluGly
1201 CTCCAACGCCCACCCCTACCAGCCCTCTTCTAAACACATCCTACACCCACTCCCAGAATCTGTCTCAGGAAGGGTAAggttctcagacactgccgacatc

1301 agcattgtctcatgtacagctcccttccctgcagggcgcccctgggagacaactggacaagatttcctactttctcctgaaacccaaagccctggtaaaa

1401 gggatacacaggactgaaaagggaatcatttttcactgtacattataaaccttcagaagctatttttttaagctatcagcaatactcatcagagcagcta

1501 gctctttggtctattttctgcagaaatttgcaactcactgattctctacatgctctttttctgtgataactctgcaaaggcctgggctggcctggcagtt

1601 gaacagagggagagactaaccttgagtcagaaaacagagaaagggtaatttcctttgcttcaaattcaaggccttccaacgcccccatcccctttactat

1701 cattctcagtgggactctgatcccatattcttaacagatctttactcttgagaaatgaataagctttctctcagaaaaaaaaaaaaaaaaaaaa
```

FIG. 2
FIG. 2A
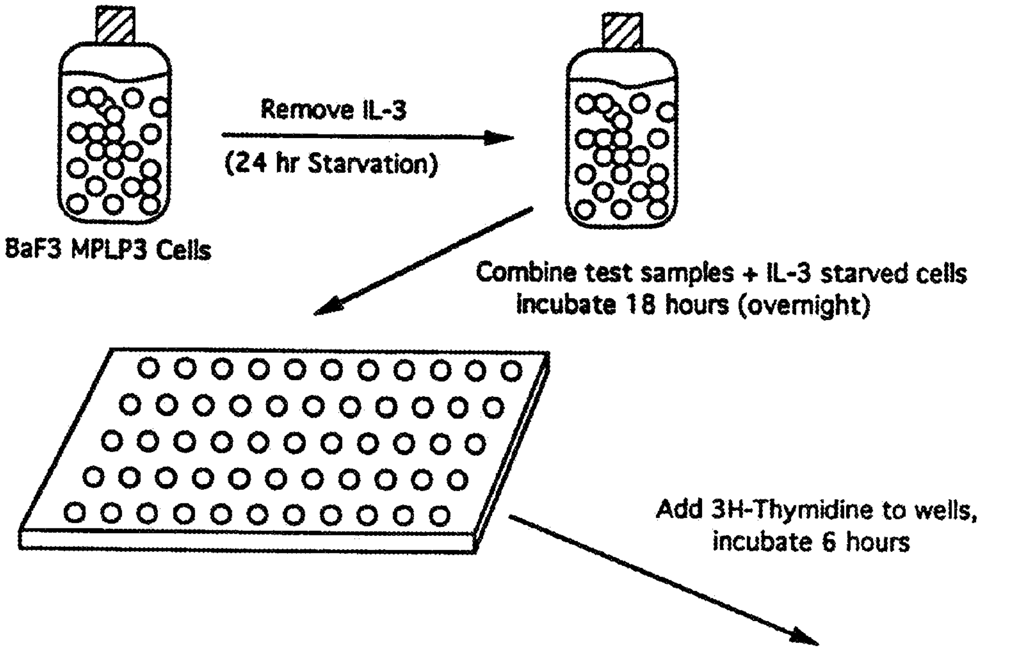
FIG. 2B
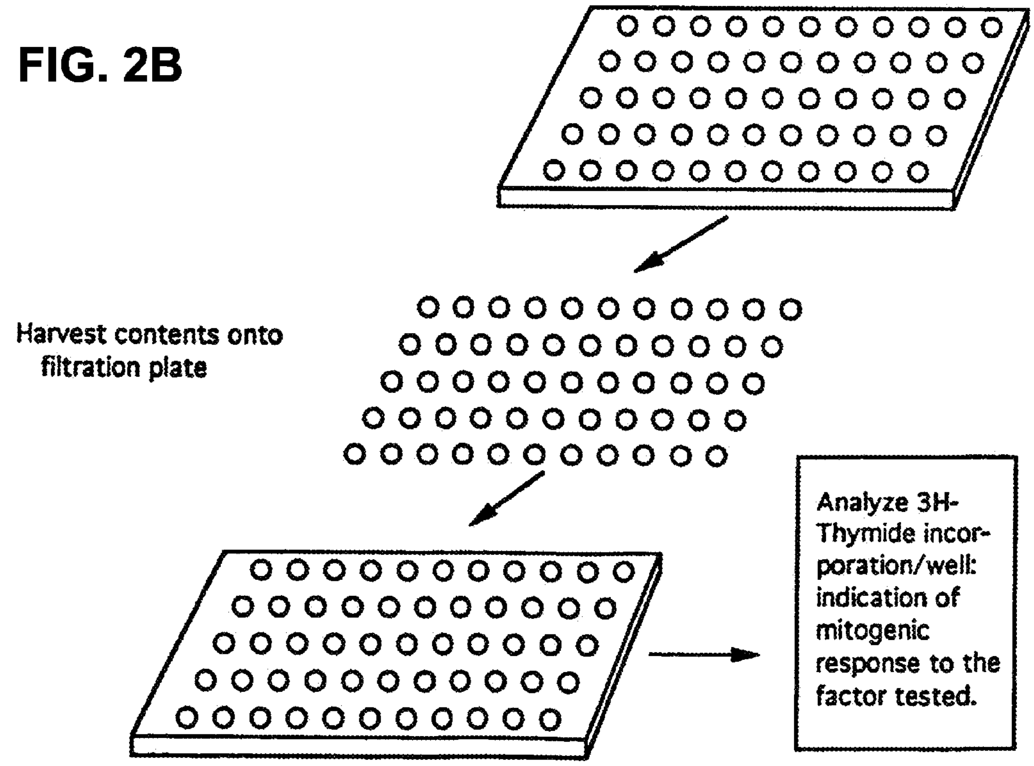

FIG. 9

```
                                                                                     -10
                                                                   ↓  L  L  L  V   V  M  L   L  L  T
  1 GAATTCCTGG AATACCAGCT GACAATGATT TCCTCCTCAT CTTTCAACCT CACCTCTCCT CATCTAAGAA TTGCTCCTCG TGGTCATGCT TCTCCTAACT
    CTTAAGGACC TTATGGTCGA CTGTTACTAA AGGAGGAGTA GAAAGTTGGA GTGGAGAGGA GTAGATTCTT AACGAGGAGC ACCAGTACGA AGAGGATTGA

                                                10                                20
     A  R  L  T   L  S  S   P  A  P   P  A  C  D   L  R  V   L  S  K   L  L  R  D   S  H  V   L  H  S   R  L ↓
101 GCAAGGCTAA CGCTGTCCAG CCCGGCTCCT CCTGCTTGTG ACCTCCGAGT CCTCAGTAAA CTGCTTCGTG ACTCCCATGT CCTTCACAGC AGACTGGTGA
    CGTTCCGATT GCGACAGGTC GGGCCGAGGA GGACGAACAC TGGAGGCTCA GGAGTCATTT GACGAAGCAC TGAGGGTACA GGAAGTGTCG TCTGACCACT

201 GAACTCCCAA CATTATCCCC TTTATCCGCG TAACTGGTAA GACACCCATA CTCCCAGGAA GACACCATCA CTTCCTCTAA CTCCTTGACC CAATGACTAT
    CTTGAGGGTT GTAATAGGGG AAATAGGCGC ATTGACCATT CTGTGGGTAT GAGGGTCCTT CTGTGGTAGT GAAGGAGATT GAGGAACTGG GTTACTGATA

301 TCTTCCCATA TTGTCCCCAC CTACTGATCA CACTCTCTGA CAAGAATTAT TCTTCACAAT ACAGCCCGCA TTTAAAAGCT CTCGTCTAGA
    AGAAGGGTAT AACAGGGGTG GATGACTAGT GTGAGAGACT GTTCTTAATA AGAAGTGTTA TGTCGGGCGT AAATTTTCGA GAGCAGATCT
```

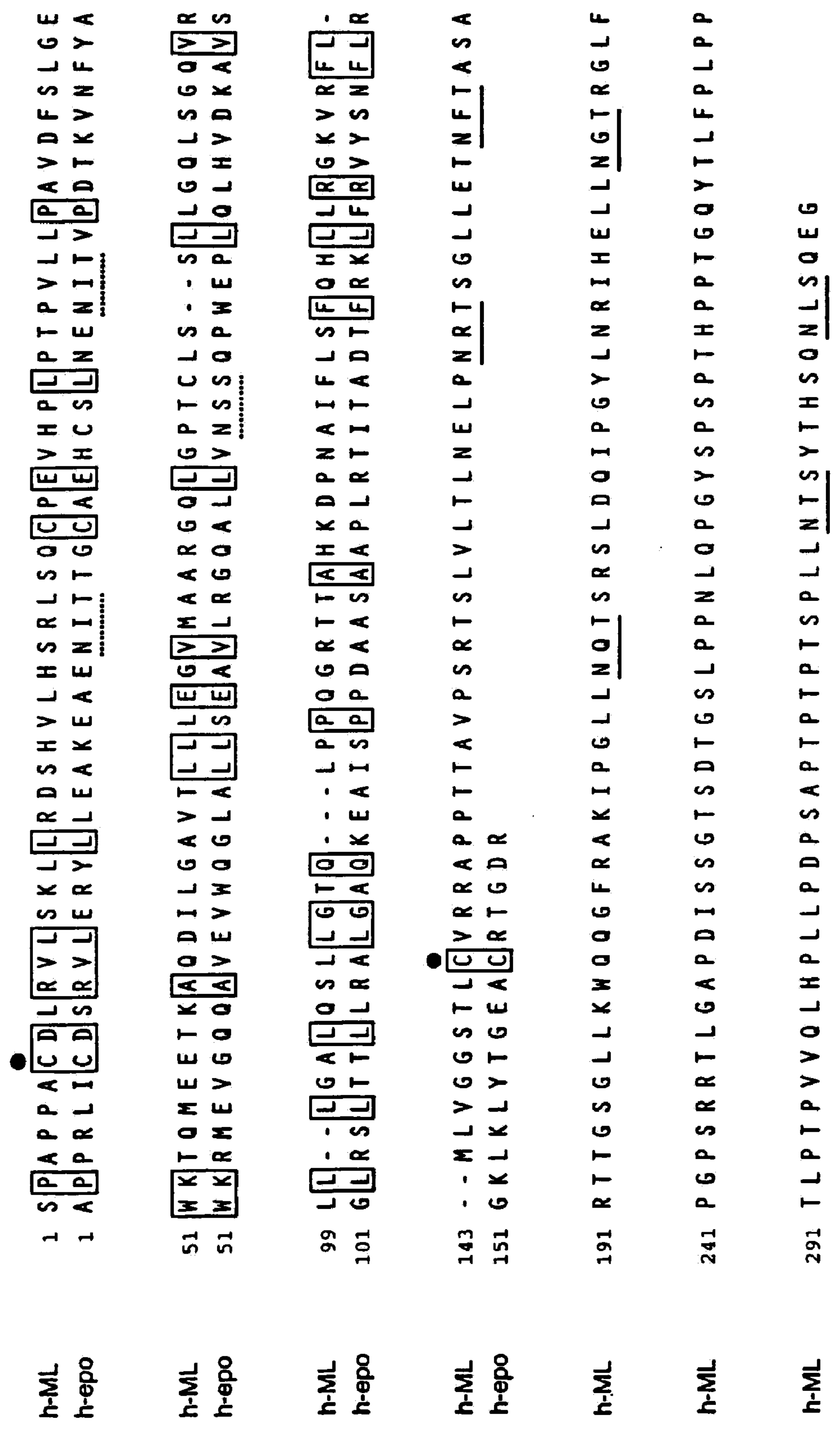

FIG. 10 h-ML    1   SPAPPACDLRVLSKLLRDSHVLHSRLSQCPEVHPLPTPVLLPAVDFSLGE
h-epo   1   APPRLICDSRVLERYLLEAKEAENITTGCAEHCSLNENITVPDTKVNFYA h-ML    51  WKTQMEETKAQDILGAVTLLLEGVMAARGQLGPTCLS--SLLGQLSGQVR
h-epo   51  WKRMEVGQQAVEVWQGLALLSEAVLRGQALLVNSSQPWEPLQLHVDKAVS h-ML    99  LL---LGALQSLLGTQ---LPPQGRTTAHKDPNAIFLSFQHLLRGKVRFL-
h-epo   101 GLRSLTTLLRALGAQKEAISPPDAASAAPLRTITADTFRKLFRVYSNFLR h-ML    143 --MLVGGSTLCVRRAPPTTAVPSRTSLVLTLNELPNRTSGLLETNFTASA
h-epo   151 GKLKLYTGEACRTGDR h-ML    191 RTTGSGLLKWQQGFRAKIPGLLNQTSRSLDQIPGYLNRIHELLNGTRGLF h-ML    241 PGPSRRTLGAPDISSGTSDTGSLPPNLQPGYSPSPTHPPTGQYTLFPLPP h-ML    291 TLPTPVVQLHPLLPDPSAPTPTPTSPLLNTSYTHSQNLSQEG

FIG. 11A

| | | |
|---|---|---|
| hML | 1 | SPAPPACDLRVLSKLLRDSHVLHSRLSQCPEVHPLPTPVLLPAVDFSLGE |
| hML2 | 1 | SPAPPACDLRVLSKLLRDSHVLHSRLSQCPEVHPLPTPVLLPAVDFSLGE |
| hML3 | 1 | SPAPPACDLRVLSKLLRDSHVLHSRLSQCPEVHPLPTPVLLPAVDFSLGE |
| hML4 | 1 | SPAPPACDLRVLSKLLRDSHVLHSRLSQCPEVHPLPTPVLLPAVDFSLGE |
| hML | 51 | WKTQMEETKAQDILGAVTLLLEGVMAARGQLGPTCLSSLLGQLSGQVRLL |
| hML2 | 51 | WKTQMEETKAQDILGAVTLLLEGVMAARGQLGPTCLSSLLGQLSGQVRLL |
| hML3 | 51 | WKTQMEETKAQDILGAVTLLLEGVMAARGQLGPTCLSSLLGQLSGQVRLL |
| hML4 | 51 | WKTQMEETKAQDILGAVTLLLEGVMAARGQLGPTCLSSLLGQLSGQVRLL |
| hML | 101 | LGALQSLLGTQLPPQGRTTAHKDPNAIFLSFQHLLRGKVRFLMLVGGSTL |
| hML2 | 101 | LGALQSLLGT....QGRTTAHKDPNAIFLSFQHLLRGKVRFLMLVGGSTL |
| hML3 | 101 | LGALQSLLGTQLPPQGRTTAHKDPNAIFLSFQHLLRGK.DFW.IVGDKLH |
| hML4 | 101 | LGALQSLLGT....QGRTTAHKDPNAIFLSFQHLLRGK.DFW.IVGDKLH |
| hML | 151 | CVRRAPPTTAVPSRTSLVLTLNELPNRTSGLLETNFTASARTTGSGLLKW |
| hML2 | 147 | CVRRAPPTTAVPSRTSLVLTLNELPNRTSGLLETNFTASARTTGSGLLKW |
| hML3 | 149 | CLSQ.........NYWL.........WASEVAAGIQSQDSWSAEPNLQ.. |
| hML4 | 145 | CLSQ.........NYWL.........WASEVAAGIQSQDSWSAEPNLQ.. |

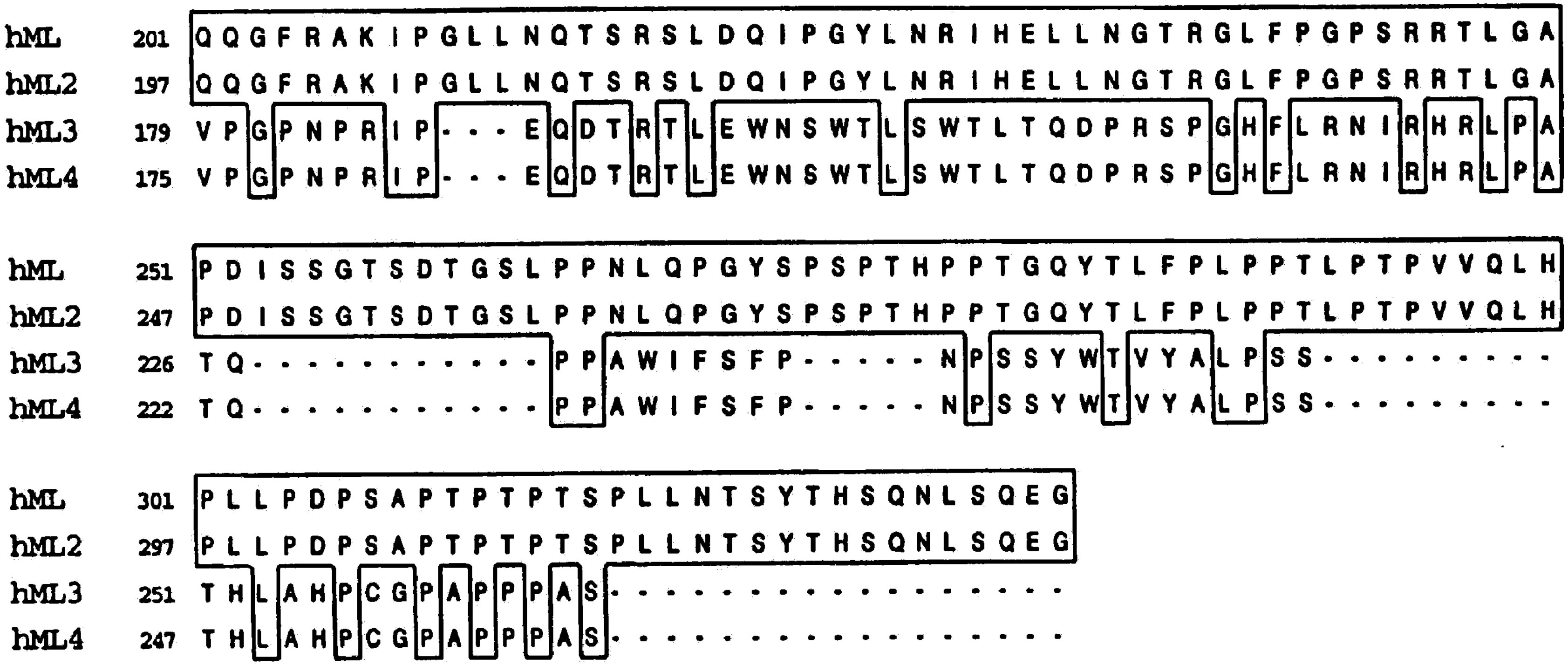

FIG. 11B

| | | |
|---|---|---|
| hML | 201 | QQGFRAKIPGLLNQTSRSLDQIPGYLNRIHELLNGTRGLFPGPSRRTLGA |
| hML2 | 197 | QQGFRAKIPGLLNQTSRSLDQIPGYLNRIHELLNGTRGLFPGPSRRTLGA |
| hML3 | 179 | VPGPNPRIP...EQDTRTLEWNSWTLTQDPRSPGHFLRNIRHRLPA |
| hML4 | 175 | VPGPNPRIP...EQDTRTLEWNSWTLTQDPRSPGHFLRNIRHRLPA |
| | | |
| hML | 251 | PDISSGTSDTGSLPPNLQPGYSPSPTHPPTGQYTLFPLPPTLPPTPVVQLH |
| hML2 | 247 | PDISSGTSDTGSLPPNLQPGYSPSPTHPPTGQYTLFPLPPTLPPTPVVQLH |
| hML3 | 226 | TQ......PPAWIFSFP......NPSSYWTVYALPSS........ |
| hML4 | 222 | TQ......PPAWIFSFP......NPSSYWTVYALPSS........ |
| | | |
| hML | 301 | PLLPDPSAPTPTSPLLNTSYTHSQNLSQEG |
| hML2 | 297 | PLLPDPSAPTPTSPLLNTSYTHSQNLSQEG |
| hML3 | 251 | THLAHPCGPAPPAS............... |
| hML4 | 247 | THLAHPCGPAPPAS............... |

FIG. 14A

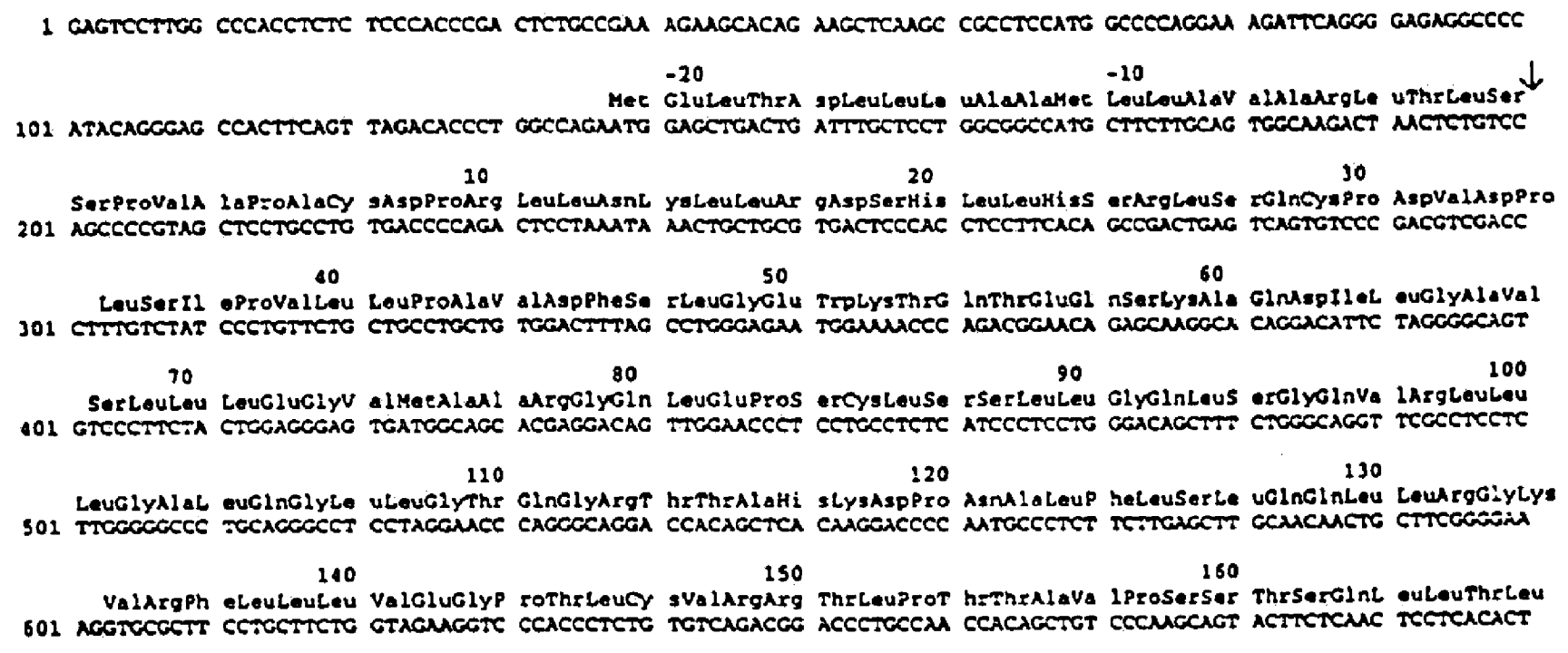

```
  1 GAGTCCTTGG CCCACCTCTC TCCCACCCGA CTCTGCCGAA AGAAGCACAG AAGCTCAAGC CGCCTCCATG GCCCCAGGAA AGATTCAGGG GAGAGGCCCC

                                                 -20                                     -10                   ↓
                                            Met GluLeuThrA spLeuLeuLe uAlaAlaMet LeuLeuAlaV alAlaArgLe uThrLeuSer
101 ATACAGGGAG CCACTTCAGT TAGACACCCT GGCCAGAATG GAGCTGACTG ATTTGCTCCT GGCGGCCATG CTTCTTGCAG TGGCAAGACT AACTCTGTCC

                                    10                              20                              30
    SerProValA laProAlaCy sAspProArg LeuLeuAsnL ysLeuLeuAr gAspSerHis LeuLeuHisS erArgLeuSe rGlnCysPro AspValAspPro
201 AGCCCCGTAG CTCCTGCCTG TGACCCCAGA CTCCTAAATA AACTGCTGCG TGACTCCCAC CTCCTTCACA GCCGACTGAG TCAGTGTCCC GACGTCGACC

                         40                              50                              60
      LeuSerIl eProValLeu LeuProAlaV alAspPheSe rLeuGlyGlu TrpLysThrG lnThrGluGl nSerLysAla GlnAspIleL euGlyAlaVal
301 CTTTGTCTAT CCCTGTTCTG CTGCCTGCTG TGGACTTTAG CCTGGGAGAA TGGAAAACCC AGACGGAACA GAGCAAGGCA CAGGACATTC TAGGGGCAGT

            70                              80                              90                             100
     SerLeuLeu LeuGluGlyV alMetAlaAl aArgGlyGln LeuGluProS erCysLeuSe rSerLeuLeu GlyGlnLeuS erGlyGlnVa lArgLeuLeu
401 GTCCCTTCTA CTGGAGGGAG TGATGGCAGC ACGAGGACAG TTGGAACCCT CCTGCCTCTC ATCCCTCCTG GGACAGCTTT CTGGGCAGGT TCGCCTCCTC

                                   110                             120                             130
    LeuGlyAlaL euGlnGlyLe uLeuGlyThr GlnGlyArgT hrThrAlaHi sLysAspPro AsnAlaLeuP heLeuSerLe uGlnGlnLeu LeuArgGlyLys
501 TTGGGGGCCC TGCAGGGCCT CCTAGGAACC CAGGGCAGGA CCACAGCTCA CAAGGACCCC AATGCCCTCT TCTTGAGCTT GCAACAACTG CTTCGGGGAA

                         140                             150                             160
      ValArgPh eLeuLeuLeu ValGluGlyP roThrLeuCy sValArgArg ThrLeuProT hrThrAlaVa lProSerSer ThrSerGlnL euLeuThrLeu
601 AGGTGCGCTT CCTGCTTCTG GTAGAAGGTC CCACCCTCTG TGTCAGACGG ACCCTGCCAA CCACAGCTGT CCCAAGCAGT ACTTCTCAAC TCCTCACACT
```

FIG. 14B

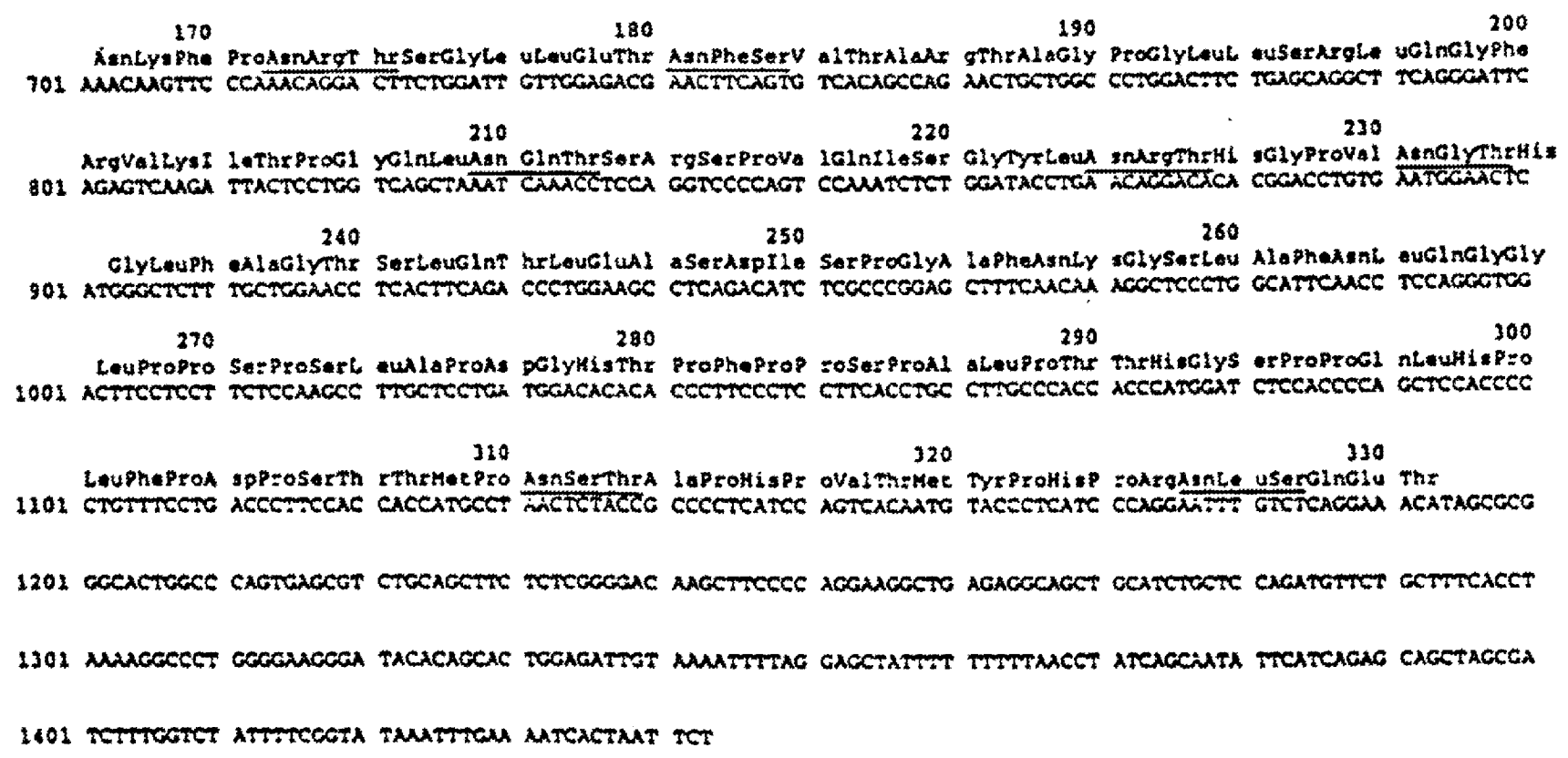

```
                170                               180                               190                               200
          AsnLysPhe  ProAsnArgT hrSerGlyLe uLeuGluThr AsnPheSerV alThrAlaAr gThrAlaGly ProGlyLeuL euSerArgLe uGlnGlyPhe
 701 AAACAAGTTC CCAAACAGGA CTTCTGGATT GTTGGAGACG AACTTCAGTG TCACAGCCAG AACTGCTGGC CCTGGACTTC TGAGCAGGCT TCAGCGATTC

                                 210                               220                               230
         ArgValLysI leThrProGl yGlnLeuAsn GlnThrSerA rgSerProVa lGlnIleSer GlyTyrLeuA snArgThrHi sGlyProVal AsnGlyThrHis
 801 AGAGTCAAGA TTACTCCTGG TCAGCTAAAT CAAACCTCCA GGTCCCCAGT CCAAATCTCT GGATACCTGA ACAGGACACA CGGACCTGTG AATGGAACTC

                           240                               250                               260
           GlyLeuPh eAlaGlyThr SerLeuGlnT hrLeuGluAl aSerAspIle SerProGlyA laPheAsnLy sGlySerLeu AlaPheAsnL euGlnGlyGly
 901 ATGGGCTCTT TGCTGGAACC TCACTTCAGA CCCTGGAAGC CTCAGACATC TCGCCCGGAG CTTTCAACAA AGGCTCCCTG GCATTCAACC TCCAGGGTGG

                270                               280                               290                               300
          LeuProPro SerProSerL euAlaProAs pGlyHisThr ProPheProP roSerProAl aLeuProThr ThrHisGlyS erProProGl nLeuHisPro
1001 ACTTCCTCCT TCTCCAAGCC TTGCTCCTGA TGGACACACA CCCTTCCCTC CTTCACCTGC CTTGCCCACC ACCCATGGAT CTCCACCCCA GCTCCACCCC

                                 310                               320                               330
         LeuPheProA spProSerTh rThrMetPro AsnSerThrA laProHisPr oValThrMet TyrProHisP roArgAsnLe uSerGlnGlu Thr
1101 CTGTTTCCTG ACCCTTCCAC CACCATGCCT AACTCTACCG CCCCTCATCC AGTCACAATG TACCCTCATC CCAGGAATTT GTCTCAGGAA ACATAGCGCG

1201 GGCACTGGCC CAGTGAGCGT CTGCAGCTTC TCTCGGGGAC AAGCTTCCCC AGGAAGGCTG AGAGGCAGCT GCATCTGCTC CAGATGTTCT GCTTTCACCT

1301 AAAAGGCCCT GGGGAAGGGA TACACAGCAC TGGAGATTGT AAAATTTTAG GAGCTATTTT TTTTTAACCT ATCAGCAATA TTCATCAGAG CAGCTAGCGA

1401 TCTTTGGTCT ATTTTCGGTA TAAATTTGAA AATCACTAAT TCT
```

FIG. 15A 1 gagtccttggcccacctctctcccacccgactctgccgaaagaagcacagaagctcaagccgcctccatggccccaggaaagattcaggggagaggcccc -20 -10
MetGluLeuThrAsnLeuLeuLeuAlaAlaMetLeuLeuAlaValAlaArgLeuThrLeuSer
101 atacagggagccacttcagttagacaccctggccagaATGGAGCTGACTGATTTGCTCCTGGCGGCCATGCTTCTTGCAGTGGCAAGACTAACTCTGTCC 10 20 30
SerProValAlaProAlaCysAspProArgLeuLeuAsnLysLeuLeuArgAspSerHisLeuLeuHisSerArgLeuSerGlnCysProAspValAspPro
201 AGCCCCGTAGCTCCTGCCTGTGACCCCAGACTCCTAAATAAACTGCTGCGTGACTCCCACCTCCTTCACAGCCGACTGAGTCAGTGTCCCGACGTCGACC 40 50 60
LeuSerIleProValLeuLeuProAlaValAspPheSerLeuGlyGluTrpLysThrGlnThrGluGlnSerLysAlaGlnAspIleLeuGlyAlaVal
301 CTTTGTCTATCCCTGTTCTGCTGCCTGCTGTGGACTTTAGCCTGGGAGAATGGAAAACCCAGACGGAACAGAGCAAGGCACAGGACATTCTAGGGGCAGT 70 80 90 100
SerLeuLeuLeuGluGlyValMetAlaAlaArgGlyGlnLeuGluProSerCysLeuSerSerLeuLeuGlyGlnLeuSerGlyGlnValArgLeuLeu
401 GTCCCTTCTACTGGAGGGAGTGATGGCAGCACGAGGACAGTTGGAACCCTCCTGCCTCTCATCCCTCCTGGGACAGCTTTCTGGGCAGGTTCGCCTCCTC 110 120 130
LeuGlyAlaLeuGlnGlyLeuLeuGlyThrGlnLeuProLeuGlnGlyArgThrThrAlaHisLysAspProAsnAlaLeuPheLeuSerLeuGlnGlnLeu
501 TTGGGGGCCCTGCAGGGCCTCCTAGGAACCCAGCTTCCTCTACAGGGCAGGACCACAGCTCACAAGGACCCCAATGCCCTCTTCTTGAGCTTGCAACAAC 140 150 160
LeuArgGlyLysValArgPheLeuLeuLeuValGluGlyProThrLeuCysValArgArgThrLeuProThrThrAlaValProSerSerThrSerGln
601 TGCTTCGGGGAAAGGTGCGCTTCCTGCTTCTGGTAGAAGGTCCCACCCTCTGTGTCAGACGGACCCTGCCAACCACAGCTGTCCCAAGCAGTACTTCTCA 170 180 190 200
LeuLeuThrLeuAsnLysPheProAsnArgThrSerGlyLeuLeuGluThrAsnPheSerValThrAlaArgThrAlaGlyProGlyLeuLeuSerArg
701 ACTCCTCACACTAAACAAGTTCCCAAACAGGACTTCTGGATTGTTGGAGACGAACTTCAGTGTCACAGCCAGAACTGCTGGCCCTGGACTTCTGAGCAGG

FIG. 15B

```
                                   210                                   220                                   230
     LeuGlnGlyPheArgValLysIleThrProGlyGlnLeuAsnGlnThrSerArgSerProValGlnIleSerGlyTyrLeuAsnArgThrHisGlyProVal
801  CTTCAGGGATTCAGAGTCAAGATTACTCCTGGTCAGCTAAATCAAACCTCCAGGTCCCCAGTCCAAATCTCTGGATACCTGAACAGGACACACGGACCTG

                 240                                   250                                   260
      AsnGlyThrHisGlyLeuPheAlaGlyThrSerLeuGlnThrLeuGluAlaSerAspIleSerProGlyAlaPheAsnLysGlySerLeuAlaPheAsn
901  TGAATGGAACTCATGGGCTCTTTGCTGGAACCTCACTTCAGACCCTGGAAGCCTCAGACATCTCGCCCGGAGCTTTCAACAAAGGCTCCCTGGCATTCAA

          270                                   280                                   290                                   300
      LeuGlnGlyGlyLeuProProSerProSerLeuAlaProAspGlyHisThrProPheProProSerProAlaLeuProThrThrHisGlySerProPro
1001 CCTCCAGGGTGGACTTCCTCCTTCTCCAAGCCTTGCTCCTGATGGACACACACCCTTCCCTCCTTCACCTGCCTTGCCCACCACCCATGGATCTCCACCC

                                   310                                   320                                   330
     GlnLeuHisProLeuPheProAspProSerThrThrMetProAsnSerThrAlaProHisProValThrMetTyrProHisProArgAsnLeuSerGlnGlu
1101 CAGCTCCACCCCCTGTTTCCTGACCCTTCCACCACCATGCCTAACTCTACCGCCCCTCATCCAGTCACAATGTACCCTCATCCCAGGAATTTGTCTCAGG

       Thr
1201 AAACATAGcgcgggcactggcccagtgagcgtctgcagcttctctcggggacaagcttccccaggaaggctgagaggcagctgcatctgctccagatgtt

1301 ctgctttcacctaaaaggccctggggaagggatacacagcactggagattgtaaaatttaggagctatttttttttaacctatcagcaatattcatcag

1401 agcagctagcgatctttggtctattttcggtataaatttgaaaatcactaaaaaaaaaaaaaaaaaaaaaaaaaaaaaaaaaaaaaaaaaaaaaaaaaa

1501 aaaaaaaaaaaaaaaaaaaaaaaaaaaaaaaaaaaa
```

FIG. 16

```
hML3   1   SPAPPACDLRVLSKLLRDSHVLHSRLSQCPEVHPLPTPVLLPAVDFSLGE
mML3   1   SPVAPACDPRLLNKLLRDSHLLHSRLSQCPDVDPLSIPVLLPAVDFSLGE

hML3   51  WKTQMEETKAQDILGAVTLLLEGVMAARGQLGPTCLSSLLGQLSGQVRLL
mML3   51  WKTQTEQSKAQDILGAVSLLLEGVMAARGQLEPSCLSSLLGQLSGQVRLL

hML3   101 LGALQSLLGTQLPPQGRTTAHKDPNAIFLSFQHLLRGKDFWIVGDKLHCL
mML3   101 LGALQGLLGTQLPLQGRTTAHKDPNALFLSLQQLLRGKDFWIVGDELQCH

hML3   151 SQNYWLWASEVAAGIQSQD.SWSAEPNLQVPGPNPRIPEQDTRTLEWNSW
mML3   151 SQNCWPWTSEQASGIQSQDYSWSAKSNLQVPSPNLWIPEQDTRTCEWNSW

hML3   200 TLSWTLTQDPRSPGHFLRNIRHRLPATQPPAWIFSFPNPSSYWTVYALPS
mML3   201 ALCWNLTSDPGSLRHLARSFQQRLPGIQPPGWTSSFSKPCS

hML3   250 STHLAHPCGPAPPPAS
```

FIG.17B

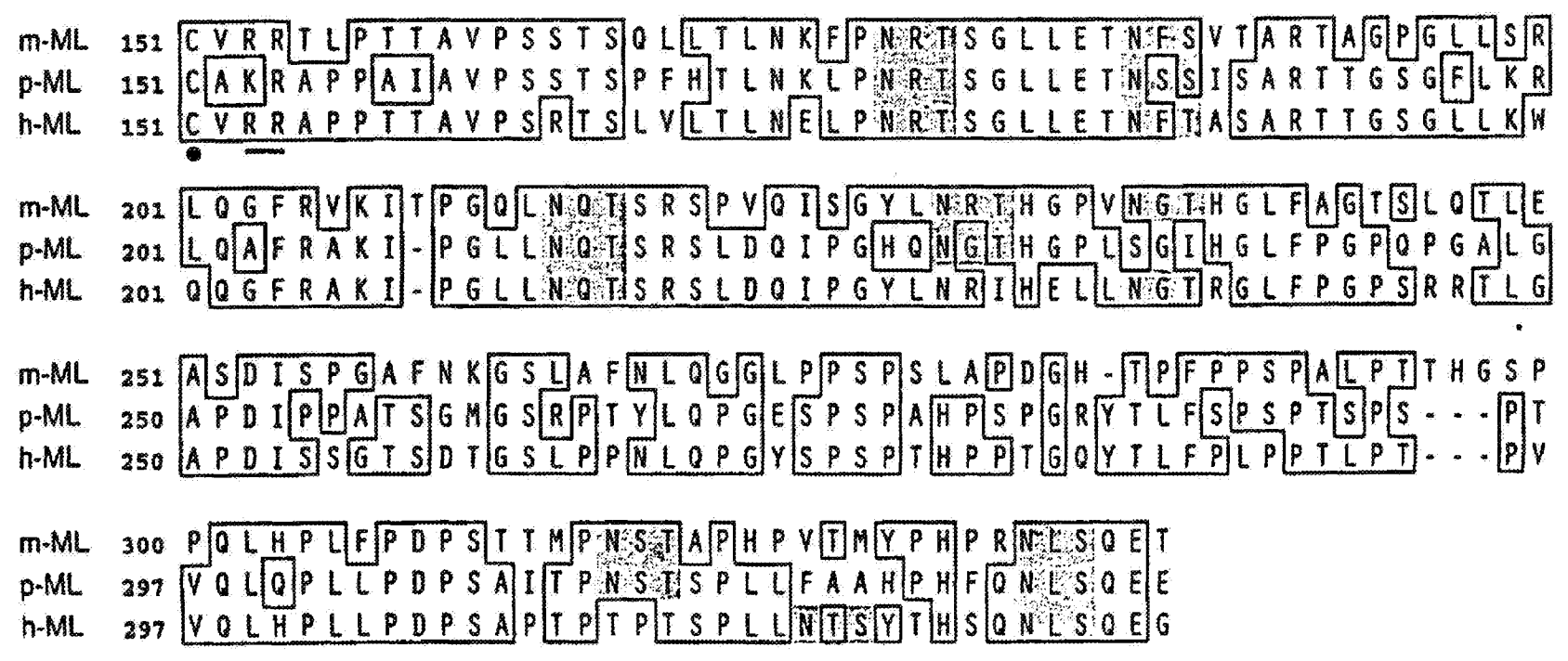

| | | |
|---|---|---|
| m-ML | 151 | CVRRTLPTTAVPSSTSQLLTLNKFPNRTSGLLETNFSVTARTAGPGLLSR |
| p-ML | 151 | CAKRAPPAIAVPSSTSPFHTLNKLPNRTSGLLETNSSISARTTGSGFLKR |
| h-ML | 151 | CVRRAPPTTAVPSRTSLVLTLNELPNRTSGLLETNFTASARTTGSGLLKW |
| m-ML | 201 | LQGFRVKITPGQLNQTSRSPVQISGYLNRTHGPVNGTHGLFAGTSLQTLE |
| p-ML | 201 | LQAFRAKI-PGLLNQTSRSLDQIPGHQNGTHGPLSGIHGLFPGPQPGALG |
| h-ML | 201 | QQGFRAKI-PGLLNQTSRSLDQIPGYLNRIHELLNGTRGLFPGPSRRTLG |
| m-ML | 251 | ASDISPGAFNKGSLAFNLQGGLPPSPSLAPDGH-TPFPPSPALPTTHGSP |
| p-ML | 250 | APDIPPATSGMGSRPTYLQPGESPSPAHPSPGRYTLFSPSPTSPS---PT |
| h-ML | 250 | APDISSGTSDTGSLPPNLQPGYSPSPTHPPTGQYTLFPLPPTLPT---PV |
| m-ML | 300 | PQLHPLFPDPSTTMPNSTAPHPVTMYPHPRNLSQET |
| p-ML | 297 | VQLQPLLPDPSAITPNSTSPLLFAAHPHFQNLSQEE |
| h-ML | 297 | VQLHPLLPDPSAPTPTPTSPLLNTSYTHSQNLSQEG |

```
                10                              20                              30
     SerProAlaProProAlaCysAspProArgLeuLeuAsnLysLeuLeuArgAspSerHisValLeuHisGlyArgLeuSerGlnCysProAspIleAsnPro
   1 AGCCCGGCTCCTCCTGCCTGTGACCCCCGACTCCTAAATAAACTGCTTCGTGACTCCCATGTCCTTCACGGCAGACTGAGCCAGTGCCCAGACATTAACC

            40                              50                              60
      LeuSerThrProValLeuLeuProAlaValAspPheThrLeuGlyGluTrpLysThrGlnThrGluGlnThrLysAlaGlnAspValLeuGlyAlaThr
 101 CTTTGTCCACACCTGTCCTGCTGCCTGCTGTGGACTTCACCTTGGGAGAATGGAAAACCCAGACGGAGCAGACAAAGGCACAGGATGTCCTGGGAGCCAC

        70                              80                              90                              100
     ThrLeuLeuLeuGluAlaValMetThrAlaArgGlyGlnValGlyProProCysLeuSerSerLeuLeuValGlnLeuSerGlyGlnValArgLeuLeu
 201 AACCCTTCTGCTGGAGGCAGTGATGACAGCACGGGGACAAGTGGGACCCCCTTGCCTCTCATCCCTGCTGGTGCAGCTTTCTGGACAGGTTCGCCTCCTC

                110                             120                             130
     LeuGlyAlaLeuGlnAspLeuLeuGlyMetGlnLeuProProGlnGlyArgThrThrAlaHisLysAspProSerAlaIlePheLeuAsnPheGlnGlnLeu
 301 CTCGGGGCCCTGCAGGACCTCCTTGGAATGCAGCTTCCTCCACAGGGAAGGACCACAGCTCACAAGGATCCCAGTGCCATCTTCCTGAACTTCCAACAAC

            140                             150                             160
      LeuArgGlyLysValArgPheLeuLeuLeuValValGlyProSerLeuCysAlaLysArgAlaProProAlaIleAlaValProSerSerThrSerPro
 401 TGCTCCGAGGAAAGGTGCGTTTCCTGCTCCTTGTAGTGGGGCCCTCCCTCTGTGCCAAGAGGGCCCCACCCGCCATAGCTGTCCCGAGCAGCACCTCTCC

        170                             180                             190                             200
     PheHisThrLeuAsnLysLeuProAsnArgThrSerGlyLeuLeuGluThrAsnSerSerIleSerAlaArgThrThrGlySerGlyPheLeuLysArg
 501 ATTCCACACACTGAACAAGCTCCCAAACAGGACCTCTGGATTGTTGGAGACAAACTCCAGTATCTCAGCCAGAACTACTGGCTCTGGATTTCTCAAGAGG
```

FIG.18B

```
                210                             220                             230
     LeuGlnAlaPheArgAlaLysIleProGlyLeuLeuAsnGlnThrSerArgSerLeuAspGlnIleProGlyHisGlnAsnGlyThrHisGlyProLeuSer
 601 CTGCAGGCATTCAGAGCCAAGATTCCTGGTCTGCTGAACCAAACCTCCAGGTCCCTAGACCAAATCCCTGGACACCAGAATGGGACACACGGACCCTTGA

            240                             250                             260
      GlyIleHisGlyLeuPheProGlyProGlnProGlyAlaLeuGlyAlaProAspIleProProAlaThrSerGlyMetGlySerArgProThrTyrLeu
 701 GTGGAATTCATGGACTCTTTCCTGGACCCCAACCCGGGGCCCTCGGAGCTCCAGACATTCCTCCAGCAACTTCAGGCATGGGCTCCCGGCCAACCTACCT

        270                             280                             290                             300
     GlnProGlyGluSerProSerProAlaHisProSerProGlyArgTyrThrLeuPheSerProSerProThrSerProSerProThrValGlnLeuGln
 801 CCAGCCTGGAGAGTCTCCTTCCCCAGCTCACCCTTCTCCTGGACGATACACTCTCTTCTCTCCTTCACCCACCTCGCCCTCCCCCACAGTCCAGCTCCAG

                310                             320                             330
     ProLeuLeuProAspProSerAlaIleThrProAsnSerThrSerProLeuLeuPheAlaAlaHisProHisPheGlnAsnLeuSerGlnGluGlu
 901 CCTCTGCTTCCTGACCCCTCTGCGATCACACCCAACTCTACCAGTCCTCTTCTATTTGCAGCTCACCCTCATTTCCAGAACCTGTCTCAGGAAGAGTAAG

1001 GTGCTCAGACCCTGCCAACTTCAGCA
```

FIG.18A

```
                                   10                                  20                                  30
    SerProAlaProProAlaCysAspProArgLeuLeuAsnLysLeuLeuArgAspSerHisValLeuHisGlyArgLeuSerGlnCysProAspIleAsnPro
  1 AGCCCGGCTCCTCCTGCCTGTGACCCCCGACTCCTAAATAAACTGCTTCGTGACTCCCATGTCCTTCACGGCAGACTGAGCCAGTGCCCAGACATTAACC

                       40                                  50                                  60
     LeuSerThrProValLeuLeuProAlaValAspPheThrLeuGlyGluTrpLysThrGlnThrGluGlnThrLysAlaGlnAspValLeuGlyAlaThr
101 CTTTGTCCACACCTGTCCTGCTGCCTGCTGTGGACTTCACCTTGGGAGAATGGAAAACCCAGACGGAGCAGACAAAGGCACAGGATGTCCTGGGAGCCAC

             70                                  80                                  90                                 100
    ThrLeuLeuLeuGluAlaValMetThrAlaArgGlyGlnValGlyProProCysLeuSerSerLeuLeuValGlnLeuSerGlyGlnValArgLeuLeu
201 AACCCTTCTGCTGGAGGCAGTGATGACAGCACGGGGACAAGTGGACCCCCTTGCCTCTCATCCCTGCTGGTGCAGCTTTCTGGACAGGTTCGCCTCCTC

                                  110                                 120                                 130
    LeuGlyAlaLeuGlnAspLeuLeuGlyMetGlnLeuProProGlnGlyArgThrThrAlaHisLysAspProSerAlaIlePheLeuAsnPheGlnGlnLeu
301 CTCGGGGCCCTGCAGGACCTCCTTGGAATGCAGCTTCCTCCACAGGGAAGGACCACAGCTCACAAGGATCCCAGTGCCATCTTCCTGAACTTCCAACAAC

                       140                                 150                                 160
     LeuArgGlyLysValArgPheLeuLeuLeuValValGlyProSerLeuCysAlaLysArgAlaProProAlaIleAlaValProSerSerThrSerPro
401 TGCTCCGAGGAAAGGTGCGTTTCCTGCTCCTTGTAGTGGGGCCCTCCCTCTGTGCCAAGAGGGCCCCACCCGCCATAGCTGTCCCGAGCAGCACCTCTCC

             170                                 180                                 190                                 200
    PheHisThrLeuAsnLysLeuProAsnArgThrSerGlyLeuLeuGluThrAsnSerSerIleSerAlaArgThrThrGlySerGlyPheLeuLysArg
501 ATTCCACACACTGAACAAGCTCCCAAACAGGACCTCTGGATTGTTGGAGACAAACTCCAGTATCTCAGCCAGAACTACTGGCTCTGGATTTCTCAAGAGG
```

FIG. 18B

```
                                              210                                       220                                       230
     LeuGlnAlaPheArgAlaLysIleProGlyLeuLeuAsnGlnThrSerArgSerLeuAspGlnIleProGlyHisGlnAsnGlyThrHisGlyProLeuSer
601  CTGCAGGCATTCAGAGCCAAGATTCCTGGTCTGCTGAACCAAACCTCCAGGTCCCTAGACCAAATCCCTGGACACCAGAATGGGACACACGGACCCTTGA

                               240                                       250                                       260
       GlyIleHisGlyLeuPheProGlyProGlnProGlyAlaLeuGlyAlaProAspIleProProAlaThrSerGlyMetGlySerArgProThrTyrLeu
701  GTGGAATTCATGGACTCTTTCCTGGACCCCAACCCGGGGCCCTCGGAGCTCCAGACATTCCTCCAGCAACTTCAGGCATGGGCTCCCGGCCAACCTACCT

           270                                       280                                       290                                       300
      GlnProGlyGluSerProSerProAlaHisProSerProGlyArgTyrThrLeuPheSerProSerProThrSerProSerProThrValGlnLeuGln
801  CCAGCCTGGAGAGTCTCCTTCCCCAGCTCACCCTTCTCCTGGACGATACACTCTCTTCTCTCCTTCACCCACCTCGCCCTCCCCCACAGTCCAGCTCCAG

                                              310                                       320                                       330
     ProLeuLeuProAspProSerAlaIleThrProAsnSerThrSerProLeuLeuPheAlaAlaHisProHisPheGlnAsnLeuSerGlnGluGlu
901  CCTCTGCTTCCTGACCCCTCTGCGATCACACCCAACTCTACCAGTCCTCTTCTATTTGCAGCTCACCCTCATTTCCAGAACCTGTCTCAGGAAGAGTAAG

1001 GTGCTCAGACCCTGCCAACTTCAGCA
```

```
                                     10                                      20                                      30
     SerProAlaProProAlaCysAspProArgLeuLeuAsnLysLeuLeuArgAspSerHisValLeuHisGlyArgLeuSerGlnCysProAspIleAsnPro
   1 AGCCCGGCTCCTCCTGCCTGTGACCCCCGACTCCTAAATAAACTGCTTCGTGACTCCCATGTCCTTCACGGCAGACTGAGCCAGTGCCCAGACATTAACC

                          40                                      50                                      60
      LeuSerThrProValLeuLeuProAlaValAspPheThrLeuGlyGluTrpLysThrGlnThrGluGlnThrLysAlaGlnAspValLeuGlyAlaThr
 101 CTTTGTCCACACCTGTCCTGCTGCCTGCTGTGGACTTCACCTTGGGAGAATGGAAAACCCAGACGGAGCAGACAAAGGCACAGGATGTCCTGGGAGCCAC

              70                                      80                                      90                                     100
      ThrLeuLeuLeuGluAlaValMetThrAlaArgGlyGlnValGlyProProCysLeuSerSerLeuLeuValGlnLeuSerGlyGlnValArgLeuLeu
 201 AACCCTTCTGCTGGAGGCAGTGATGACAGCACGGGGACAAGTGGACCCCCTTGCCTCTCATCCCTGCTGGTGCAGCTTTCTGGACAGGTTCGCCTCCTC

                                     110                                     120                                     130
     LeuGlyAlaLeuGlnAspLeuLeuGlyMetGlnGlyArgThrThrAlaHisLysAspProSerAlaIlePheLeuAsnPheGlnGlnLeuLeuArgGlyLys
 301 CTCGGGGCCCTGCAGGACCTCCTTGGAATGCAGGGAAGGACCACAGCTCACAAGGATCCCAGTGCCATCTTCCTGAACTTCCAACAACTGCTCCGAGGAA

                          140                                     150                                     160
      ValArgPheLeuLeuLeuValValGlyProSerLeuCysAlaLysArgAlaProProAlaIleAlaValProSerSerThrSerProPheHisThrLeu
 401 AGGTGCGTTTCCTGCTCCTTGTAGTGGGGCCCTCCCTCTGTGCCAAGAGGGCCCCACCCGCCATAGCTGTCCCGAGCAGCACCTCTCCATTCCACACACT
```

FIG. 19B

```
              170                                     180                                     190                                     200
      AsnLysLeuProAsnArgThrSerGlyLeuLeuGluThrAsnSerSerIleSerAlaArgThrThrGlySerGlyPheLeuLysArgLeuGlnAlaPhe
 501 GAACAAGCTCCCAAACAGGACCTCTGGATTGTTGGAGACAAACTCCAGTATCTCAGCCAGAACTACTGGCTCTGGATTTCTCAAGAGGCTGCAGGCATTC

                                     210                                     220                                     230
     ArgAlaLysIleProGlyLeuLeuAsnGlnThrSerArgSerLeuAspGlnIleProGlyHisGlnAsnGlyThrHisGlyProLeuSerGlyIleHisGly
 601 AGAGCCAAGATTCCTGGTCTGCTGAACCAAACCTCCAGGTCCCTAGACCAAATCCCTGGACACCAGAATGGGACACACGGACCCTTGAGTGGAATTCATG

                          240                                     250                                     260
      LeuPheProGlyProGlnProGlyAlaLeuGlyAlaProAspIleProProAlaThrSerGlyMetGlySerArgProThrTyrLeuGlnProGlyGlu
 701 GACTCTTTCCTGGACCCCAACCCGGGGCCCTCGGAGCTCCAGACATTCCTCCAGCAACTTCAGGCATGGGCTCCCGGCCAACCTACCTCCAGCCTGGAGA

              270                                     280                                     290                                     300
      SerProSerProAlaHisProSerProGlyArgTyrThrLeuPheSerProSerProThrSerProSerProThrValGlnLeuGlnProLeuLeuPro
 801 GTCTCCTTCCCCAGCTCACCCTTCTCCTGGACGATACACTCTCTTCTCTCCTTCACCCACCTCGCCCTCCCCCACAGTCCAGCTCCAGCCTCTGCTTCCT

                                     310                                     320
     AspProSerAlaIleThrProAsnSerThrSerProLeuLeuPheAlaAlaHisProHisPheGlnAsnLeuSerGlnGluGlu
 901 GACCCCTCTGCGATCACACCCAACTCTACCAGTCCTCTTCTATTTGCAGCTCACCCTCATTTCCAGAACCTGTCTCAGGAAGAGTAAGGTGCTCAGACCC

1001 TGCCAACTTCAGCA
```

FIG. 19A

```
                                          10                                      20                                      30
    SerProAlaProProAlaCysAspProArgLeuLeuAsnLysLeuLeuArgAspSerHisValLeuHisGlyArgLeuSerGlnCysProAspIleAsnPro ·
  1 AGCCCGGCTCCTCCTGCCTGTGACCCCCGACTCCTAAATAAACTGCTTCGTGACTCCCATGTCCTTCACGGCAGACTGAGCCAGTGCCCAGACATTAACC

                            40                                      50                                      60
      LeuSerThrProValLeuLeuProAlaValAspPheThrLeuGlyGluTrpLysThrGlnThrGluGlnThrLysAlaGlnAspValLeuGlyAlaThr
101 CTTTGTCCACACCTGTCCTGCTGCCTGCTGTGGACTTCACCTTGGGAGAATGGAAAACCCAGACGGAGCAGACAAAGGCACAGGATGTCCTGGGAGCCAC

              70                                      80                                      90                                     100
     ThrLeuLeuLeuGluAlaValMetThrAlaArgGlyGlnValGlyProProCysLeuSerSerLeuLeuValGlnLeuSerGlyGlnValArgLeuLeu
201 AACCCTTCTGCTGGAGGCAGTGATGACAGCACGGGGACAAGTGGACCCCCTTGCCTCTCATCCCTGCTGGTGCAGCTTTCTGGACAGGTTCGCCTCCTC

                                          110                                     120                                     130
    LeuGlyAlaLeuGlnAspLeuLeuGlyMetGlnGlyArgThrThrAlaHisLysAspProSerAlaIlePheLeuAsnPheGlnGlnLeuLeuArgGlyLys
301 CTCGGGGCCCTGCAGGACCTCCTTGGAATGCAGGGAAGGACCACAGCTCACAAGGATCCCAGTGCCATCTTCCTGAACTTCCAACAACTGCTCCGAGGAA

                            140                                     150                                     160
      ValArgPheLeuLeuLeuValValGlyProSerLeuCysAlaLysArgAlaProProAlaIleAlaValProSerSerThrSerProPheHisThrLeu
401 AGGTGCGTTTCCTGCTCCTTGTAGTGGGGCCCTCCCTCTGTGCCAAGAGGGCCCCACCCGCCATAGCTGTCCCGAGCAGCACCTCTCCATTCCACACACT
```

FIG. 19B

```
              170                                 180                                 190                                 200
         AsnLysLeuProAsnArgThrSerGlyLeuLeuGluThrAsnSerSerIleSerAlaArgThrThrGlySerGlyPheLeuLysArgLeuGlnAlaPhe
501 GAACAAGCTCCCAAACAGGACCTCTGGATTGTTGGAGACAAACTCCAGTATCTCAGCCAGAACTACTGGCTCTGGATTTCTCAAGAGGCTGCAGGCATTC

                                    210                                 220                                 230
        ArgAlaLysIleProGlyLeuLeuAsnGlnThrSerArgSerLeuAspGlnIleProGlyHisGlnAsnGlyThrHisGlyProLeuSerGlyIleHisGly
601 AGAGCCAAGATTCCTGGTCTGCTGAACCAAACCTCCAGGTCCCTAGACCAAATCCCTGGACACCAGAATGGGACACACGGACCCTTGAGTGGAATTCATG

                        240                                 250                                 260
          LeuPheProGlyProGlnProGlyAlaLeuGlyAlaProAspIleProProAlaThrSerGlyMetGlySerArgProThrTyrLeuGlnProGlyGlu
701 GACTCTTTCCTGGACCCCAACCCGGGGCCCTCGGAGCTCCAGACATTCCTCCAGCAACTTCAGGCATGGGCTCCCGGCCAACCTACCTCCAGCCTGGAGA

              270                                 280                                 290                                 300
         SerProSerProAlaHisProSerProGlyArgTyrThrLeuPheSerProSerProThrSerProSerProThrValGlnLeuGlnProLeuLeuPro
801 GTCTCCTTCCCCAGCTCACCCTTCTCCTGGACGATACACTCTCTTCTCTCCTTCACCCACCTCGCCCTCCCCCACAGTCCAGCTCCAGCCTCTGCTTCCT

                                    310                                 320
        AspProSerAlaIleThrProAsnSerThrSerProLeuLeuPheAlaAlaHisProHisPheGlnAsnLeuSerGlnGluGlu
901 GACCCCTCTGCGATCACACCCAACTCTACCAGTCCTCTTCTATTTGCAGCTCACCCTCATTTCCAGAACCTGTCTCAGGAAGAGTAAGGTGCTCAGACCC

1001 TGCCAACTTCAGCA
```

FIG. 20

FIG.20A pML 1 SPAPPACDPRLLNKLLRDSHVLHGRLSQCPDINPLSTPVLLPAVDFTLGE
pML2 1 SPAPPACDPRLLNKLLRDSHVLHGRLSQCPDINPLSTPVLLPAVDFTLGE pML 51 WKTQTEQTKAQDVLGATTLLLEAVMTARGQVGPPCLSSLLVQLSGQVRLL
pML2 51 WKTQTEQTKAQDVLGATTLLLEAVMTARGQVGPPCLSSLLVQLSGQVRLL pML 101 LGALQDLLGMQLPPQGRTTAHKDPSAIFLNFQQLLRGKVRFLLLVVGPSL
pML2 101 LGALQDLLGM----QGRTTAHKDPSAIFLNFQQLLRGKVRFLLLVVGPSL

FIG.20B pML 151 CAKRAPPAIAVPSSTSPFHTLNKLPNRTSGLLETNSSISARTTGSGFLKR
pML2 147 CAKRAPPAIAVPSSTSPFHTLNKLPNRTSGLLETNSSISARTTGSGFLKR pML 201 LQAFRAKIPGLLNQTSRSLDQIPGHQNGTHGPLSGIHGLFPGPQPGALGA
pML2 197 LQAFRAKIPGLLNQTSRSLDQIPGHQNGTHGPLSGIHGLFPGPQPGALGA pML 251 PDIPPATSGMGSRPTYLQPGESPSPAHPSPGRYTLFSPSPTSPSPTVQLQ
pML2 247 PDIPPATSGMGSRPTYLQPGESPSPAHPSPGRYTLFSPSPTSPSPTVQLQ pML 301 PLLPDPSAITPNSTSPLLFAAHPHFQNLSQEE
pML2 297 PLLPDPSAITPNSTSPLLFAAHPHFQNLSQEE

FIG. 20A

```
pML    1   SPAPPACDPRLLNKLLRDSHVLHGRLSQCPDINPLSTPVLLPAVDFTLGE
pML2   1   SPAPPACDPRLLNKLLRDSHVLHGRLSQCPDINPLSTPVLLPAVDFTLGE

pML    51  WKTQTEQTKAQDVLGATTLLLEAVMTARGQVGPPCLSSLLVQLSGQVRLL
pML2   51  WKTQTEQTKAQDVLGATTLLLEAVMTARGQVGPPCLSSLLVQLSGQVRLL

pML    101 LGALQDLLGMQLPPQGRTTAHKDPSAIFLNFQQLLRGKVRFLLLVVGPSL
pML2   101 LGALQDLLGM....QGRTTAHKDPSAIFLNFQQLLRGKVRFLLLVVGPSL
```

METHOD OF TREATMENT OF THROMBOCYTOPENIA OR RISK THEREOF USING MPL LIGAND (THROMBOPOIETIN), VARIANTS, AND FRAGMENTS THEREOF

CROSS REFERENCES

This is a divisional of pending U.S. patent application Ser. No. 08/249,376 filed May 25, 1994, which is a continuation-in-part of pending U.S. patent application Ser. No. 08/223,263 filed Apr. 4, 1994, which is a continuation-in-part of pending U.S. patent application Ser. No. 08/196,689 filed Feb. 15, 1994, which is a continuation-in-part of pending U.S. patent application Ser. No. 08/185,607 filed Jan. 21, 1994, now abandoned, which is a continuation-in-part of pending U.S. patent application Ser. No. 08/176,553 filed Jan. 3, 1994, now abandoned, which applications are incorporated herein by reference and to which applications priority is claimed under 35 USC §120.

FIELD OF THE INVENTION

This invention relates to the isolation, purification and recombinant or chemical synthesis of proteins that influence survival, proliferation, differentiation or maturation of hematopoietic cells, especially platelet progenitor cells. This invention specifically relates to the cloning and expression of nucleic acids encoding a protein ligand capable of binding to and activating mpl, a member of the cytokine receptor superfamily. This invention further relates to the use of these proteins alone or in combination with other cytokines to treat immune or hematopoietic disorders including thrombocytopenia.

BACKGROUND OF THE INVENTION

I. The Hematopoietic System

The hematopoietic system produces the mature highly specialized blood cells known to be necessary for survival of all mammals. These mature cells include; erythrocytes, specialized to transport oxygen and carbon dioxide, T- and B-lymphocytes, responsible for cell- and antibody-mediated immune responses, platelets or thrombocytes, specialized to form blood clots, and granulocytes and macrophages, specialized as scavengers and as accessory cells to combat infection. Granulocytes are further subdivided into; neutrophils, eosinophils, basophils and mast cells, specialized cell types having discrete functions. Remarkably, all of these specialized mature blood cells are derived from a single common primitive cell type, referred to as the pluripotent (or totipotent) stem cell, found primarily in bone marrow (Dexter at al., *Ann. Rev. Cell Biol.,* 3:423-441 [1987]).

The mature highly specialized blood cells must be produced in large numbers continuously throughout the life of a mammal. The vast majority of these specialized blood cells are destined to remain functionally active for only a few hours to weeks (Cronkite et al., *Blood Cells,* 2:263-284 [1976]). Thus, continuous renewal of the mature blood cells, the primitive stem cells themselves, as well as any intermediate or lineage-committed progenitor cell lines lying between the primitive and mature cells, is necessary in order to maintain the normal steady state blood cell needs of the mammal.

At the heart of the hematopoietic system lies the pluripotent stem cell(s). These cells are relatively few in number and undergo self-renewal by proliferation to produce daughter stem cells or are transformed, in a series of differentiation steps, into increasingly mature lineage-restricted progenitor cells, ultimately forming the highly specialized mature blood cell(s).

For example, certain multipotent progenitor cells, referred to as CFC-Mix, derived from stem cells undergo proliferation (self-renewal) and development to produce colonies containing all the different myeloid cells; erythrocytes, neutrophils, megakaryocytes (predecessors of platelets), macrophages, basophils, eosinophils, and mast cells. Other progenitor cells of the lymphoid lineage undergo proliferation and development into T-cells and B-cells.

Additionally, between the CFC-Mix progenitor cells and myeloid cells lie another rank of progenitor cells of intermediate commitment to their progeny. These lineage-restricted progenitor cells are classified on the basis of the progeny they produce. Thus, the known immediate predecessors of the myeloid cells are: erythroid colony-forming units (CFU-E) for erythrocytes, granulocyte/macrophage colony-forming cells (GM-CFC) for neutrophils and macrophages, megakaryocyte colony-forming cells (Meg-CFC) for megakaryocytes, eosinophil colony-forming cells (Eos-CFC) for eosinophils, and basophil colony-forming cells (Bas-CFC) for mast cells. Other intermediate predecessor cells between the pluripotent stem cells and mature blood cells are known (see below) or will likely be discovered having varying degrees of lineage-restriction and self-renewal capacity.

The underlying principal of the normal hematopoietic cell system appears to be decreased capacity for self-renewal as multipotency is lost and lineage-restriction and maturity is acquired. Thus, at one end of the hematopoietic cell spectrum lies the pluripotent stem cell possessing the capacity for self-renewal and differentiation into all the various lineage-specific committed progenitor cells. This capacity is the basis of bone marrow transplant therapy where primitive stem cells repopulate the entire hematopoietic cell system. At the other end of the spectrum lie the highly lineage-restricted progenitors and their progeny which have lost the ability of self-renewal but have acquired mature functional activity.

The proliferation and development of stem cells and lineage-restricted progenitor cells is carefully controlled by a variety of hematopoietic growth factors or cytokines. The role of these growth factors in vivo is complex and incompletely understood. Some growth factors, such as interleukin-3 (IL-3), are capable of stimulating both multipotent stem cells as well as committed progenitor cells of several lineages, including for example, megakaryocytes. Other factors such as granulocyte/macrophage colony-stimulating factor (GM-CSF) was initially thought to be restricted in its action to GM-CFC's. Later, however, it was discovered GM-CSF also influenced the proliferation and development of interalia megakaryocytes. Thus, IL-3 and GM-CSF were found to have overlapping biological activities, although with differing potency. More recently, both interleukin-6 (IL-6) and interleukin-11 (IL-11), while having no apparent influence on meg-colony formation alone, act synergistically with IL-3 to stimulate maturation of megakaryocytes (Yonemura et al., *Exp. Hematol.,* 20:1011-1016 [1992]).

Thus, hematopoietic growth factors may influence growth and differentiation of one or more lineages, may overlap with other growth factors in affecting a single progenitor cell line, or may act synergistically with other factors.

It also appears that hematopoietic growth factors can exhibit their effect at different stages of cell development from the totipotent stem cell through various committed lineage-restricted progenitors to the mature blood cell. For example, erythropoietin (epo) appears to promote proliferation only of mature erythroid progenitor cells. IL-3 appears to exert its effect earlier influencing primitive stem cells and intermediate lineage-restricted progenitor cells. Other growth factors such as stem cell factor (SCF) may influence even more primitive cell development.

It will be appreciated from the foregoing that novel hematopoietic growth factors that affect survival, proliferation, differentiation or maturation of any of the blood cells or predecessors thereof would be useful, especially to assist in the re-establishment of a diminished hematopoietic system caused by disease or after radiation- or chemo-therapy.

II. Megakaryocytopoiesis—Platelet Production

Regulation of megakaryocytopoiesis and platelet production has been reviewed by: Mazur, *Exp. Hematol.,* 15:248 [1987] and Hoffman, *Blood,* 74:1196-1212 [1989]. Briefly, bone marrow pluripotent stem cells differentiate into megakaryocytic, erythrocytic, and myelocytic cell lines. It is believed there is a hierarchy of committed megakaryocytic progenitor cells between stem cells and megakaryocytes. At least three classes of megakaryocytic progenitor cells have been identified, namely; burst forming unit megakaryocytes (BFU-MK), colony-forming unit megakaryocytes (CFU-MK), and light density megakaryocyte progenitor cells (LD-CFU-MK). Megakaryocytic maturation itself is a continuum of development that has been separated into stages based on standard morphologic criteria. The earliest recognizable member of the megakaryocyte (MK or meg) family are the megakaryoblasts. These cells are initially 20 to 30 μm in diameter having basophilic cytoplasm and a slightly irregular nucleus with loose, somewhat reticular chromatin and several nucleoli. Later, megakaryoblasts may contain up to 32 (polyploid), but the cytoplasm remains sparse and immature. As maturation proceeds, the nucleus becomes more lobulate and pyknotic, the cytoplasm increases in quantity and becomes more acidophilic and granular. The most mature cells of this family may give the appearance of releasing platelets at their periphery. Normally, less than 10% of megakaryocytes are in the blast stage and more than 50% are mature. Arbitrary morphologic classifications commonly applied to the megakaryocyte series are megakaryoblast for the earliest form; promegakaryocyte or basophilic megakaryocyte for the intermediate form; and mature (acidophilic, granular, or platelet-producing) megakaryocyte for the late forms. The mature megakaryocyte extends filaments of cytoplasm into sinusoidal spaces where they detach and fragment into individual platelets (Williams et al., *Hematology,* 1972).

Megakaryocytopoiesis is believed to involve several regulatory factors (Williams et al., *Br. J. Haematol.,* 52:173 [1982] and Williams et al., *J. Cell Physiol.,* 110:101 [1982]). The early level of megakaryocytopoiesis is postulated as being mitotic, concerned with cell proliferation and colony initiation from CFU-MK but is not affected by platelet count (Burstein et al., *J. Cell Physiol.,* 109:333 [1981] and Kimura et al., *Exp. Hematol.,* 13:1048 [1985]). The later stage of maturation is non-mitotic, involved with nuclear polyploidization and cytoplasmic maturation and is probably regulated in a feedback mechanism by peripheral platelet number (Odell et al., *Blood,* 48:765 [1976] and Ebbe et al., *Blood,* 32:787 [1968]).

The existence of a distinct and specific megakaryocyte colony-stimulating factor (MK-CSF) has been disputed (Mazur, *Exp. Hematol.,* 15:340-350 [1987]). However most authors believe that a process so vital to survival as platelet production would be regulated by cytokine(s) exclusively responsible for this process. The hypothesis that megakaryocyte/platelet specific cytokine(s) exist has provided the basis for more than 30 years of search—but to date no such cytokine has been purified, sequenced and established by assay as a unique MK-CSF (TPO).

Although it has been reported that MK-CSF's have been partly purified from experimentally produced thrombocytopenia (Hill et al., *Exp. Hematol.,* 14:752 [1986]) and human embryonic kidney conditioned medium [CM] (McDonald et al., *J. Lab. Clin. Med.,* 85:59 [1975]) and in man from a plastic anemia and idiopathic thrombocytopenic purpura urinary extracts (Kawakita et al., *Blood,* 6:556 [1983]) and plasma (Hoffman et al., *J. Clin. Invest.,* 75:1174 [1985]), their physiological function is as yet unknown in most cases.

The conditioned medium of pokeweed mitogen-activated spleen cells (PWM-SpCM) and the murine myelomonocyte cell line WEHI-3 (WEHI-3CM) have been used as megakaryocyte potentiators. PWM-SpCM contains factors enhancing CFU-MK growth (Metcalf et al., *Pro. Natl. Acad. Sci., USA,* 72:1744-1748 [1975]; Quesenberry et al., *Blood,* 65:214 [1985]; and Iscove, N. N., in *Hematopoietic Cell Differentiation, ICN-UCLA Symposia on Molecular and Cellular Biology*, Vol. 10, Golde et al., eds. [New York, Academy Press] pp 37-52 [1978]), one of which is interleukin-3 (IL-3), a multilineage colony stimulating factor (multi-CSF [Burstein, *Blood Cells,* 11:469 [1986]). The other factors in this medium have not yet been identified and isolated. WEHI-3 is a murine myelomonocytic cell line secreting relatively large amounts of IL-3 and smaller amounts of GM-CSF. IL-3 has been found to potentiate the growth of a wide range of hematopoietic cells (Ihle et al., *J. Immunol.,* 13:282 [1983]). IL-3 has also been found to synergize with many of the known hematopoietic hormones or growth factors (Bartelmez et al., *J. Cell Physiol.,* 122:362-369 [1985] and Warren et al., *Cell,* 46:667-674 [1988]), including both erythropoietin (EPO) and interleukin-1 (IL-1), in the induction of very early multipotential precursors and the formation of very large mixed hematopoietic colonies.

Other sources of megakaryocyte potentiators have been found in the conditioned media of murine lung, bone, macrophage cell lines, peritoneal exudate cells and human embryonic kidney cells. Despite certain conflicting data (Mazur, *Exp. Hematol.,* 15:340-350 [1987]), there is some evidence (Geissler et al., *Br. J. Haematol.,* 60:233-238 [1985]) that activated T lymphocytes rather than monocytes play an enhancing role in megakaryocytopoiesis. These findings suggest that activated T-lymphocyte secretions such as interleukins may be regulatory factors in MK development (Geissler et al., *Exp. Hematol.,* 15:845-853 [1987]). A number of studies on megakaryocytopoiesis with purified erythropoietin EPO (Vainchenker et al., *Blood,* 54:940 [1979]; McLeod et al., *Nature,* 261:492-4 [1976]; and Williams et al., *Exp. Hematol.,* 12:734 [1984]) indicate that this hormone has an enhancing effect on MK colony formation. This has also been demonstrated in both serum-free and serum-containing cultures and in the absence of accessory cells (Williams et al., *Exp. Hematol.,* 12:734 [1984]). EPO was postulated to be involved more in the single and two-cell stage aspects of megakaryocytopoiesis as opposed to the effect of PWM-SpCM which was involved in the four-cell stage of megakaryocyte development. The interaction of all these factors on both early and late phases of megakaryocyte development remains to be elucidated.

Data produced from several laboratories suggests that the only multi-lineage factors that individually have MK-colony stimulating activity are GM-CSF and IL-3 and, to a lesser extent, the B-cell stimulating factor IL-6 (Ikebuchi et al., *Proc. Natl. Acad. Sci. USA,* 84:9035 [1987]). More recently, several authors have reported that IL-11 and leukemia inhibitory factor (LIF) act synergistically with IL-3 to increase megakaryocyte size and ploidy (Yonemura et al., *British Journal of Hematology,* 84:16-23 [1993]; Burstein et al., *J. Cell. Physiol.,* 153:305-312 [1992]; Metcalf et al., *Blood,* 76:50-56 [1990]; Metcalf et al., *Blood,* 77:2150-2153 [1991]; Bruno et al., *Exp. Hematol.,* 19:378-381 [1991]; and Yonemura et al., *Exp. Hematol.,* 20:1011-1016 [1992]).

Other documents of interest include: Eppstein et al., U.S. Pat. No. 4,962,091; Chong, U.S. Pat. No. 4,879,111; Fernandes et al., U.S. Pat. No. 4,604,377; Wissler et al., U.S. Pat. No. 4,512,971; Gottlieb, U.S. Pat. No. 4,468,379; Bennett et al., U.S. Pat. No. 5,215,895; Kogan et al., U.S. Pat. No. 5,250,732; Kimura et al., *Eur. J. Immunol.,* 20(9):1927-1931 [1990]; Secor et al., *J. of Immunol.,* 144(4):1484-1489 [1990]; Warren et al., *J. of Immunol.,* 140(1):94-99 [1988]; Warren et al., *Exp. Hematol.,* 17(11):1095-1099 [1989]; Bruno et al., *Exp. Hematol.,* 17(10):1038-1043 [1989]; Tanikawa et al., *Exp. Hematol.,* 17(8):883-888 [1989]; Koike et al., *Blood,* 75(12):2286-2291 [1990]; Lotem, *Blood,* 75(5): 1545-1551 [1989]; Rennick et al., *Blood,* 73(7):1828-1835 [1989]; and Clutterbuck et al., *Blood,* 73(6):1504-1512 [1989].

III. Thrombocytopenia

Platelets are critical elements of the blood clotting mechanism. Depletion of the circulating level of platelets, called thrombocytopenia, occurs in various clinical conditions and disorders. Thrombocytopenia is commonly defined as a platelet count below $150\times10^9$ per liter. The major causes of thrombocytopenia can be broadly divided into three categories on the basis of platelet life span, namely; (1) impaired production of platelets by the bone marrow, (2) platelet sequestration in the spleen (splenomegaly), or (3) increased destruction of platelets in the peripheral circulation (e.g., autoimmune thrombocytopenia or chemo- and radiation-therapy). Additionally, in patients receiving large volumes of rapidly administered platelet-poor blood products, thrombocytopenia may develop due to dilution.

The clinical bleeding manifestations of thrombocytopenia depend on the severity of thrombocytopenia, its cause, and possible associated coagulation defects. In general, patients with platelet counts between 20 and $100\times10^9$ per liter are at risk of excessive post traumatic bleeding, while those with platelet counts below $20\times10^9$ per liter may bleed spontaneously. These latter patients are candidates for platelet transfusion with attendant immune and viral risk. For any given degree of thrombocytopenia, bleeding tends to be more severe when the cause is decreased production rather than increased destruction of platelets. In the latter situation, accelerated platelet turnover results in the circulation of younger, larger and hemostatically more effective platelets. Thrombocytopenia may result from a variety of disorders briefly described below. A more detailed description may be found in Schafner, A. I., "Thrombocytopenia and Disorders of Platelet Function," *Internal Medicine,* 3rd Ed., John J. Hutton et al., Eds., Little Brown and Co., Boston/Toronto/London [1990].

(a) Thrombocytopenia Due to Impaired Platelet Production

Causes of congenital thrombocytopenia include constitutional aplastic anemia (Fanconi syndrome) and congenital amegakaryocytic thrombocytopenia, which may be associated with skeletal malformations. Acquired disorders of platelet production are caused by either hypoplasia of megakaryocytes or ineffective thrombopoiesis. Megakaryocytic hypoplasia can result from a variety of conditions, including marrow aplasia (including idiopathic forms or myelosuppression by chemotherapeutic agents or radiation therapy), myelfibrosis, leukemia, and invasion of the bone marrow by metastatic tumor or granulomas. In some situations, toxins, infectious agents, or drugs may interfere with thrombopoiesis relatively selectively; examples include transient thrombocytopenias caused by alcohol and certain viral infections and mild thrombocytopenia associated with the administration of thiazide diuretics. Finally, ineffective thrombopoiesis secondary to megaloblastic processes (folate or $B_{12}$ deficiency) can also cause thrombocytopenia, usually with coexisting anemia and leukopenia.

Current treatment of thrombocytopenias due to decreased platelet production depends on identification and reversal of the underlying cause of the bone marrow failure. Platelet transfusions are usually reserved for patients with serious bleeding complications, or for coverage during surgical procedures, since isoimmunization may lead to refractoriness to further platelet transfusions. Mucosal bleeding resulting from severe thrombocytopenia may be ameliorated by the oral or intravenous administration of the antifibrinolytic agents. Thrombotic complications may develop, however, if antifibrinolytic agents are used in patients with disseminated intravascular coagulation (DIC).

(b) Thrombocytopenia Due to Splenic Sequestration

Splenomegaly due to any cause may be associated with mild to moderate thrombocytopenia. This is a largely passive process (hypersplenism) of splenic platelet sequestration, in contrast to the active destruction of platelets by the spleen in cases of immunomediated thrombocytopenia discussed below. Although the most common cause of hypersplenism is congestive splenomegaly from portal hypertension due to alcoholic cirrhosis, other forms of congestive, infiltrative, or lymphoproliferative splenomegaly are also associated with thrombocytopenia. Platelet counts generally do not fall below $50\times10^9$ per liter as a result of hypersplenism alone.

(c) Thrombocytopenia Due to Nonimmune-Mediated Platelet Destruction

Thrombocytopenia can result from the accelerated destruction of platelets by various nonimmunologic processes. Disorders of this type include disseminated intravascular coagulation, prosthetic intravascular devices, extra corporeal circulation of the blood, and thrombotic microangiopathies such as thrombotic thrombocytic purpura. In all of these situations, circulating platelets that are exposed to either artificial surfaces or abnormal vascular intima either are consumed at these sites or are damaged and then prematurely cleared by the reticuloendothelial system. Disease states or disorders in which disseminated intravascular coagulation (DIC) may arise are set forth in greater detail in Braunwald et al. (eds), *Harrison's Principles of Internal Medicine,* 11th Ed., p.1478, McGraw Hill [1987]. Intravascular prosthetic devices, including cardiac valves and intra-aortic balloons can cause a mild to moderate destructive thrombocytopenia and transient thrombocytopenia in patients undergoing cardiopulmonary bypass or hemodialysis may result from consumption or damage of platelets in the extra corporeal circuit.

(d) Drug-Induced Immune Thrombocytopenia

More than 100 drugs have been implicated in immunologically mediated thrombocytopenia. However, only quinidine, quinine, gold, sulfonamides, cephalothin, and heparin have been well characterized. Drug-induced thrombocytopenia is frequently very severe and typically occurs precipitously within days while patients are taking the sensitizing medication.

(e) Immune (Autoimmune) Thrombocytopenic Purpura (ITP)

ITP in adults is a chronic disease characterized by autoimmune platelet destruction. The autoantibody is usually IgG although other immunoglobulins have also been reported. Although the autoantibody of ITP has been found to be associated with platelet membrane $GPII_bIII_a$, the platelet antigen specificity has not been identified in most cases. Extravascular destruction of sensitized platelets occurs in the reticuloendothelial system of the spleen and liver. Although over one-half of all cases of ITP are idiopathic, many patients have underlying rheumatic or autoimmune diseases (e.g., systemic lupus erythematosus) or lymphoproliferative disorders (e.g., chronic lymphocytic leukemia).

(f) HIV-Induced ITP

ITP is an increasingly common complication of HIV infection (Morris et al., *Ann. Intern. Med.,* 96:714-717 [1982]), and can occur at any stage of the disease progression, both in patients diagnosed with the Acquired Immune Deficiency Syndrome (AIDS), those with AIDS-related complex, and those with HIV infection but without AIDS symptoms. HIV infection is a transmissible disease ultimately characterized by a profound deficiency of cellular immune function as well as the occurrence of opportunistic infection and malignancy. The primary immunologic abnormality resulting from infection by HIV is the progressive depletion and functional impairment of T lymphocytes expressing the CD4 cell surface glycoprotein (Lane et al., *Ann. Rev. Immunol.,* 3:477 [1985]). The loss of CD4 helper/inducer T cell function probably underlies the profound defects in cellular and humoral immunity leading to the opportunistic infections and malignancies characteristic of AIDS (H. Lane supra).

Although the mechanism of HIV-associated ITP is unknown, it is believed to be different from the mechanism of ITP not associated with HIV infection. (Walsh et al., *N. Eng. J. Med.,* 311:635-639 [1984]; and Ratner, *Am. J. Med.,* 86:194-198 [1989]).

IV. Current Therapy for Thrombocytopenia

The therapeutic approach to the treatment of patients with thrombocytopenia is dictated by the severity and urgency of the clinical situation. The treatment is similar for HIV-associated and non-HIV-related thrombocytopenia, and although a number of different therapeutic approaches have been used, the therapy remains controversial.

Platelet counts in patients diagnosed with thrombocytopenia have been successfully increased by glucocorticoid (e.g., prednisolone) therapy, however in most patients, the response is incomplete, or relapse occurs when the glucocorticoid dose is reduced or its administration is discontinued. Based upon studies with patients having HIV-associated ITP, some investigators have suggested that glucocorticoid therapy may result in predisposition to AIDS. Glucocorticoids are usually administered if platelet count falls below $20\times10^9$/liter or when spontaneous bleeding occurs.

For patients refractory to glucocorticoids, the compound 4-(2-chlorphenyl)-9-methyl-2-[3-(4-morpholinyl)-3-propanon-1-yl]6H-thieno[3,2,f][1,2,4]triazolo[4,3,a,][1,4] diazepin (WEB 2086) has been successfully used to treat a severe case of non HIV-associated ITP. A patient having platelet counts of 37,000-58,000/μl was treated with WEB 2086 and after 1-2 weeks treatment platelet counts increased to 140,000-190,000/μl. (EP 361,077 and Lohman et al., *Lancet,* 1147 [1988]).

Although the optimal treatment for acquired amegakaryocytic thrombocytopenia purpura (AATP) is uncertain, antithymocyte globulin (ATG), a horse antiserum to human thymus tissue, has been shown to produce prolonged complete remission (Trimble et al., *Am. J. Hematol.,* 37:126-127 [1991]). A recent report however, indicates that the hematopoletic effects of ATG are attributable to thimerosal, where presumably the protein acts as a mercury carrier (Panella et al., *Cancer Research,* 50:4429-4435 [1990]).

Good results have been reported with splenectomy. Splenectomy removes the major site of platelet destruction and a major source of autoantibody production in many patients. This procedure results in prolonged treatment-free remissions in a large number of patients. However, since surgical procedures are generally to be avoided in immune compromised patients, splenectomy is recommended only in severe cases of thrombocytopenia (e.g. severe HIV-associated ITP), in patients who fail to respond to 2 to 3 weeks of glucocorticoid treatment, or do not achieve sustained response after discontinuation of glucocorticoid administration. Based upon current scientific knowledge, it is unclear whether splenectomy predisposes patients to AIDS.

In addition to prednisolone therapy and splenectomy, certain cytotoxic agents, e.g., vincristine, and azidothimidine (AZT, zidovudine) also show promise in treating HIV-induced ITP; however, the results are preliminary.

It will be appreciated from the foregoing that one way to treat thrombocytopenia would be to obtain an agent capable of accelerating the differentiation and maturation of megakaryocytes or precursors thereof into the platelet-producing form. Considerable efforts have been expended on identifying such an agent, commonly referred to as "thrombopoletin" (TPO). Other names for TPO commonly found in the literature include; thrombocytopoiesis stimulating factor (TSF), megakaryocyte colony-stimulating factor (MK-CSF), megakaryocyte-stimulating factor and megakaryocyte potentiator. TPO activity was observed as early as 1959 (Rak et al., *Med. Exp.,* 1:125) and attempts to characterize and purify this agent have continued to the present day. While reports of partial purification of TPO-active polypeptides exist (see, for example, Tayrien et al., *J. Biol. Chem.,* 262:3252 [1987] and Hoffman et al., *J. Clin. Invest.* 75:1174 [1985]), others have postulated that TPO is not a discrete entity in its own right but rather is simply the polyfunctional manifestation of a known hormone (IL-3, Sparrow et al., *Prog. Clin. Biol. Res.,* 215:123 [1986]). Regardless of its form or origin, a molecule possessing thrombopoietic activity would be of significant therapeutic value. Although no protein has been unambiguously identified as TPO, considerable interest surrounds the recent discovery that mpl, a putative cytokine receptor, may transduce a thrombopoietic signal.

V. Mpl is a Megakaryocytopoletic Cytokine Receptor

It is believed that the proliferation and maturation of hematopoietic cells is tightly regulated by factors that positively or negatively modulate pluripotential stem cell proliferation and multilineage differentiation. These effects are mediated through the high-affinity binding of extracellular protein factors to specific cell surface receptors. These cell surface receptors share considerable homology and are generally classified as members of the cytokine receptor superfamily. Members of the superfamily include receptors for: IL-2 (β and γ chains) (Hatakeyama et al., *Science,* 244:551-556 [1989]; Takeshita et al., *Science,* 257:379-382 [1991]), IL-3 (Itoh et al., *Science,* 247:324-328 [1990]; Gorman et al., *Proc. Natl. Acad. Sci. USA,* 87:5459-5463 [1990]; Kitamura et al., *Cell,* 66:1165-1174 [1991a]; Kitamura et al., *Proc. Natl. Acad. Sci. USA,* 88:5082-5086 [1991b]), IL-4 (Mosley et al., *Cell,* 59:335-348 [1989], IL-5 (Takaki et al., *EMBO J.,* 9:4367-4374 [1990]; Tavernier et al., *Cell,* 66:1175-1184 [1991]), IL-6 (Yamasaki et al., *Science,* 241:825-828 [1988]; Hibi et al., *Cell,* 63:1149-1157 [1990]), IL-7 (Goodwin et al., *Cell,* 60:941-951 [1990]), IL-9 (Renault et al., *Proc. Natl. Acad. Sci. USA,* 89:5690-5694 [1992]), granulocyte-macrophage colony-stimulating factor (GM-CSF) (Gearing et al.,

*EMBO J.,* 8:3667-3676 [1991]; Hayashida et al., *Proc. Natl. Acad. Sci. USA,* 244:9655-9659 [1990]), granulocyte colony-stimulating factor (G-CSF) (Fukunaga et al., *Cell,* 61:341-350 [1990a]; Fukunaga et al., *Proc. Natl. Acad. Sci. USA,* 87:8702-8706 [1990b]; Larsen et al., *J. Exp. Med.,* 172:1559-1570 [1990]), EPO (D'Andrea et al., *Cell,* 57:277-285 [1989]; Jones et al., *Blood,* 76:31-35 [1990]), Leukemia inhibitory factor (LIF) (Gearing et al., *EMBO J.,* 10:2839-2848 [1991]), oncostatin M (OSM) (Rose et al., *Proc. Natl. Acad. Sci. USA,* 88:8641-8645 [1991]) and also receptors for prolactin (Boutin et al., *Proc. Natl. Acad. Sci. USA,* 88:7744-7748 [1988]; Edery et al., *Proc. Natl. Acad. Sci. USA,* 86:2112-2116 [1989]), growth hormone (GH) (Leung et al., *Nature,* 330:537-543 [1987]) and ciliary neurotrophic factor (CNTF) (Davis et al., *Science,* 253:59-63 [1991].

Members of the cytokine receptor superfamily may be grouped into three functional categories (for review see Nicola et al., *Cell,* 67:1-4 [1991]). The first class comprises single chain receptors, such as erythropoietin receptor (EPO-R) or granulocyte colony stimulating factor receptor (G-CSF-R), which bind ligand with high affinity via the extracellular domain and also generate an intracellular signal. A second class of receptors, so called α-subunits, includes interleukin-6 receptor (IL6-R), granulocyte-macrophage colony stimulating factor receptor (GM-CSF-R), interleukin-3 receptor (IL3-Rα) and other members of the cytokine receptor superfamily. These α-subunits bind ligand with low affinity but cannot transduce an intracellular signal. A high affinity receptor capable of signaling is generated by a heterodimer between an α-subunit and a member of a third class of cytokine receptors, termed β-subunits, e.g., $\beta_c$, the common β-subunit for the three α-subunits of L3-Rα, IL-5R and GM-CSF-R.

Evidence that mpl is a member of the cytokine receptor superfamily comes from sequence homology (Gearing, *EMBO J.,* 8:3667-3676 [1988]; Bazan, *Proc. Natl. Aced. Sci. USA,* 87:6834-6938 [1990]; Davis et al., *Science,* 253:59-63 [1991] and Vigon et al., *Proc. Natl. Acad. Sci. USA,* 89:5640-5644 [1992]) and its ability to transduce proliferative signals.

Deduced protein sequence from molecular cloning of murine c-mpl reveals this protein is homologous to other cytokine receptors. The extracellular domain contains 465 amino acid residues and is composed of two subdomains each with four highly conserved cysteines and a particular motif in the N-terminal subdomain and in the C-terminal subdomain. The ligand-binding extracellular domains are predicted to have similar double β-barrel fold structural geometries. This duplicated extracellular domain is highly homologous to the signal transducing chain common to IL-3, IL-5 and GM-CSF receptors as well as the low-affinity binding domain of LIF (Vigon et al., *Oncogene,* 8:2607-2615 [1993]). Thus mpl may belong to the low affinity ligand binding class of cytokine receptors.

A comparison of murine mpl and mature human mpl P, reveals these two proteins show 81% sequence identity. More specifically, the N-terminus and C-terminus extracellular subdomains share 75% and 80% sequence identity respectively. The most conserved mpl region is the cytoplasmic domain showing 91% amino acid identity, with a sequence of 37 residues near the transmembrane domain being identical in both species. Accordingly, mpl is reported to be one of the most conserved members of the cytokine receptor superfamily (Vigon supra).

Evidence that mpl is a functional receptor capable of transducing a proliferative signal comes from construction of chimeric receptors containing an extracellular domain from a cytokine receptor having high affinity for a known cytokine with the mpl cytoplasmic domain. Since no known ligand for mpl has been reported, it was necessary to construct the chimeric high affinity ligand binding extracellular domain from a class one cytokine receptor such as IL-4R or G-CSFB. Vigon et al., supra fused the extracellular domain of G-CSFR with both the transmembrane and cytoplasmic domain of c-mpl. An IL-3 dependent cell line, BAF/B03 (Ba/F3) was transfected with the G-CSFR/mpl chimera along with a full length G-CSFR control. Cells transfected with the chimera grew equally well in the presence of cytokine IL-3 or G-CSF. Similarly, cells transfected with G-CSFR also grew well in either IL-3 or G-CSF. All cells died in the absence of growth factors. A similar experiment was conducted by Skoda et al., *EMBO J.,* 12(7):2645-2653 [1993] in which both the extracellular and transmembrane domains of human IL-4 receptor (hIL-4-R) were fused to the murine mpl cytoplasmic domain, and transfected into a murine IL-3 dependent Ba/F3 cell line. Ba/F3 cells transfected with wildtype hIL-4-R proliferated normally in the presence of either of the species specific IL-4 or IL-3. Ba/F3 cells transfected with hIL-4R/mpl proliferated normally in the presence of hIL-4 (in the presence or absence of IL-3) demonstrating that in Ba/F3 cells the mpl cytoplasmic domain contains all the elements necessary to transduce a proliferative signal.

These chimeric experiments demonstrate the proliferation signaling capability of the mpl extracellular domain but are silent regarding whether the mpl extracellular domain can bind a ligand. These results are consistent with at least two possibilities, namely, mpl is a single chain (class one) receptor like EPO-R or G-CSFR or it is a signal transducing β-subunit (class three) requiring an α-subunit like IL-3 (Skoda at al. supra).

VI. Mpl Ligand is a Thrombopoietin (TPO)

As described above, it has been suggested that serum contains a unique factor, sometimes referred to as thrombopoietin (TPO), that acts synergistically with various other cytokines to promote growth and maturation of megakaryocytes. No such natural factor has ever been isolated from serum or any other source even though considerable effort has been expended by numerous groups. Even though it is not known whether mpl is capable of directly binding a megakaryocyte stimulating factor, recent experiments demonstrate that mpl is involved in proliferative signal transduction from a factor or factors found in the serum of patients with aplastic bone marrow (Methia et al., *Blood,* 82(5):1395-1401 [1993]).

Evidence that a unique serum colony-forming factor distinct from IL-1α, IL-3, IL-4, IL-6, IL-11, SCF, EPO, G-CSF, and GM-CSF transduces a proliferative signal through mpl comes from examination of the distribution of c-mpl expression in primitive and committed hematopoietic cell lines and from mpl antisense studies in one of these cell lines.

Using reverse transcriptase (RT)-PCR in immuno-purified human hematopoietic cells, Methia et al., supra demonstrated that strong mpl mRNA messages were only found in $CD34^+$ purified cells, megakaryocytes and platelets. $CD34^+$ cells purified from bone marrow (BM) represents about 1% of all BM cells and are enriched in primitive and committed progenitors of all lineages (e.g., erythroid, granulomacrophage, and megakaryocytic).

Mpl antisense oligodeoxynucleotides were shown to suppress megakaryocytic colony formation from the pluripotent $CD34^+$ cells cultured in serum from patients with aplastic marrow (a rich source of megakaryocyte colony-stimulating activity [MK-CSA]). These same antisense oligodeoxynucleotides had no effect on erythroid or granulomacrophage colony formation.

Whether mpl directly binds a ligand and whether the serum factor shown to cause megakaryocytopoiesis acts through mpl is still unknown. It has been suggested, however, that if mpl does directly bind a ligand, its amino acid sequence is likely to be highly conserved and have species cross-reactivity owing to the considerable sequence identity between human and murine mpl extracellular domains (Vigon at al., supra [1993]).

In view of the foregoing, it will be appreciated there is a current and continuing need in the art to isolate and identify molecules capable of stimulating proliferation, differentiation and maturation of hematopoietic cells, especially megakaryocytes or their predecessors for therapeutic use in the treatment of thrombocytopenia. It is believed such a molecule is a mpl ligand and thus there exists a further need to isolate such ligand(s) to evaluate their role(s) in cell growth and differentiation.

Accordingly, it is an object of this invention to obtain a pharmaceutically pure molecule capable of stimulating proliferation, differentiation and/or maturation of megakaryocytes into the mature platelet-producing form.

It is another object to provide the molecule in a form for therapeutic use in the treatment of a hematopoietic disorder, especially thrombocytopenia.

It is a further object of the present invention to isolate, purify and specifically identify protein ligands capable of binding in vivo a cytokine superfamily receptor known as mpl and to transduce a proliferative signal.

It is still another object to provide nucleic acid molecules encoding such protein ligands and to use these nucleic acid molecules to produce mpl binding ligands in recombinant cell culture for diagnostic and therapeutic use.

It is yet another object to provide derivatives and modified forms of the protein ligands including amino acid sequence variants, variant glycoprotein forms and covalent derivatives thereof.

It is an additional object to provide fusion polypeptide forms combining a mpl ligand and a heterologous protein and covalent derivatives thereof.

It is still an additional object to provide variant polypeptide forms combining a mpl ligand with amino acid additions and substitutions from the EPO sequence to produce a protein capable of regulating proliferation and growth of both platelets and red blood cell progenitors.

It is yet an additional object to prepare immunogens for raising antibodies against mpl ligands or fusion forms thereof, as well as to obtain antibodies capable of binding such ligands.

These and other objects of the invention will be apparent to the ordinary artisan upon consideration of the specification as a whole.

SUMMARY OF THE INVENTION

The objects of the invention are achieved by providing an isolated mammalian megakaryocytopoietic proliferation and maturation promoting protein, denominated the "mpl ligand" (ML), capable of stimulating proliferation, maturation and/or differentiation of megakaryocytes into the mature platelet-producing form.

This substantially homogeneous protein may be purified from a natural source by a method comprising; (1) contacting a source plasma containing the mpl ligand molecules to be purified with an immobilized receptor polypeptide, specifically mpl or a mpl fusion polypeptide immobilized on a support, under conditions whereby the mpl ligand molecules to be purified are selectively adsorbed onto the immobilized receptor polypeptide, (2) washing the immobilized receptor polypeptide and its support to remove non-adsorbed material, and (3) eluting the mpl ligand molecules from the immobilized receptor polypeptide to which they are adsorbed with an elution buffer. Preferably the natural source is mammalian plasma or urine containing the mpl ligand. Optionally the mammal is aplastic and the immobilized receptor is a mpl-IgG fusion.

Optionally, the preferred megakaryocytopoietic proliferation and maturation promoting protein is an isolated substantially homogeneous mpl ligand polypeptide made by synthetic or recombinant means.

The "mpl ligand" polypeptide of this invention preferably has at least 70% overall sequence identity with the amino acid sequence of the highly purified substantially homogeneous porcine mpl ligand polypeptide and at least 80% sequence identity with the "epo-domain" of the porcine mpl ligand polypeptide. Optionally, the mpl ligand of this invention is mature human mpl ligand (hML), having the mature amino acid sequence provided in FIG. 10 (SEQ ID NO:6), or a variant or posttranscriptionally modified form thereof or a protein having about 80% sequence identity with mature human mpl ligand. The mpl ligand comprises amino acid residues 1-X of FIG. 1 (SEQ ID NO 6) where X is selected from 153, 164, 191, 205, 207, 217, 229, 245 or 332. Optionally the mpl ligand polypeptide or fragment thereof may be fused to a heterologous polypeptide (chimera). A preferred heterologous polypeptide is a cytokine, colony stimulating factor or interleukin or fragment thereof, especially kit-ligand, IL-1, IL-3, IL-6, IL-11, EPO, GM-CSF or LIF. An optional preferred heterologous polypeptide is an immunoglobin chain, especially human IgG1, IgG2, IgG3, IgG4, IgA, IgE, IgD, IgM or fragment thereof, especially comprising the constant domain of an IgG heavy chain.

Another aspect of this invention provides a composition comprising an isolated mpl agonist that is biologically active and is preferably capable of stimulating the incorporation of labeled nucleotides (e.g., $^3$H-thymidine) into the DNA of IL-3 dependent Ba/F3 cells transfected with human mpl. Optionally the mpl agonist is biologically active mpl ligand and is preferably capable of stimulating the incorporation of $^{35}$S into circulating platelets in a mouse platelet rebound assay. Suitable mpl agonist include $hML_{153}$, hML(R153A, R154A), hML2, hML3, hML4, mML, mML2, mML3, pML, and pML2 or fragments thereof.

In another embodiment, this invention provides an isolated antibody capable of binding to the mpl ligand. The isolated antibody capable of binding to the mpl ligand may optionally be fused to a second polypeptide and the antibody or fusion thereof may be used to isolate and purify mpl ligand from a source as described above for immobilized mpl. In a further aspect of this embodiment, the invention provides a method for detecting the mpl ligand in vitro or in vivo comprising contacting the antibody with a sample, especially a serum sample, suspected of containing the ligand and detecting if binding has occurred.

In still further embodiments, the invention provides an isolated nucleic acid molecule, encoding the mpl ligand or fragments thereof, which nucleic acid molecule may optionally be labeled with a detectable moiety, and a nucleic acid molecule having a sequence that is complementary to, or hybridizes under moderate to highly stringent conditions with, a nucleic acid molecule having a sequence encoding a mpl ligand. Preferred nucleic acid molecules are those encoding human, porcine, and murine mpl ligand, and include RNA and DNA, both genomic and cDNA. In a further aspect of this embodiment, the nucleic acid molecule is DNA encoding the mpl ligand and further comprises a replicable vector in which the DNA is operably linked to control sequences recognized by a host transformed with the vector. Optionally the DNA is cDNA having the sequence provided in FIG. 1 5'-3' (SEQ ID NO: 2), 3'-5' or a fragment thereof. This aspect further includes host cells transformed with the vector and a method of using the DNA to effect production of mpl ligand, preferably comprising expressing the cDNA encoding the mpl ligand in a culture of the transformed host cells and recovering the mpl ligand from the host cells or the host cell culture. The mpl ligand prepared in this manner is preferably human mpl ligand.

The invention further includes a method for treating a mammal having a hematopoietic disorder, especially thrombocytopenia, comprising administering a therapeutically effective amount of a mpl ligand to the mammal. Optionally the mpl ligand is administered in combination with a cytokine, especially a colony stimulating factor or interleukin. Preferred colony stimulating factors or interleukins include; kit-ligand, LIF, G-CSF, GM-CSF, M-CSF, EPO, IL-1, IL-3, IL-6, and IL-11.

BRIEF DESCRIPTION OF THE FIGURES

FIG. 9. shows both strands of a 390 bp fragment of human genomic DNA encoding the mpl ligand. The deduced amino acid sequence of “exon 3” (SEQ ID NO: 3), the coding sequence (SEQ ID NO: 4), and its compliment (SEQ ID NO: 5) are shown.

FIG. 10. shows deduced amino acid sequence of mature human mpl ligand (h-ML) (SEQ ID NO: 6) and mature human erythropoietin (h-epo) (SEQ ID NO: 7). The predicted amino acid sequence for the human mpl ligand is aligned with the human erythropoietin sequence. Identical amino acids are boxed and gaps introduced for optimal alignment are indicated by dashes. Potential N-glycosylation sites are underlined with a plain line for the h-ML and with a broken line for h-epo. The two cysteines important for erythropoietin activity are indicated by a large dot.

Two hundred ninety-three cells were transfected by the $CaPO_4$ method (Gorman, C in *DNA Cloning: A New Approach* 2:143-190 [1985]) with pRK5 vector alone, pRK5-hML or with pRK5-$ML_{153}$ overnight (pRK5-$ML_{153}$ was generated by introducing a stop codon after residue 153 of hML by PCR). Media was then conditioned for 36 h and assayed for stimulation of cell proliferation of Ba/F3-mpl as described in Example 1 (A) or in vitro human megakaryocytopoiesis (B). Megakaryocytopoiesis was quantitated using a $^{125}$I radiolabeled murine IgG monoclonal antibody (HP1-1D) to the megakaryocyte specific glycoprotein GPIIbIIIa as described (Grant et al. *Blood* 69:1334-1339 [1987]). The effect of partially purified recombinant ML (rML) on in vivo platelet production (C) was determined using the rebound thrombocytosis assay described by McDonald, T. P. *Proc. Soc. Exp. Biol. Med.* 144:1006-10012 (1973). Partially purified rML was prepared from 200 ml of conditioned media containing the recombinant ML. The media was passed through a 2 ml Blue-Sepharose column equilibrated in PBS and the column was washed with PBS and eluted with PBS containing 2M each of urea and NaCl. The active fraction was dialyzed into PBS and made 1 mg/ml with endotoxin free BSA. The sample contained less than one unit of endotoxin/ml. Mice were injected with either 64,000, 32,000 or 16,000 units of rML or excipient alone. Each group consisted of six mice. The mean and standard deviation of each group is shown in FIGS. C and D. p values were determined by a 2 tailed T-test comparing medians.

Figure 13:
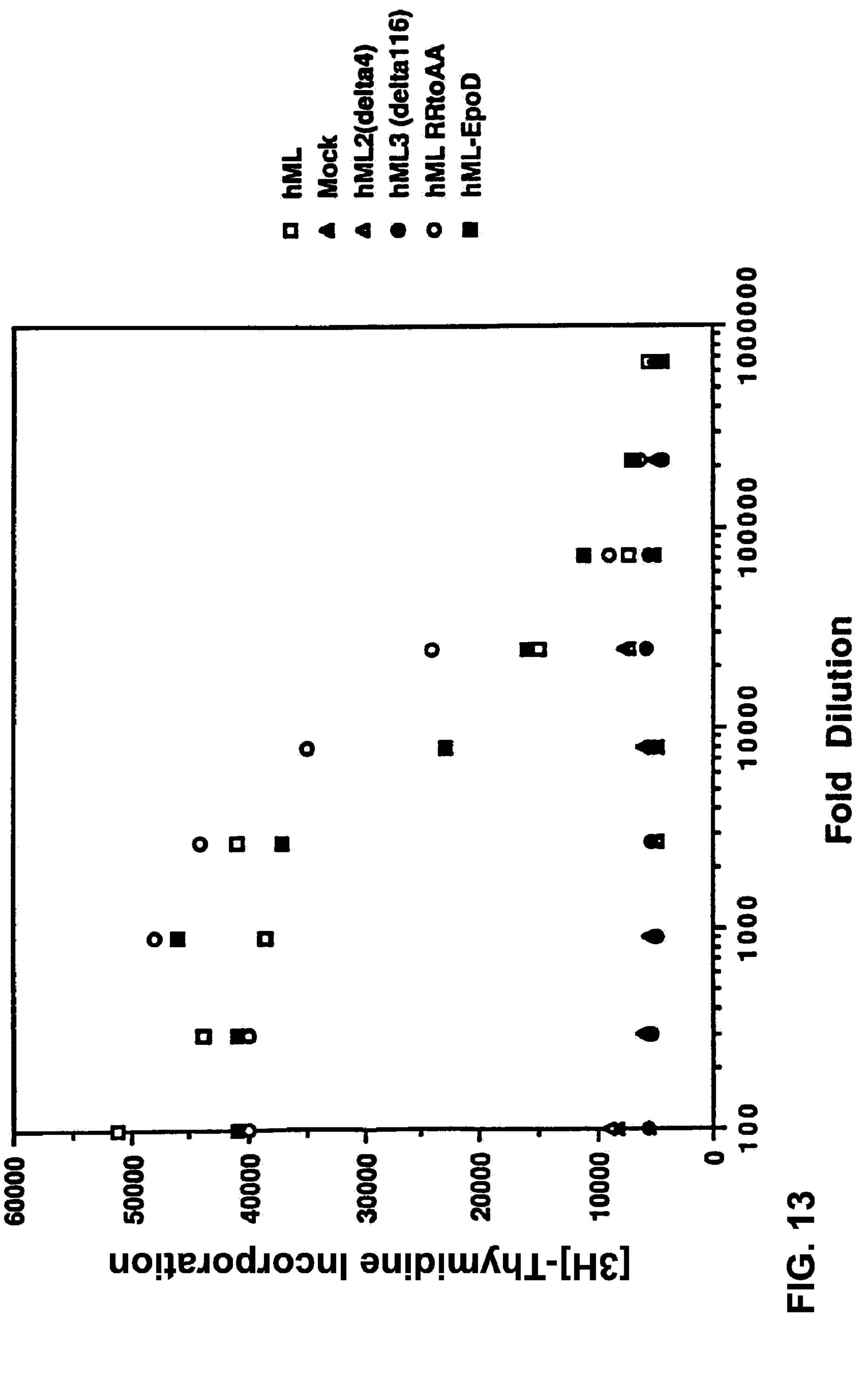

FIG. 13. compares the effect of human mpl ligand isoforms and variants in the Ba/F3-mpl cell proliferation assay. hML, mock, hML2, hML3, hML(R153A, R154A), and $hML_{153}$ were assayed at various dilutions as described in Example 1.

Figure 14:
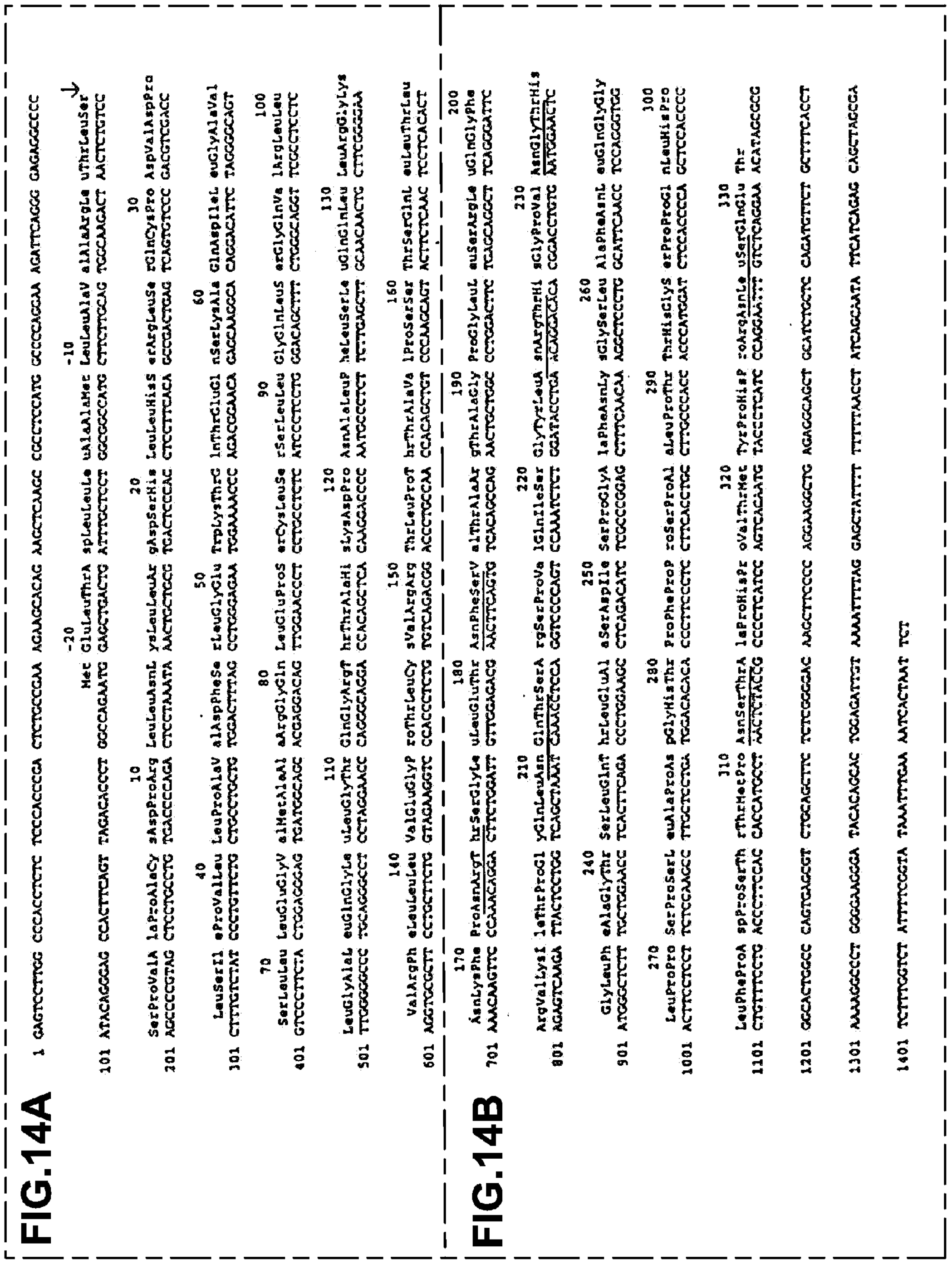

FIGS. 14 A and B show the nucleotide sequence: cDNA coding (SEQ ID NO: 11) and deduced amino acid sequence (SEQ ID NO: 12) of the open reading frame of a murine ML isoform. This mature murine mpl ligand isoform contains 331 amino acid residues, four fewer than the putative full length mML, and is therefore designated mML2. Nucleotides are numbered at the beginning of each line. Amino acid residues are numbered above the sequence starting with Ser 1. The potential N-glycosylation sites are underlined. Cysteine residues are indicated by a dot above the sequence.

Figure 15:
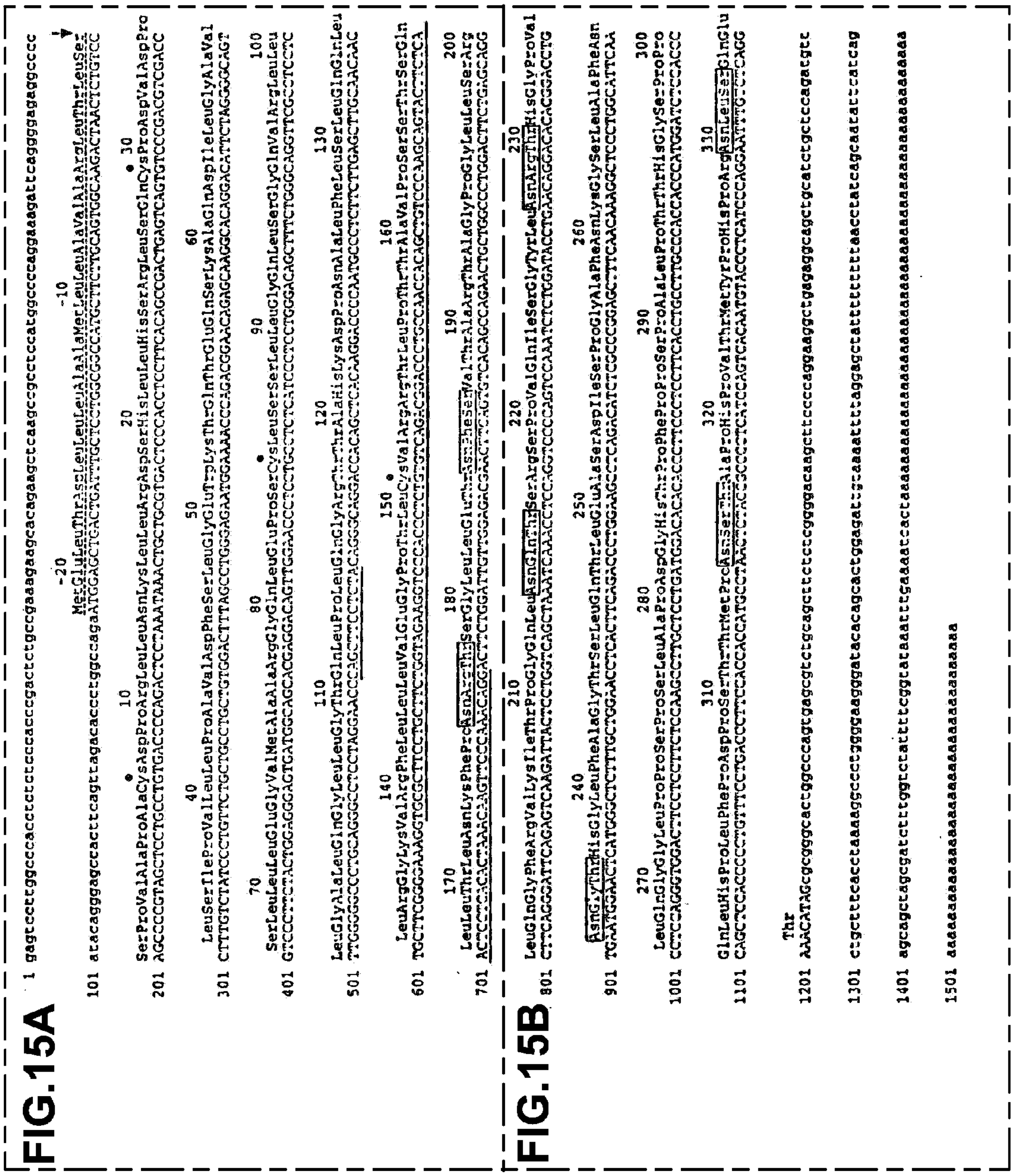

FIGS. 15 A and B show the cDNA sequence (SEQ ID NO: 13) and predicted protein sequence (SEQ ID NO: 14) of this murine ML isoform (mML). Nucleotides are numbered at the beginning of each line. Amino acid residues are numbered above the sequence starting with Ser 1. This mature murine mpl ligand isoform contains 335 amino acid residues and is believed to be the full length mpl ligand, designated mML. The signal sequence is indicated with a dashed underline and the likely cleavage point is denoted with an arrow. The 5' and 3' untranslated regions are indicated with lower case letters. The two deletions found as a result of alternative splicing (mML2 and mML3) are underlined. The four cysteine residues are indicated by a dot. The seven potential N-glycosylation sites are boxed.

FIG. 16. compares the deduced amino acid sequence of the human ML isoform hML3 (SEQ ID NO: 9) and a murine ML isoform designated mML3 (SEQ ID NO: 15). The predicted amino acid sequence for the human mpl ligand is aligned with the murine mpl ligand sequence. Identical amino acids are boxed and gaps introduced for optimal alignment are indicated by dashes. Amino acids are numbered at the beginning of each line.

Figure 17:
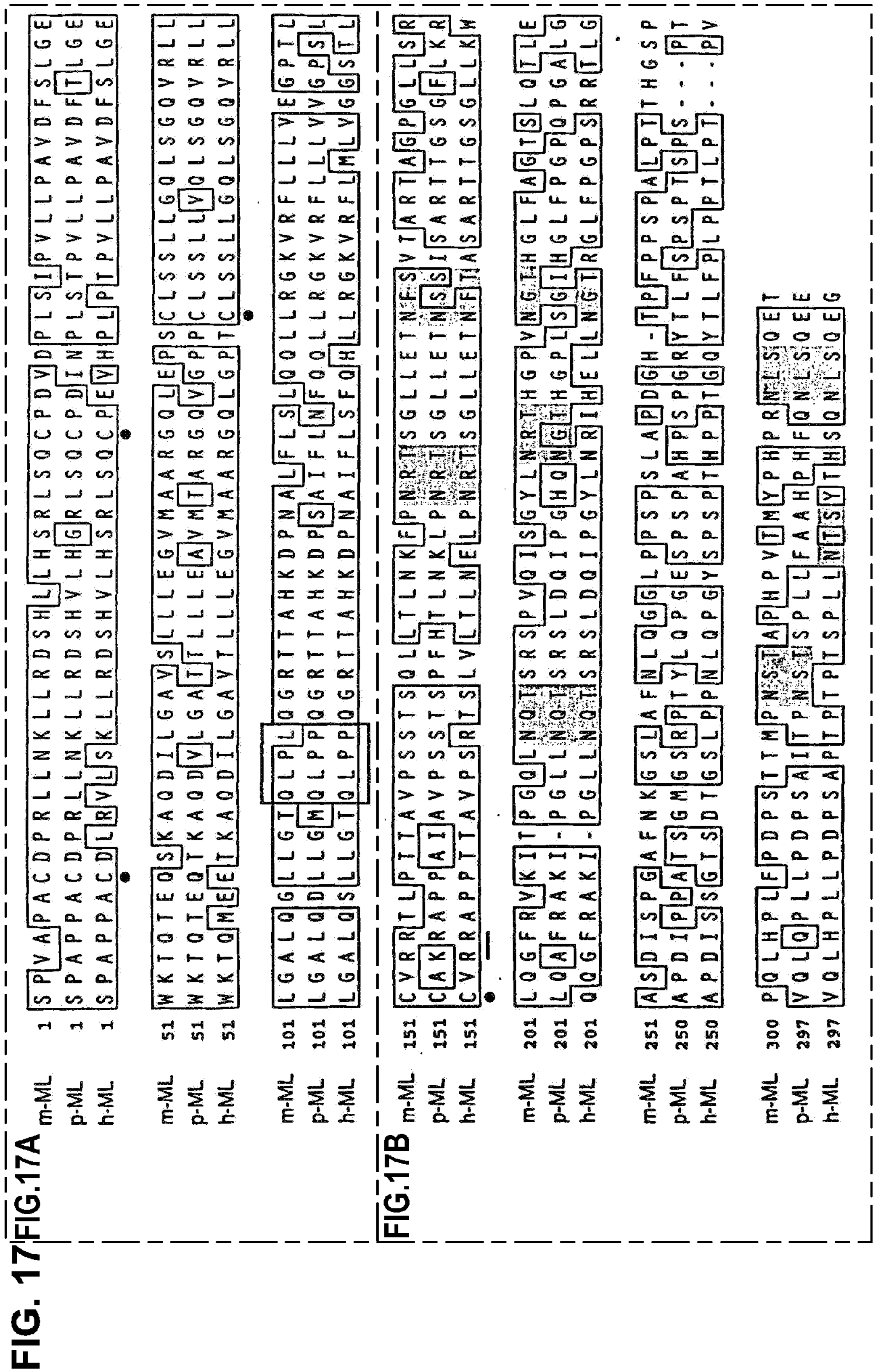
Figure 17A:
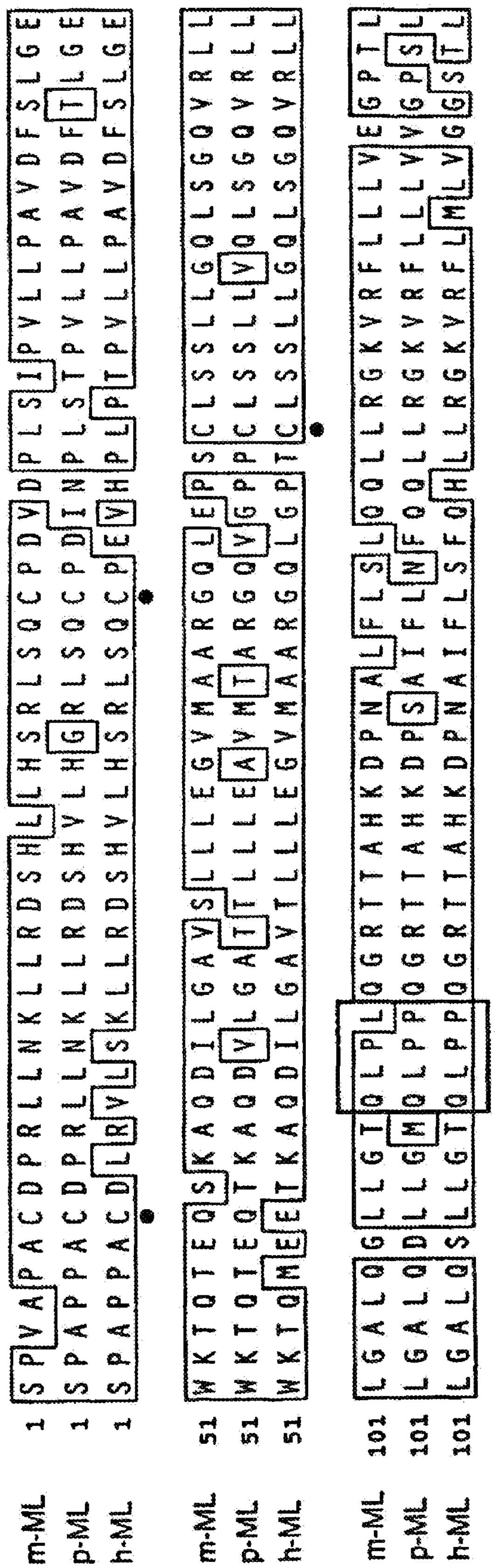

FIGS. 17 A and B compare the predicted amino acid sequences of mature ML isoforms from mouse-ML (SEQ ID NO: 16), pig-ML (SEQ ID NO: 17) and human-ML (SEQ ID NO: 6). Amino acid sequences are aligned with gaps, indicated by dashes, introduced for optimal alignment. Amino acids are numbered at the beginning of each line with identical residues boxed. Potential N-glycosylation sites are indicated by a shaded box and cysteine residues are designated with a dot. The conserved di-basic amino acid motif that presents a potential protease cleavage site is underlined. The four amino acid deletion found to occur in all three species (ML2) is outlined with a bold box.

FIGS. 18 A and B show the cDNA sequence (SEQ ID NO: 18) and predicted mature protein sequence (SEQ ID NO: 17) of a porcine ML isoform (pML). This porcine mpl ligand isoform contains 332 amino acid residues and is believed to be the full length porcine mpl ligand, designated pML. Nucleotides are numbered at the beginning of each line. Amino acid residues are numbered above the sequence starting with Ser 1.

FIGS. 19 A and B show the cDNA sequence (SEQ ID NO: 19) and predicted mature protein sequence (SEQ ID NO: 20) of a porcine ML isoform (pML2). This porcine mpl ligand isoform contains 328 amino acid residues and is a four residues deletion form of the full length porcine mpl ligand, designated pML2. Nucleotides are numbered at the beginning of each line. Amino acid residues are numbered above the sequence starting with Ser 1.

Figure 20B:
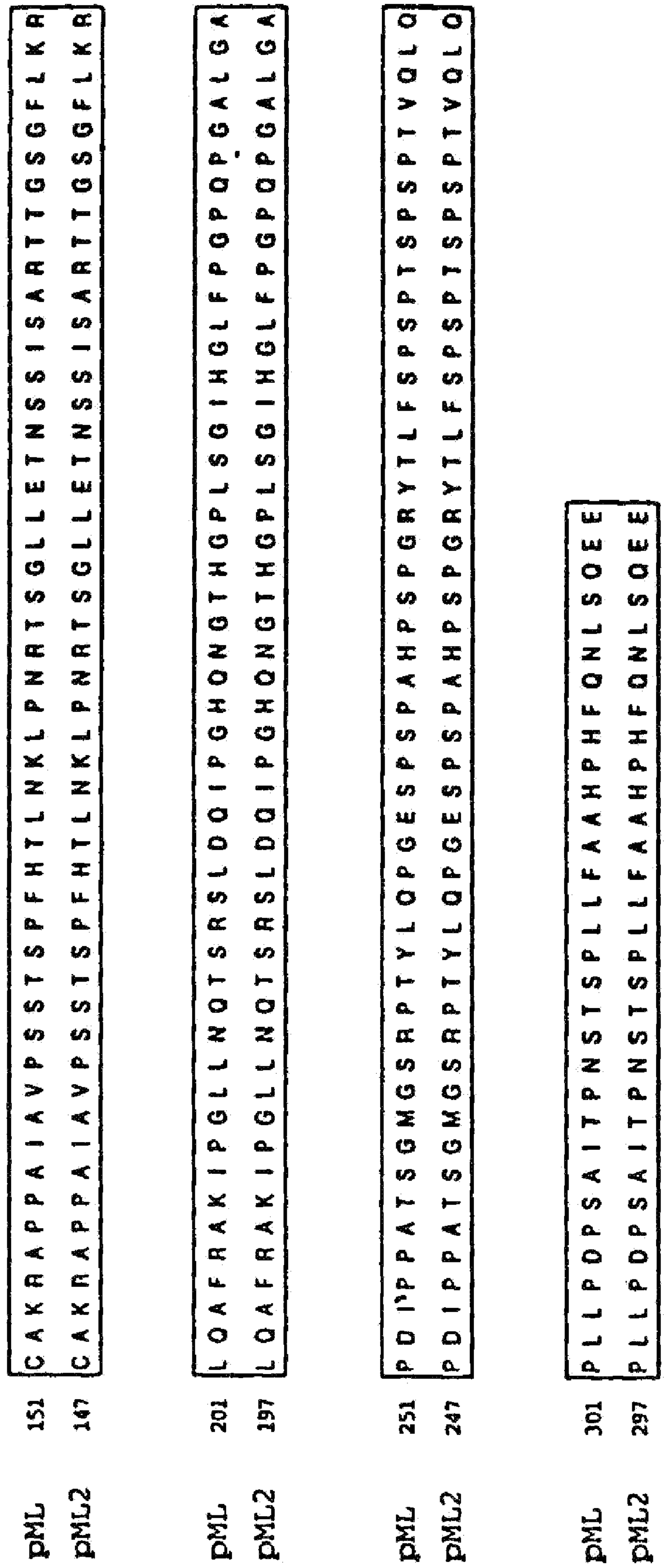

FIGS. 20 A and B compare the deduced amino acid sequence of the full length porcine ML isoform pML (SEQ ID NO: 17) and a porcine ML isoform designated pML2 (SEQ ID NO: 20). The predicted amino acid sequence for the pML is aligned with pML2 sequence. Identical amino acids are boxed and gaps introduced for optimal alignment are indicated by dashes. Amino acids are numbered at the beginning of each line.

DETAILED DESCRIPTION OF THE INVENTION

I. Definitions

In general, the following words or phrases have the indicated definition when used in the description, examples, and claims.

"Cytokine" is a generic term for proteins released by one cell population which act on another cell as intercellular mediators. Examples of such cytokines are lymphokines, monokines, and traditional polypeptide hormones. Included among the cytokines are growth hormone, insulin-like growth factors, human growth hormone, N-methionyl human growth hormone, bovine growth hormone, parathyroid hormone, thyroxine, insulin, proinsulin, relaxin, prorelaxin, glycoprotein hormones such as follicle stimulating hormone (FSH), thyroid stimulating hormone (TSH), and leutinizing hormone (LH), hematopoletic growth factor, hepatic growth factor, fibroblast growth factor, prolactin, placental lactogen, tumor necrosis factor-α (TNF-α and TNF-β) mullerian-inhibiting substance, mouse gonadotropin-associated peptide, inhibin, activin, vascular endothelial growth factor, integrin, nerve growth factors such as NGF-β, platelet-growth factor, transforming growth factors (TGFs) such as TGF-α and TGF-β, insulin-like growth factor-I and -II, erythropoietin (EPO), osteoinductive factors, interferons such as interferon-α, -β, and -γ, colony stimulating factors (CSFs) such as macrophage-CSF (M-CSF), granulocyte-macrophage-CSF (GM-CSF), and granulocyte-CSF (G-CSF), interleukins (IL's) such as IL-1, IL-1a, IL-2, IL-3, IL-4, IL-5, IL-6, IL-7, IL-8, IL-9, IL-11, IL-12 and other polypeptide factors including LIF, SCF, and kit-ligand. As used herein the foregoing terms are meant to include proteins from natural sources or from recombinant cell culture. Similarly, the terms are intended to include biologically active equivalents: e.g., differing in amino acid sequence by one or more amino acids or in type or extent of glycosylation.

A "mpl ligand", "mpl ligand polypeptide" or "ML" comprises any polypeptide that possesses the property of binding to mpl, a member of the cytokine receptor superfamily, and having a biological property of the ML as defined below. An exemplary and preferred biological property is the ability to stimulate the incorporation of labeled nucleotides (e.g., $^{3}H$ -thymidine) into the DNA of IL-3 dependent Ba/F3 cells transfected with human mpl P. Another exemplary and preferred biological property is the ability to stimulate the incorporation of $^{35}S$ into circulating platelets in a mouse platelet rebound assay. This definition encompasses the polypeptide isolated from a mpl ligand source such as aplastic porcine plasma described herein or from another source, such as another animal species, including humans or prepared by recombinant or synthetic methods and includes variant forms including functional derivatives, fragments, alleles, isoforms and analogues thereof.

A "mpl ligand fragment" is a portion of a naturally occurring mature full length mpl ligand sequence having one or more amino acid residues or carbohydrate units deleted. The deleted amino acid residue(s) may occur anywhere in the peptide including at either the N-terminal or C-terminal end or internally. The fragment will share at least one biological property in common with mpl ligand. Mpl/ligand fragments typically will have a consecutive sequence of at least 10, 15, 20, 25, 30, or 40 amino acid residues that are identical to the sequences of the mpl ligand isolated from a mammal including the ligand isolated from aplastic porcine plasma or the human or murine ligand.

"Mpl ligand variants" or "mpl ligand sequence variants" as defined herein means a biologically active mpl ligand as defined below having less than 100% sequence identity with the mpl ligand isolated from recombinant cell culture or aplastic porcine plasma or the human ligand having the deduced sequence described in FIG. 1 (SEQ ID NO: 1). Ordinarily, a biologically active mpl ligand variant will have an amino acid sequence having at least about 70% amino acid sequence identity with the mpl ligand isolated from aplastic porcine plasma or the mature murine or human ligand or fragments thereof (see FIG. 1 (SEQ ID NO: 1)), preferably at least about 75%, more preferably at least about 80%, still more preferably at least about 85%, even more preferably at least about 90%, and most preferably at least about 95%.

A "chimeric mpl ligand" is a polypeptide comprising full length mpl ligand or one or more fragments thereof fused or bonded to a second heterologous polypeptide or one or more fragments thereof. The chimera will share at least one biological property in common with mpl ligand. The second polypeptide will typically be a cytokine, immunoglobin or fragment thereof.

"Isolated mpl ligand", "highly purified mpl ligand" and "substantially homogeneous mpl ligand" are used interchangeably and mean a mpl ligand that has been purified from a mpl ligand source or has been prepared by recombinant or synthetic methods and is sufficiently free of other peptides or proteins (1) to obtain at least 15 and preferably 20 amino acid residues of the N-terminal or of an internal amino acid sequence by using a spinning cup sequenator or the best commercially available amino acid sequenator marketed or as modified by published methods as of the filing date of this application, or (2) to homogeneity by SDS-PAGE under non-reducing or reducing conditions using Coomassie blue or, preferably, silver stain. Homogeneity here means less than about 5% contamination with other source proteins.

"Biological property" when used in conjunction with either the "mpl ligand" or "Isolated mpl ligand" means having thrombopoietic activity or having an in vivo effector or antigenic function or activity that is directly or indirectly caused or performed by a mpl ligand (whether in its native or denatured conformation) or a fragment thereof. Effector functions include mpl binding and any carrier binding activity, agonism or antagonism of mpl, especially transduction of a proliferative signal including replication, DNA regulatory function, modulation of the biological activity of other cytokines, receptor (especially cytokine) activation, deactivation, up- or down regulation, cell growth or differentiation and the like. An antigenic function means possession of an epitope or antigenic site that is capable of cross-reacting with antibodies raised against the native mpl ligand. The principal antigenic function of a mpl ligand polypeptide is that it binds with an affinity of at least about $10^6$ Vmole to an antibody raised against the mpl ligand isolated from aplastic porcine plasma. Ordinarily, the polypeptide binds with an affinity of at least about $10^7$ I/mole. Most preferably, the antigenically active mpl ligand polypeptide is a polypeptide that binds to an antibody raised against the mpl ligand having one of the above described effector functions. The antibodies used to define "biologically activity" are rabbit polyclonal antibodies raised by formulating the mpl ligand isolated from recombinant cell culture or aplastic porcine plasma in Freund's complete adjuvant, subcutaneously injecting the formulation, and boosting the immune response by intraperitoneal injection of the formulation until the titer of mpl ligand antibody plateaus.

"Biologically active" when used in conjunction with either the "mpl ligand" or "Isolated mpl ligand" means a mpl ligand or polypeptide that exhibits thrombopoietic activity or shares an effector function of the mpl ligand isolated from aplastic porcine plasma or expressed in recombinant cell culture described herein. A principal known effector function of the mpl ligand or polypeptide herein is binding to mpl and stimulating the incorporation of labeled nucleotides ($^3$H-thymidine) into the DNA of IL-3 dependent Ba/F3 cells transfected with human mpl P. Another known effector function of the mpl ligand or polypeptide herein is the ability to stimulate the incorporation of $^{35}$S into circulating platelets in a mouse platelet rebound assay. Yet another known effector function of mpl ligand is the ability to stimulate in vitro human megakaryocytopoiesis that may be quantitated by using a radio labeled monoclonal antibody specific to the megakaryocyte glycoprotein $GPII_bIII_a$.

Figure 1:
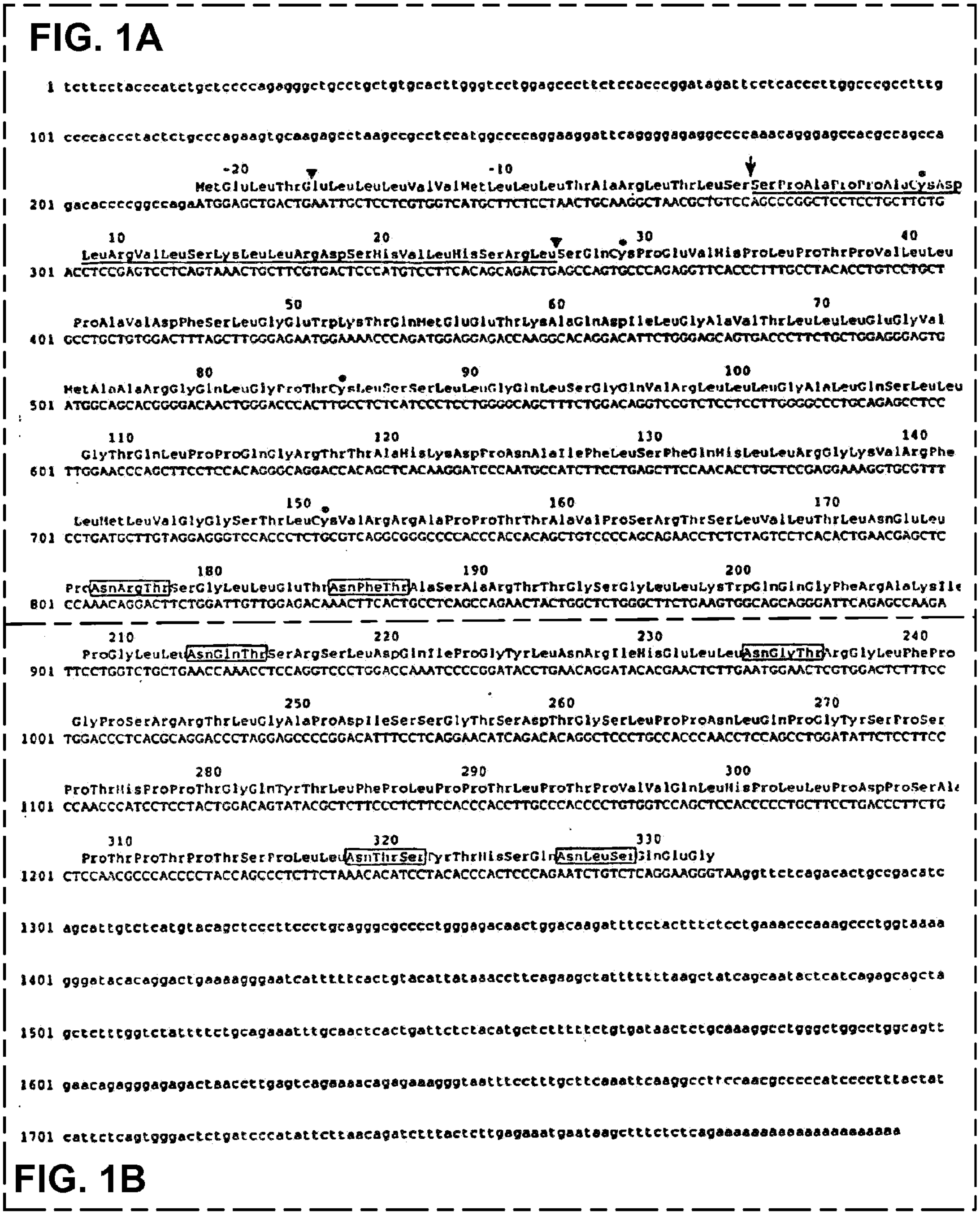
FIGS. 1A and B show the deduced amino acid sequence (SEQ ID NO: 1) of human mpl ligand (hML) cDNA and the coding nucleotide sequence (SEQ ID NO: 2). Nucleotides are numbered at the beginning of each line. The 5' and 3' untranslated regions are indicated in lower case letters. Amino acid residues are numbered above the sequence starting at Ser 1 of the mature mpl ligand (ML) protein sequence. The boundaries of presumed exon 3 are indicated by the arrows and the potential N-glycosylation sites are boxed. Cysteine residues are indicated by a dot above the sequence. The underlined sequence corresponds to the N-terminal sequence determined from mpl ligand purified from porcine plasma.

"Percent amino acid sequence identity" with respect to the mpl ligand sequence is defined herein as the percentage of amino acid residues in the candidate sequence that are identical with the residues in the mpl ligand sequence isolated from aplastic porcine plasma or the murine or human ligand having the deduced amino acid sequence described in FIG. 1 (SEQ ID NO: 1), after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the mpl ligand sequence shall be construed as affecting sequence identity or homology. Thus exemplary biologically active mpl ligand polypeptides considered to have identical sequences include; prepro-mpl ligand, pro-mpl ligand, and mature mpl ligand.

"Mpl ligand microsequencing" may be accomplished by any appropriate standard procedure provided the procedure is sensitive enough. In one such method, highly purified polypeptide obtained from SDS gels or from a final HPLC step are sequenced directly by automated Edman (phenyl isothiocyanate) degradation using a model 470A Applied Biosystems gas phase sequencer equipped with a 120A phenyithiohydantion (PTH) amino acid analyzer. Additionally, mpl ligand fragments prepared by chemical (e.g., CNBr, hydroxylamine, 2-nitro-5-thiocyanobenzoate) or enzymatic (e.g., trypsin, clostripain, staphylococcal protease) digestion followed by fragment purification (e.g., HPLC) may be similarly sequenced. PTH amino acids are analyzed using the ChromPerfect data system (Justice Innovations, Palo Alto, Calif.). Sequence interpretation is performed on a VAX 11/785 Digital Equipment Co. computer as described by Henzel et al., *J. Chromatography,* 404:41.52 [1987]. Optionally, aliquots of HPLC fractions may be electrophoresed on 5-20% SDS-PAGE, electrotransferred to a PVDF membrane (ProBlott, AlB, Foster City, Calif.) and stained with Coomassie Brilliant Blue (Matsurdiara, *J. Biol. Chem.,* 262:10035-10038 [1987]. A specific protein identified by the stain is excised from the blot and N-terminal sequencing is carried out with the gas phase sequenator described above. For internal protein sequences, HPLC fractions are dried under vacuum (SpeedVac), resuspended in appropriate buffers, and digested with cyanogen bromide, the Lys-specific enzyme Lys-C (Wako Chemicals, Richmond, Va.), or Asp-N (Boehringer Mannheim, Indianapolis, Ind.). After digestion, the resultant peptides are sequenced as a mixture or after HPLC resolution on a C4 column developed with a propanol gradient in 0.1% TFA prior to gas phase sequencing.

"Thrombocytopenia" is defined as a platelet count below $150\times10^9$ per liter of blood.

"Thrombopoietic activity" is defined as biological activity that consists of accelerating the proliferation, differentiation and/or maturation of megakaryocytes or megakaryocyte precursors into the platelet producing form of these cells. This activity may be measured in various assays including an in vivo mouse platelet rebound synthesis assay, induction of platelet cell surface antigen assay as measured by an anti-platelet immunoassay (anti-$GPII_bIII_a$) for a human leukemia megakaryoblastic cell line (CMK), and induction of polyploidization in a megakaryoblastic cell line (DAMI).

"Thrombopoietin" (TPO) is defined as a compound having thrombopoietic activity or being capable of increasing serum platelet counts in a mammal. TPO is preferably capable of increasing endogenous platelet counts by at least 10%, more preferably by 50%, and most preferably capable of elevating platelet counts in a human to greater that $150\times10^9$ per liter of blood.

"Isolated mpl ligand nucleic acid" is RNA or DNA containing greater than 16 and preferably 20 or more sequential nucleotide bases that encode biologically active mpl ligand or a fragment thereof, is complementary to the RNA or DNA, or hybridizes to the RNA or DNA and remains stably bound under moderate to stringent conditions. This RNA or DNA is free from at least one contaminating source nucleic acid with which it is normally associated in the natural source and preferably substantially free of any other mammalian RNA or DNA. The phrase "free from at least one contaminating source nucleic acid with which it is normally associated" includes the case where the nucleic acid is present in the source or natural cell but is in a different chromosomal location or is otherwise flanked by nucleic acid sequences not normally found in the source cell. An example of isolated mpl ligand nucleic acid is RNA or DNA that encodes a biologically active mpl ligand sharing at least 75% sequence identity, more preferably at least 80%, still more preferably at least 85%, even more preferably 90%, and most preferably 95% sequence identity with the human, murine or porcine mpl ligand.

"Control sequences" when referring to expression means DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

"Operably linked" when referring to nucleic acids means that the nucleic acids are placed in a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

"Exogenous" when referring to an element means a nucleic acid sequence that is foreign to the cell, or homologous to the cell but in a position within the host cell nucleic acid in which the element is ordinarily not found.

"Cell," "cell line," and "cell culture" are used interchangeably herein and such designations include all progeny of a cell or cell line. Thus, for example, terms like "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

"Plasmids" are autonomously replicating circular DNA molecules possessing independent origins of replication and are designated herein by a lower case "p" preceded and/or followed by capital letters and/or numbers. The starting plasmids herein are either commercially available, publicly available on an unrestricted basis, or can be constructed from such available plasmids in accordance with published procedures. In addition, other equivalent plasmids are known in the art and will be apparent to the ordinary artisan.

"Restriction enzyme digestion" when referring to DNA means catalytic cleavage of internal phosphodiester bonds of DNA with an enzyme that acts only at certain locations or sites in the DNA sequence. Such enzymes are called "restriction endonucleases". Each restriction endonuclease recognizes a specific DNA sequence called a "restriction site" that exhibits two-fold symmetry. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 μg of plasmid or DNA fragment is used with about 1-2 units of enzyme in about 20 μl of buffer solution. Appropriate buffers and substrate amounts for particular restriction enzymes are specified by the manufacturer. Incubation of about 1 hour at 37° C. is ordinarily used, but may vary in accordance with the supplier's instructions. After incubation, protein or polypeptide is removed by extraction with phenol and chloroform, and the digested nucleic acid is recovered from the aqueous fraction by precipitation with ethanol. Digestion with a restriction enzyme may be followed with bacterial alkaline phosphatase hydrolysis of the terminal 5' phosphates to prevent the two restriction-cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional as described in sections 1.56-1.61 of Sambrook et al., *Molecular Cloning: A Laboratory Manual* [New York: Cold Spring Harbor Laboratory Press, 1989].

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al., *Nucleic Acids Res.,* 9:6103-6114 [1981], and Goeddel et al., *Nucleic Acids Res.,* 8:4057 [1980].

"Southern analysis" or "Southern blotting" is a method by which the presence of DNA sequences in a restriction endonuclease digest of DNA or DNA-containing composition is confirmed by hybridization to a known, labeled oligonucleotide or DNA fragment. Southern analysis typically involves electrophoretic separation of DNA digests on agarose gels, denaturation of the DNA after electrophoretic separation, and transfer of the DNA to nitrocellulose, nylon, or another suitable membrane support for analysis with a radiolabeled, biotinylated, or enzyme-labeled probe as described in sections 9.37-9.52 of Sambrook et at, supra.

"Northern analysis" or "Northern blotting" is a method used to identify RNA sequences that hybridize to a known probe such as an oligonucleotide, DNA fragment, cDNA or fragment thereof, or RNA fragment. The probe is labeled with a radioisotope such as $^{32}P$, or by biotinylation, or with an enzyme. The RNA to be analyzed is usually electrophoretically separated on an agarose or polyacrylamide gel, transferred to nitrocellulose, nylon, or other suitable membrane, and hybridized with the probe, using standard techniques well known in the art such as those described in sections 7.39-7.52 of Sambrook et al., supra.

"Ligation" is the process of forming phosphodiester bonds between two nucleic acid fragments. For ligation of the two fragments, the ends of the fragments must be compatible with each other. In some cases, the ends will be directly compatible after endonuclease digestion. However, it may be necessary first to convert the staggered ends commonly produced after endonuclease digestion to blunt ends to make them compatible for ligation. For blunting the ends, the DNA is treated in a suitable buffer for at least 15 minutes at 15° C. with about 10 units of the Klenow fragment of DNA polymerase I or T4 DNA polymerase in the presence of the four deoxyribonucleotide triphosphates. The DNA is then purified by phenol-chloroform extraction and ethanol precipitation. The DNA fragments that are to be ligated together are put in solution in about equimolar amounts. The solution will also contain ATP, ligase buffer, and a ligase such as T4 DNA ligase at about 10 units per 0.5 μg of DNA. If the DNA is to be ligated into a vector, the vector is first linearized by digestion with the appropriate restriction endonuclease(s). The linearized fragment is then treated with bacterial alkaline phosphatase or calf intestinal phosphatase to prevent self-ligation during the ligation step.

"Preparation" of DNA from cells means isolating the plasmid DNA from a culture of the host cells. Commonly used methods for DNA preparation are the large- and small-scale plasmid preparations described in sections 1.25-1.33 of Sambrook et al., supra. After preparation of the DNA, it can be purified by methods well known in the art such as that described in section 1.40 of Sambrook et al., supra.

"Oligonucleotides" are short-length, single- or double-stranded polydeoxynucleotides that are chemically synthesized by known methods (such as phosphotriester, phosphite, or phosphoramidite chemistry, using solid-phase techniques such as described in EP 266,032 published 4 May 1988, or via deoxynucleoside H-phosphonate intermediates as described by Froehler et al., *Nucl. Acids Res.,* 14:5399-5407 [1986]. Further methods include the polymerase chain reaction defined below and other autoprimer methods and oligonucleotide syntheses on solid supports. All of these methods are described in Engels et al., *Agnew. Chem. Int. Ed. Engl.,* 28:716-734 [1989]). These methods are used if the entire nucleic acid sequence of the gene is known, or the sequence of the nucleic acid complementary to the coding strand is available. Alternatively, if the target amino acid sequence is known, one may infer potential nucleic acid sequences using known and preferred coding residues for each amino acid residue. The oligonucleotides are then purified on polyacrylamide gels.

"Polymerase chain reaction" or "PCR" refers to a procedure or technique in which minute amounts of a specific piece of nucleic acid, RNA and/or DNA, are amplified as described in U.S. Pat. No. 4,683,195 issued 28 Jul. 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.,* 51:263 [1987]; Erlich, ed., *PCR Technology*, (Stockton Press, NY, 1989). As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

"Stringent conditions" are those that (1) employ low ionic strength and high temperature for washing, for example, 0.015 M NaCl/0.0015 M sodium citrate/0.1% $NaDodSO_4$ (SDS) at 50° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS.

"Moderately stringent conditions" are described in Sambrook at al., supra, and include the use of a washing solution and hybridization conditions (e.g., temperature, ionic strength, and % SDS) less stringent than described above. An example of moderately stringent conditions are conditions such as overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 μl/ml denatured sheared salmon sperm DNA, followed by washing the fitters in 1×SSC at about 37-50° C. The skilled artisan will recognize how to adjust the temperature, ionic strength etc. as necessary to accommodate factors such as probe length and the like.

"Antibodies" (Abs) and "Immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one and ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., *J. Mol. Biol.,* 186:651-663 [1985]; Novotny and Haber, *Proc. Natl. Acad. Sci. USA,* 82:4592-4596 [1985]).

The term "variable" refers to the fact that certain portions of the variable domains differ extensively in sequence among antibodies and are used in the binding and specificity of each particular antibody for its particular antigen. However, the variability is not evenly distributed through the variable domains of antibodies. It is concentrated in three segments called complementarity determining regions (CDRs) or hypervariable regions both in the light chain and the heavy chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat et al., *Sequences of Proteins of Immunological Interest*, National Institute of Health, Bethesda, Md. [1987]). The constant domains are not involved directly in binding an antibody to an antigen, but exhibit various effector functions, such as participation of the antibody in antibody-dependent cellular toxicity.

Papain digestion of antibodies produces two identical antigen binding fragments, called "Fab" fragments, each with a single antigen binding site, and a residual "Fc" fragment, whose name reflects its ability to crystallize readily. Pepsin treatment yields an $F(ab')_2$ fragment that has two antigen combining sites and is still capable of cross-linking antigen.

"Fv" is the minimum antibody fragment which contains a complete antigen recognition and binding site. This region consists of a dimer of one heavy and one light chain variable domain in tight, non-covalent association. It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other, chemical couplings of antibody fragments are also known.

The "light chains" of antibodies (immunoglobulins) from any vertebrate species can be assigned to one of two clearly distinct types, called kappa and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called α, delta, epsilon, γ, and μ, respectively. The subunit structures and three-dimensional configurations of different classes of immunoglobulins are well known.

The term "antibody" is used in the broadest sense and specifically covers single monoclonal antibodies (including agonist and antagonist antibodies), antibody compositions with polyepitopic specificity, as well as antibody fragments (e.g., Fab, $F(ab')_2$, and Fv), so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler & Milstein, *Nature,* 256:495 [1975], or may be made by recombinant DNA methods [see, e.g., U.S. Pat. No. 4,816,567 (Cabilly et al.)].

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567 (Cabilly et al.; Morrison et al., *Proc. Natl. Acad. Sci. USA,* 81:6851-6855 [1984]).

"Humanized" forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues which are found—neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details see: Jones at al., *Nature,* 921:522-525 [1986]; Reichmann et al., *Nature,* 332: 323-329 [1988]; and Presta, *Curr. Op. Struct. Biol.,* 2:593-596 [1992]).

"Non-immunogenic in a human" means that upon contacting the polypeptide in a pharmaceutically acceptable carrier and in a therapeutically effective amount with the appropriate tissue of a human, no state of sensitivity or resistance to the polypeptide is demonstrable upon the second administration of the polypeptide after an appropriate latent period (e.g., 8 to 14 days).

II. Preferred Embodiments of the Invention

Preferred polypeptides of this invention are substantially homogeneous polypeptide(s), referred to as mpl ligand(s), that possess the property of binding to mpl, a member of the receptor cytokine superfamily, and having the biological property of stimulating the incorporation of labeled nucleotides ($^3$H-thymidine) into the DNA of IL-3 dependent Ba/F3 cells transfected with human mpl P. More preferred mpl ligand(s) are isolated mammalian protein(s) having hematopoietic, especially megakaryocytopoietic or thrombocytopoietic activity—namely, being capable of stimulating proliferation, maturation and/or differentiation of immature megakaryocytes or their predecessors into the mature platelet-producing form. Most preferred polypeptides of this invention are human mpl ligand(s) including fragments thereof having hematopoietic, megakaryocytopoietic or thrombopoietic activity. Optionally these human mpl ligand(s) lack glycosylation. Other preferred human mpl ligands are the "epo-domain" of hML referred to as $hML_{153}$, the mature full length polypeptide having the amino acid sequence shown in FIG. 1 (SEQ ID NO: 1), referred to as hML or $hML_{332}$, and the biologically active substitutional variant hML(R153A, R154A).

Optional preferred polypeptides of this invention are biologically or immunologically active mpl ligands variants selected from hML2, hML3, hML4, mML, mML2, mML3, pML and pML2.

Optional preferred polypeptides of this invention are biologically active mpl ligand variant(s) that have an amino acid sequence having at least 70% amino acid sequence identity with the human mpl ligand (see FIG. 1 (SEQ ID NO: 1)), the murine mpl ligand (see FIG. 15 (SEQ ID NOS: 13 & 14)), the recombinant porcine mpl ligand (see FIG. 18 (SEQ ID NOS: 16 & 17)) or the porcine mpl ligand isolated from aplastic porcine plasma, preferably at least 75%, more preferably at least 80%, still more preferably at least 85%, even more preferably at least 90%, and most preferably at least 95%.

The mpl ligand isolated from aplastic porcine plasma has the following characteristics:

(1) The partially purified ligand elutes from a gel filtration column run in either PBS, PBS containing 0.1% SDS or PBS containing 4M $MgCl_2$ with Mr of 60,000-70,000;

(2) The ligand's activity is destroyed by pronase;

(3) The ligand is stable to low pH (2.5), SDS to 0.1%, and 2M urea;

(4) The ligand is a glycoprotein, based on its binding to a variety of lectin columns;

(5) The highly purified ligand elutes from non-reduced SDS-PAGE with a Mr of 25,000-35,000. Smaller amounts of activity also elute with Mr of −18,000 and 60,000;

(6) The highly purified ligand resolves on reduced SDS-PAGE as a doublet with Mr of 28,000 and 31,000;

(7) The amino-terminal sequence of the 18,000, 28,000 and 31,000 bands is the same—SPAPPACDPRLLNKLLRDDH-VLHGR (SEQ ID NO: 21); and (8) The ligand binds and elutes from the following affinity columns Blue-Sepharose,
CM Blue-Sepharose,
MONO-Q,
MONO-S,
Lentil lectin-Sepharose,
WGA-Sepharose,
Con A-Sepharose,
Ether 650 m Toyopearl,
Butyl 650 m Toyopearl,
Phenyl 650 m Toyopearl, and
Phenyl-Sepharose.

More preferred mpl ligand polypeptides are those encoded by human genomic or cDNA having an amino acid sequence described in FIG. 1 (SEQ ID NO: 1).

Other preferred naturally occurring biologically active mpl ligand polypeptides of this invention include prepro-mpl ligand, pro-mpl ligand, mature mpl ligand, mpl ligand fragments and glycosylation variants thereof.

Still other preferred polypeptides of this invention include mpl ligand sequence variants and chimeras. Ordinarily, preferred mpl ligand sequence variants and chimeras are biologically active mpl ligand variants that have an amino acid sequence having at least 70% amino acid sequence identity with the human mpl ligand or the mpl ligand isolated from aplastic porcine plasma, preferably at least 75%, more preferably at least 80%, still more preferably at least 85%, even more preferably at least 90%, and most preferably at least 95%. An exemplary preferred mpl ligand variant is a N-terminal domain hML variant referred to as the "epo-domain" because of its sequence homology to erythropoietin). The preferred hML epo-domain comprises about the first 153 amino acid residues of mature hML and is referred to as $hML_{153}$. An optionally preferred hML sequence variant comprises one in which one or more of the basic or dibasic amino acid residue(s) in the C-terminal domain is substituted with a non-basic amino acid residue(s) (e.g., hydrophobic, neutral, acidic, aromatic, Gly, Pro and the like). A preferred hML C-terminal domain sequence variant comprise one in which Arg residues 153 and 154 are replaced with Ala residues. This variant is referred to as $hML_{332}$(R153A, R154A). An alternative preferred hML variant comprises either $hML_{332}$ or $hML_{153}$ in which amino residues 111-114 (QLPP or LPPQ) are deleted or replaced with a different tetrapeptide sequence (e.g. AGAG or the like). The foregoing deletion mutants are referred to as $\Delta 4hML_{332}$ or $\Delta 4hML_{153}$.

A preferred chimera is a fusion between mpl ligand or fragment (defined below) thereof with a heterologous polypeptide or fragment thereof. For example, $hML_{153}$ may be fused to an IgG fragment to improve serum half-life or to IL-3, G-CSF or EPO to produce a molecule with enhanced thrombopoietic or chimeric hematopoietic activity.

An alternative preferred human mpl ligand chimera is a "ML-EPO domain chimera" that consists of the N-terminus 153 to 157 hML residues substituted with one or more, but not all, of the human epo residues approximately aligned as shown in FIG. 10 (SEQ ID NO: 7). In this embodiment, the hML chimera would be about 153-166 residues in length in which individual or blocks of residues from the human epo sequence are added or substituted into the hML sequence at positions corresponding to the alignment shown in FIG. 10 (SEQ ID NO: 6). Exemplary block sequence inserts into the N-terminus portion of hML would include one or more of the N-glycosylation sites at positions (epo) 24-27, 38-40, and 83-85; one or more of the four predicted amphipathic α-helical bundles at positions (epo) 9-22, 59-76, 90-107, and 132-152; and other highly conserved regions including the N-terminus and C-terminus regions and residue positions (epo) 44-52 (see e.g., Wen et al., *Blood,* 82:1507-1516 [1993] and Boissel et al., *J. Biol. Chem.,* 268(21):15983-15993 [1993]). It is contemplated this "ML-EPO domain chimera" will have mixed thrombopoietic-erythropoietic (TEPO) biological activity.

Other preferred polypeptides of this invention include mpl ligand fragments having a consecutive sequence of at least 10, 15, 20, 25, 30, or 40 amino acid residues that are identical to the sequences of the mpl ligand isolated from aplastic porcine plasma or the human mpl ligand described herein (see e.g. Table 4, Example 16). A preferred mpl ligand fragment is human ML[1-X] where X is 153, 164, 191, 205, 207, 217, 229, or 245 (see FIG. 1 (SEQ ID NO: 1) for the sequence of residues 1-X). Other preferred mpl ligand fragments include those produced as a result of chemical or enzymatic hydrolysis or digestion of the purified ligand.

Another preferred aspect of the invention is a method for purifying mpl ligand molecules comprises contacting a mpl ligand source containing the mpl ligand molecules with an immobilized receptor polypeptide, specifically mpl or a mpl fusion polypeptide, under conditions whereby the mpl ligand molecules to be purified are selectively adsorbed onto the immobilized receptor polypeptide, washing the immobilized support to remove non-adsorbed material, and eluting the molecules to be purified from the immobilized receptor polypeptide with an elution buffer. The source containing the mpl ligand may be plasma where the immobilized receptor is preferably a mpl-IgG fusion.

Alternatively, the source containing the mpl ligand is recombinant cell culture where the concentration of mpl ligand in either the culture medium or in cell lysates is generally higher than in plasma or other natural sources. In this case the above described mpl-IgG immunoaffinity method, while still useful, is usually not necessary and more traditional protein purification methods known in the art may be applied. Briefly, the preferred purification method to provide substantially homogeneous mpl ligand comprises: removing particulate debris, either host cells or lysed fragments by, for example, centrifugation or ultrafiltration; optionally, protein may be concentrated with a commercially available protein concentration filter; followed by separating the ligand from other impurities by one or more steps selected from; immunoaffinity, ion-exchange (e.g., DEAE or matricies containing carboxymethyl or sulfopropyl groups), Blue-Sepharose, CM Blue-Sepharose, MONO-Q, MONO-S, lentil lectin-Sepharose, WGA-Sepharose, Con A-Sepharose, Ether Toypearl, Butyl Toypearl, Phenyl Toypearl, protein A Sepharose, SDS-PAGE, reverse phase HPLC (e.g., silica gel with appended aliphatic groups) or Sephadex molecular sieve or size exclusion chromatography, and ethanol or ammonium sulfate precipitation. A protease inhibitor such as methyisulfonylfluoride (PMSF) may be included in any of the foregoing steps to inhibit proteolysis.

In another preferred embodiment, this invention provides an isolated antibody capable of binding to the mpl ligand. A preferred mpl ligand isolated antibody is monoclonal (Kohler and Milstein, *Nature,* 256:495-497 [1975]; Campbell, *Laboratory Techniques in Biochemistry and Molecular Biology*, Burdon et al., Eds, Volume 13, Elsevier Science Publishers, Amsterdam [1985]; and Huse et al., *Science,* 246:1275-1281 [1989]). Preferred mpl ligand isolated antibody is one that binds to mpl ligand with an affinity of at least about $10^6$ l/mole. More preferably the antibody binds with an affinity of at least about $10^7$ l/mole. Most preferably, the antibody is raised against the mpl ligand having one of the above described effector functions. The isolated antibody capable of binding to the mpl ligand may optionally be fused to a second polypeptide and the antibody or fusion thereof may be used to isolate and purify mpl ligand from a source as described above for immobilized mpl polypeptide. In a further preferred aspect of this embodiment, the invention provides a method for detecting the mpl ligand in vitro or in vivo comprising contacting the antibody with a sample, especially a serum sample, suspected of containing the ligand and detecting if binding has occurred.

In still further preferred embodiments, the invention provides an isolated nucleic acid molecule encoding the mpl ligand or fragments thereof, which nucleic acid molecule may be labeled or unlabeled with a detectable moiety, and a nucleic acid molecule having a sequence that is complementary to, or hybridizes under stringent or moderately stringent conditions with, a nucleic acid molecule having a sequence encoding a mpl ligand. A preferred mpl ligand nucleic acid is RNA or DNA that encodes a biologically active mpl ligand sharing at least 75% sequence identity, more preferably at least 80%, still more preferably at least 85%, even more preferably 90%, and most preferably 95% sequence identity with the human mpl ligand. More preferred isolated nucleic acid molecules are DNA sequences encoding biologically active mpl ligand, selected from: (a) DNA based on the coding region of a mammalian mpl ligand gene (e.g., DNA comprising the nucleotide sequence provided in FIG. 1 (SEQ ID NO: 2), or fragments thereof); (b) DNA capable of hybridizing to a DNA of (a) under at least moderately stringent conditions; and (c) DNA that is degenerate to a DNA defined in (a) or (b) which results from degeneracy of the genetic code. It is contemplated that the novel mpl ligands described herein may be members of a family of ligands or cytokines having suitable sequence identity that their DNA may hybridize with the DNA of FIG. 1 (SEQ ID NO: 2) (or the complement or fragments thereof) under low to moderate stringency conditions. Thus a further aspect of this invention includes DNA that hybridizes under low to moderate stringency conditions with DNA encoding the mpl ligand polypeptides.

In a further preferred embodiment of this invention, the nucleic acid molecule is cDNA encoding the mpl ligand and further comprises a replicable vector in which the cDNA is operably linked to control sequences recognized by a host transformed with the vector. This aspect further includes host cells transformed with the vector and a method of using the cDNA to effect production of mpl ligand, comprising expressing the cDNA encoding the mpl ligand in a culture of the transformed host cells and recovering the mpl ligand from the host cell culture. The mpl ligand prepared in this manner is preferably substantially homogeneous human mpl ligand.

The invention further includes a preferred method for treating a mammal having an immunological or hematopoietic disorder, especially thrombocytopenia comprising administering a therapeutically effective amount of a mpl ligand to the mammal. Optionally, the mpl ligand is administered in combination with a cytokine, especially a colony stimulating factor or interleukin. Preferred colony stimulating factors or interleukins include; kit-ligand, LIF, G-CSF, GM-CSF, M-CSF, EPO, IL-1, IL-2, IL-3, IL-5, IL-6, IL-7, IL-8, IL-9 or IL-11.

III. Methods of Making

Platelet production has long been thought to be controlled by lineage specific humoral factors. It has been postulated that two distinct cytokine activities, referred to as megakaryocyte colony-stimulating factor (meg-CSF) and thrombopoietin, regulate megakaryocytopoiesis and thrombopoiesis (Williams et al., *J. Cell Physiol.,* 110:101-104 [1982]; Williams et al., *Blood Cells,* 15:123-133 [1989]; and Gordon at al., *Blood,* 80:302-307 [1992]). Meg-CSF stimulates the proliferation of progenitor megakaryocytes while thrombopoietin primarily affects maturation of more differentiated cells and ultimately platelet release. Since the 1960's the induction and appearance of meg-CSF and thrombopoietin activities in the plasma, serum and urine of animals and humans following thrombocytopenic episodes has been well documented (Odell et al., *Proc. Soc. Exp. Biol. Med.,* 108:428-431 [1961]; Nakeff et al., *Acta Haematol.,* 54:340-344 [1975]; Specter, *Proc. Soc. Exp. Biol.,* 108:146-149 [1961]; Schreiner et al., *J.Clin-.Invest.,* 49:1709-1713 [1970; Ebbe, *Blood,* 44:605-608 [1974]; Hoffman et al., *N. Engl. J. Med.,* 305:533 [1981]; Straneva et al., *Exp. Hematol.,* 17:1122-1127 [1988]; Mazur et al., *Exp. Hematol.,* 13:1164 [1985]; Mazur et al., *J.Clin. Invest.,* 68:733-741 [1981]; Sheiner et al., *Blood,* 56:183-188 [1980]; Hill et al., *Exp. Hematol.,* 20:354-360 [1992]; and Hegyi et al., *Int. J. Cell Cloning,* 8:236-244 [1990]). These activities are reported to be lineage specific and distinct from known cytokines (Hill R. J. et al., *Blood* 80:346 (1992); Erickson-Miller C. L. et al., *Brit. J. Haematol.* 84:197-203 (1993); Straneva J. E. et al., *Exp. Hematol.* 20:4750(1992); and Tsukada J. et al., *Blood* 81:866-867 (1993)). Heretofore, attempts to purify meg-CSF or thrombopoietin from thrombocytopenic plasma or urine have been unsuccessful.

Consistent with the above observations describing thrombocytopenic plasma, we have found that aplastic porcine plasma (APP) obtained from irradiated pigs stimulates human megakaryocytopoiesis in vitro. Here we report that this stimulatory activity is abrogated by the soluble extracellular domain of c-mpl, confirming APP as a potential source of the putative mpl ligand (ML). The ML was purified from APP and amino acid sequence information used to isolate murine, porcine and human ML cDNA. These ML's have sequence homology to erythropoietin and have both meg-CSF and thrombopoietin-like activities.

1. Purification an Identification of mpl Ligand from Plasma

Aplastic plasma from a variety of species has been reported to contain activities that stimulate hematopoiesis in vitro, however no hematopoietic stimulatory factor has previously been reported isolated from plasma. One source of aplastic plasma is that obtained from irradiated pigs. This aplastic porcine plasma (APP) stimulates human hematopoiesis in vitro. To determine if APP contained the mpl ligand, its effect on $^3$H-thymidine incorporation into Ba/F3 cells transfected with human mpl P (Ba/F3-mpl) was measured by the procedure shown in FIG. 2. APP stimulated $^3$H-thymidine incorporation into Ba/F3-mpl cells but not Ba/F3 control cells (i.e., not transfected with human mpl P). Additionally, no such activity was observed in normal porcine plasma. These results indicated that APP contained a factor or factors that transduced a proliferative signal through the mpl receptor and therefore might be the natural ligand for this receptor. This was further supported by the finding that treatment of APP with soluble mpl-IgG blocked the stimulatory effects of APP on Ba/F3-mpl cells.

Figure 3:
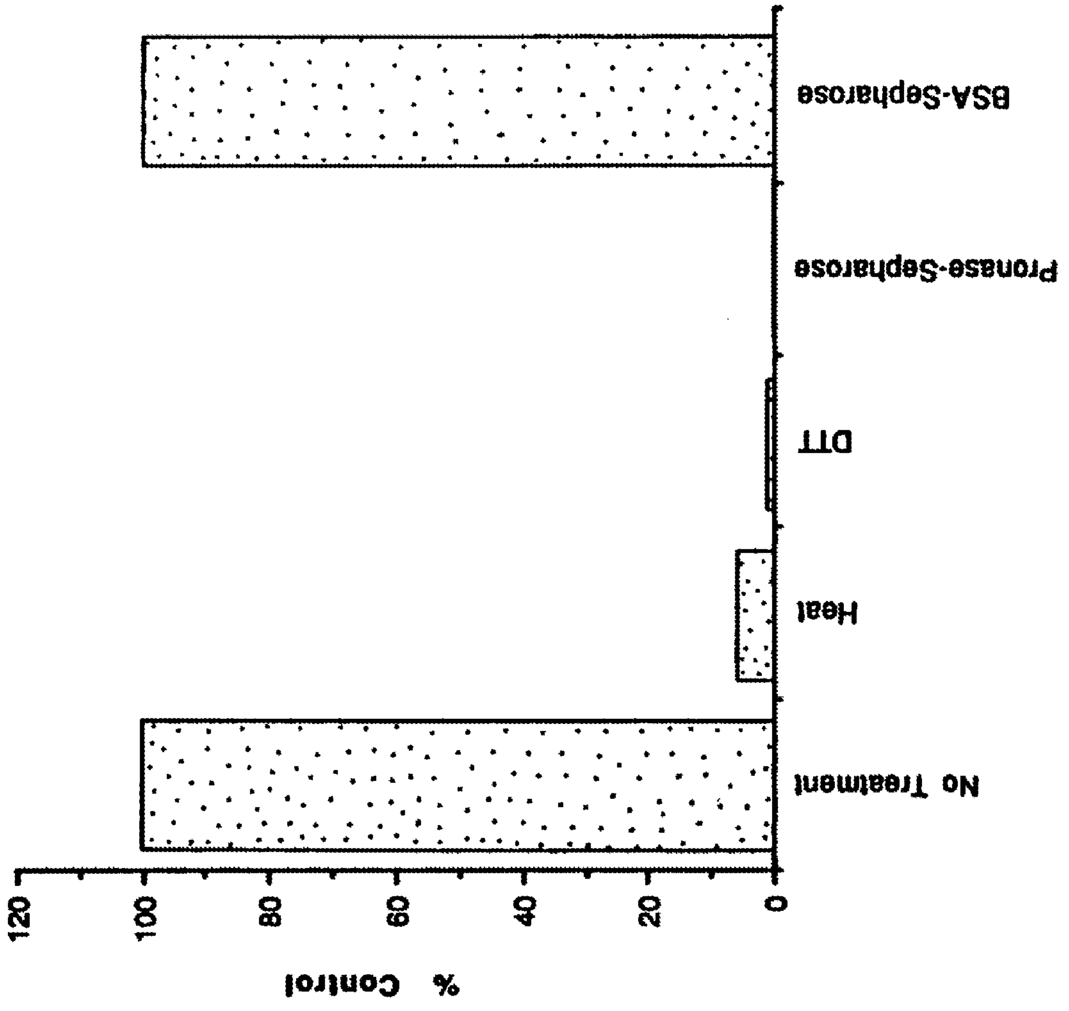
FIG. 3 shows the effect of pronase, DTT and heat on the ability of APP to stimulate Ba/F3-mpl cell proliferation. For pronase digestion of APP, pronase (Boehringer Mannheim) or bovine serum albumin was coupled to Affi-gel10 (Biorad) and incubated individually with APP for 18 hrs. at 37° C. Subsequently, the resins were removed by centrifugation and supernatants assayed. APP was also heated to 80° C. for 4 min. or made 100 μM DTT followed by dialysis against PBS.

The activity in APP appeared to be a protein since pronase, DTT, or heat destroy the activity in APP (FIG. 3). The activity was also non-dialyzable. The activity was, however, stable to low pH (pH 2.5 for 2 hrs.) and was shown to bind and elute from several lectin-affinity columns, indicating that it was a glycoprotein. To further elucidate the structure and identity of this activity it was affinity purified from APP.

Figure 4:
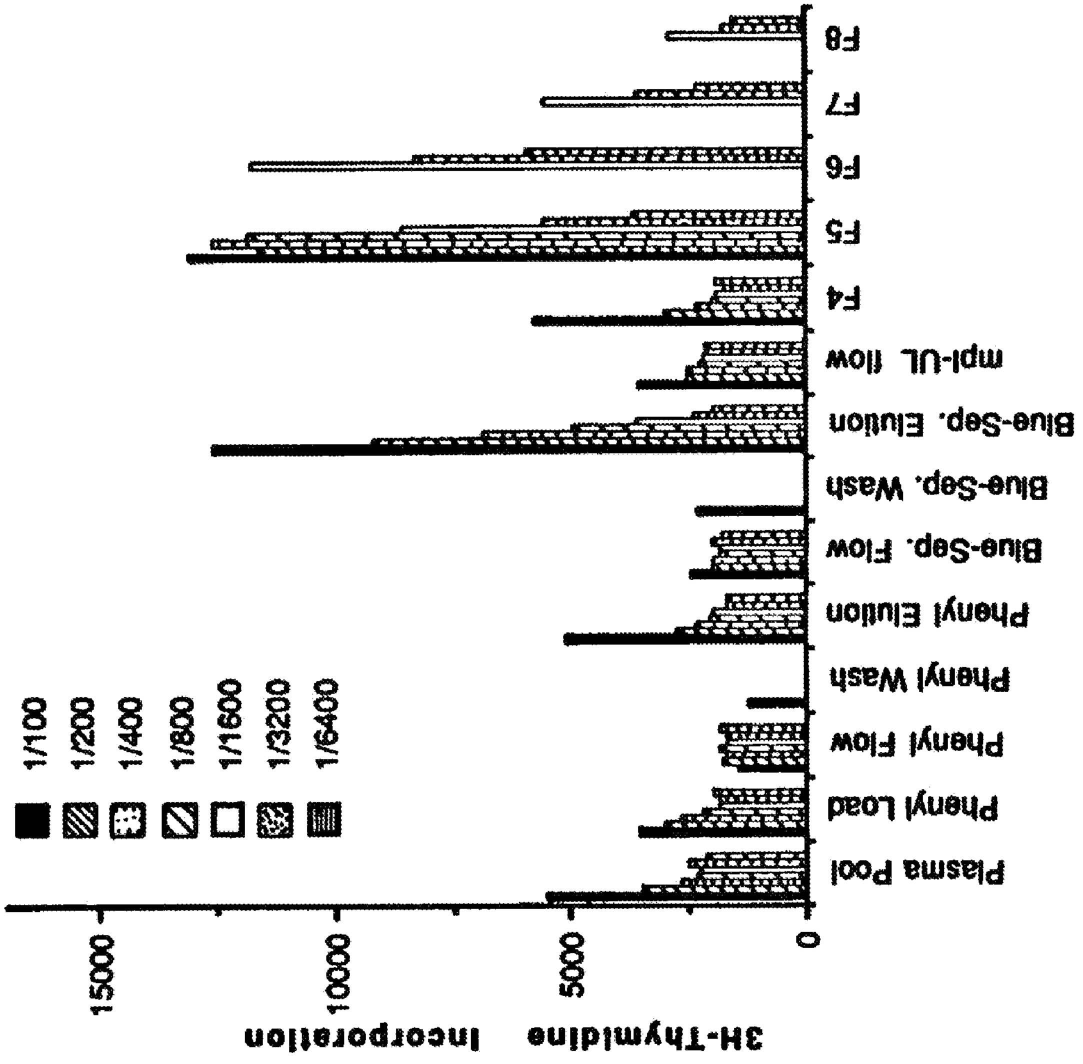
FIG. 4 shows the elution of mpl ligand activity from Phenyl-Toyopearl, Blue-Sepharose and Ultralink-mpl columns. Fractions 4-8 from the mpl affinity column were the peak activity fractions eluted from the column.

APP was treated according to the protocol set forth in Examples 1 and 2. Briefly, mpl ligand was purified using hydrophobic interaction chromatography (HIC), immobilized dye chromatography, and mpl-affinity chromatography. The recovery of activity from each step is shown in FIG. 4 and the fold purification is provided in Table 1. The overall recovery of activity through the mpl-affinity column was approximately 10%. The peak activity fraction (F6) from the mpl-affinity column has an estimated specific activity of 9.8×10$^6$ units/mg. The overall purification from 5 liters of APP was approximately 4×10$^6$ fold (0.8 units/mg to 3.3×10$^6$ units/mg) with a 83×10$^6$ fold reduction in protein (250 gms to 3 μg). We estimated the specific activity of the ligand eluted from the mpl-affinity column to be −3×10$^6$ units/mg.

TABLE 1

Purification of mpl Ligand

| Sample | Volume mls | Protein mg/ml | Units/ml | Units | Specific Activity Units/mg | Yield % | Fold Purification |
|---|---|---|---|---|---|---|---|
| APP | 5000 | 50 | 40 | 200,000 | 0.8 | — | 1 |
| Phenyl | 4700 | 0.8 | 40 | 200,000 | 50 | 94 | 62 |
| Blue-Sep. | 640 | 0.93 | 400 | 256,000 | 430 | 128 | 538 |
| mpl (μl) (Fxns 5-7) | 12 | $5 \times 10^{-4}$ | 1666 | 20,000 | 3,300,000 | 10 | 4,100,000 |

Protein was determined by the Bradford assay. Protein concentration of mpl-eluted fractions 5-7 are estimates based on staining intensity of a silver stained SDS-gel. One unit is defined as that causing 50% maximal stimulation of Ba/F3-mpl cell proliferation.

Figure 5:
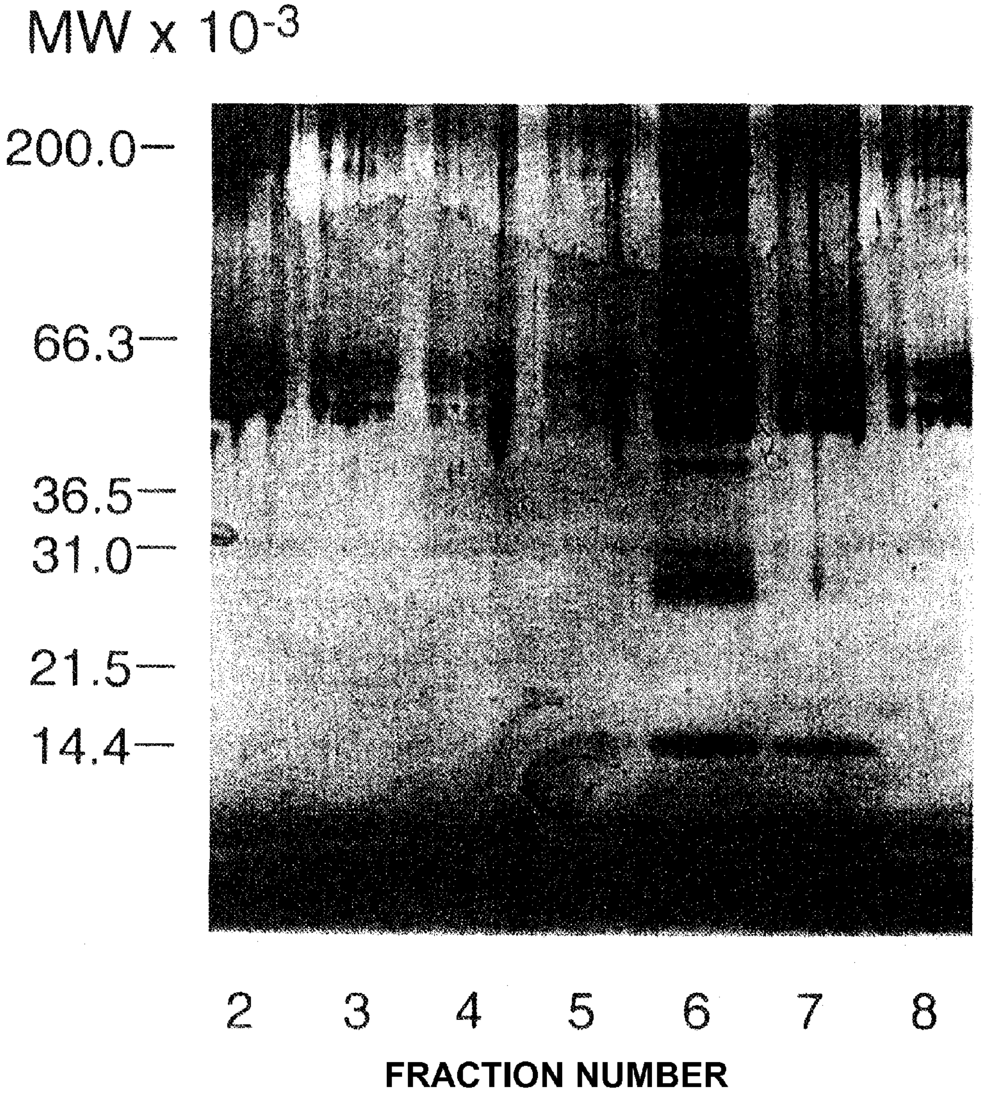
FIG. 5 shows the SDS-PAGE of eluted Ultralink-mpl fractions. To 200 μl of each fraction 2-8, 1 ml of acetone containing 1 mM HCl at −20° C. was added. After 3 hrs. at −20° C. samples were centrifuged and resultant pellets were washed 2× with acetone at −20° C. The acetone pellets were subsequently dissolved in 30 μl of SDS-solubilization buffer, made 100 μM DTT and heated at 90° C. for 5 min. The samples were then resolved on a 4-20% SDS-polyacrylamide gel and proteins were visualized by silver staining.

Analysis of eluted fractions from the mpl affinity column by SDS-PAGE (4-20%, Novex gel) run under reducing conditions, revealed the presence of several proteins (FIG. 5). Proteins that silver stained with the strongest intensity resolved with apparent Mr of 66,000, 55,000, 30,000, 28,000 and 14,000. To determine which of these proteins stimulated proliferation of Ba/F3-mpl cell cultures, the proteins were eluted from the gel as described in Example 2.

Figure 6:
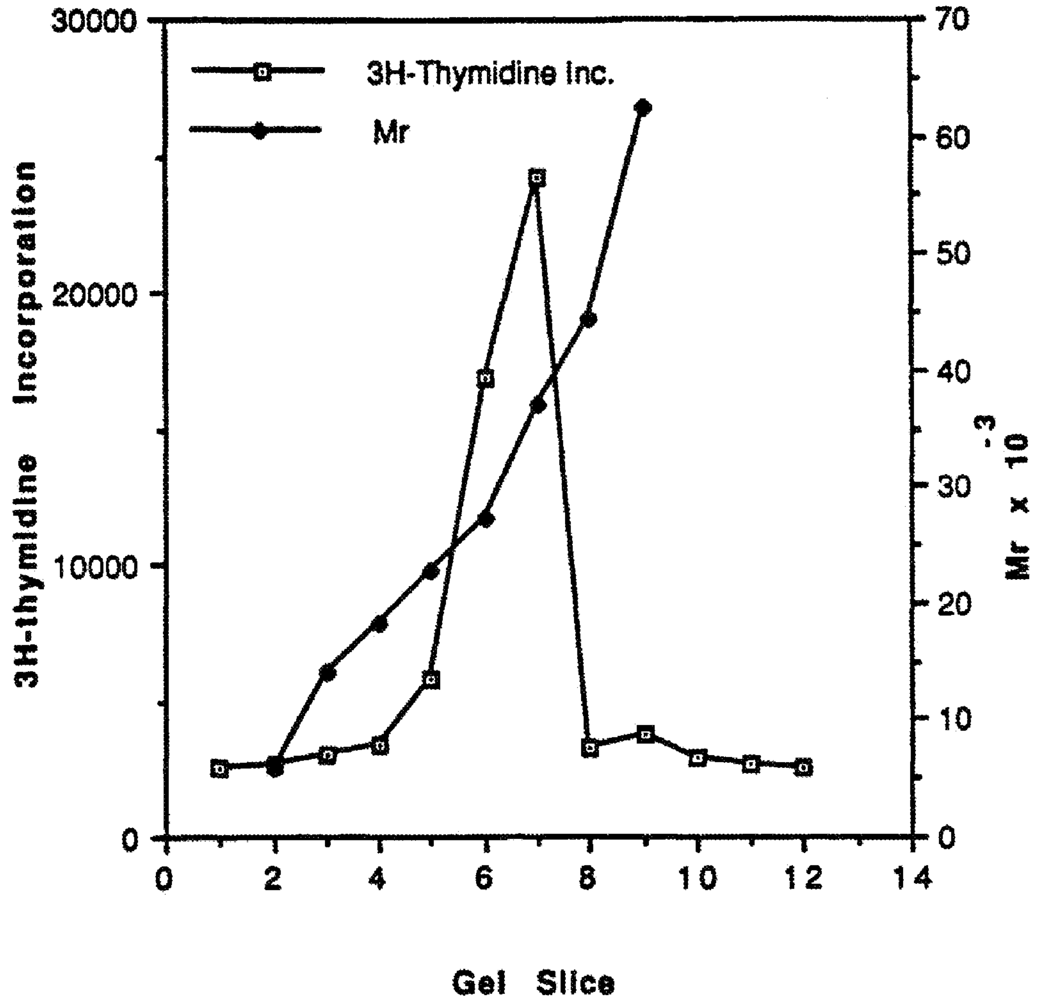
FIG. 6 shows elution of mpl ligand activity from SDS-PAGE. Fraction 6 from the mpl-affinity column was resolved on a 4-20% SDS-polyacrylamide gel under non-reducing conditions. Following electrophoresis the gel was sliced into 12 equal regions and electroeluted as described in the examples. The electroeluted samples were dialyzed into PBS and assayed at a 1/20 dilution. The Mr standards used to calibrate the gel were Novex Mark 12 standards.

The results of this experiment showed that most of the activity eluted from a gel slice that included proteins with Mr 28,000-32,000, with lesser activity eluting in the 18,000-20,000 region of the gel (FIG. 6). The only proteins visible in these regions had Mr of 30,000, 28,000 and 18,000. To identify and obtain protein sequence for the proteins resolving in this region of the gel (i.e. bands at 30, 28 and 18 kDa), these three proteins were electroblotted to PVDF and sequenced as described in Example 3. Protein sequences obtained were as follows:

```
1) 30 kDa                                        (SEQ ID NO: 22)
      1         5         10         15          20           25
    (S) P A P P A(C)D P R L L N K L L R D D (H/S) V L H (G) R L

2) 28 kDa                                        (SEQ ID NO: 23)
      1         5         10         15          20           25
    (S) P A P P A X D P R L L N K L L R D D (H) V L (H) G R

3) 18 kDa                                        (SEQ ID NO: 24)
      1         5         10
      X P A P P A X D P R L X (N) (K)
```

Computer-assisted analysis revealed these sequences to be novel. Because all three sequences were the same, it is believed the 30 kDa, 28 kDa and 18 kDa proteins are related and may be different forms of the same novel protein. Furthermore, this protein(s) was a likely candidate as the natural mpl ligand because the activity resolved on SDS-PAGE in the same region (28,000-32,000) of a 4-20% gel. In addition, the partially purified ligand migrated with a Mr of 17,000-30,000 when subjected to gel filtration chromatography using a Superose 12 (Pharmacia) column. It is believed the different Mr forms of the ligand are a result of proteolysis or glycosylation differences or other post or pre-translational modifications.

Figure 7:
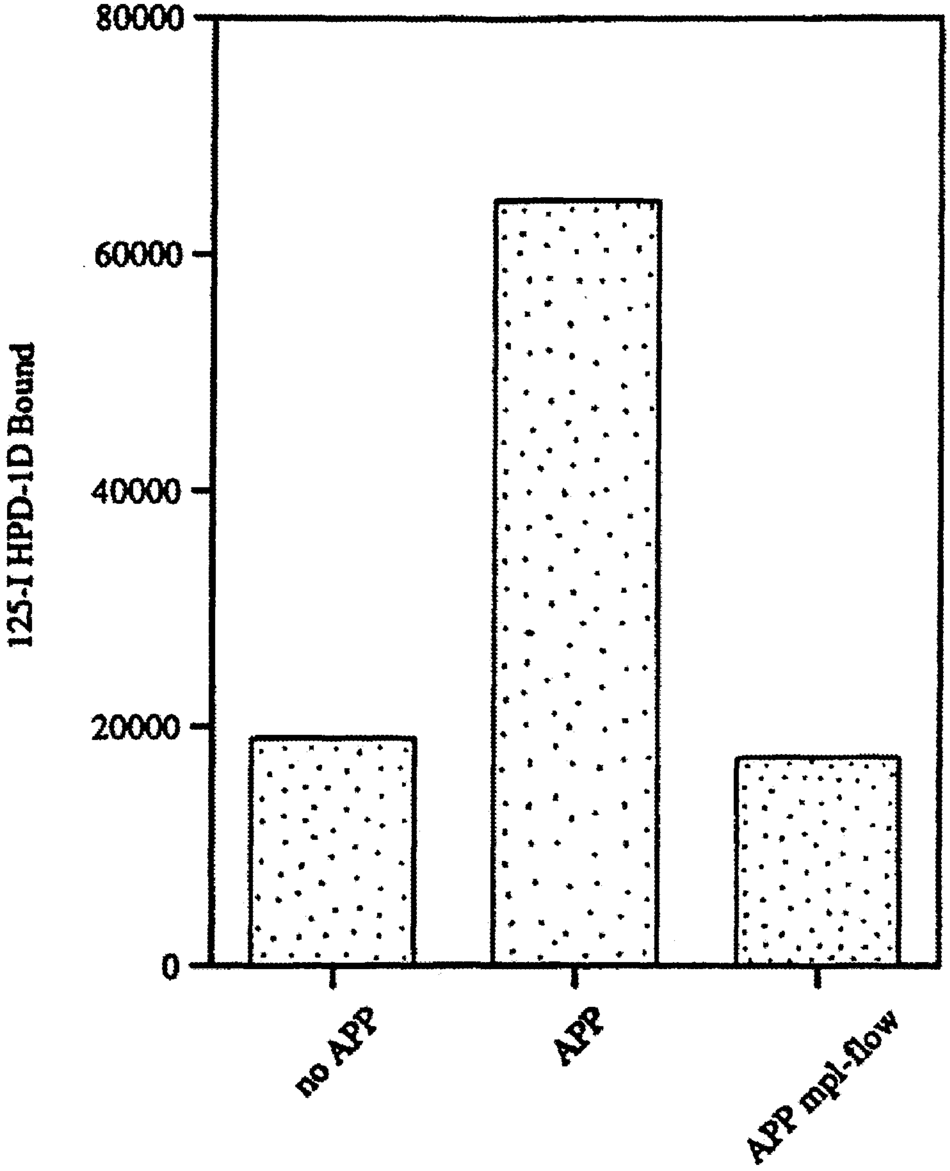
FIG. 7 shows the effect of mpl ligand depleted APP on human megakaryocytopoiesis. mpl ligand depleted APP was made by passing 1 ml over a 1 ml mpl-affinity column (700 μg mpl-IgG/ml NHS-superose, Pharmacia). Human peripheral stem cell cultures were made 10% APP or 10% mpl ligand depleted APP and cultured for 12 days. Megakaryocytopoiesis was quantitated as described in the examples.

As described earlier, antisense human mpl RNA abrogated megakaryocytopoiesis in human bone marrow cultures enriched with CD $34^+$ progenitor cells without affecting the differentiation of other hematopoietic cell lineages (Methia et al., supra). This result suggested that the mpl receptor plays a role in the differentiation and proliferation of megakaryocytes in vitro. To further elucidate the role of the mpl ligand in megakaryocytopoiesis, the effects of APP and mpl ligand depleted APP on in vitro human megakaryocytopoiesis was compared. The effect of APP on human megakaryocytopoiesis was determined using a modification of the liquid suspension megakaryocytopoiesis assay described in Example 4. In this assay, human peripheral stem cells (PSC) were treated with APP before and after mpl-IgG affinity chromatography. $GPII_bIII_a$ stimulation of megakaryocytopoiesis was quantitated with an $^{125}I$-anti-$II_bIII_a$ antibody (FIG. 7). Shown in FIG. 7 10% APP caused approximately a 3-fold stimulation while APP depleted of mpl ligand had no effect. Significantly, the mpl ligand depleted APP did not induce proliferation of the Ba/F3-mpl cells.

Figure 8:
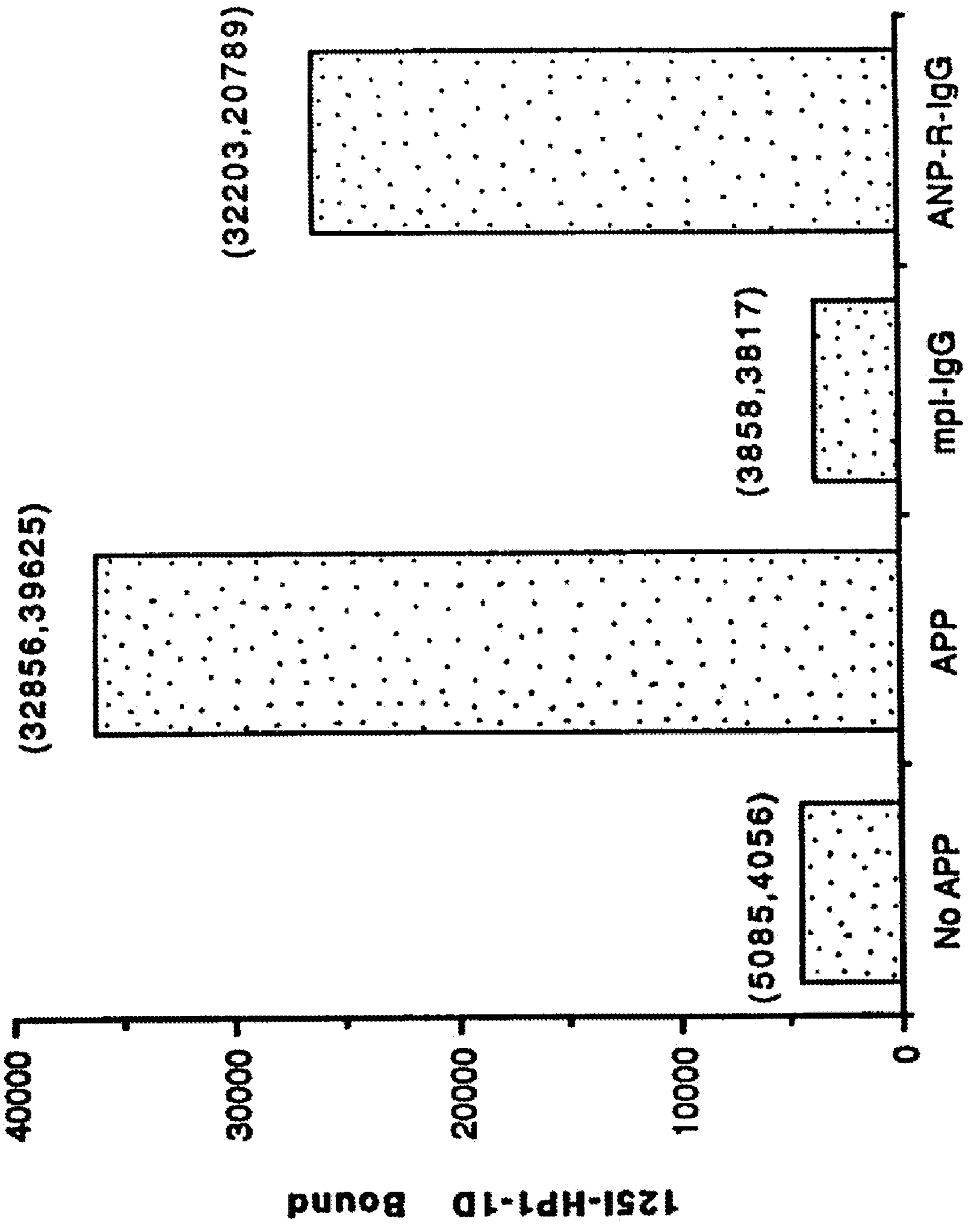
FIG. 8. shows the effect of mpl-IgG on the stimulation of human megakaryocytopoiesis by APP. Human peripheral stem cell cultures were made 10% with APP and cultured for 12 days. At day 0, 2 and 4, mpl-IgG (0.5 μg) or ANP-R-IgG (0.5 μg) was added. After 12 days megakaryocytopoiesis was quantitated as described in the examples. The average of duplicate samples is graphed with the actual duplicate data in parenthesis.

In another experiment, soluble human mpl-IgG added at days 0, 2 and 4 to cultures containing 10% APP neutralized the stimulatory effects of APP on human megakaryocytopoiesis (FIG. 8). These results indicate that the mpl ligand plays a role in regulating human megakaryocytopoiesis and therefore may be useful for the treatment of thrombocytopenia.

2. Molecular Cloning of the mpl Ligand

Based on the amino-terminal amino acid sequence obtained from the 30 kDa, 28 kDa and 18 kDa proteins (see above), two degenerate oligonucleotide primer pools were designed and used to amplify porcine genomic DNA by PCR. It was reasoned that if the amino-terminal amino acid sequence was encoded by a single exon then the correct PCR product was expected to be 69 bp long. A DNA fragment of this size was found and subcloned into pGEMT. The sequences of the oligonucleotide PCR primers and the three clones obtained are shown in Example 5. The amino acid sequence (PRLLNKLLR (SEQ ID NO: 25)) of the peptide encoded between the PCR primers was identical to that obtained by amino-terminal protein sequencing of the porcine ligand (see residues 9-17 for the 28 and 30 kDa porcine protein sequences above).

A synthetic oligonucleotide based on the sequence of the PCR fragment was used to screen a human genomic DNA library. A 45-mer oligonucleotide was designed and synthesized based on the sequence of the PCR fragment. This oligonucleotide had the following sequence:

5' GCC-GTG-AAG-GAC-GTG-GTC-GTC-ACG-
AAG-CAG-TTT-ATT-TAG-GAG-TCG 3' (SEQ ID NO:26)

This deoxyoligonucleotide was used to screen a human genomic DNA library in λgem12 under low stringency hybridization and wash conditions according to Example 6. Positive clones were picked, plaque purified and analyzed by restriction mapping and southern blotting. A 390 by EcoRI-XbaI fragment that hybridized to the 45-mer was subcloned into pBluescript SK-. DNA sequencing of this clone confirmed that DNA encoding the human homolog of the porcine mpl ligand had been isolated. The human DNA sequence and deduced amino acid sequence are shown in FIG. 9 (SEQ ID NOS: 3 & 4). The predicted positions of introns in the genomic sequence are also indicated by arrows, and define a putative exon ("exon 3").

Based on the human "exon 3" sequence (Example 6) oligonucleotides corresponding to the 3' and 5' ends of the exon sequence were synthesized. These 2 primers were used in PCR reactions employing as a template cDNA prepared from various human tissues. The expected size of the correct PCR product was 140 bp. After analysis of the PCR products on a 12% polyacrylamide gel, a DNA fragment of the expected size was detected in cDNA libraries prepared from human adult kidney, 293 fetal kidney cells and cDNA prepared from human fetal liver.

A fetal liver cDNA library ($7\times10^6$ clones) in lambda DR2 was next screened with the same 45-mer oligonucleotide used to screen the human genomic library and the fetal liver cDNA library under low stringency hybridization conditions. Positive clones were picked, plaque purified and the insert size was determined by PCR. One clone with a 1.8 kb insert was selected for further analysis. Using the procedures described in Example 7 the nucleotide and deduced amino acid sequence of the human mpl ligand (hML) were obtained. These sequences are presented in FIG. 1 (SEQ ID NO: 1).

3. Structure of the Human mpl Ligand (hML)

The human mpl ligand (hML) cDNA sequence (FIG. 1 (SEQ ID NO: 2)) comprises 1774 nucleotides followed by a poly(A) tail. It contains 215 nucleotides of 5' untranslated sequence and a 3' untranslated region of 498 nucleotides. The presumed initiation codon at nucleotide position (216-218) is within a consensus sequence favorable for eukaryotic translation initiation. The open reading frame is 1059 nucleotides long and encodes a 353 amino acid residue polypeptide, beginning at nucleotide position 220. The N-terminus of the predicted amino acid sequence is highly hydrophobic and probably corresponds to a signal peptide. Computer analysis of the predicted amino acid sequence (von Heijne et al., *Eur. J. Biochem.,* 133:17-21 [1983]) indicates a potential cleavage site for signal peptidase between residues 21 and 22. Cleavage at that position would generate a mature polypeptide of 332 amino acid residues beginning with the amino-terminal sequence obtained from mpl ligand purified from porcine plasma. The predicted non-glycosylated molecular weight of the 332 amino acid residue ligand is about 38 kDa. There are 6 potential N-glycosylation sites and 4 cysteine residues.

Comparison of the mpl ligand sequence with the Genbank sequence database revealed 23% identity between the amino terminal 153 residues of the hML and human erythropoietin (FIG. 10 (SEQ ID NOS: 6 & 7)). When conservative substitutions are taken into account, this region of hML shows 50% similarity to human erythropoietin (h-epo). Both h-epo and the hML contain four cysteines. Three of the 4 cysteines are conserved in hML, including the first and last cysteines, but none of the glycosylation sites. Site-directed mutagenesis experiments have shown that the first and last cysteines of erythropoietin form a disulfide bond that is required for function (Wang, F. F. et al., *Endocrinology* 116:2286-2292 (1983)). By analogy, the first and last cysteines of hML may also form a critical disulfide bond. All potential hML N-glycosylation sites are located in the carboxy-terminal half of the hML polypeptide.

Similar to h-epo, the hML mRNA does not contain the consensus polyadenylation sequence AAUAAA, nor the regulatory element AUUUA that is present in 3' untranslated regions of many cytokines and is thought to influence mRNA stability (Shaw et al., *Cell,* 46:659-667 [1986]). Northern blot analysis reveals low levels of a single 1.8 kb hML RNA transcript in both fetal and adult liver. After longer exposure, a weaker band of the same size could be detected in adult kidney. By comparison, human erythropoietin is expressed in fetal liver and, in response to hypoxia, the adult kidney and liver (Jacobs et al., *Nature,* 313:804-809 [1985] and Bondurant et al., *Molec. Cell. Biol.,* 6:2731-2733 [1986]).

The importance of the C-terminal region of the hML remains to be elucidated. Based on the presence of the six potential sites for N-linked glycosylation and the ability of the ligand to bind lectin-affinity columns, this region of the hML is likely glycosylated. In some gel elution experiments, we observed activity resolving with a $M_r$ around 60,000 which may represent the full length, glycosylated molecule. The C-terminal region may therefore act to stabilize and increase the half-life of circulating hML. In the case of erythropoietin, the non-glycosylated form has full in vitro biological activity, but has a significantly reduced plasma half-life relative to glycosylated erythropoietin (Takeuchi et al., *J. Biol. Chem.,* 265:12127-12130 [1990]; Narhi et al., *J. Biol. Chem.,* 266: 23022-23026 [1991] and Spivack et al., *Blood,* 7:90-99 [1989]). The C-terminal domain of hML contains two dibasic amino acid sequences [Arg-Arg motifs at positions 153-154 and 245-246] that could serve as potential processing sites. Cleavage at these sites may be responsible for generating the 30, 28 and 18 kDa forms of the ML isolated from APP. Significantly, the $Arg_{153}$-$Arg_{154}$ sequence occurs immediately following the erythropoietin-like domain of the ML. These observations indicate that full length ML may represent a precursor protein that undergoes limited proteolysis to generate the mature ligand.

4. Isoforms and Variants of the Human mpl Ligand

Figures 11, 11A, 11B:
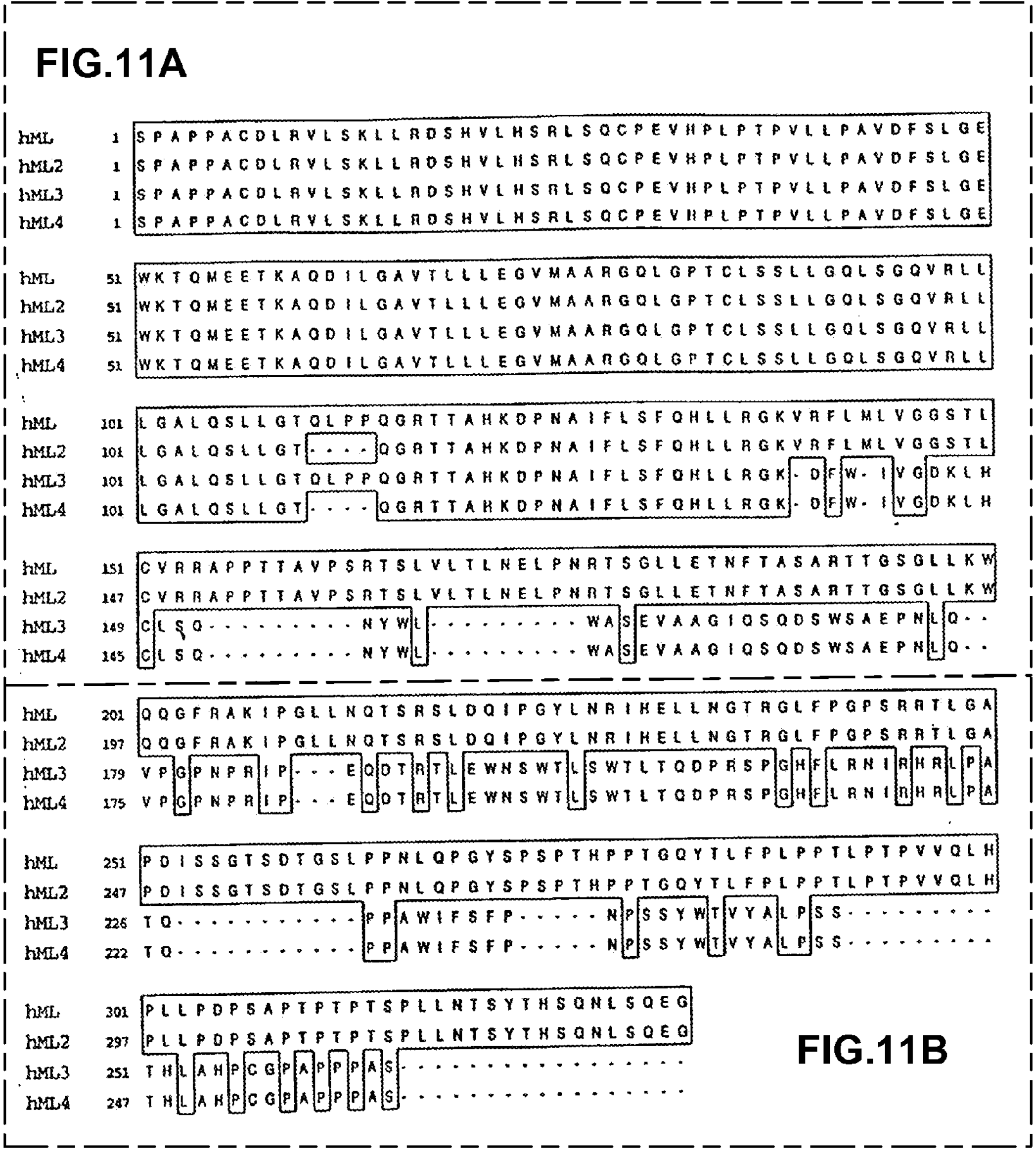
FIGS. 11 A and B show deduced amino acid sequence of mature human mpl ligand isoforms h-ML (SEQ ID NO: 6), h-ML2 (SEQ ID NO: 8), h-ML3 (SEQ ID NO: 9), and h-ML4 (SEQ ID NO: 10). Identical amino acids are boxed and gaps introduced for optimal alignment are indicated by dashes.

Isoforms or alternatively spliced forms of human mpl ligand were detected by PCR in human adult liver. Briefly, primers were synthesized corresponding to each end as well as selected internal regions of the coding sequence of hML. These primers were used in RT-PCR to amplify human adult liver RNA as described in Example 9. In addition to the full length form, designated hML, three other forms, designated hML2, hML3 and hML4, were observed or deduced. The mature deduced amino acid sequences of all four isoforms is presented in FIG. 11 (SEQ ID NOS: 6, 8, 9 & 10). hML3 has a 116 nucleotide deletion at position 700 which results in both an amino acid deletion and a frameshift. The cDNA now encodes a mature polypeptide that is 265 amino acid long and diverges from the hML sequence at amino acid residue 139. Finally, hML4 has both a 12 nucleotide deletion following nucleotide position 618 (also found in the mouse and the pig sequences [see below]) and the 116 bp deletion found in hML3. Although clones with only the 12 bp deletion (following nucleotide 619) have been isolated in the human (designated hML2), this form is likely to exist because such a isoform has been identified in both the mouse and pig (see below), and because it has been identified in conjunction with the 116 nucleotide deletion in hML4.

Both a substitutional variant of hML in which the dibasic $Arg_{153}$-$Arg_{154}$ sequence was replaced with two alanine residues and a "epo-domain" truncated form of hML were constructed to determine whether the full length ML was necessary for biological activity. The $Arg_{153}$-$Arg_{154}$ dibasic sequence substitutional variant, referred to as hML(R153A, R154A), was constructed using PCR as described in Example 10. The "epo-domain" truncated form, $hML_{153}$, was also made using PCR by introducing a stop codon following Arg153.

5. Expression of Recombinant Human mpl Ligand

Figure 12A:
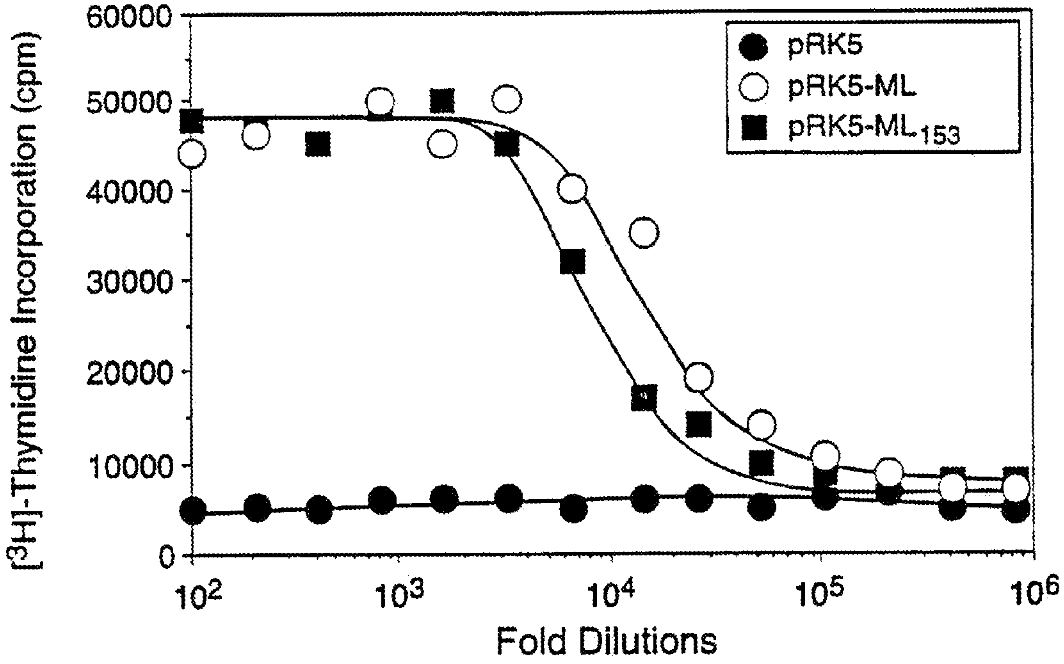
FIGS. 12 A, B, C, and D show the effect of human mpl ligand on Ba/F3-mpl cell proliferation (A), in vitro human megakaryocytopoiesis quantitated using a radiolabeled murine IgG monoclonal antibody specific to the megakaryocyte glycoprotein GPIIbIIIa (B), and murine thrombopoiesis measured in a platelet rebound assay (C).

To confirm that the cloned human cDNA encoded a ligand for mpl, the ligand was expressed in mammalian cells under the control of the cytomegalovirus immediate early promoter using the expression vectors pRK5-hML or pRK5-$hML_{153}$. Supernatants from transiently transfected human embryonic kidney 293 cells were found to stimulate $^3H$-thymidine incorporation in Ba/F3-mpl cells, but not in parental Ba/F3 cells (FIG. 12A). Media from the 293 cells transfected with the pRK vector alone did not contain this activity. Addition of mpl-IgG to the media abolished the stimulation (data not shown). These results show that the cloned cDNA encodes a functional human ML (hML).

To determine if the "epo-domain" alone could bind and activate mpl, the truncated form of hML, $rhML_{153}$, was expressed in 293 cells. Supernatants from transfected cells were found to have activity similar to that present in supernatants from cells expressing the full length hML (FIG. 12A), indicating that the C-terminal domain of ML is not required for binding and activation of c-mpl.

6. mpl Ligand Stimulates Megakaryocytopoiesis and Thrombopoiesis

Figure 12B:
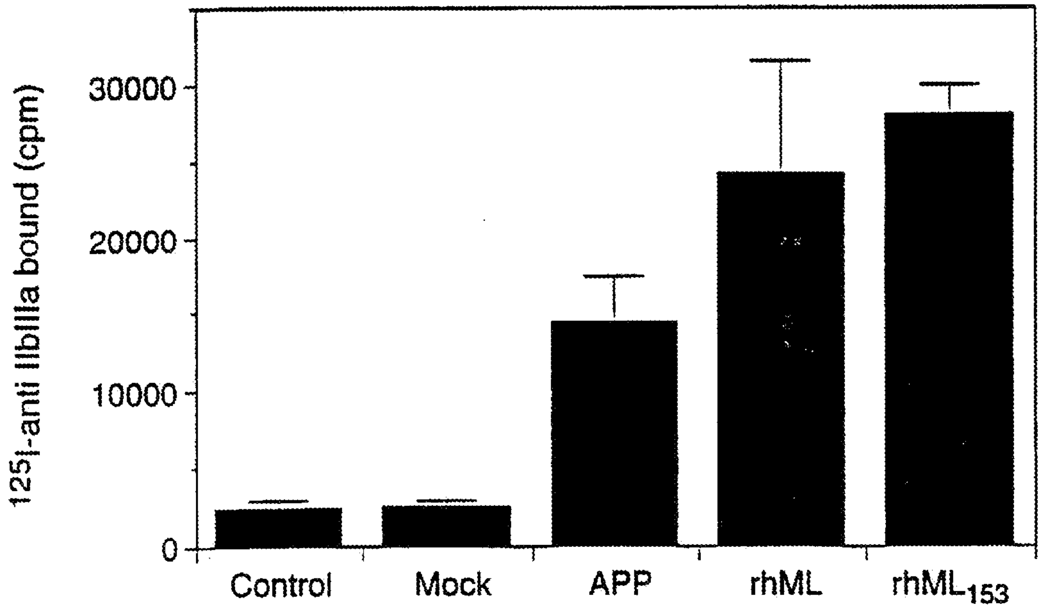
Figure 12D:
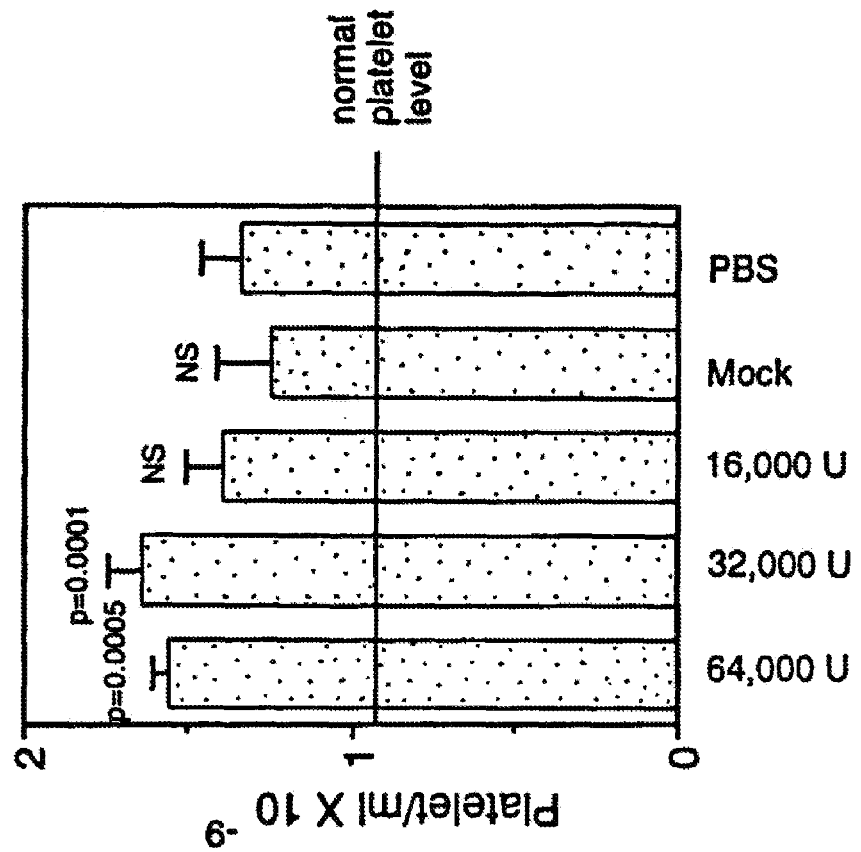

Both the full length rhML and the truncated $rhML_{153}$ forms of recombinant hML stimulated human megakaryocytopoiesis in vitro (FIG. 12B). This effect was observed in the absence of other exogenously added hematopoietic growth factors. With the exception of IL-3, the ML was the only hematopoietic growth factor tested that exhibited this activity. IL-11, IL-6, IL-1, erythropoietin, G-CSF, IL-9, LIF, kit ligand, M-CSF, OSM and GM-CSF had no effect on megakaryocytopoiesis when tested separately in our assay (data not shown). This result demonstrates that the ML has megakaryocyte-stimulating activity, and indicates a role for ML in regulating megakaryocytopoiesis.

Figure 12C:
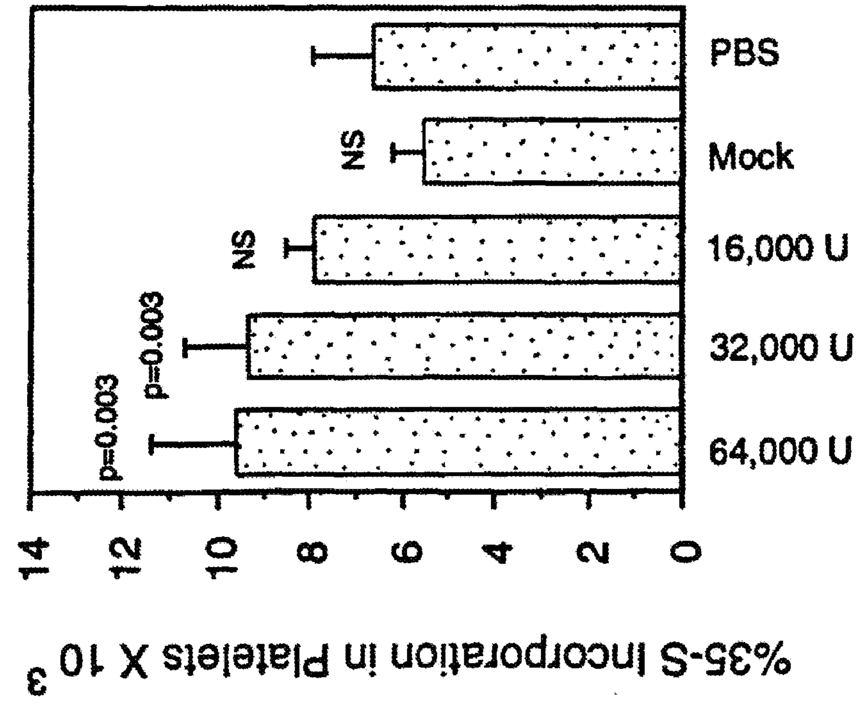

Thrombopoietic activities present in plasma of thrombocytopenic animals have been shown to stimulate platelet production in a mouse rebound thrombocytosis assay (McDonald, *Proc. Soc. Exp. Biol. Med.*, 14:1006-1001 [1973] and McDonald et al., *Scand. J. Haematol.*, 16:326-334 [1976]). In this model mice are made acutely thrombocytopenic using specific antiplatelet serum, resulting in a predictable rebound thrombocytosis. Such immunothrombocythemic mice are more responsive to exogenous thrombopoietin-like activities than are normal mice (McDonald, *Proc. Soc. Exp. Biol. Med.*, 14:1006-1001 [1973]), just as exhypoxic mice are more sensitive to erythropoietin than normal are mice (McDonald, et al., *J. Lab. Clin. Med.*, 77:134-143 [1971]). To determine whether the rML stimulates platelet production in vivo, mice in rebound thrombocytosis were injected with partially purified rhML. Platelet counts and incorporation of $^{35}$S into platelets were then quantitated. Injection of mice with 64,000 or 32,000 units of rML significantly increased platelet production, as evidenced by a −20% increase in platelet counts (p=0.0005 and 0.0001, respectively) and a −40% increase in $^{35}$S incorporation into platelets (p=0.003) in the treated mice versus control mice injected with excipient alone (FIG. 12C). This level of stimulation is comparable to that which we have observed with IL-6 in this model (data not shown). Treatment with 16,000 units of rML did not significantly stimulate platelet production. These results indicate that ML stimulates platelet production in a dose-dependent manner and therefore possesses thrombopoietin-like activity.

293 cells were also transfected with the other hML isoform constructs described above and the supernatants were assayed using the Ba/F3-mpl proliferation assay (see FIG. 13). hML2 and hML3 showed no detectable activity in this assay, however the activity of hML(R153A, R154A) was similar to hML and hML$_{153}$ indicating that processing at the Arg$_{153}$-Arg$_{154}$ di-basic site is neither required for nor detrimental to activity.

7. Megakaryocytopoiesis and the mpl Ligand

It has been proposed that megakaryocytopoiesis is regulated at multiple cellular levels (Williams et al., *J.Cell Physiol.*, 110:101-104 [1982] and Williams et al., *Blood Cells*, 15:123-133 [1989]). This is based largely on the observation that certain hematopoietic growth factors stimulate proliferation of megakaryocyte progenitors while others appear to primarily affect maturation. The results presented here suggest that the ML acts both as a proliferative and maturation factor. That ML stimulates proliferation of megakaryocyte progenitors is supported by several lines of evidence. First, APP stimulates both proliferation and maturation of human megakaryocytes in vitro, and this stimulation is completely inhibited by mpl-IgG (FIGS. 7 and 8). Furthermore, the inhibition of megakaryocyte colony formation by c-mpl antisense oligonucleotides (Methia et al., *Blood*, 82:1395-1401 [1993]) and the finding that c-mpl can transduce a proliferative signal in cells into which it is transfected (Skoda et al., *EMBO*, 12:2645-2653 [1993] and Vigon et al., *Oncogene*, 8:2607-2615 [1993]) also indicate that ML stimulates proliferation. The apparent expression of c-mpl during all stages of megakaryocyte differentiation (Methia et al., *Blood*, 82:1395-1401 [1993]) and the ability of recombinant ML to rapidly stimulate platelet production in vivo indicate that ML also affects maturation. The availability of recombinant ML makes possible a careful evaluation of its role in regulating megakaryocytopoiesis and thrombopoiesis as well as its potential to influence other hematopoietic lineages.

8. The Murine mpl Ligand

A DNA fragment corresponding to the coding region of the human mpl ligand was obtained by PCR, gel purified and labeled in the presence of $^{32}$P-dATP and $^{32}$P-dCTP. This probe was used to screen $10^6$ clones of a mouse liver cDNA library in λGT10. A murine clone (FIG. 14 (SEQ ID NOS: 11 & 12)) containing a 1443 base pair insert was isolated and sequenced. The presumed initiation codon at nucleotide position 138-141 was within a consensus sequence favorable for eukaryotic translation initiation (Kozak, M. *J.Cell Biol.* 108: 229-241 (1989)). This sequence defines an open reading frame of 1056 nucleotides, which predicts a primary translation product of 352 amino acids. Flanking this open reading frame are 137 nucleotides of 5' and 247 nucleotides of 3' untranslated sequence. There is no poly(A) tail following the 3' untranslated region indicating that the clone is probably not complete. The N-terminus of the predicted amino acid sequence is highly hydrophobic and probably represents a signal peptide. Computer analysis (von Heijne, G. *Eur. J. Biochem.* 133:17-21 (1983)) indicated a potential cleavage site for signal peptidase between residues 21 and 22. Cleavage at that position would generate a mature polypeptide of 331 amino acids (35 kDa) identified as mML$_{331}$ (or mML2 for reasons described below). The sequence contains 4 cysteines, all conserved in the human sequence, and seven potential N-glycosylation sites, 5 of which are conserved in the human sequence. Again, as with hML, all seven potential N-glycosylation sites are located in the C-terminal half of the protein.

When compared with the human ML, considerable identity for both nucleotide and deduced amino acid sequences were observed in the "epo-domains" of these ML's. However, when deduced amino acid sequences of human and mouse ML's were aligned, the mouse sequence appeared to have a tetrapeptide deletion between residues 111-114 corresponding to the 12 nucleotide deletion following nucleotide position 618 seen in both the human (see above) and pig (see below) cDNA's. Accordingly, additional clones were examined to detect possible murine ML isoforms. One clone encoded a 335 amino acid deduced sequence polypeptide containing the "missing" tetrapeptide LPLQ. This form is believed to be the full length murine ML and is referred to as mML or mML$_{335}$. The nucleotide and deduced amino acid sequence for mML are provided in FIG. 15 (SEQ ID NOS: 13 & 14). This cDNA clone consists of 1443 base pairs followed by a poly(A) tail. It possesses an open reading frame of 1068 by flanked by 134 bases of 5' and 241 bases of 3' untranslated sequence. The presumed initiation codon lies at nucleotide position 138-140. The open reading frame encodes a predicted protein of 356 amino acids, the first 21 of which are highly hydrophobic and likely function as a secretion signal.

Finally, a third murine clone was isolated, sequenced and was found to contained the 116 nucleotide deletion corresponding to hML3. This murine isoform is therefore denominated mML3. Comparison of the deduced amino acid sequences of these two isoforms is shown in FIG. 16 (SEQ ID NOS: 9 & 15).

The overall amino acid sequence identity between human and mouse ML (FIG. 17 (SEQ ID NOS: 6 & 16)) is 72% but this homology is not evenly distributed. The region defined as the "epo-domain" (amino acids 1-153 for the human sequence and 1-149 for the mouse) is better conserved (86% homology) than the carboxy-terminal region of the protein (62% homology). This may further indicate that only the "epo-domain" is important for the biological activity of the protein. Interestingly, of the two di-basic amino acid motifs found in hML, only the di-basic motif immediately following the "epo-domain" (residue position 153-154) in the human sequence is present in the murine sequence. This is consistent with the possibility that the full length ML may represent a precursor protein that undergoes limited proteolysis to generate the mature ligand.

An expression vector containing the entire coding sequence of mML was transiently transfected into 293 cells as described in Example 1. Conditioned media from these cells stimulated $^3$H-thymidine incorporation into Ba/F3 cells expressing either murine or human mpl but had no effect on the parental (mpl-less) cell line. This indicates that the cloned murine ML cDNA encodes a functional ligand that is able to activate both the murine and human ML receptor (mpl).

9. The Porcine mpl Ligand

Porcine ML (pML) cDNA was isolated by RACE PCR as described in Example 12. A PCR cDNA product of 1342 bp was found in kidney and subcloned. Several clones were sequenced and found to encode a pig mpl ligand of 332 amino acid residues referred to as pML (or $pML_{332}$) having the nucleotide and deduced amino acid sequence shown in FIG. 18 (SEQ ID NOS: 17 & 18).

Again, a second form, designated pML2, encoding a protein with a 4 amino acid residue deletion (228 amino acid residues) was identified (see FIG. 19 (SEQ ID NO: 20). Comparison of pML and pML2 amino acid sequences shows the latter form is identical except that the tetrapeptide QLPP corresponding to residues 111-114 inclusive have been deleted (see FIG. 20 (SEQ ID NOS: 17 & 20)). The four amino acid deletions observed in both murine and porcine ML cDNA occur at precisely the same position within the predicted proteins.

Comparison of the predicted amino acid sequences of the mature ML from human, mouse, and pig (FIG. 17 (SEQ ID NOS: 6, 16 & 17)) indicates that overall sequence identity is 72 percent between mouse and human, 68 percent between mouse and pig and 73 percent between pig and human. The homology is substantially greater in the amino-terminal half of the ML (epo homologous domain). This domain is 80 to 84 percent identical between any two species whereas the carboxy-terminal half (carbohydrate domain) is only 57 to 67 percent identical. A di-basic amino acid motif that could represent a protease cleavage site is present at the carboxyl end of the erythropoeitin homology domain. This motif is conserved between the three species at this position (FIG. 17 (SEQ ID NOS: 6, 16 & 17)). A second di-basic site present at position 245 and 246 in the human sequence is not present in the mouse or pig sequences. The murine and the pig ML sequence contain 4 cysteines, all conserved in the human sequence. There are seven potential N-glycosylation sites within the mouse ligand and six within the porcine ML, 5 of which are conserved within the human sequence. Again, all the potential N-glycosylation sites are located in the C-terminal haft of the protein.

10. Methods for Measurement of Thrombopoietic Activity

Thrombopoietic activity may be measured in various assays including an in vivo mouse platelet rebound synthesis assay, induction of platelet cell surface antigen assay as measured by an anti-platelet immunoassay (anti-$GPII_bIII_a$) for a human leukemia megakaryoblastic cell line (CMK) (see Sato et al., *Brit. J. Heamatol.,* 72:184-190 [1989]), and induction of polyploidization in a megakaryoblastic cell line (DAMI) (see Ogura et al., *Blood,* 72(1):49-60 [1988]). Maturation of megakaryocytes from immature, largely non-DNA synthesizing cells, to morphologically identifiable megakaryocytes involves a process that includes appearance of cytoplasmic organelles, acquisition of membrane antigens ($GPII_bIII_a$), endoreplication and release of platelets as described in the background. A lineage specific promoter (i.e., the mpl ligand) of megakaryocyte maturation would be expected to induce at least some of these changes in immature megakaryocytes leading to platelet release and alleviation of thrombocytopenia. Thus, assays were designed to measure the emergence of these parameters in immature megakaryocyte cell lines, i.e., CMK and DAMI cells. The CMK assay (Example 13) measures the appearance of a specific platelet marker, $GPII_bIII_a$., and platelet shedding. The DAMI assay (Example 14) measures endoreplication since increases in ploidy are hallmarks of mature megakaryocytes. Recognizable megakaryocytes have ploidy values of 2N, 4N, 8N, 16N, 32N, etc. Finally, the in vivo assay (Example 15) is useful in demonstrating that administration of the test compound (here the mpl ligand) results in elevation of platelet numbers.

11. General Recombinant Preparation of mpl Ligand and Variants

Preferably mpl ligand is prepared by standard recombinant procedures which involve production of the mpl ligand polypeptide by culturing cells transfected to express mpl ligand nucleic acid (typically by transforming the cells with an expression vector) and recovering the polypeptide from the cells. However, it is optionally envisioned that the mpl ligand may be produced by homologous recombination, or with recombinant production methods utilizing control elements introduced into cells already containing DNA encoding the mpl ligand. For example, a powerful promoter/enhancer element, a suppressor, or an exogenous transcription modulatory element may be inserted in the genome of the intended host cell in proximity and orientation sufficient to influence the transcription of DNA encoding the desired mpl ligand polypeptide. The control element does not encode the mpl ligand, rather the DNA is indigenous to the host cell genome. One next screens for cells making the receptor polypeptide of this invention, or for increased or decreased levels of expression, as desired.

Thus, the invention contemplates a method for producing mpl ligand comprising inserting into the genome of a cell containing the mpl ligand nucleic acid molecule a transcription modulatory element in sufficient proximity and orientation to the nucleic acid molecule to influence transcription thereof, with an optional further step comprising culturing the cell containing the transcription modulatory element and the nucleic acid molecule. The invention also contemplates a host cell containing the indigenous mpl ligand nucleic acid molecule operably linked to exogenous control sequences recognized by the host cell.

A. Isolation of DNA Encoding mpl Ligand Polypeptide

The DNA encoding mpl ligand polypeptide may be obtained from any cDNA library prepared from tissue believed to possess the mpl ligand mRNA and to express it at a detectable level. The mpl ligand gene may also be obtained from a genomic DNA library or by in vitro oligonucleotide synthesis from the complete nucleotide or amino acid sequence.

Libraries are screened with probes designed to identify the gene of interest or the protein encoded by it. For cDNA expression libraries, suitable probes include monoclonal or polyclonal antibodies that recognize and specifically bind to the mpl ligand. For cDNA libraries suitable probes include oligonucleotides of about 20-80 bases in length that encode known or suspected portions of the mpl ligand cDNA from the same or different species; and/or complementary or homologous cDNAs or fragments thereof that encode the same or a similar gene. Appropriate probes for screening genomic DNA libraries include, but are not limited to, oligonucleotides, cDNAs, or fragments thereof that encode the same or a similar gene, and/or homologous genomic DNAs or fragments thereof. Screening the cDNA or genomic library with the selected probe may be conducted using standard procedures as described in Chapters 10-12 of Sambrook et al., supra.

An alternative means to isolate the gene encoding mpl ligand is to use PCR methodology as described in section 14 of Sambrook et al., supra. This method requires the use of oligonucleotide probes that will hybridize to DNA encoding the mpl ligand. Strategies for selection of oligonucleotides are described below.

A preferred method of practicing this invention is to use carefully selected oligonucleotide sequences to screen cDNA libraries from various tissues, preferably human or porcine kidney (adult or fetal) or liver cell lines. For example, human fetal liver cell line cDNA libraries are screened with the oligonucleotide probes. Alternatively, human genomic libraries may be screened with the oligonucleotide probes.

The oligonucleotide sequences selected as probes should be of sufficient length and sufficiently unambiguous that false positives are minimized. The actual nucleotide sequence(s) is usually designed based on regions of the mpl ligand which have the least codon redundancy. The oligonucleotides may be degenerate at one or more positions. The use of degenerate oligonucleotides is of particular importance where a library is screened from a species in which preferential codon usage is not known.

The oligonucleotide must be labeled such that it can be detected upon hybridization to DNA in the library being screened. The preferred method of labeling is to use ATP (e.g., $\gamma^{32}P$) and polynucleotide kinase to radiolabel the 5' end of the oligonucleotide. However, other methods may be used to label the oligonucleotide, including, but not limited to, biotinylation or enzyme labeling.

Of particular interest is the mpl ligand nucleic acid that encodes a full-length mpl ligand polypeptide. In some preferred embodiments, the nucleic acid sequence includes the native mpl ligand signal sequence. Nucleic acid having all the protein coding sequence is obtained by screening selected cDNA or genomic libraries using the deduced amino acid sequence.

B. Amino Acid Sequence Variants of Native mpl Ligand

Amino acid sequence variants of mpl ligand are prepared by introducing appropriate nucleotide changes into the mpl ligand DNA, or by in vitro synthesis of the desired mpl ligand polypeptide. Such variants include, for example, deletions from, or insertions or substitutions of, residues within the amino acid sequence for the porcine mpl ligand. For example, carboxy terminus portions of the mature full length mpl ligand may be removed by proteolytic cleavage, either in vivo or in vitro, or by cloning and expressing a fragment or the DNA encoding full length mpl ligand to produce a biologically active variant. Any combination of deletion, insertion, and substitution is made to arrive at the final construct, provided that the final construct possesses the desired biological activity. The amino acid changes also may after post-translational processes of the mpl ligand, such as changing the number or position of glycosylation sites. For the design of amino acid sequence variants of the mpl ligand, the location of the mutation site and the nature of the mutation will depend on the mpl ligand characteristic(s) to be modified. The sites for mutation can be modified individually or in series, e.g., by (1) substituting first with conservative amino acid choices and then with more radical selections depending upon the results achieved, (2) deleting the target residue, or (3) inserting residues of the same or a different class adjacent to the located site, or combinations of options 1-3.

A useful method for identification of certain residues or regions of the mpl ligand polypeptide that are preferred locations for mutagenesis is called "alanine scanning mutagenesis," as described by Cunningham and Wells, *Science,* 244: 1081-1085 [1989]. Here, a residue or group of target residues are identified (e.g., charged residues such as arg, asp, his, lys, and glu) and replaced by any, but preferably a neutral or negatively charged, amino acid (most preferably alanine or polyalanine) to affect the interaction of the amino acids with the surrounding aqueous environment in or outside the cell. Those domains demonstrating functional sensitivity to the substitutions then are refined by introducing further or other variants at or for the sites of substitution. Thus, while the site for introducing an amino acid sequence variation is predetermined, the nature of the mutation per se need not be predetermined. For example, to optimize the performance of a mutation at a given site, ala scanning or random mutagenesis is conducted at the target codon or region and the expressed mpl ligand variants are screened for the optimal combination of desired activity.

There are two principal variables in the construction of amino acid sequence variants: the location of the mutation site and the nature of the mutation. For example, variants of the mpl ligand polypeptide include variants from the mpl ligand sequence, and may represent naturally occurring alleles (which will not require manipulation of the mpl ligand DNA) or predetermined mutant forms made by mutating the DNA, either to arrive at an allele or a variant not found in nature. In general, the location and nature of the mutation chosen will depend upon the mpl ligand characteristic to be modified.

Amino acid sequence deletions generally range from about 1 to 30 residues, more preferably about 1 to 10 residues, and typically are contiguous. Amino acid sequence deletions for the mpl ligand may include the entire carboxy-terminus glycoprotein domain. Contiguous deletions ordinarily are made in even numbers of residues, but single or odd numbers of deletions are within the scope hereof. Deletions may be introduced into regions of low homology among the mpl ligands that share the most sequence identity to modify the activity of the mpl ligand. Or deletions may be introduced into regions of low homology among human mpl ligand and other mammalian mpl ligand polypeptides that share the most sequence identity to the human mpl ligand. Deletions from a mammalian mpl ligand polypeptide in areas of substantial homology with other mammalian mpl ligands will be more likely to modify the biological activity of the mpl ligand more significantly. The number of consecutive deletions will be selected so as to preserve the tertiary structure of mpl ligands in the affected domain, e.g., beta-pleated sheet or alpha helix.

Amino acid sequence insertions include amino- and/or carboxyl-terminal fusions ranging in length from one residue to polypeptides containing a hundred or more residues, as well as intrasequence insertions of single or multiple amino acid residues. Intrasequence insertions (i.e., insertions within the mature mpl ligand sequence) may range generally from about 1 to 10 residues, more preferably 1 to 5, most preferably 1 to 3. An exemplary preferred fusion is that of mpl ligand or fragment thereof and another cytokine or fragment thereof. Examples of terminal insertions include mature mpl ligand with an N-terminal methionyl residue, an artifact of the direct expression of mature mpl ligand in recombinant cell culture, and fusion of a heterologous N-terminal signal sequence to the N-terminus of the mature mpl ligand molecule to facilitate the secretion of mature mpl ligand from recombinant hosts. Such signal sequences generally will be obtained from, and thus homologous to, the intended host cell species. Suitable sequences include STII or Ipp for *E. coli*, alpha factor for yeast, and viral signals such as herpes gD for mammalian cells.

Other insertional variants of the mpl ligand molecule include the fusion to the N- or C-terminus of mpl ligand of immunogenic polypeptides (i.e., not endogenous to the host to which the fusion is administered), e.g., bacterial polypeptides such as beta-lactamase or an enzyme encoded by the *E. coli* trp locus, or yeast protein, and C-terminal fusions with proteins having a long half-life such as immunoglobulin constant regions (or other immunoglobulin regions), albumin, or ferritin, as described in WO 89/02922 published 6 Apr. 1989.

A third group of variants are amino acid substitution variants. These variants have at least one amino acid residue in the mpl ligand molecule removed and a different residue inserted in its place. The sites of greatest interest for substitutional mutagenesis include sites identified as the active site(s) of mpl ligand and sites where the amino acids found in other analogues are substantially different in terms of side-chain bulk, charge, or hydrophobicity, but where there is also a high degree of sequence identity at the selected site among various mpl ligand species and/or within the various animal analogues of one mpl ligand member.

Other sites of interest are those in which particular residues of the mpl ligand obtained from various family members and/or animal species within one member are identical. These sites, especially those failing within a sequence of at least three other identically conserved sites, are substituted in a relatively conservative manner. Such conservative substitutions are shown in Table 2 under the heading of preferred substitutions. If such substitutions result in a change in biological activity, then more substantial changes, denominated exemplary substitutions in Table 2, or as further described below in reference to amino acid classes, are introduced and the products screened.

TABLE 2

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

Substantial modifications in function or immunological identity of the mpl ligand are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, Ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another. Such substituted residues also may be introduced into the conservative substitution sites or, more preferably, into the remaining (non-conserved) sites.

In one embodiment of the invention, it is desirable to inactivate one or more protease cleavage sites that are present in the molecule. These sites are identified by inspection of the encoded amino acid sequence, in the case of trypsin, e.g., for an arginyl or lysinyl residue. When protease cleavage sites are identified, they are rendered inactive to proteolytic cleavage by substituting the targeted residue with another residue, preferably a basic residue such as glutamine or a hydrophobic residue such as serine; by deleting the residue; or by inserting a prolyl residue immediately after the residue.

In another embodiment, any methionyl residues other than the starting methionyl residue of the signal sequence, or any residue located within about three residues N- or C-terminal to each such methionyl residue, is substituted by another residue (preferably in accordance with Table 2) or deleted. Alternatively, about 1-3 residues are inserted adjacent to such sites.

Any cysteine residues not involved in maintaining the proper conformation of the mpl ligand also may be substituted, generally with serine, to improve the oxidative stability of the molecule and prevent aberrant crosslinking.

Nucleic acid molecules encoding amino acid sequence variants of mpl ligand are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of mpl ligand polypeptide.

Oligonucleotide-mediated mutagenesis is a preferred method for preparing substitution, deletion, and insertion variants of mpl ligand DNA. This technique is well known in the art as described by Adelman et al., *DNA,* 2:183 [1983]. Briefly, mpl ligand DNA is altered by hybridizing an oligonucleotide encoding the desired mutation to a DNA template, where the template is the single-stranded form of a plasmid or bacteriophage containing the unaltered or native DNA sequence of mpl ligand. After hybridization, a DNA polymerase is used to synthesize an entire second complementary strand of the template that will thus incorporate the oligonucleotide primer, and will code for the selected alteration in the mpl ligand DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. USA,* 75:5765 [1978].

The DNA template can be generated by those vectors that are either derived from bacteriophage M13 vectors (the commercially available M13mp18 and M13mp19 vectors are suitable), or those vectors that contain a single-stranded phage origin of replication as described by Viera et al., *Meth. Enzymol.,* 153:3 [1987]. Thus, the DNA that is to be mutated may be inserted into one of these vectors to generate single-stranded template. Production of the single-stranded template is described in Sections 4.21-4.41 of Sambrook et al., *Molecular Cloning: A Laboratory Manual* (Cold Spring Harbor Laboratory Press, NY 1989).

Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the mpl ligand, and the other strand (the original template) encodes the native, unaltered sequence of the mpl ligand. This heteroduplex molecule is then transformed into a suitable host cell, usually a prokaryote such as *E. coli* JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for protein production, generally an expression vector of the type typically employed for transformation of an appropriate host.

The method described immediately above may be modified such that a homoduplex molecule is created wherein both strands of the plasmid contain the mutation(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thio-deoxyribocytosine called dCTP-(aS) (which can be obtained from the Amersham Corporation). This mixture is added to the template-oligonucleotide complex. Upon addition of DNA polymerase to this mixture, a strand of DNA identical to the template, except for the mutated bases is generated. In addition, this new strand of DNA will contain dCTP-(aS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101, as described above.

DNA encoding mpl ligand mutants with more than one amino acid to be substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions.

The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

PCR mutagenesis is also suitable for making amino acid variants of mpl ligand polypeptide. While the following discussion refers to DNA, it is understood that the technique also finds application with RNA. The PCR technique generally refers to the following procedure (see Erlich, supra, the chapter by R. Higuchi, p. 61-70): When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer, or performing a second PCR with different mutant primers and ligating the two resulting PCR fragments simultaneously to the vector fragment in a three (or more)-part ligation.

In a specific example of PCR mutagenesis, template plasmid DNA (1 μg) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide triphosphates and is included in the GeneAmp® kits (obtained from Perkin-Elmer Cetus, Norwalk, Conn. and Emeryville, Calif.), and 25 pmole of each oligonucleotide primer, to a final volume of 50 μl. The reaction mixture is overlaid with 35 μl mineral oil. The reaction mixture is denatured for five minutes at 100° C., placed briefly on ice, and then 1 μl *Thermus aquaticus* (Taq) DNA polymerase (5 units/μl, purchased from Perkin-Elmer Cetus) is added below the mineral oil layer. The reaction mixture is then inserted into a DNA Thermal Cycler (purchased from Perkin-Elmer Cetus) programmed as follows:

2 min. 55° C.

30 sec. 72° C., then 19 cycles of the following:

30 sec. 94° C.

30 sec. 55° C., and 30 sec. 72° C.

At the end of the program, the reaction vial is removed from the thermal cycler and the aqueous phase transferred to a new vial, extracted with phenol/chloroform (50:50 vol), and ethanol precipitated, and the DNA is recovered by standard procedures. This material is subsequently subjected to the appropriate treatments for insertion into a vector.

Another method for preparing variants, cassette mutagenesis, is based on the technique described by Wells et al., *Gene,* 34:315 [1985]. The starting material is the plasmid (or other vector) comprising the mpl ligand DNA to be mutated. The codon(s) in the mpl ligand DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the mpl ligand DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated mpl ligand DNA sequence.

C. Insertion of Nucleic Acid into a Replicable Vector

The nucleic acid (e.g., cDNA or genomic DNA) encoding native or variant mpl ligand polypeptide is inserted into a replicable vector for further cloning (amplification of the DNA) or for expression. Many vectors are available, and selection of the appropriate vector will depend on (1) whether it is to be used for DNA amplification or for DNA expression, (2) the size of the nucleic acid to be inserted into the vector, and (3) the host cell to be transformed with the vector. Each vector contains various components depending on its function (amplification of DNA or expression of DNA) and the host cell with which it is compatible. The vector components generally include, but are not limited to, one or more of the following: a signal sequence, an origin of replication, one or more marker genes, an enhancer element, a promoter, and a transcription termination sequence.

(i) Signal Sequence Component

The mpl ligand of this invention may be expressed not only directly, but also as a fusion with a heterologous polypeptide, preferably a signal sequence or other polypeptide having a specific cleavage site at the N-terminus of the mature protein or polypeptide. In general, the signal sequence may be a component of the vector, or it may be a part of the mpl ligand DNA that is inserted into the vector. The heterologous signal sequence selected should be one that is recognized and processed (i.e., cleaved by a signal peptidase) by the host cell. For prokaryotic host cells that do not recognize and process the native mpl ligand signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase, alpha factor, or acid phosphatase leaders, the *C. albicans* glucoamylase leader (EP 362,179 published 4 Apr. 1990), or the signal described in WO 90/13646 published 15 Nov. 1990. In mammalian cell expression the native signal sequence (i.e., the mpl ligand presequence that normally directs secretion of mpl ligand from its native mammalian cells in vivo) is satisfactory, although other mammalian signal sequences may be suitable, such as signal sequences from other mpl ligand polypeptides or from the same mpl ligand from a different animal species, signal sequences from a mpl ligand, and signal sequences from secreted polypeptides of the same or related species, as well as viral secretory leaders, for example, the herpes simplex gD signal.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2 μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e., they are capable of replication in at least one class of organisms but can be transfected into another organism for expression. For example, a vector is cloned in *E. coil* and then the same vector is transfected into yeast or mammalian cells for expression even though it is not capable of replicating independently of the host cell chromosome.

DNA may also be amplified by insertion into the host genome. This is readily accomplished using *Bacillus* species as hosts, for example, by including in the vector a DNA sequence that is complementary to a sequence found in *Bacillus* genomic DNA. Transfection of *Bacillus* with this vector results in homologous recombination with the genome and insertion of mpl ligand DNA. However, the recovery of genomic DNA encoding mpl ligand is more complex than that of an exogenously replicated vector because restriction enzyme digestion is required to excise the mpl ligand DNA.

(iii) Selection Gene Component

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c)

supply critical nutrients not available from complex media, e.g., the gene encoding D-alanine racemase for *Bacilli.*

One example of a selection scheme utilizes a drug to arrest growth of a host cell. Those cells that are successfully transformed with a heterologous gene express a protein conferring drug resistance and thus survive the selection regimen. Examples of such dominant selection use the drugs neomycin (Southern et al., *J. Molec. Appl. Genet.,* 1:327 [1982]) mycophenolic acid (Mulligan et al., *Science,* 209:1422 [1980]) or hygromycin Sugden et al., *Mol. Cell. Biol.,* 5:410-413 [1985]). The three examples given above employ bacterial genes under eukaryotic control to convey resistance to the appropriate drug G418 or neomycin (geneticin), xgpt (mycophenolic acid), or hygromycin, respectively.

Examples of other suitable selectable markers for mammalian cells are those that enable the identification of cells competent to take up the mpl ligand nucleic acid, such as dihydrofolate reductase (DHFR) or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes mpl ligand polypeptide. Amplification is the process by which genes in greater demand for the production of a protein critical for growth are reiterated in tandem within the chromosomes of successive generations of recombinant cells. Increased quantities of mpl ligand are synthesized from the amplified DNA.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc. Natl. Acad. Sci. USA,* 77:4216 [1980]. The transformed cells are then exposed to increased levels of Mtx. This leads to the synthesis of multiple copies of the DHFR gene, and, concomitantly, multiple copies of other DNA comprising the expression vectors, such as the DNA encoding mpl ligand. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060). Alternatively, host cells [particularly wild-type hosts that contain endogenous DHFR] transformed or co-transformed with DNA sequences encoding mpl ligand, wild-type DHFR protein, and another selectable marker such as aminoglycoside 3' phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature,* 282:39 [1979]; Kingsman et al., *Gene,* 7:141 [1979]; or Tschemper et al., *Gene,* 10:157 [1980]). The trp1 gene provides a selection marker for a mutant strain of yeast lacking the ability to grow in tryptophan, for example, ATCC No. 44076 or PEP4-1 (Jones, *Genetics,* 85:12 [1977]). The presence of the trp1 lesion in the yeast host cell genome then provides an effective environment for detecting transformation by growth in the absence of tryptophan. Similarly, Leu2-deficient yeast strains (ATCC No. 20,622 or 38,626) are complemented by known plasmids bearing the Leu2 gene.

(iv) Promoter Component

Expression and cloning vectors usually contain a promoter that is recognized by the host organism and is operably linked to the mpl ligand nucleic acid. Promoters are untranslated sequences located upstream (5') to the start codon of a structural gene (generally within about 100 to 1000 bp) that control the transcription and translation of particular nucleic acid sequence, such as the mpl ligand nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to mpl ligand encoding DNA by removing the promoter from the source DNA by restriction enzyme digestion and inserting the isolated promoter sequence into the vector. Both the native mpl ligand promoter sequence and many heterologous promoters may be used to direct amplification and/or expression of the mpl ligand DNA. However, heterologous promoters are preferred, as they generally permit greater transcription and higher yields of expressed mpl ligand as compared to the native mpl ligand promoter.

Promoters suitable for use with prokaryotic hosts include the β-lactamase and lactose promoter systems (Chang et al., *Nature,* 275:615 [1978]; and Goeddel et al., *Nature,* 281:544 [1979]), alkaline phosphatase, a tryptophan (trp) promoter system (Goeddel, *Nucleic Acids Res.,* 8:4057 [1980] and EP 36,776) and hybrid promoters such as the tac promoter (deBoer et al., *Proc. Natl. Acad. Sci. USA,* 80:21-25 [1983]). However, other known bacterial promoters are suitable. Their nucleotide sequences have been published, thereby enabling a skilled worker operably to ligate them to DNA encoding mpl ligand (Siebenlist et al., *Cell,* 20:269 [1980]) using linkers or adaptors to supply any required restriction sites. Promoters for use in bacterial systems also will contain a Shine-Dalgarno (S.D.) sequence operably linked to the DNA encoding mpl ligand polypeptide.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase (Hitzeman et al., *J. Biol. Chem.,* 255:2073 [1980]) or other glycolytic enzymes (Hess et al., *J. Adv. Enzyme Reg.,* 7:149 [1968]; and Holland, *Biochemistry,* 17:4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657A. Yeast enhancers also are advantageously used with yeast promoters.

Mpl ligand transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, and from the promoter normally associated with the mpl ligand sequence, provided such promoters are compatible with the host cell systems.

The early and late promoters of the SV40 virus are conveniently obtained as an SV40 restriction fragment that also contains the SV40 viral origin of replication. Fiers et al., *Nature,* 273:113 [1978]; Mulligan and Berg, *Science,* 209: 1422-1427 [1980]; Pavlakis et al., *Proc. Natl. Acad. Sci. USA,* 78:7398-7402 [1981]. The immediate early promoter of the human cytomegalovirus is conveniently obtained as a HindIII E restriction fragment. Greenaway et al., *Gene,* 18:355-360 [1982]. A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature,* 295:503-508 [1982] on expressing cDNA encoding immune interferon in monkey cells; Reyes et al., *Nature,* 297:598-601 [1982] on expression of human β-interferon cDNA in mouse cells under the control of a thymidine kinase promoter from herpes simplex virus; Canaani and Berg, *Proc. Natl. Acad. Sci. USA,* 79:5166-5170 [1982] on expression of the human interferon β1 gene in cultured mouse and rabbit cells; and Gorman et al., *Proc. Natl. Acad. Sci. USA,* 79:6777-6781 [1982] on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

(v) Enhancer Element Component

Transcription of a DNA encoding the mpl ligand of this invention by higher eukaryotes is often increased by inserting an enhancer sequence into the vector. Enhancers are cis-acting elements of DNA, usually about from 10 to 300 bp, that act on a promoter to increase its transcription. Enhancers are relatively orientation and position independent, having been found 5' (Laimins et al., *Proc. Natl. Acad. Sci. USA,* 78:993 [1981]) and 3' (Lusky et al., *Mol. Cell Bio.,* 3:1108 [1983]) to the transcription unit, within an intron (Banerji et al., *Cell,* 33:729 [1983]), as well as within the coding sequence itself (Osborne et al., *Mol. Cell Bio.,* 4:1293 [1984]). Many enhancer sequences are now known from mammalian genes (globin, elastase, albumin, a-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature,* 297:17-18 [1982] on enhancing elements for activation of eukaryotic promoters. The enhancer may be spliced into the vector at a position 5' or 3' to the mpl ligand encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding mpl ligand.

(vii) Construction and Analysis of Vectors

Construction of suitable vectors containing one or more of the above listed components employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC No. 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.,* 9:309 [1981] or by the method of Maxam et al., *Methods in Enzymology,* 65:499 [1980].

(viii) Transient Expression Vectors

Particularly useful in the practice of this invention are expression vectors that provide for the transient expression in mammalian cells of DNA encoding the mpl ligand polypeptide. In general, transient expression involves the use of an expression vector that is able to replicate efficiently in a host cell, such that the host cell accumulates many copies of the expression vector and, in turn, synthesizes high levels of a desired polypeptide encoded by the expression vector. Sambrook et al., supra, pp. 16.17-16.22. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogues and variants of mpl ligand polypeptide that have mpl ligand polypeptide biological activity.

(ix) Suitable Exemplary Vertebrate Cell Vectors

Other methods, vectors, and host cells suitable for adaptation to the synthesis of mpl ligand in recombinant vertebrate cell culture are described in Gething et al., *Nature,* 293:620-625 [1981]; Mantei et al., *Nature,* 281:40-46 [1979]; Levinson et al.; EP 117,060; and EP 117,058. A particularly useful plasmid for mammalian cell culture expression of mpl ligand is pRK5 (EP 307,247 U.S. Pat. No. 5,258,287) or pSVI6B (PCT Publication No. WO 91/08291).

D. Selection and Transformation of Host Cells

Suitable host cells for cloning or expressing the vectors herein are the prokaryote, yeast, or higher eukaryotic cells described above. Suitable prokaryotes include eubacteria, such as Gram-negative or Gram-positive organisms, for example, *E. coli, Bacilli* such as *B. subtilis, Pseudomonas* species such as *P. aeruginosa, Salmonella typhimurium*, or *Serratia marcescans*. One preferred *E. coli* cloning host is *E. coli* 294 (ATCC No. 31,446), although other strains such as *E. coli* B, *E. coil* X1776 (ATCC No. 31,537), and *E. coil* W3110 (ATCC No. 27,325) are suitable. These examples are illustrative rather than limiting. Preferably the host cell should secrete minimal amounts of proteolytic enzymes. Alternatively, in vitro methods of cloning, e.g., PCR or other nucleic acid polymerase reactions, are suitable.

In addition to prokaryotes, eukaryotic microbes such as filamentous fungi or yeast are suitable hosts for mpl ligand encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe* (Beach and Nurse, *Nature,* 290:140 [1981]; EP 139,383 published 2 May 1985), *Kluyveromyces* hosts (U.S. Pat. No. 4,943,529) such as, e.g., *K. lactis* (Louvencourt et al., *J. Bacteriol.,* 737 [1983]), *K. fragile, K. bulgaricus, K. thermotolerans*, and *K. marxianus, yarrowia* [EP 402,226], *Pichia pastoris* (EP 183,070; Sreekrishna et al., *J. Basic Microbiol.,* 28:265-278 [1988]), *Candida, Trichoderma reesia* (EP 244,234), *Neurospora crassa* (Case et al., *Proc. Natl. Acad. Sci. USA,* 76:5259-5263 [1979]), and filamentous fungi such as, e.g, *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.,* 112: 284-289 [1983]; Tilburn et al., *Gene,* 26:205-221 [1983]; Yelton et al., *Proc. Natl. Acad. Sci. USA,* 81:1470-1474 [1984]) and *A. niger* (Kelly and Hynes, *EMBO J.,* 4:475-479 [1985]).

Suitable host cells for the expression of glycosylated mpi ligand are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow et al., *Bio/Technology,* 6:47-55 [1988]; Miller et al., *Genetic Engineering*, Setlow et al., eds., Vol. 8 (Plenum Publishing, 1986), pp. 277-279; and Maeda et al., *Nature,* 315:592-594 [1985]. A variety of viral strains for transfection are publicly available, e.g., the L-1 variant of *Autographs californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the mpl ligand DNA. During incubation of the plant cell culture with *A. tumefaciens*, the DNA encoding the mpl ligand is transferred to the plant cell host such that it is transfected, and will, under appropriate conditions, express the mpl ligand DNA. In addition, regulatory and signal sequences compatible with plant cells are available, such as the nopaline synthase promoter and polyadenylation signal sequences. Depicker et al., *J. Mol. Appl. Gen.,* 1:561 [1982]. In addition, DNA segments isolated from the upstream region of the T-DNA 780 gene are capable of activating or increasing transcription levels of plant-expressible genes in recombinant DNA-containing plant tissue. EP 321,196 published 21 Jun. 1989.

However, interest has been greatest in vertebrate cells, and propagation of vertebrate cells in culture (tissue culture) has become a routine procedure in recent years (Tissue Culture, Academic Press, Kruse and Patterson, editors [1973]). Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.,* 36:59 [1977]); baby hamster kidney cells (BHK, ATCC CCL 10); Chinese hamster ovary cells/-DHFR (CHO, Urlaub and Chasin, *Proc. Natl. Acad. Sci. USA,* 77:4216 [1980]); mouse sertoli cells (TM4, Mather, *Biol. Reprod.,* 23:243-251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.,* 383:44-68 [1982]); MRC 5 cells; FS4 cells; and a human hepatoma line (Hep G2).

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, is generally used for prokaryotes or other cells that contain substantial cell-wall barriers. Infection with *Agrobacterium tumefaciens* is used for transformation of certain plant cells, as described by Shaw et al., *Gene,* 23:315 [1983] and WO 89/05859 published 29 Jun. 1989. In addition, plants may be transfected using ultrasound treatment as described in WO 91/00358 published 10 Jan. 1991. For mammalian cells without such cell walls, the calcium phosphate precipitation method of Graham and van der Eb, *Virology,* 52:456-457 [1978] is preferred. General aspects of mammalian cell host system transformations have been described by Axel in U.S. Pat. No. 4,399,216 issued 16 Aug. 1983. Transformations into yeast are typically carried out according to the method of Van Solingen et al., *J. Bact.,* 130:946 [1977] and Hsiao et al., *Proc. Natl. Acad. Sci.* (*USA*), 76:3829 [1979]. However, other methods for introducing DNA into cells such as by nuclear injection, electroporation, or protoplast fusion may also be used.

E. Culturing the Host Cells

Prokaryotic cells used to produce the mpl ligand polypeptide of this invention are cultured in suitable media as described generally in Sambrook et al., supra.

The mammalian host cells used to produce the mpl ligand of this invention may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the host cells. In addition, any of the media described in Ham and Wallace, *Meth. Enz.,* 58:44 [1979], Barnes and Sato, *Anal. Biochem.,* 102:255 [1980], U.S. Pat. Nos. 4,767,704; 4,657,866; 4,927,762; or 4,560,655; WO 90/03430; WO 87/00195; U.S. Pat. No. Re. 30,985; or copending U.S. Ser. Nos. 07/592,107 or 07/592,141, both filed on 3 Oct. 1990, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The host cells referred to in this disclosure encompass cells in in vitro culture as well as cells that are within a host animal.

F. Detecting Gene Amplification/Expression

Gene amplification and/or expression may be measured in a sample directly, for example, by conventional Southern blotting, northern blotting to quantitate the transcription of mRNA (Thomas, *Proc. Natl. Acad. Sci. USA,* 77:5201-5205 [1980]), dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., *Am. J. Clin. Path.,* 75:734-738 [1980].

Antibodies useful for immunohistochemical staining and/or assay of sample fluids may be either monoclonal or polyclonal, and may be prepared in any mammal. Conveniently, the antibodies may be prepared against a native mpl ligand polypeptide or against a synthetic peptide based on the DNA sequences provided herein as described further below.

G. Purification of mpl Ligand Polypeptide

Mpl ligand preferably is recovered from the culture medium as a secreted polypeptide, although it also may be recovered from host cell lysates when directly expressed without a secretory signal.

When mpl ligand is expressed in a recombinant cell other than one of human origin, the mpl ligand is completely free of proteins or polypeptides of human origin. However, it is still usually necessary to purify mpl ligand from other recombinant cell proteins or polypeptides to obtain preparations that are substantially homogeneous as to the mpl ligand per se. As a first step, the culture medium or lysate is centrifuged to remove particulate cell debris. The membrane and soluble protein fractions are then separated. Alternatively, a commercially available protein concentration filter (e.g., Amicon or Millipore Pellicon ultrafiltration units) may be used. The mpl ligand may then be purified from the soluble protein fraction and from the membrane fraction of the culture lysate, depending on whether the mpl ligand is membrane bound. Mpl ligand thereafter is purified from contaminant soluble proteins and polypeptides by salting out and exchange or chromatographic procedures employing various gel matrices. These matrices include; acrylamide, agarose, dextran, cellulose and others common to protein purification. Exemplary chromatography procedures suitable for protein purification include; immunoaffinity (e.g., anti-hmpl ligand Mab), receptoraffinity (e.g., mpl-IgG or protein A Sepharose), hydrophobic interaction chromatography (HIC) (e.g., ether, butyl, or phenyl Toyopearl), lectin chromatography (e.g., Con A-Sepharose, lentil-lectin-Sepharose), size exclusion (e.g., Sephadex G-75), cation- and anion-exchange columns (e.g., DEAE or carboxymethyl- and sulfopropyl-cellulose), and reverse-phase high performance liquid chromatography (RP-HPLC) (see e.g., Urdal et al., *J. Chromatog.,* 296:171 [1984] where two sequential RP-HPLC steps are used to purify recombinant human IL-2). Other purification steps optionally include; ethanol precipitation; ammonium sulfate precipitation; chromatofocusing; preparative SDS-PAGE, and the like.

Mpl ligand variants in which residues have been deleted, inserted, or substituted are recovered in the same fashion as native mpl ligand, taking account of any substantial changes in properties occasioned by the variation. For example, preparation of a mpl ligand fusion with another protein or polypeptide, e.g., a bacterial or viral antigen, facilitates purification; an immunoaffinity column containing antibody to the antigen can be used to adsorb the fusion polypeptide. Immunoaffinity columns such as a rabbit polyclonal anti-mpl ligand column can be employed to absorb the mpl ligand variant by binding it to at least one remaining immune epitope. Alternatively, the mpl ligand may be purified by affinity chromatography using a purified mpl-IgG coupled to a (preferably) immobilized resin such as Affi-Gel 10 (Bio-Rad, Richmond, Calif.) or the like, by means well known in the art. A protease inhibitor such as phenyl methyl sulfonyl fluoride (PMSF) also may be useful to inhibit proteolytic degradation during purification, and antibiotics may be included to prevent the growth of adventitious contaminants. One skilled in the art will appreciate that purification methods suitable for native mpl ligand may require modification to account for changes in the character of mpl ligand or its variants upon expression in recombinant cell culture.

H. Covalent Modifications of mpl Ligand Polypeptide

Covalent modifications of mpl ligand polypeptides are included within the scope of this invention. Both native mpl ligand and amino acid sequence variants of the mpl ligand may be covalently modified. One type of covalent modification included within the scope of this invention is a mpl ligand fragment. Variant mpl ligand fragments having up to about 40 amino acid residues may be conveniently prepared by chemical synthesis or by enzymatic or chemical cleavage of the full-length or variant mpl ligand polypeptide. Other types of covalent modifications of the mpl ligand or fragments thereof are introduced into the molecule by reacting targeted amino acid residues of the mpl ligand or fragments thereof with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R—N═C═N—R'), where R and R' are different alkyl groups, such as 1-cyclohexyl-3-(2-morpholinyl-4-ethyl)carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

Derivatization with bifunctional agents is useful for crosslinking mpl ligand to a water-insoluble support matrix or surface for use in the method for purifying anti-mpl ligand antibodies, and vice versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W.H. Freeman & Co., San Francisco, pp. 79-86 [1983]), acetylation of the N-terminal amine, and amidation of any C-terminal carboxyl group.

Another type of covalent modification of the mpl ligand polypeptide included within the scope of this invention comprises altering the native glycosylation pattern of the polypeptide. By altering is meant deleting one or more carbohydrate moieties found in native mpl ligand, and/or adding one or more glycosylation sites that are not present in the native mpl ligand.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the mpl ligand polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the native mpl ligand sequence (for O-linked glycosylation sites). For ease, the mpl ligand amino acid sequence is preferably altered through changes at the DNA level, particularly by mutating the DNA encoding the mpl ligand polypeptide at preselected bases such that codons are generated that will translate into the desired amino acids. The DNA mutation(s) may be made using methods described above under the heading of "Amino Acid Sequence Variants of mpl Ligand."

Another means of increasing the number of carbohydrate moieties on the mpl ligand is by chemical or enzymatic coupling of glycosides to the polypeptide. These procedures are advantageous in that they do not require production of the polypeptide in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published 11 Sep. 1987, and in Aplin and Wriston, *CRC Crit. Rev. Biochem.*, pp. 259-306 [1981].

Removal of carbohydrate moieties present on the mpl ligand polypeptide may be accomplished chemically or enzymatically. Chemical deglycosylation requires exposure of the polypeptide to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin, et al., *Arch. Biochem. Biophys.*, 259:52 [1987] and by Edge et al., *Anal. Biochem.*, 118:131 [1981]. Enzymatic cleavage of carbohydrate moieties on polypeptides can be achieved by the use of a variety of endo- and exo-glycosidases as described by Thotakura et al., *Meth. Enzymol.*, 138:350 [1987].

Glycosylation at potential glycosylation sites may be prevented by the use of the compound tunicamycin as described by Duskin et al., *J. Biol. Chem.*, 257:3105 [1982]. Tunicamycin blocks the formation of protein-N-glycoside linkages.

Another type of covalent modification of mpl ligand comprises linking the mpl ligand polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

It will be appreciated that some screening of the recovered mpl ligand variant will be needed to select the optimal variant for binding to a mpl and having the immunological and/or biological activity defined above. One can screen for stability in recombinant cell culture or in plasma (e.g., against proteolytic cleavage), high affinity to a mpl member, oxidative stability, ability to be secreted in elevated yields, and the like. For example, a change in the immunological character of the mpl ligand polypeptide, such as affinity for a given antibody, is measured by a competitive-type immunoassay. Other potential modifications of protein or polypeptide properties such as redox or thermal stability, hydrophobicity, or susceptibility to proteolytic degradation are assayed by methods well known in the art.

12. General Methods for Preparation of Antibodies to mpl Ligand

Antibody Preparation (i) Polyclonal Antibodies

Polyclonal antibodies to mpl ligand polypeptides or fragments are generally raised in animals by multiple subcutaneous (sc) or intraperitoneal (ip) injections of the mpl ligand and an adjuvant. It may be useful to conjugate the mpl ligand or a fragment containing the target amino acid sequence to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glytaraldehyde, succinic anhydride, $SOCl_2$, or $R^1N{=}C{=}NR$, where R and $R^1$ are different alkyl groups.

Animals are immunized against the mpl ligand polypeptide or fragment, immunogenic conjugates or derivatives by combining 1 mg of 1 μg of the peptide or conjugate (for rabbits or mice, respectively) with 3 volumes of Freund's complete adjuvant and injecting the solution intradermally at multiple sites. One month later the animals are boosted with 1/5 to 1/10 the original amount of peptide or conjugate in Freund's complete adjuvant by subcutaneous injection at multiple sites. Seven to 14 days later the animals are bled and the serum is assayed for mpl ligand antibody titer. Animals are boosted until the titer plateaus. Preferably, the animal boosted with the conjugate of the same mpl ligand, but conjugated to a different protein and/or through a different cross-linking reagent. Conjugates also can be made in recombinant cell culture as protein fusions. Also, aggregating agents such as alum are used to enhance the immune response.

(ii) Monoclonal Antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the mpl ligand monoclonal antibodies of the invention may be made using the hybridoma method first described by Kohler & Milstein, *Nature*, 256:495 [1975], or may be made by recombinant DNA methods (U.S. Pat. No. 4,816,567 (Cabilly et al.)).

In the hybridoma method, a mouse or other appropriate host animal, such as hamster is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp.59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high level expression of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 [1984]; Brodeur et al., *Monoclonal Antibody Production Techniques and Applications*, pp.51-63, Marcel Dekker, Inc., New York, 1987).

Culture medium in which hybridoma cells are growing is assayed for production of monoclonal antibodies directed against mpl ligand. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson & Pollard, *Anal. Biochem.*, 107:220 [1980].

After hybridoma cells are identified that produce antibodies of the desired specificity, affinity, and/or activity, the clones may be subcloned by limiting dilution procedures and grown by standard methods (Goding, supra). Suitable culture media for this purpose include, for example, Dulbecco's Modified Eagle's Medium or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, (Cabilly et al., supra; Morrison, et al., *Proc. Nat. Acad. Sci.,* 81:6851 [1984]), or by covalently joining to the immunoglobulin coding sequence all or part of the coding sequence for a non-immunoglobulin polypeptide.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for a mpl ligand and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

For diagnostic applications, the antibodies of the invention typically will be labeled with a detectable moiety. The detectable moiety can be any one which is capable of producing, either directly or indirectly, a detectable signal. For example, the detectable moiety may be a radioisotope, such as $^{3}H$, $^{14}C$, $_{32}P$, $^{35}S$, or $^{125}I$, a fluorescent or chemiluminescent compound, such as fluorescein isothiocyanate, rhodamine, or luciferin; radioactive isotopic labels, such as, e.g., $^{125}I$, $^{32}P$, $^{14}C$, or $^{3}H$, or an enzyme, such as alkaline phosphatase, beta-galactosidase or horseradish peroxidase.

Any method known in the art for separately conjugating the antibody to the detectable moiety may be employed, including those methods described by Hunter, et al., *Nature,* 144:945 [1962]; David, et al., *Biochemistry,* 13:1014 [1974]; Pain, et al., *J. Immunol. Meth.,* 40:219 [1981]; and Nygren, *J. Histochem. and Cytochem.,* 30:407 [1982].

The antibodies of the present invention may be employed in any known assay method, such as competitive binding assays, direct and indirect sandwich assays, and immunoprecipitation assays. Zola, *Monoclonal Antibodies: A Manual of Techniques*, pp.147-158 (CRC Press, Inc., 1987).

Competitive binding assays rely on the ability of a labeled standard (which may be a mpl ligand or an immunologically reactive portion thereof) to compete with the test sample analyte (mpl ligand) for binding with a limited amount of antibody. The amount of mpl ligand in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein (mpl ligand) to be detected. In a sandwich assay, the test sample analyte is bound by a first antibody which is immobilized on a solid support, and thereafter a second antibody binds to the analyte, thus forming an insoluble three part complex. David & Greene, U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme (e.g., horseradish peroxidase).

(iii) Humanized and Human Antibodies

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature,* 321:522-525 [1986]; Riechmann et al., *Nature,* 332:323-327 [1988]; Verhoeyen et al., *Science,* 239:1534-1536 [1988]), by substituting rodent CDRs or CDR sequences for the corresponding sequences of a human antibody. Accordingly, such "humanized" antibodies are chimeric antibodies (Cabilly et al., supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the so called "best-fit" method, the sequence of the variable domain of a rodent antibody is screened against the entire library of known human variable domain sequences. The human sequence which is closest to that of the rodent is then accepted as the human framework (FR) for the humanized antibody (Sims et al., *J. Immunol.,* 151:2296 [1993]; Chothia and Lesk, *J. Mol. Biol.,* 196:901 [1987]). Another method uses a particular framework derived from the concensus sequence of all human antibodies of a particular subgroup of light or heavy chains. The same framework may be used for several different humanized antibodies (Carter et al., *Proc. Natl. Acad. Sci. USA,* 89:4285 [1992]; Presta et al., *J. Immnol.,* 151:2623 [1993]).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details see U.S. application Ser. No. 07/934,373 filed 21 Aug. 1992, which is a continuation-in-part of application Ser. No. 07/715,272 filed 14 Jun. 1991.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90:2551-255 [1993]; Jakobovits et al., *Nature,* 362:255-258 [1993]; Bruggermann et al., *Year In Immuno.,* 7:33 [1993]. Human antibodies can also be produced in phage display libraries (Hoogenboom and Winter, J. Mol. Biol. 227, 381 [1991]; Marks et al., *J. Mol. Biol.* 222, 581 [1991]).

(iv) Bispecific Antibodies

Bispecific antibodies are monoclonal, preferably human or humanized, antibodies that have binding specificities for at least two different antigens. Methods for making bispecific antibodies are known in the art.

Traditionally, the recombinant production of bispecific antibodies is based on the coexpression of two immunoglobulin heavy chain-light chain pairs, where the two heavy chains have different specificities (Millstein and Cuello, *Nature,* 305:537-539 [1983]). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in PCT publication No. WO 93/08829 (published 13 May 1993), and in Traunecker et al., *EMBO,* 10:3655-3659 [1991].

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in copending application Ser. No. 07/931,811 filed 17 Aug. 1992.

For further details of generating bispecific antibodies see, for example, Suresh et al., *Methods in Enzymology,* 121:210 [1986].

(v) Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (PCT publication Nos. WO 91/00360 and WO 92/00373; EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

IV. Therapeutic Use of the Megakaryocytopoletic Protein mpl Ligand

The biologically active mpl ligand having hematopoietic effector function and referred to here as a megakaryocytopoietic or thrombocytopoietic protein (TPO) may be used in a sterile pharmaceutical preparation or formulation to stimulate megakaryocytopoietic or thrombopoietic activity in patients suffering from thrombocytopenia due to impaired production, sequestration, or increased destruction of platelets. Thrombocytopenia-associated bone marrow hypoplasia (e.g., aplastic anemia following chemotherapy or bone marrow transplant) may be effectively treated with the compounds of this invention as well as disorders such as disseminated intravascular coagulation (DIC), immune thrombocytopenia (including HIV-induced ITP and non HIV-induced ITP), idiopathic thrombocytopenia, and thrombotic thrombocytopenia. Additionally, these megakaryocytopoietic proteins may be useful in treating myeloproliferative thrombocytotic diseases as well as thrombocytosis from inflammatory conditions and in iron deficiency.

Still other disorders usefully treated with the megakaryocytopoietic proteins of this invention include defects or damage to platelets resulting from drugs, poisoning or activation on artificial surfaces. In these cases, the instant compounds may be employed to stimulate "shedding" of new "undamaged" platelets. For a more complete list of useful applications, see the "Background" supra, especially section (a)-(f) and references cited therein.

The megakaryocytopoietic proteins of the instant invention may be employed alone or in combination with other cytokines, hematopoietins, interleukins, growth factors, or antibodies in the treatment of the above-identified disorders and conditions. Thus, the instant compounds may be employed in combination with other protein or peptide having thrombopoietic activity including; G-CSF, GM-CSF, LIF, M-CSF, IL-1, IL-3, erythropoietin (epo), kit ligand, IL-6, and IL-11.

The megakaryocytopoietic proteins of the instant invention are prepared in a mixture with a pharmaceutically acceptable carrier. This therapeutic composition can be administered intravenously or through the nose or lung. The composition may also be administered parenterally or subcutaneously as desired. When administered systematically, the therapeutic composition should be pyrogen-free and in a parenterally acceptable solution having due regard for pH, isotonicity, and stability. These conditions are known to those skilled in the art. Briefly, dosage formulations of the compounds of the present invention are prepared for storage or administration by mixing the compound having the desired degree of purity with physiologically acceptable carriers, excipients, or stabilizers. Such materials are non-toxic to the recipients at the dosages and concentrations employed, and include buffers such as phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sobitol; counterions such as sodium and/or nonionic surfactants such as Tween, Pluronics or polyethyleneglycol.

About 0.5 to 500 mg of a compound or mixture of the megakaryocytopoietic protein as the free acid or base form or as a pharmaceutically acceptable salt, is compounded with a physiologically acceptable vehicle, carrier, excipient, binder, preservative, stabilizer, flavor, etc., as called for by accepted pharmaceutical practice. The amount of active ingredient in these compositions is such that a suitable dosage in the range indicated is obtained.

Sterile compositions for injection can be formulated according to conventional pharmaceutical practice. For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice.

Suitable examples of sustained-release preparations include semipermeable matrices of solid hydrophobic polymers containing the polypeptide, which matrices are in the form of shaped articles, e.g., films, or microcapsules. Examples of sustained-release matrices include polyesters, hydrogels [e.g., poly(2-hydroxyethyl-methacrylate) as described by Langer et al., *J. Biomed. Mater. Res.,* 15:167-277 [1981] and Langer, *Chem. Tech.,* 12:98-105 [1982] or poly(vinylalcohol)], polylactides (U.S. Pat. No. 3,773,919, EP 58,481), copolymers of L-glutamic acid and gamma ethyl-L-glutamate (Sidman et al., *Biopolyers,* 22:547-556 [1983]), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release megakaryocytopoietic protein compositions also include liposomally entrapped megakaryocytopoietic protein. Liposomes containing megakaryocytopoietic protein are prepared by methods known per se: DE 3,218,121; Epstein et al., *Proc. Natl. Acad. Sci. USA,* 82:3688-3692 [1985]; Hwang et al., *Proc. Natl. Acad. Sci. USA,* 77:4030-4034 [1980]; EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200-800 Angstroms) unilamellar type in which the lipid content is greater than about 30 mol. % cholesterol, the selected proportion being adjusted for the optimal megakaryocytopoietic protein therapy.

The dosage will be determined by the attending physician taking into consideration various factors known to modify the action of drugs including severity and type of disease, body weight, sex, diet, time and route of administration, other medications and other relevant clinical factors. Typically, the daily regimen will range from 1-1000 μg/kg body weight. Preferably the dosage will range from 1-100 μg/kg body weight. More preferably, the dosage will range from 1 to 50 μg/kg/day, and most preferably the dosage range will be the same as that of other cytokines, especially G-CSF, GM-CSF, and epo. Therapeutically effective dosages may be determined by either in vitro or in vivo methods.

EXAMPLES

Without further description, it is believed that one of ordinary skill in the art can, using the preceding description and illustrative examples, make and utilize the present invention to the fullest extent. The following working examples therefore specifically point out preferred embodiments of the present invention, and are not to be construed as limiting in any way of the remainder of the disclosure.

Example 1

Partial Purification of the Porcine mpl Ligand

Platelet-poor plasma was collected from normal or aplastic anemic pigs. Pigs were rendered aplastic by irradiation with 900 cGy of total body irradiation using a 4 mEV linear accelerator. The irradiated pigs were supported for 6-8 days with intramuscular injections of cefazolin. Subsequently, their total blood volume was removed under general anesthesia, heparinized, and centrifuged at 1800×g for 30 min. to make platelet-poor plasma. The megakaryocyte stimulating activity was found to peak 6 days after irradiation.

Aplastic porcine plasma obtained from irradiated pigs is made 4M with NaCl and stirred for 30 min. at room temperature. The resultant precipitate is removed by centrifugation at 3800 rpm in a Sorvall RC3B and the supernatant is loaded onto a Phenyl-Toyopearl column (220 ml) equilibrated in 10 mM $NaPO_4$ containing 4M NaCl. The column is washed with this buffer until $A_{280}$ is <0.05 and eluted with $dH_2O$. The eluted protein peak is diluted with $dH_2O$ to a conductivity of 15 mS and loaded onto a Blue-Sepharose column equilibrated (240 ml) in PBS. Subsequently, the column is washed with 5 column volumes each of PBS and 10 mM $NaPO_4$ (pH 7.4) containing 2M urea. Proteins are eluted from the column with 10 mM $NaPO_4$ (pH 7.4) containing 2M urea and 1M NaCl. The eluted protein peak is made 0.01% octyl glucoside(n-octyl b-D-glucopyranoside) and 1 mM each with EDTA and Pefabloc (Boehinger Mannheim) and loaded directly onto tandemly linked CD4-IgG (Capon, D. J. et al. *Nature* 337:

525-531 [1989]) and mpl-IgG Ultralink (Pierce) columns (see below). The CD4-IgG (2 ml) column is removed after the sample is loaded and the mpl-IgG (4 ml) column is washed with 10 column volumes each of PBS and PBS containing 2 M NaCl and eluted with 0.1M glycine-HCl pH 2.25. Fractions are collected into 1/10th volume 1M Tris-HCl (pH 8.0).

Analysis of eluted fractions from the mpl-affinity column by SDS-PAGE (4.20%, Novex gel) run under reducing conditions, revealed the presence of several proteins (FIG. 5). Proteins that silver stain with the strongest intensity resolve with apparent Mr of 66,000, 55,000, 30,000, 28,000 and 14,000. To determine which of these proteins stimulate proliferation of Ba/F3-mpl cell cultures these proteins were eluted from the gel as described in Example 2 below.

Ultralink Affinity Columns 10-20 mg of mpl-IgG or CD4-IgG in PBS are coupled to 0.5 grams of Ultralink resin (Pierce) as described by the manufacturer's instructions.

Construction and Expression of mpl-IgG

A chimeric molecule comprising the entire extracellular domain of human mpl (amino acids 1-491) and the Fc region of a human IgG1 molecule was expressed in 293 cells. A cDNA fragment encoding amino acids 1-491 of human mpl was obtained by PCR from a human megakaryocytic CMK cell cDNA library and sequenced. A ClaI site was inserted at the 5' end and a BstEII site at the 3' end. This fragment was cloned upstream of the IgG1 Fc coding region in a Bluescript vector between the ClaI and the BstEII sites after partial digestion of the PCR product with BstEII because of 2 other BstEII sites present in the DNA encoding the extracellular domain of mpl. The BstEII site introduced at the 3' end of the mpl PCR product was designed to have the Fc region in frame with the mpl extracellular domain. The construct was subcloned into pRK5-tkneo vector between the ClaI and XbaI sites and transfected into 293 human embryonic kidney cells by the calcium phosphate method. The cells were selected in 0.4 mg/ml G418 and individual clones were isolated. Mpl-IgG expression from isolated clones was determined using a human Fc specific ELISA. The best expression clone had an expression level of 1-2 mg/ml of mpl-IgG.

Ba/F3 mpl P Expressing Cells

A cDNA corresponding to the entire coding region of human mpl P was cloned into pRK5-tkneo which was subsequently linearized with NotI and transfected into the IL-3 dependent cell line Ba/F3 by electroporation ($1\times10^7$ cells, 9605F, 250 Volts). Three days later selection was started in the presence of 2 mg/ml of G418. The cells were selected as pools or individual clones were obtained by limiting dilution in 96 well plates. Selected cells were maintained in RPMI containing 15% FBS, 1 mg/ml G418, 20 mM Glutamine, 10 mM HEPES and 100 μg/ml of Pen-Strep. Expression of mpl P in selected clones was determined by FACS analysis using a anti-mpl P rabbit polyclonal antibody.

mpl Ligand Assay

Figure 2A:
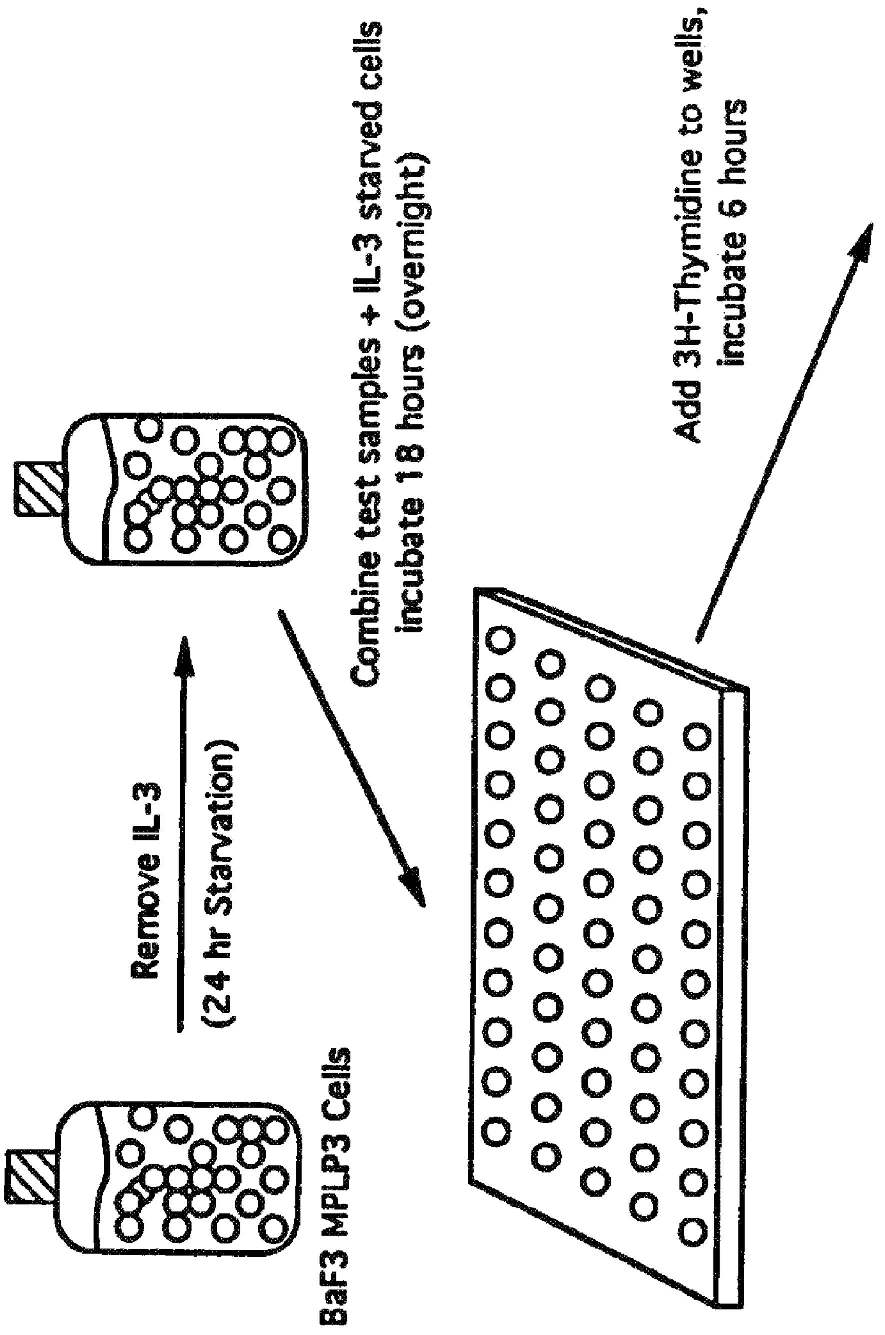
FIGS. 2 A and B show the procedure used for the mpl ligand $^3$H-thymidine incorporation assay. To determine the presence of mpl ligand from various sources, the mpl P Ba/F3 cells were starved of IL-3 for 24 hours in a humidified incubator at 37° C. in 5% $CO_2$ and air. Following IL-3 starvation the cells were plated out in 96 well culture dishes with or without diluted samples and cultured for 24 hrs in a cell culture incubator. 20 μl of serum free RPMI media containing 1 μCi of $^3$H-thymidine was added to each well for the last 6-8 hours. The cells were then harvested on 96 well filter plates and washed with water. The filters were then counted.
Figure 2B:
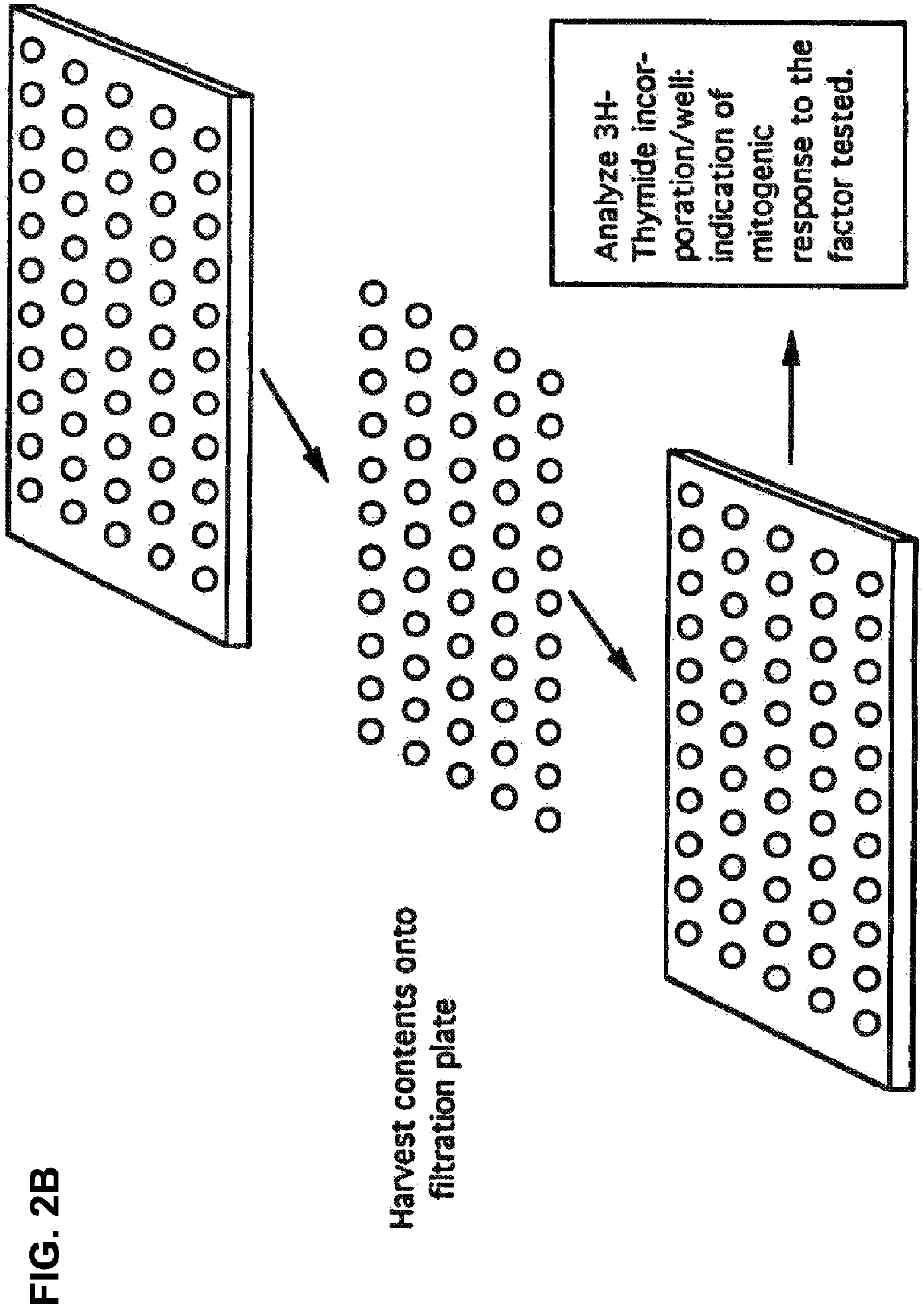

The mpl ligand assay was conducted as shown is FIG. 2. To determine the presence of mpl ligand from various sources, the mpl P Ba/F3 cells were starved of IL-3 for 24 hours at a cell density of $5\times10^5$ cells/ml in a humidified incubator at 37° C. in 5% $CO_2$ and air. Following IL-3 starvation the cells were plated out in 96 well culture dishes at a density of 50,000 cells in 200 μl of media with or without diluted samples and cultured for 24 hrs in a cell culture incubator. 20 μl of serum free RPMI media containing 1 μCi of $^3$H-thymidine was added to each well for the last 6-8 hours. The cells were then harvested on 96 well GF/C filter plates and washed 5 times with water. The lifters were counted in the presence of 40 μl of scintillation fluid (microscint 20) in a Packard Top Count counter.

Example 2

Highly Purified Porcine mpl Ligand Gel Elution Protocol

Equal amounts of affinity purified mpl ligand (fraction 6 eluted from the mpl-IgG column) and 2×Laemmli sample buffer were mixed at room temperature without reducing agent and loaded onto a Novex 4-20% polyacrylamide gel as quickly as possible. The sample was not heated. As a control, sample buffer without ligand was run in an adjacent lane. The gel was run at 4-6° C. at 135 volts for approximately 2¼ hours. The running buffer was initially at room temperature. The gel was then removed from the gel box and the plate on one side of the gel removed.

A replica of the gel was made on nitrocellulose as follows: A piece of nitrocellulose was wet with distilled water and carefully laid on top of the exposed gel face so air bubbles were excluded. Fiducial marks were placed on the nitrocellulose and the gel plate so the replica could be accurately repositioned after staining. After approximately 2 minutes, the nitrocellulose was carefully removed, and the gel was wrapped in plastic wrap and placed in the refrigerator. The nitrocellulose was stained with Biorad's gold total protein stain by first agitating it in 3×10 ml 0.1% Tween 20+0.5 M NaCl+0.1 M Tris-HCl pH 7.5 over approximately 45 minutes followed by 3×10 ml purified water over 5 minutes. The gold stain was then added and allowed to develop until the bands in the standards were visible. The replica was then rinsed with water, placed over the plastic wrap on the gel and carefully aligned with the fiducial marks. The positions of the Novex standards were marked on the gel plate and lines were drawn to indicate the cutting positions. The nitrocellulose and plastic wrap were then removed and the gel cut along the indicated lines with a sharp razor blade. The cuts were extended beyond the sample lanes so they could be used to determine the positions of the slices when the gel was stained. After the slices were removed, the remaining gel was silver stained and the positions of the standards and the cut marks were measured. The molecular weights corresponding to the cut positions were determined from the Novex standards.

The 12 gel slices were placed into the cells in two Biorad model 422 electro-eluters. 12-14 K molecular weight cutoff membrane caps were used in the cells. 50 mM ammonium bicarbonate+0.05% SDS (approximately pH 7.8) was the elution buffer. One liter of buffer was chilled approximately 1 hour in a 4-6° C. coldroom before use. Gel slices were eluted at 10 ma/cell (40 v initially) in a 4-6° C. coldroom. Elution took approximately 4 hours. The cells were then carefully removed and the liquid above the kit removed with a pipet. The elution chamber was removed and any liquid above the membrane cap removed with a pipet. The liquid in the membrane cap was removed with a Pipetman and saved. Fifty μl aliquots of purified water were then placed in the cap, agitated and removed until all the SDS crystals dissolved. These washes were combined with the saved liquid above. Total elution sample volume was 300-500 μl per gel slice. Samples were placed in 10 mm Spectrapor 4 12-14 K cutoff dialysis tubing which had been soaked several hours in purified water. They were dialyzed overnight at 4-6° C. against 600 ml of phosphate buffered saline (PBS is approximately 4 mM in potassium) per 6 samples. The buffer was replaced the next morning and dialysis continued for 2.5 hours. Samples were then removed from the dialysis bags and placed in microfuge tubes. The tubes were placed on ice for 1 hour, microfuged at 14 K rpm for 3 min. and the supernatants carefully removed from the precipitated SDS. The supernatants were then placed on ice for approximately 1 hour more and microfuged again for 4 min. The supernatants were diluted in phosphate buffered saline and submitted for the activity assay. Remaining samples were frozen at −70° C.

Example 3

Porcine mpl Ligand Microsequencing

Fraction 6 (2.6 ml) from the mpl-IgG affinity column was concentrated on a Microcon-10 (Amicon). In order to prevent the mpl ligand from absorbing to the Microcon, the membrane was rinsed with 1% SDS and 5 μl of 10% SDS was added to fraction 6. Sample buffer (20 μl) of 2× was added to the fraction #6 after Microcon concentration (20 μl) and the total volume (40 μl) was loaded on a single lane of a 4-20% gradient acrylamide gel (Novex). The gel was run following Novex protocol. The gel was then equilibrated for 5 min. prior to electroblotting in 10 mM 3-(cyclohexylamino)-1-propanesulfonic acid (CAPS) buffer, pH 11.0, containing 10% methanol. Electroblotting onto Immobilon-PSQ membranes (Millipore) was carried out for 45 min. at 250 mA constant current in a BioRad Trans-Blot transfer cell (32). The PVDF membrane was stained with 0.1% Coomassie Blue R-250 in 40% methanol, 0.1% acetic acid for 1 min. and destained for 2-3 min. with 10% acetic acid in 50% methanol. The only proteins that were visible in the Mr 18,000-35,000 region of the blot had Mr of 30,000, 28,000 and 22,000.

Bands at 30, 28 and 22 kDa were subjected to protein sequencing. Automated protein sequencing was performed on a model 470A Applied Biosystem sequencer equipped with an on-line PTH analyzer. The sequencer was modified to inject 80-90% of the sample (Rodriguez, J. *Chromatogr.,* 350:217-225 [1985]). Acetone (−12 μl/l) was added to solvent A to balance the UV absorbance. Electroblotted proteins were sequenced in the Blott cartridge. Peaks were integrated with Justice Innovation software using Nelson Analytical 970 interfaces. Sequence interpretation was performed on a VAX 5900 (Henzel et al., *J. Chromatogr.,* 404:41-52 [1987]). N-terminal sequences (using one letter code with uncertain residues in parenthesis) of indicated gel bands were:

Example 4

Liquid Suspension Megakaryocytopoiesis Assay

Human peripheral stem cells (PSC) (obtained from consenting patients) were diluted 5 fold with IMDM media (Gibco) and centrifuged for 15 min. at room temp. at 800×g. The cell pellets were resuspended in IMDM and layered onto 60% Percoll (density 1.077 gm/ml) (Pharmacia) and centrifuged at 800×g for 30 min. The light density mononuclear cells were aspirated at the interface and washed 2× with IMDM and plated out at 1-2×$10^6$ cells/ml in IMDM containing 30% FBS (1 ml final volume) in 24 well tissue culture clusters (Costar). APP or mpl ligand depleted APP was added to 10% and cultures were grown for 12-14 days in a humidified incubator at 37° C. in 5% $CO_2$ and air. The cultures were also grown in the presence of 10% APP with 0.5 μg of mpl-IgG added at days 0, 2 and 4. APP was depleted of mpl ligand by passing APP through a mpl-IgG affinity column.

To quantitate megakaryocytopoiesis in these liquid suspension cultures, a modification of Solberg et al. was used and employs a radiolabeled murine IgG monoclonal antibody (HP1-1D) to GPIIbIIIa (provided by Dr. Nichols, Mayo Clinic). 100 μg of HP1-1D (see Grant, B. et al. *Blood* 69:1334-1339 [1987]). was radiolabeled with 1 mCi of $Na^{125}I$ using enzymobeads (Biorad, Richmond, Calif.) as described by the manufacturer's instructions. Radiolabeled HP1-1D was stored at −70° C. in PBS containing 0.01% octyl-glucoside. Typical specific activities were 1-2×$10^6$ cpm/μg (>95% precipitated by 12.5% trichloroacetic acid).

Liquid suspension cultures were set up in triplicate for each experimental point. After 12-14 days in culture the 1 ml cultures were transferred to 1.5 ml eppendorf tubes and centrifuged at 800×g for 10 min. at room temp. and the resultant cell pellets were resuspended in 100 μl of PBS containing 0.02% EDTA and 20% bovine calf serum. 10 ng of $^{125}I$-HP1-1D in 50 μl of assay buffer was added to the resuspended cultures and incubated for 60 min. at room temperature (RT) with occasional shaking. Subsequently, cells were collected by centrifugation at 800×g for 10 min. at RT and washed 2× with assay buffer. The pellets were counted for 1 min. in a gamma counter (Packard). Non-specific binding was determined by adding 1 μg of unlabeled HP1-1D for 60 min. before the addition of labeled HP1-1D. Specific binding was determined as the total $^{125}I$-HP1-1D bound minus that bound in the presence of excess unlabeled HP1-1D.

Example 5

Oligonucleotide PCR Primers

Based on the amino-terminal amino acid sequence obtained from the 30 kDa, 28 kDa and 22 kDa proteins, degenerate oligonucleotides were designed for use as poly-

```
1) 30 kDa (1.8 pmol)                          (SEQ ID NO: 22)
       1      5      10      15       20        25
    (S) P A P P A(C)D P R L L N K L L R D D (H/S) V L H (G) R L;

2) 28 kDa (0.5 pmol)                          (SEQ ID NO: 23)
       1      5      10      15       20        25
    (S) P A P P A X D P R L L N K L L R D D (H) V L (H) G R; and

3) 22 kDa (0.5 pmol)                          (SEQ ID NO: 24)
       1      5      10
    X P A P P A X D P R L X (N) (K).
```

merase chain reaction (PCR) primers. Two primer pools were synthesized, a positive sense 20 mer pool encoding amino acid residues 2-8 (mpl 1) and an anti-sense 21-mer pool complimentary to sequences encoding amino acids 18-24 (mpl 2).

```
                                    (SEQ ID NO: 27)
mpl 1 5' CCN GCN CCN CCN GCN TGY GA 3'
(2,048-fold degenerate)

                                    (SEQ ID NO: 28)
mpl 2 5' NCC RTG NAR NAC RTG RTC RTC 3'
(2,048-fold degenerate)
```

Porcine genomic DNA, isolated from porcine peripheral blood lymphocytes, was used as a template for PCR. The 50 μl reaction contained: 0.8 μg of porcine genomic DNA in 10 mM Tris-HCl (pH 8.3), 50 mM KCl, 3 mM $MgCl_2$, 100 μg/ml BSA, 400 μM dNTPs, 1 μM of each primer pool and 2.5 units of Taq polymerase. Initial template denaturation was at 94° C. for 8 min. followed by 35 cycles of 45 seconds at 94° C., 1 min. at 55° C. and 1 min. at 72° C. The final cycle was allowed to extend for 10 min. at 72° C. PCR products were separated by electrophoresis on a 12% polyacrylamide gel and visualized by staining with ethidium bromide. If the amino-terminal amino acid sequence is encoded by a single exon then the correct PCR product is expected to be 69 bp. A DNA fragment of this size was eluted from the gel and subcloned into pGEMT (Promega) . Sequences of three clones are shown below:

This oligonucleotide was $^{32}$P-labeled with ($\gamma^{32}$P)-ATP and T4 kinase and used to screen a human genomic DNA library in λgem12 under low stringency hybridization and wash conditions (see Example 7). Positive clones were picked, plaque purified and analyzed by restriction mapping and southern blotting. Clone #4 was selected for additional analysis.

A 2.8 kb BamHI-XbaI fragment that hybridized to the 45-mer was subcloned into pBluescript SK-. Partial DNA sequencing of this clone was performed using as primers oligonucleotides specific to the porcine mpl ligand DNA sequence. The sequence obtained confirmed that DNA encoding the human homolog of the porcine mpl ligand had been isolated. An EcoRI restriction site was detected in the sequence allowing us to isolate a 390 bp EcoRI-XbaI fragment from the 2.8 kb BamHI-XbaI and to subclone it in pBluescript SK-.

Both strands of this fragment were sequenced. The human DNA sequence and deduced amino acid sequence are shown in FIG. 9 (SEQ ID NOS: 3 & 4). The predicted positions of introns in the genomic sequence are also indicated by arrows, and define a putative exon ("exon 3").

Examination of the predicted amino acid sequence confirms that a serine residue is the first amino acid of the mature mpl ligand, as determined from direct amino acid sequence analysis. Immediately upstream from this codon the predicted amino acid sequence is highly suggestive of a signal sequence involved in secretion of the mature mpl ligand. This signal sequence coding region is probably interrupted at nucleotide position 68 by an intron.

```
(1) gemT3
                                                                           (SEQ ID NO: 29)
5' CCAGCGCCGC CAGCCTGTGA CCCCCGACTC CTAAATAAAC TGCCTCGTGA TGACCACGTT CAGCACGGC 69

                                                                           (SEQ ID NO: 30)
3' GGTCGCGGCG GTCGGACACT GGGGGCTGAG GATTTATTTG ACGGAGCACT ACTGGTGCAA GTCGTGCCG

(2) gemT7
                                                                           (SEQ ID NO: 31)
5' CCAGCACCTC CGGCATGTGA CCCCCGACTC CTAAATAAAC TGCTTCGTGA CGACCACGTC CATCACGGC 69

                                                                           (SEQ ID NO: 32)
3' GGTCGTGGAG GCCGTACACT GGGGGCTGAG GATTTATTTG ACGAAGCACT GCTGGTGCAG GTAGTGCCG

(3) gemT9
                                                                           (SEQ ID NO: 25)
                    P  R  L  L  N  K  L  L  R

                                                                           (SEQ ID NO: 33)
5' CCAGCACCGCCGGCATGTGACCCCCGACTCCTAAATAAACTGCTTCGTGACGATCATGTCTATCACGGT 3'

                                                                           (SEQ ID NO: 34)
3' GGTCGTGGCGGCCGTACACTGGGGGCTGAGGATTTATTTGACGAAGCACTGCTAGTACAGATAGTGCCA 5'
```

The position of the PCR primers is indicated by the underlined bases. These results verify the N-terminal sequence obtained for amino acids 9-17 for the 30 kDa, 28 kDa and 18 kDa proteins and indicated that this sequence is encoded by a single exon of porcine DNA.

Example 6

Human mpl Ligand Gene

Based on the results from Example 5, a 45-mer deoxyoligonucleotide was designed and synthesized to screen a genomic library. The 45-mer had the following sequence:

5' GCC-GTG-AAG-GAC-GTG-GTC-GTC-ACG-
AAG-CAG-TTT-ATT-TAG-GAG-TCG 3' (SEQ ID NO: 26)

In the 3' direction the exon appears to terminate at nucleotide 196. This exon therefore encodes a sequence of 42 amino acids, 16 of which are likely to be part of a signal sequence and 26 of which are part of the mature human mpl ligand.

Example 7

Full Length Human mpl Ligand cDNA

Based on the human "exon 3" sequence (Example 6) 2 non-degenerate oligonucleotides corresponding to the 3' and 5' ends of the exon sequence were synthesized.

```
Forward primer:
                                        (SEQ ID NO: 35)
5' GCT AGC TCT AGA AAT TGC TCC TCG TGG TCA TGC
TTC T 3'

Reverse primer:
                                        (SEQ ID NO: 36)
5' CAG TCT GCC GTG AAG GAC ATG G 3'
```

These 2 primers were used in PCR reactions employing as a template DNA from various human cDNA libraries or 1 ng of Quick Clone cDNA (Clonetech) from various tissues using the conditions described in the Example 5. The expected size of the correct PCR product was 140 bp. After analysis of the PCR products on a 12% polyacrylamide gel, a DNA fragment of the expected size was detected in cDNA libraries prepared from adult kidney, 293 fetal kidney cells and cDNA prepared from human fetal liver (Clonetech cat. #7171-1).

A fetal liver cDNA library in lambda DR2 (Clonetech cat. # HL1151x) was screened with the same 45 mer oligonucleotide used to screen the human genomic library. The oligonucleotide was labelled with ($\gamma^{32}$P)-ATP using T4 polynucleotide kinase. The library was screened under low stringency hybridization conditions. The filters were prehybridized for 2 h then hybridized with the probe overnight at 42° C. in 20% formamide, 5×SSC, 10×Denhardt's, 0.05M sodium phosphate (pH 6.5), 0.1% sodium pyrophosphate, 50 μg/ml of sonicated salmon sperm DNA for 16 h. Fitters were then rinsed in 2×SSC and then washed once in 0.5×SSC, 0.1% SDS at 42° C. Filters were exposed overnight to Kodak X-Ray film. Positive clones were picked, plaque purified and the insert size was determined by PCR using oligonucleotides flanking the BamHI-XbaI cloning in lambda DR2 (Clonetech cat. #6475-1). 5 μl of phage stock was used as a template source. Initial denaturation was for 7 min. at 94° C. followed by 30 cycles of amplification (1 min. at 94° C., 1 min. at 52° C. and 1.5 min. at 72° C.). Final extention was for 15 min. at 72° C. Clone #FL2b had a 1.8 kb insert and was selected for further analysis.

The plasmid pDR2 (Clonetech, Lambda DR2 & pDR2 cloning and Expression System Library Protocol Handbook, p 42) contained within the lambda DR2 phage arms, was rescued as described per manufacturer's instructions (Clonetech, Lambda DR2 & pDR2 cloning and Expression System Library Protocol Handbook, p 29-30). Restriction analysis of the plasmid pDR2-FL2b with BamHI and XbaI indicated the presence of an internal BamHI restriction site in the insert approximately at position 650. Digestion of the plasmid with BamHI-XbaI cut the insert in two fragments, one of 0.65 kb and one of 1.15 kb. DNA sequence was determined with three different classes of template derived from the plasmid pDR2-FL2b. DNA sequencing of double-stranded plasmid DNA was carried out with the ABI373 (Applied Biosystems, Foster City, Calif.) automated fluorescent DNA sequencer using standard protocols for dye-labeled dideoxy nucleoside triphosphate terminators (dye-terminators) and custom synthesized walking primers (Sanger et al., *Proc. Natl. Acad. Sci. USA,* 74:5463-5467 [1977]; Smith et al., *Nature,* 321:674-679 [1986]). Direct sequencing of polymerase chain reaction amplified fragments from the plasmid was done with the ABI373 sequencer using custom primers and dye-terminator reactions. Single stranded template was generated with the M13 Janus vector (DNASTAR, Inc., Madison, Wis.) (Burland et al., *Nucl. Acids Res.,* 21:3385-3390 [1993]). BamHI-XbaI (1.15 kb) and BamHI (0.65 kb) fragments were isolated from the plasmid pDR2-FL2b, the ends filled in with T4 DNA polymerase in the presence of deoxynucleotides, and then subcloned into the SmaI site of M13 Janus. Sequencing was carried out with standard protocols for dye-labeled M13 Universal and Reverse primers, or walking primers and dye-terminators. Manual sequencing reactions were carried out on single strand M13 DNA using walking primers and standard dideoxy-terminator chemistry (Sanger et al., *Proc. Natl. Acad. Sci. USA,* 74:5463-5467 [1977]), $^{33}$P-labeled alpha-dATP and Sequenase (United States Biochemical Corp., Cleveland, Ohio). DNA sequence assembly was carried out with Sequencher V2.1b12 (Gene Codes Corporation, Ann Arbor, Mich.). The nucleotide and deduced sequences of hML are provided in FIG. 1 (SEQ ID NO: 1).

Example 8

Transient Expression of Human mpl Ligand hML

In order to subclone the full length insert contained in pDR2-FL2b, the plasmid was digested with XbaI to completion, then partially digested with BamHI. A DNA fragment corresponding to the 1.8 kb insert was gel purified and subcloned in pRK5 (pRK5-hmpl I) (see U.S. Pat. No. 5,258,287 for construction of pRK5) under the control of the cytomegalovirus immediate early promoter. DNA from the construct pRK5-hmpl I was prepared by the PEG method and transfected in Human embryonic kidney 293 cells maintained in Dulbecco's modified Eagle's medium (DMEM) supplemented with F-12 nutrient mixture, 20 mM Hepes (pH 7.4) and 10% fetal bovine serum. Cells were transfected by the calcium phosphate method as described (Gorman, C. [1985] in *DNA Cloning: A Practical Approach* (Glover, D. M., ed) Vol. II, pp. 143-190, IRL Press, Washington, D.C.). 36 h after transfection, the supernatant of the transfected cells was assayed for activity in the proliferation assay (see Example 1). Supernatant of 293 cells transfected with pRK vector only gave no stimulation of the Ba/F3 or Ba/F3-mpl cells (FIG. 12A). Supernatant of cells transfected with pRK5-hmpl I had no effect on the Ba/F3 cells but dramatically stimulates the proliferation of Ba/F3-mpl cells (FIG. 12A), indicating that this cDNA encodes a functionally active human mpl ligand.

Example 9

Human Mpl Ligand Isoforms hML2, hML3, and hML4

In order to identify alternatively spliced forms of hML, primers were synthesized corresponding to each end of the coding sequence of hML. These primers were employed in RT-PCR to amplify human adult liver RNA. Additionally, internal primers flanking selected regions of interest (see below) were constructed and similarly employed. Direct sequencing of the ends of the PCR product revealed a single sequence corresponding exactly to the sequence of the cDNA isolated from the human fetal liver library (see FIG. 1 (SEQ ID NO: 1)). However, a region near the C-terminus of the EPO-domain (in the middle of the PCR product) exhibited a complex sequence pattern suggesting the existence of possible splice variants in that region. To isolate these splice variants, the following primers flanking the region of interest were used in a PCR as templates for human adult liver cDNA.

phmpllcdna.3e1: 5'TGTGGACTTTAGCTTGGGAGAATG3' (SEQ ID NO: 37)and pbx4.f2: 5'GGTCCAGGGACCTGGAGGTTTG3' (SEQ ID NO: 38)

The PCR products were subcloned blunt into M13. Sequencing of individual subclones revealed the existence of at least 3 ML isoforms. One of them, hML (also referred to as $hML_{332}$), is the longest form and corresponds exactly to the sequence isolated from the fetal liver library. Sequences of the four human mpl ligand isoforms listed from longest (hML) to shortest (hML4) are provided in (FIG. 11 (SEQ ID NOS: 6, 8, 9 & 10)).

Example 10

Construction and Transient Expression of Human Mpl Ligand Isoforms and Substitutional Variants hML2, hML3, and hML(R153A, R154A)

Isoforms hML2 and hML3 and substitutional variant hML (R153A, R154A) were reconstituted from hML using the recombinant PCR technique described by Russell Higuchi, in PCR Protocols, *A guide to Methods and Applications*, Acad. Press, M. A. Innis, D. H. Gelfand, J. J. Sninsky & T. J. White Editors.

In all contructs, the "outside" primers used were:

```
Cla.FL.F2:
                                        (SEQ ID NO: 39)
5'ATC GAT ATC GAT AGC CAG ACA CCC CGG CCA G3'

HMPLL-R:
                                        (SEQ ID NO: 40)
5'GCT AGC TCT AGA CAG GGA AGG GAG CTG TAC ATG
AGA3'
```

with the following overlapping primers:

hML2:

```
                                        (SEQ ID NO: 41)
MLΔ4.F: 5'CTC CTT GGA ACC CAG GGC AGG ACC 3'

                                        (SEQ ID NO: 42)
MLΔ4.R  5'GGT CCT GCC CTG GGT TCC AAG GAG 3'
```

hML3:

```
hMLΔ116+:
                                        (SEQ ID NO: 43)
5'CTG CTC CGA GGA AAG GAC TTC TGG ATT 3'

hMLΔ116-:
                                        (SEQ ID NO: 44)
5'AAT CCA GAA GTC CTT TCC TCG GAG CAG 3'
```

hML(R153A, R154A):

```
                                        (SEQ ID NO: 45)
RR-KO-F: 5'CCC TCT GCG TCG CGG CGG CCC CAC
CCA C 3'
                                        (SEQ ID NO: 46)
RR-KO-R: 5'GTG GGT GGG GCC GCC GCG ACG CAG
AGG G 3'
```

All PCR amplifications were performed with cloned Pfu DNA polymerase (Stratagene) using the following conditions: Initial template denaturation was at 94° C. for 7 min. followed by 30 cycles of 1 min. at 94° C., 1 min. at 55° C. and 1.5 min. at 72° C. The final cycle was allowed to extend for 10 min at 72° C. The final PCR product was digested with ClaI-XbaI, gel purified and cloned in pRK5tkneo. 293 cells were transfected with the various constructs as described above and the supernatant was assayed using the Ba/F3-mpl proliferation assay. hML2 and hML3 showed no detectable activity in this assay, however the activity of hML(R153A, R154A) was similar to hML indicating that processing at this di-basic site is not required for activity (see FIG. 13).

Example 11

Murine mpl Ligand cDNA mML, mML2 and mML3

Isolation of m-ML cDNA. A DNA fragment corresponding to the entire coding region of the human mpl ligand was obtained by PCR, gel purified and labeled by random priming in the presence of $^{32}$P-dATP and $^{32}$P-dCTP. This probe was used to screen $10^6$ clones of a mouse liver cDNA library in λGT10 (Clontech cat# ML3001a). Duplicate filters were hybridized in 35% formamide, 5×SSC, 10×Denhardt's, 0.1% SDS, 0.05M sodium phosphate (pH 6.5), 0.1% sodium pyrophosphate, 100 μg/ml of sonicated salmon sperm DNA overnight in the presence of the probe. Filters were rinsed in 2×SSC and then washed once in 0.5×SSC, 0.1% SDS at 42° C. Hybridizing phage were plaque-purified and the cDNA inserts were subcloned into the Eco R1 site of Bluescript SK-plasmid. Clone "LD" with a 1.5 kb insert was chosen for further analysis and both strands were sequenced as described above for the human ML cDNA. The nucleotide and deduced amino acid sequences from clone LD are provided in FIG. 14 (SEQ ID NOS: 11 & 12). The deduced mature ML sequence from this clone was 331 amino acid residues long and identified as $mML_{331}$ (or mML2 for reasons described below). Considerable identity for both nucleotide and deduced amino acid sequences were observed in the EPO-like domains of these ML's. However, when deduced amino acid sequences of human and mouse ML's were aligned, the mouse sequence appeared to have a tetrapeptide deletion between human residues 111-114 corresponding to the 12 nucleotide deletion following nucleotide position 618 seen in both the human (see above) and pig (see below) cDNA's. Accordingly, additional clones were examined to detect possible murine ML isoforms. One clone, "L7", had a 1.4 kb insert with a 335 amino acid deduced sequence containing the "missing" tetrapeptide LPLQ. This form is believed to be the full length murine ML and is referred to as mML or $mML_{335}$. The nucleotide and deduced amino acid sequence for mML are provided in FIG. 15 (SEQ ID NOS: 13 & 14). Finally, clone "L2" was isolated and sequenced. This clone has the 116 nucleotide deletion corresponding to hML3 and is therefore denominated mML3. Comparison of the deduced amino acid sequences of these two isoforms is shown in FIG. 16.

Expression of recombinant m-ML. Expression vectors for murine ML were prepared essentially as described in Example 8. Clones encoding mML and mML2 were subcloned into pRK5tkneo, a mammalian expression vector that provides expression under the control of the CMV promoter and an SV40 polyadenylation signal. The resulting expression vectors, mMLpRKtkneo and mML2pRKtkneo were transiently transfected into 293 cells using the calcium phosphate method. Following transient transfection, media was conditioned for five days. The cells were maintained in high glucose DMEM media supplemented with 10% fetal calf serum.

Expression of murine-mpl (m-mpl) in Ba/F3 cells. Stable cell lines expressing c-mpl were obtained by transfection of m-mpl pRKtkneo, essentially as described for human mpl in Example 1. Briefly, an expression vector (20 μg; linearized) containing the entire coding sequence of murine mpl (Skoda, R. C., et al., *EMBO J.* 12:2645-2653 [1993]) was transfected into Ba/F3 cells by electroporation ($5\times10^6$ cells, 250 volts, 960 μF) followed by selection for neomycine resistance with 2 mg/ml G418. Expression of mpl was assessed by flow cytometry analysis using rabbit anti-murine mpl-IgG antisera. Ba/F3 cells were maintained in RPMI 1640 media from WEHI-3B cells as a source of IL-3. Supernatants from 293 cells transiently transfected with both mML and mML2 were assayed in BaF3 cells transfected with both m-mpl and h-mpl as described in Example 1.

Example 12

Porcine mpl Ligand cDNA pML and pML2

Porcine ML (pML) cDNA was isolated by RACE PCR. Briefly, an oligo dT primer and 2 specific primers were designed based on the sequence of the exon of the porcine ML gene encoding the amino terminus of the ML purified from the aplastic pig serum. cDNA prepared from various aplastic pig tissues was obtained and amplified. A PCR cDNA product of 1342 bp was found in kidney and subcloned. Several clones were sequenced and found to encode the mature pig mpl ligand (not including a complete secretion signal). The cDNA was found to encode a 332 amino acid mature protein ($pML_{332}$) having the sequence shown in FIG. 18 (SEQ ID NOS: 16 & 17).

Method

Isolation of p-ML gene and cDNA. Genomic clones of the porcine ML gene were isolated by screening a pig genomic library in EMBL3 (Clontech Inc.) with pR45. The library was screened essentially as described in Example 7. Several clones were isolated and the exon encoding amino acid sequence identical to that obtained from the purified ML was sequenced. Porcine ML cDNA were obtained using a modification of the RACE PCR protocol. Two specific ML primers were designed based on the sequence of the pig ML gene. Polyadenylated mRNA was isolated from the kidney of aplastic pigs essentially as previously described. cDNA was prepared by reverse transcription with a primer (BamdT: 5' GACTCGAGGATCCATCGATTTTTTTTTTTTTTTTTT 3' (SEQ ID NO: 47)) directed against the polyadenosine tail of the mRNA. An initial round of PCR amplification (28 cycles of 95° C. for 60 seconds, 58° C. for 60 seconds, and 72° C. for ninety seconds) was conducted using the ML specific primer h-forward-1 (5' GCTAGCTCTAGAAATTGCTCCTCGTGGTCATGCTTCT 3' (SEQ ID NO: 35)) and primer BAMAD (5' GACTCGAGGATCCATCG 3' (SEQ ID NO: 48)) in a 100 ml reaction (50 mM KCl, 1.5 mM MgCl, 10 mM Tris pH 8.0, 0.2 mM dNTPs, with 0.05 U/ml Amplitaq polymerase (Perkin Elmer inc.)) The PCR product was then digested with Cla1, extracted with phenol-chloroform (1:1), ethanol precipitated, and ligated to 0.1 mg of Bluescript SK-vector (Stratagene inc.) that had been cut with Cla1 and Kpn 1. After incubation for two hours at room temperature, one fourth of the ligation mixture was added directly to a second round of PCR (22 cycles as described above) using a second ML specific primer Forward-1 (5' GCTAGCTCTAGAAGCCCGGCTCCTCCTGCCTG 3' (SEQ ID NO: 49) and T3-21 (an oligonucleotide that binds to a sequence adjacent to the multiple cloning region within the Bluescript SK-vector: 5' CGAAATTAACCCTCACTAAAG 3' (SEQ ID NO: 50)). The resulting PCR product was digested with Xba1 and Cla1 and subcloned into Bluescript SK-. Several clones from independent PCR reactions were sequenced.

Again, a second form, designated pML2, encoding a protein with a 4 amino acid residue deletion (228 amino acid residues) was identified (see FIG. 19 (SEQ ID NO: 20)). Comparison of pML and pML2 amino acid sequences shows the latter form is identical except that the tetrapeptide QLPP corresponding to residues 111-114 inclusive have been deleted (see FIG. 20 (SEQ ID NOS: 17 & 20)). The four amino acid deletions observed in murine, human and porcine ML cDNA occur at precisely the same position within the predicted proteins.

Example 13

CMK Assay for Thrombopoietin (TPO) Induction of Platelet Antigen $GPII_bIII_a$ Expression CMK cells are maintained in RMPI 1640 medium (Sigma) supplemented with 10% fetal bovine serum and 10 mM glutamine. In preparation for the assay, the cells are harvested, washed and resuspended at $5\times10^5$ cells/ml in serum-free GIF medium supplemented with 5 mg/l bovine insulin, 10 mg/l apo-transferrin, 1×trace elements. In a 96-well flat-bottom plate, the TPO standard or experimental samples are added to each well at appropriate dilutions in 100 μl volumes. 100 μl of the CMK cell suspension is added to each well and the plates are incubated at 37° C., in a 5% $CO_2$ incubator for 48 hours. After incubation, the plates are spun at 1000 rpm at 4° C. for five minutes. Supernatants are discarded and 100 μl of the FITC-conjugated $GPII_bIII_a$ monoclonal 2D2 antibody is added to each well. Following incubation at 4° C. for 1 hour, plates are spun again at 1000 rpm for five minutes. The supernatants containing unbound antibody are discarded and 200 μl of 0.1% BSA-PBS wash is added to each well. The 0.1% BSA-PBS wash step is repeated three times. Cells are then analyzed on a FASCAN using standard one parameter analysis measuring relative fluorescence intensity.

Example 14

DAMI Assay for Thrombopoietin (TPO) by Measuring Endomitotic Activity of DAMI Cells on 96-well Microtiter Plates DAMI cells are maintained in IMDM+10% horse serum (Gibco) supplemented with 10 mM glutamine, 100 ng/ml Penicillin G, and 50 μg/ml streptomycin. In preparation for the assay, the cells are harvested, washed, and resuspended at $1\times10^6$ cells/ml in IMDM+1% horse serum. In a 96-well round-bottom plate, 100 μl of the TPO standard or experimental samples is added to DAMI cell suspension. Cells are then incubated for 48 hours at 37° C. in a 5% $CO_2$ incubator. After incubation, plates are spun in a Sorvall 6000B centrifuge at 1000 rpm for five minutes at 4° C. Supernatants are discarded and 200 μl of PBS-0.1% BSA wash step is repeated. Cells are fixed by the addition of 200 μl ice-cold 70% Ethanol-PBS and resuspended by aspiration. After incubation at 4° C. for 15 minutes, the plates are spun at 2000 rpm for five minutes and 150 μl of 1 mg/ml RNAse containing 0.1 mg/ml propidium iodide and 0.05% Tween-20 is added to each well. Following a one hour incubation at 37° C. the changes in DNA content are measured by flow cytometry. Polyploidy is measured and quantitated as follows:

$$\text{Normalized Polyploid Ratio } (NPR) = \frac{(\%\text{ Cells in} > G2+M\,/\,\%\text{ Cells in} < G2+M)\text{ with }TPO}{(\%\text{ Cells in} > G2+M\,/\,\%\text{ Cells in} < G2+M)\text{ in control}}$$

Example 15

Thrombopoietin (TPO) In Vivo Assay (Mouse Platelet Rebound Assay)

In Vivo Assay for $^{35}S$ Determination of Platelet Production

C57BL6 mice (obtained from Charles River) are injected intraperitoneally (IP) with 1 ml goat anti-mouse platelet serum (6 amps) on day 1 to produce thrombocytopenia. On days 5 and 6, mice are given two IP injections of the factor or PBS as the control. On day 7, thirty μCi of $Na_2{}^{35}SO_4$ in 0.1 ml saline are injected intravenously and the percent $^{35}S$ incorporation of the injected dose into circulating platelets is measured in blood samples obtained from treated and control mice. Platelet counts and leukocyte counts are made at the same time from blood obtained from the retro-orbital sinus.

Example 16

Synthetic mpl-ligand

Although Human mpl-ligand (hML) is usually made using recombinant methods, it can also be synthesized via enzymatic ligation of synthetic peptide fragments using methods described below. Synthetic production of hML allows the incorporation of unnatural amino acids or synthetic functionalities such as polyethylene glycol. Previously, a mutant of the serine protease subtilisin BPN, subtiligase (S221C/P225A) was engineered to efficiently ligate peptide esters in aqueous solution (Abrahmsen et al., *Biochem.*, 30:4151-4159 [1991]). It has now been shown that synthetic peptides can be enzymatically ligated in a sequential manor to produce enzymatically active long peptides and proteins such as ribonuclease A (Jackson et al., *Science*, *[*1994]). This technology, described in more detail below, has enabled us to chemically synthesize long proteins that previously could be made only with recombinant DNA technology.

A general strategy for $hML_{153}$ synthesis using subtiligase is shown (Scheme 1). Beginning with a fully deprotected peptide corresponding to the C-terminal fragment of the protein, an N-terminal protected, C-terminal activated ester peptide is added along with subtiligase. When the reaction is complete, the product is isolated by reverse phase HPLC and the protecting group is removed from the N-terminus. The next peptide fragment is ligated, deprotected and the process is repeated using successive peptides until full length protein is obtained. The process is similar to solid phase methodology in that an N-terminal protected C-terminal activated peptide is ligated to the N-terminus of the preceding peptide and protein is synthesized in a C->N direction. However because each coupling results in addition of up to 50 residues and the products are isolated after each ligation, much longer highly pure proteins can be synthesized in reasonable yields.

Scheme 1. Strategy for Synthesis of h-ML Using Subtiligase

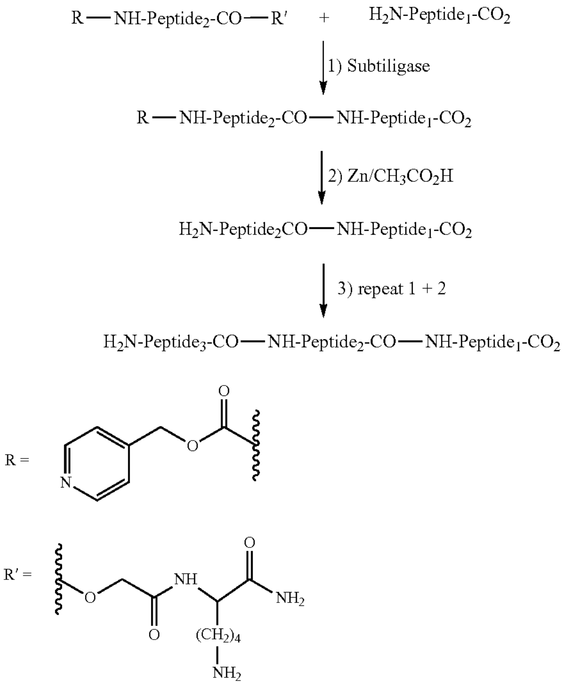

Based on our knowledge of the sequence specificity of the subtiligase as well as the amino acid sequence of the biologically active "epo-domain" of hML, we divided $hML_{153}$ into seven fragments 18-25 residues in length. Test ligation tetrapeptides were synthesized to determine suitable ligation junctions for the 18-25 mer's. Table 3 shows the results of these test ligations.

TABLE 3 hML Test Ligations. Donor and nucleophile peptides were dissolved at 10 mM in 100 mM tricine (pH 7.8) at 22° C. Ligase was added to a final concentration of 10 μM from a 1.6 mg/mL stock (~70 μM) and the ligation allowed to proceed overnight. Yields are based on % ligation vs. hydrolysis of the donor peptides.

| | Site # | Donor (glc-K-$NH_2$) | Nucleophile-$NH_2$ | % Hydrolysis | % Ligation |
|---|---|---|---|---|---|
| 1 | (23/24) | HVLH (SEQ ID NO: 51) | SRLS (SEQ ID NO: 52) | 92 | 08 |
| | (22/23) | SHVL (SEQ ID NO: 53) | HSRL (SEQ ID NO: 54) | 48 | 52 |
| 2 | (46/47) | AVDF (SEQ ID NO: 55) | SLGE (SEQ ID NO: 56) | 22 | 78 |
| 3 | (69/70) | AVTL (SEQ ID NO: 57) | LLEG (SEQ ID NO: 58) | 53 | 47 |

TABLE 3-continued hML Test Ligations. Donor and nucleophile peptides were dissolved at 10 mM in 100 mM tricine (pH 7.8) at 22° C. Ligase was added to a final concentration of 10 μM from a 1.6 mg/mL stock (~70 μM) and the ligation allowed to proceed overnight. Yields are based on % ligation vs. hydrolysis of the donor peptides.

| Site # | Donor (glc-K-$NH_2$) | Nucleophile-$NH_2$ | % Hydrolysis | % Ligation |
|---|---|---|---|---|
| 4 (89/90) | LSSL (SEQ ID NO: 59) | LGQL (SEQ ID NO: 60) | 95 | 05 |
| (88/89) | C(acm)LSS (SEQ ID NO: 61) | LLGQ (SEQ ID NO: 62) | 00 | 00 |
| (90/91) | SSLL (SEQ ID NO: 63) | GQLS (SEQ ID NO: 64) | 45 | 55 |
| (88/89) | CLSS (SEQ ID NO: 61) | LLGQ (SEQ ID NO: 62) | 90 | 10 |
| 5 (107/108) | LQSL (SEQ ID NO: 65) | LGTQ (SEQ ID NO: 66) | 99 | 01 |
| (106/107) | ALQS (SEQ ID NO: 67) | LLGT (SEQ ID NO: 68) | 70 | 30 |
| 6 (128/129) | NAIF (SEQ ID NO: 69) | LSFQ (SEQ ID NO: 70) | 60 | 40 |

Based on these experiments, the ligation peptides indicated in Table 4 should be efficiently ligated by the subtiligase. A suitable protecting group for the N-terminus of each donor ester peptide was needed to prevent self-ligation. We chose an isonicotinyl (INOC) protecting group (Veber et al., *J. Org. Chem.*, 42:3286-3289 [1977]) because it is water soluble, it can be incorporated at the last step of solid phase peptide synthesis and it is stable to anhydrous HF used to deprotect and cleave peptides from the solid phase resin. In addition, it can be removed from the peptide after each ligation under mild reducing conditions ($Zn/CH_3CO_2H$) to afford a free N-terminus for subsequent ligations. A glycolate-lysyl-amide (glc-K-$NH_2$) ester was used for C-terminal activation based on previous experiments which showed this to be efficiently acylated by subtiligase (Abrahmsen et al., *Biochem.*, 30:4151-4159 [1991]). The INOC-protected, glc-K-amide activated peptides can be synthesized using standard solid phase methods as outlined (Scheme 2). The peptides are then seqentially ligated until the full protein is produced and the final product refolded in vitro. Based on homology with EPO, disulfide pairs are believed to be formed between cysteine residues 7 and 151 and between 28 and 85. Oxidation of the disulfides may be accomplished by simply stirring the reduced material under an oxygen atmosphere for several hours. The refolded material can then be purified by HPLC and fractions containing active protein pooled and lyophilized. As an alternative, disulfides can be differentially protected to control sequential oxidation between specific disulfide pairs. Protection of cysteines 7 and 151 with acetamidomethyl (acm) groups would ensure oxidation of 28 and 85. The acm groups could then be removed and residues 7 and 151 oxidized. Conversely, residues 28 and 85 could be acm protected and oxidized in case sequential oxidation is required for correct folding. Optionally, Cysteins 28 and 85 may be substituted with another natural or unnatural residue other than Cys to insure proper oxidation of cysteins 7 and 151.

TABLE 4

Peptide Fragments Used For Total Synthesis of h-ML Using Subtiligase

| Fragment | Sequence | |
|---|---|---|
| 1 (SEQ ID NO: 71) | INOC-HN-SPAPPACDLRVLSKLLRDSHVL-glc-K-$NH_2$ | (1-22) |
| 2 (SEQ ID NO: 72) | INOC-HN-HSRLSQCPEVHPLPTPVLLPAVDF-glc-K-$NH_2$ | (23-46) |
| 3 (SEQ ID NO: 73) | INOC-HN-SLGEWKTQMEETKAQDILGAVTL-glc-K-$NH_2$ | (47-69) |
| 4 (SEQ ID NO: 74) | INOC-HN-LLEGVMAARGQLGPTCLSSLL-glc-K-$NH_2$ | (70-90) |
| 5 (SEQ ID NO: 75) | INOC-HN-GQLSGQVRLLLGALQS-glc-K-$NH_2$ | (90-106) |
| 6 (SEQ ID NO: 76) | INOC-HN-LLGTQLPPQGRTTAHKDPNAIF-glc-K-$NH_2$ | (107-128) |
| 7 (SEQ ID NO: 77) | $H_2N$-LSFQHLLRGKVRFLMLVGGSTLCVR-$CO_2$ | (129-153) |

Peptide ligations are carried out at 25° C. in 100 mM tricine, pH 8 (freshly prepared and degassed by vacuum filtration through a 5 μM filter). Typically the C-terminal fragment is dissolved in buffer (2-5 mM peptide) and a 10× stock solution of subtiligase (1 mg/ml in 100 mM tricine, pH 8) is added to bring the final enzyme concentration to ~5 μM. A 3-5 molar excess of the glc-K-$NH_2$ activated donor peptide is then added as a solid, dissolved, and the mixture allowed to stand at 25° C. The ligations are monitored by analytical reverse phase C18 HPLC ($CH_3CN/H_2O$ gradient with 0.1% TFA). The ligation products are purified by preparative HPLC and lyophilized. Isonicotinyl (iNOC) deprotection was performed by stirring HCl activated zinc dust with the protected peptide in acetic acid. The zinc dust is removed by filtration and the acetic acid evaporated under vacuum. The resulting peptide can be used directly in the next ligation and the process is repeated. Synthetic $hML_{153}$ can be ligated by procedures analogous to those described above to synthetic or recombinant $hML_{154-332}$ to produce synthetic or semisynthetic full length hML.

Synthetic hML has many advantages over recombinant. Unnatural side chains can be introduced in order to improve potency or specificity. Polymer functionalities such as polyethylene glycol can be incorporated to improve duration of action. For example, polyethylene glycol can be attached to lysine residues of the individual fragments (Table 4) before or after one or more ligation steps have been performed. Protease sensitive peptide bonds can be removed or altered to improve stability in vivo. In addition, heavy atom derivatives can be synthesized to aid in structure determination.

C. in dimethylacetamide (DMA) to afford the bromoacetyl derivative 2. b) The resin is washed extensively with DMA and individual Boc-protected amino acids (3 eq., Bachem) are esterified by stirring with sodium bicarbonate (6 eq.) in dimethylformamide (DMF) for 24 h. at 50° C. to afford the corresponding glycolate-phenylalanyl-amide-resin 3. The amino acetylated resin 3 is washed with DMF (3×) and dichloromethane ($CH_2Cl_2$) (3×) and can be stored at room temperature for several months. The resin 3 can then be loaded into an automated peptide synthesizer (Applied Biosystems 430A) and the peptides elongated using standard solid phase procedures (5). c) The N-α-Boc group is removed with a solution of 45% trifluoroacetic acid in $CH_2Cl_2$. d) Subsequent Boc-protected amino acids (5 eq.) are preactivated using benzotriazol-1-yl-oxy-tris-(dimethylamino) phosphonium hexafluorophosphate (BOP, 4 eq.) and N-methylmorpholine (NMM, 10 eq.) in DMA and coupled for 1-2 h. e) The final N-α-Boc group is removed ($TFA/CH_2Cl_2$) to afford 4 and the isonicotinyl (iNOC) protecting group is introduced as described previously (4) via stirring with of 4-isonicotinyl-2-4-dinitrophenyl carbonate (3 eq.) and NMM (6 eq.) in DMA at 25° C. for 24 h. f) Cleavage and deprotection of the peptide via treatment with anhydrous HF (5%

Scheme 2. Solid Phase Synthesis of Peptide Fragments for Segment Ligation.

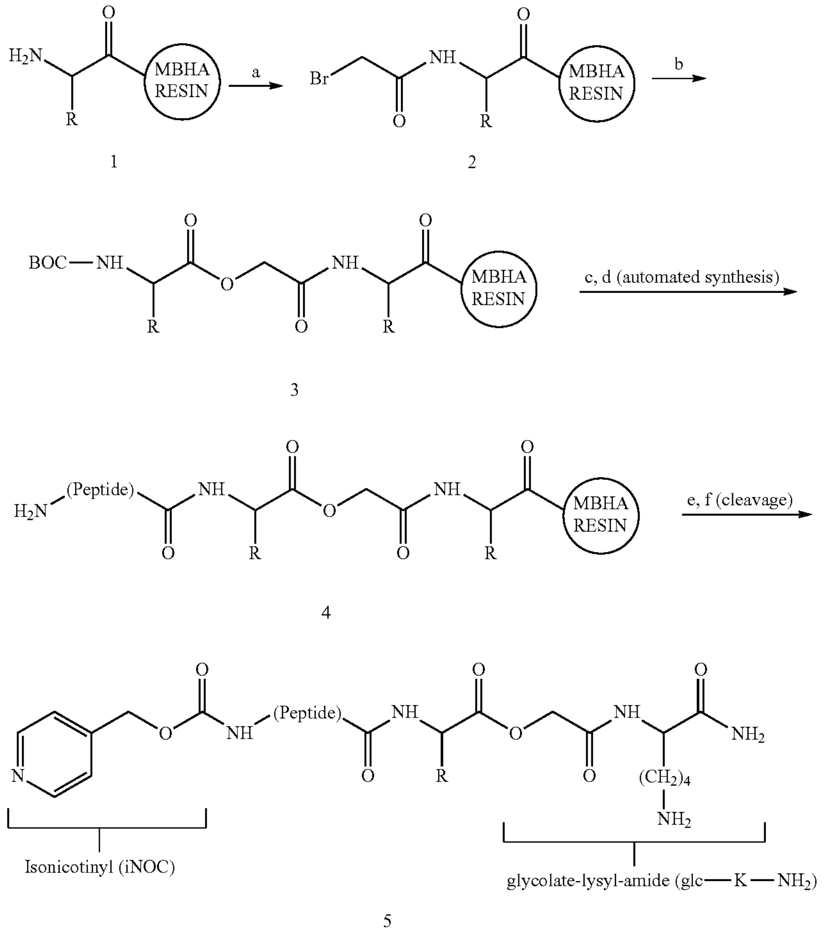

1 2 3 4 5 a) Lysyl-paramethylbenzhydrylamine (MBHA) resin 1 (0.63 meq./gm., Advanced ChemTech) is stirred with bromoacetic acid (5 eq.) and diisopropyl carbodiimide (5 eq.) for 1 h. at 25° anisole/5% ethylmethyl sufide) at 0° C. for 1 h. affords the iNOC-protected, glycolate-lys-amide activated peptide 5 which is purified by reverse phase C18 HPLC ($CH_3CN/H_2O$ gradient, 0.1% TFA). The identity of all substrates is confirmed by mass spectrometry.

SUPPLEMENTAL ENABLEMENT

The invention as claimed is enabled in accordance with the above specification and readily available references and starting materials. Nevertheless, Applicants have deposited with the American Type Culture Collection, Rockville, Md., USA (ATCC) the cell line listed below:

*Escherichia coli*. DH10B-pBSK-hmp/l 1.8, ATCC accession no. CRL 69575, deposited Feb. 24, 1994.

This deposit was made under the provisions of the Budapest Treaty on the International Recognition of the Deposit of Microorganisms for the Purposes of Patent Procedure and the regulations thereunder (Budapest Treaty). This assures maintenance of a viable culture for 30 years from date of deposit. The organisms will be made available by ATCC under the terms of the Budapest Treat, and subject to an agreement between Applicants and ATCC which assures unrestricted availability upon issuance of the pertinent U.S. patent. Availability of the deposited strain is not to be construed as a license to practice the invention in contravention of the rights granted under the authority of any government in accordance with its patent laws.

While the invention has necessarily been described in conjunction with preferred embodiments and specific working examples, one of ordinary skill, after reading the foregoing specification, will be able to effect various changes, substitutions of equivalents, and alterations to the subject matter set forth herein, without departing from the spirit and scope thereof. Hence, the invention can be practiced in ways other than those specifically described herein. It is therefore intended that the protection granted by letters patent hereon be limited only by the appended claims and equivalents thereof.

All references cited herein are hereby expressly incorporated by reference.

We claim:

1. A method for treating a mammal having or at risk for thrombocytopenia comprising administering to a mammal in need of such treatment a therapeutically effective amount of a pharmaceutical composition comprising an isolated human mpl ligand having the amino acid sequence as shown in SEQ ID NO:1 and FIG. 1 or a biologically active fragment thereof.

2. The method of claim 1 wherein the biologically active human mpl ligand fragment comprises amino acid residues 1 to X as shown in SEQ. ID NO:1 and FIG. 1 where X is selected from the group 153, 164, 191, 205, 207, 217, 229 and 245.

3. The method of claim 2 wherein the fragment further comprises an N-terminal methionyl residue.

4. The method of claim 3 wherein the fragment is administered subcutaneously.

5. The method of claim 4 wherein the fragment is administered at a dosage of from 1 to 50 μg/kg/day.

6. The method of claim 2 wherein the fragment further comprises a covalent modification comprising a nonproteinaceous polymer selected from the group consisting of polyethylene glycol, polypropylene glycol and polyoxyalkylenes.

7. The method of claim 6 wherein the fragment is administered subcutaneously.

8. The method of claim 7 wherein the fragment is administered at a dosage of from 1 to 50 μg/kg/day.

9. The method of claim 1 therein the human mpl ligand comprises amino acid residues 1-332 as shown in SEQ ID NO:1 and FIG. 1.

10. The method of claim 9 wherein the human mpl ligand is administered intravenously.

11. A method of treating a human patient prior to or following radiation therapy, chemotherapy or bone marrow transplant comprising administering a therapeutically effective amount of an isolated human mpl ligand having the amino acid sequence as shown in SEQ ID NO:1 and FIG. 1 or a biologically active fragment thereof.

12. The method of claim 11 further comprising administering a therapeutically effective amount of an agent selected from the group consisting of cytokines, colony-stimulating factors, and interleukins.

13. The method of claim 12 wherein the agent is selected from EPO, G-CSF and GM-CSF.

14. The method of claim 11 wherein the therapeutically effective amount of human mpl ligand is a dose ranging from 1 to 50 μg/kg body weight/day.

15. A method for treating a mammal having a hematopoietic disorder comprising administering a pharmaceutical composition comprising an isolated substantially homogenous human mpl ligand wherein the amino acid sequence of the ligand consists of amino acid residues 1 to X as shown in SEQ ID NO:1 and wherein X is selected from the group consisting of residues 153-166 and wherein the mpl ligand is unglycosylated.

16. The method of claim 15 wherein the mpl ligand further comprises an N-terminal methionyl amino acid residue.

17. The method of claim 16 wherein the mpl ligand is covalently modified with polyethylene glycol.

18. The method of claim 15 further comprising administering in combination with the mpl ligand a therapeutically effective amount of an agent selected from the group consisting of a cytokine, a colony stimulating factor and an interleukin.

19. A method for treating a human having or at risk for a hematopoietic disorder comprising administering a pharmaceutical composition comprising an isolated substantially homogeneous human mpl ligand comprising amino acid residues 1 to 153 as shown in SEQ ID NO:1 and FIG. 1.

20. The method of claim 19 wherein the pharmaceutical composition is sterile.

21. The method of claim 19 wherein the amino acid sequence comprises amino acid residue numbers 1 to X as shown in SEQ ID NO:1 and FIG. 1 where X is selected from the group consisting of 153-166 and 332.

22. The method of claim 21 wherein the amino acid sequence comprises amino acid residue numbers 1 to X as shown in SEQ ID NO:1 and FIG. 1 where X is 153 to 166.

23. The method of claim 22 wherein the mpl ligand is unglycosylated.

24. The method of claim 21 wherein the mpl ligand is glycosylated.

25. The method of claim 22 wherein the mpl ligand is linked to a nonproteinaceous polymer selected from the group consisting of polyethylene glycol, polypropylene glycol and polyoxyalkylene.

26. A method for treating a human having or at risk for thrombocytopenia comprising administering to a human in need of such treatment a therapeutically effective amount of a pharmaceutical composition comprising an isolated substantially homogeneous mpl ligand capable of binding to and activating human mpl selected from the group consisting of:

(a) a substantially homogeneous human mpl ligand wherein the amino acid sequence of the mpl ligand consists of amino acid residues 1 to X as shown in SEQ ID NO:1 and FIG. 1 where X is selected from the group consisting of amino acid residues 153, 164, 191, 205, 207, 217, 229, 245 and 332, the mpl ligand optionally further containing an N-terminal methionyl residue, and (b) a substantially homogenous mpl ligand insertion, deletion or substitution variant having an amino acid sequence that is at least 95% identical to the human mpl ligand in (a).

27. The method of claim 26 wherein the mpl ligand further comprises a nonproteinaceous polymer selected from the group consisting of polyethylene glycol, polypropylene glycol and polyoxyalkylene.

* * * * *

```
                              SEQUENCE LISTING


(1) GENERAL INFORMATION:

   (iii) NUMBER OF SEQUENCES: 77


(2) INFORMATION FOR SEQ ID NO:1:

     (i) SEQUENCE CHARACTERISTICS:
          (A) LENGTH: 353 amino acids
          (B) TYPE: Amino Acid
          (D) TOPOLOGY: Linear

    (xi) SEQUENCE DESCRIPTION: SEQ ID NO:1:

Met Glu Leu Thr Glu Leu Leu Leu Val Val Met Leu Leu Leu Thr
-21 -20                 -15                 -10

Ala Arg Leu Thr Leu Ser Ser Pro Ala Pro Pro Ala Cys Asp Leu
     -5                  1               5

Arg Val Leu Ser Lys Leu Leu Arg Asp Ser His Val Leu His Ser
 10                  15                  20

Arg Leu Ser Gln Cys Pro Glu Val His Pro Leu Pro Thr Pro Val
 25                  30                  35

Leu Leu Pro Ala Val Asp Phe Ser Leu Gly Glu Trp Lys Thr Gln
 40                  45                  50

Met Glu Glu Thr Lys Ala Gln Asp Ile Leu Gly Ala Val Thr Leu
 55                  60                  65

Leu Leu Glu Gly Val Met Ala Ala Arg Gly Gln Leu Gly Pro Thr
 70                  75                  80

Cys Leu Ser Ser Leu Leu Gly Gln Leu Ser Gly Gln Val Arg Leu
 85                  90                  95

Leu Leu Gly Ala Leu Gln Ser Leu Leu Gly Thr Gln Leu Pro Pro
100                 105                 110

Gln Gly Arg Thr Thr Ala His Lys Asp Pro Asn Ala Ile Phe Leu
115                 120                 125

Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr
145                 150                 155

Ala Val Pro Ser Arg Thr Ser Leu Val Leu Thr Leu Asn Glu Leu
160                 165                 170
```

```
Pro Asn Arg Thr Ser Gly Leu Leu Glu Thr Asn Phe Thr Ala Ser
175                 180                 185

Ala Arg Thr Thr Gly Ser Gly Leu Leu Lys Trp Gln Gln Gly Phe
190                 195                 200

Arg Ala Lys Ile Pro Gly Leu Leu Asn Gln Thr Ser Arg Ser Leu
205                 210                 215

Asp Gln Ile Pro Gly Tyr Leu Asn Arg Ile His Glu Leu Leu Asn
220                 225                 230

Gly Thr Arg Gly Leu Phe Pro Gly Pro Ser Arg Arg Thr Leu Gly
235                 240                 245

Ala Pro Asp Ile Ser Ser Gly Thr Ser Asp Thr Gly Ser Leu Pro
250                 255                 260

Pro Asn Leu Gln Pro Gly Tyr Ser Pro Ser Pro Thr His Pro Pro
265                 270                 275

Thr Gly Gln Tyr Thr Leu Phe Pro Leu Pro Pro Thr Leu Pro Thr
280                 285                 290

Pro Val Val Gln Leu His Pro Leu Leu Pro Asp Pro Ser Ala Pro
295                 300                 305

Thr Pro Thr Pro Thr Ser Pro Leu Leu Asn Thr Ser Tyr Thr His
310                 315                 320

Ser Gln Asn Leu Ser Gln Glu Gly
325                 330     332
```

(2) INFORMATION FOR SEQ ID NO:2:

(i) SEQUENCE CHARACTERISTICS:
(A) LENGTH: 1795 base pairs
(B) TYPE: Nucleic Acid
(C) STRANDEDNESS: Single
(D) TOPOLOGY: Linear (xi) SEQUENCE DESCRIPTION: SEQ ID NO:2:

```
TCTTCCTACC CATCTGCTCC CCAGAGGGCT GCCTGCTGTG CACTTGGGTC     50

CTGGAGCCCT TCTCCACCCG GATAGATTCC TCACCCTTGG CCCGCCTTTG    100

CCCCACCCTA CTCTGCCCAG AAGTGCAAGA GCCTAAGCCG CCTCCATGGC    150

CCCAGGAAGG ATTCAGGGGA GAGGCCCCAA ACAGGGAGCC ACGCCAGCCA    200

GACACCCCGG CCAGAATGGA GCTGACTGAA TTGCTCCTCG TGGTCATGCT    250

TCTCCTAACT GCAAGGCTAA CGCTGTCCAG CCCGGCTCCT CCTGCTTGTG    300

ACCTCCGAGT CCTCAGTAAA CTGCTTCGTG ACTCCCATGT CCTTCACAGC    350

AGACTGAGCC AGTGCCCAGA GGTTCACCCT TTGCCTACAC CTGTCCTGCT    400

GCCTGCTGTG GACTTTAGCT TGGGAGAATG GAAAACCCAG ATGGAGGAGA    450

CCAAGGCACA GGACATTCTG GGAGCAGTGA CCCTTCTGCT GGAGGGAGTG    500

ATGGCAGCAC GGGGACAACT GGGACCCACT TGCCTCTCAT CCCTCCTGGG    550

GCAGCTTTCT GGACAGGTCC GTCTCCTCCT TGGGGCCCTG CAGAGCCTCC    600

TTGGAACCCA GCTTCCTCCA CAGGGCAGGA CCACAGCTCA CAAGGATCCC    650

AATGCCATCT TCCTGAGCTT CCAACACCTG CTCCGAGGAA AGGTGCGTTT    700

CCTGATGCTT GTAGGAGGGT CCACCCTCTG CGTCAGGCGG GCCCCACCCA    750

CCACAGCTGT CCCCAGCAGA ACCTCTCTAG TCCTCACACT GAACGAGCTC    800

CCAAACAGGA CTTCTGGATT GTTGGAGACA AACTTCACTG CCTCAGCCAG    850

AACTACTGGC TCTGGGCTTC TGAAGTGGCA GCAGGGATTC AGAGCCAAGA    900
```

```
TTCCTGGTCT GCTGAACCAA ACCTCCAGGT CCCTGGACCA AATCCCCGGA        950
TACCTGAACA GGATACACGA ACTCTTGAAT GGAACTCGTG GACTCTTTCC       1000
TGGACCCTCA CGCAGGACCC TAGGAGCCCC GGACATTTCC TCAGGAACAT       1050
CAGACACAGG CTCCCTGCCA CCCAACCTCC AGCCTGGATA TTCTCCTTCC       1100
CCAACCCATC CTCCTACTGG ACAGTATACG CTCTTCCCTC TTCCACCCAC       1150
CTTGCCCACC CCTGTGGTCC AGCTCCACCC CCTGCTTCCT GACCCTTCTG       1200
CTCCAACGCC CACCCCTACC AGCCCTCTTC TAAACACATC CTACACCCAC       1250
TCCCAGAATC TGTCTCAGGA AGGGTAAGGT TCTCAGACAC TGCCGACATC       1300
AGCATTGTCT CATGTACAGC TCCCTTCCCT GCAGGGCGCC CCTGGGAGAC       1350
AACTGGACAA GATTTCCTAC TTTCTCCTGA AACCCAAAGC CCTGGTAAAA       1400
GGGATACACA GGACTGAAAA GGGAATCATT TTTCACTGTA CATTATAAAC       1450
CTTCAGAAGC TATTTTTTTA AGCTATCAGC AATACTCATC AGAGCAGCTA       1500
GCTCTTTGGT CTATTTTCTG CAGAAATTTG CAACTCACTG ATTCTCTACA       1550
TGCTCTTTTT CTGTGATAAC TCTGCAAAGG CCTGGGCTGG CCTGGCAGTT       1600
GAACAGAGGG AGAGACTAAC CTTGAGTCAG AAAACAGAGA AAGGGTAATT       1650
TCCTTTGCTT CAAATTCAAG GCCTTCCAAC GCCCCCATCC CCTTTACTAT       1700
CATTCTCAGT GGGACTCTGA TCCCATATTC TTAACAGATC TTTACTCTTG       1750
AGAAATGAAT AAGCTTTCTC TCAGAAAAAA AAAAAAAAAA AAAAA            1795
```

(2) INFORMATION FOR SEQ ID NO:3:

(i) SEQUENCE CHARACTERISTICS:
(A) LENGTH: 42 amino acids
(B) TYPE: Amino Acid
(D) TOPOLOGY: Linear (xi) SEQUENCE DESCRIPTION: SEQ ID NO:3:

```
Leu Leu Leu Val Val Met Leu Leu Leu Thr Ala Arg Leu Thr Leu
-16 -15                 -10                 -5

Ser Ser Pro Ala Pro Pro Ala Cys Asp Leu Arg Val Leu Ser Lys
     1               5                  10

Leu Leu Arg Asp Ser His Val Leu His Ser Arg Leu
 15                  20                 25  26
```

(2) INFORMATION FOR SEQ ID NO:4:

(i) SEQUENCE CHARACTERISTICS:
(A) LENGTH: 390 base pairs
(B) TYPE: Nucleic Acid
(C) STRANDEDNESS: Single
(D) TOPOLOGY: Linear (xi) SEQUENCE DESCRIPTION: SEQ ID NO:4:

```
GAATTCCTGG AATACCAGCT GACAATGATT TCCTCCTCAT CTTTCAACCT         50
CACCTCTCCT CATCTAAGAA TTGCTCCTCG TGGTCATGCT TCTCCTAACT        100
GCAAGGCTAA CGCTGTCCAG CCCGGCTCCT CCTGCTTGTG ACCTCCGAGT        150
CCTCAGTAAA CTGCTTCGTG ACTCCCATGT CCTTCACAGC AGACTGGTGA        200
GAACTCCCAA CATTATCCCC TTTATCCGCG TAACTGGTAA GACACCCATA        250
CTCCCAGGAA GACACCATCA CTTCCTCTAA CTCCTTGACC CAATGACTAT        300
TCTTCCCATA TTGTCCCCAC CTACTGATCA CACTCTCTGA CAAGAATTAT        350
```

-continued

TCTTCACAAT ACAGCCCGCA TTTAAAAGCT CTCGTCTAGA 390

(2) INFORMATION FOR SEQ ID NO:5:

(i) SEQUENCE CHARACTERISTICS:
(A) LENGTH: 390 base pairs
(B) TYPE: Nucleic Acid
(C) STRANDEDNESS: Single
(D) TOPOLOGY: Linear (xi) SEQUENCE DESCRIPTION: SEQ ID NO:5:

TCTAGACGAG AGCTTTTAAA TGCGGGCTGT ATTGTGAAGA ATAATTCTTG 50

TCAGAGAGTG TGATCAGTAG GTGGGGACAA TATGGGAAGA ATAGTCATTG 100

GGTCAAGGAG TTAGAGGAAG TGATGGTGTC TTCCTGGGAG TATGGGTGTC 150

TTACCAGTTA CGCGGATAAA GGGGATAATG TTGGGAGTTC TCACCAGTCT 200

GCTGTGAAGG ACATGGGAGT CACGAAGCAG TTTACTGAGG ACTCGGAGGT 250

CACAAGCAGG AGGAGCCGGG CTGGACAGCG TTAGCCTTGC AGTTAGGAGA 300

AGCATGACCA CGAGGAGCAA TTCTTAGATG AGGAGAGGTG AGGTTGAAAG 350

ATGAGGAGGA AATCATTGTC AGCTGGTATT CCAGGAATTC 390

(2) INFORMATION FOR SEQ ID NO:6:

(i) SEQUENCE CHARACTERISTICS:
(A) LENGTH: 332 amino acids
(B) TYPE: Amino Acid
(D) TOPOLOGY: Linear (xi) SEQUENCE DESCRIPTION: SEQ ID NO:6:

Ser Pro Ala Pro Pro Ala Cys Asp Leu Arg Val Leu Ser Lys Leu
1 5 10 15

Leu Arg Asp Ser His Val Leu His Ser Arg Leu Ser Gln Cys Pro
20 25 30

Glu Val His Pro Leu Pro Thr Pro Val Leu Leu Pro Ala Val Asp
35 40 45

Phe Ser Leu Gly Glu Trp Lys Thr Gln Met Glu Glu Thr Lys Ala
50 55 60

Gln Asp Ile Leu Gly Ala Val Thr Leu Leu Leu Glu Gly Val Met
65 70 75

Ala Ala Arg Gly Gln Leu Gly Pro Thr Cys Leu Ser Ser Leu Leu
80 85 90

Gly Gln Leu Ser Gly Gln Val Arg Leu Leu Leu Gly Ala Leu Gln
95 100 105

Ser Leu Leu Gly Thr Gln Leu Pro Pro Gln Gly Arg Thr Thr Ala
110 115 120

His Lys Asp Pro Asn Ala Ile Phe Leu Ser Phe Gln His Leu Leu
125 130 135

Arg Gly Lys Val Arg Phe Leu Met Leu Val Gly Gly Ser Thr Leu
140 145 150

Cys Val Arg Arg Ala Pro Pro Thr Thr Ala Val Pro Ser Arg Thr
155 160 165

Ser Leu Val Leu Thr Leu Asn Glu Leu Pro Asn Arg Thr Ser Gly
170 175 180

Leu Leu Glu Thr Asn Phe Thr Ala Ser Ala Arg Thr Thr Gly Ser
185 190 195

Gly Leu Leu Lys Trp Gln Gln Gly Phe Arg Ala Lys Ile Pro Gly

-continued

```
                200                 205                 210

Leu Leu Asn Gln Thr Ser Arg Ser Leu Asp Gln Ile Pro Gly Tyr
                215                 220                 225

Leu Asn Arg Ile His Glu Leu Leu Asn Gly Thr Arg Gly Leu Phe
                230                 235                 240

Pro Gly Pro Ser Arg Arg Thr Leu Gly Ala Pro Asp Ile Ser Ser
                245                 250                 255

Gly Thr Ser Asp Thr Gly Ser Leu Pro Pro Asn Leu Gln Pro Gly
                260                 265                 270

Tyr Ser Pro Ser Pro Thr His Pro Pro Thr Gly Gln Tyr Thr Leu
                275                 280                 285

Phe Pro Leu Pro Pro Thr Leu Pro Thr Pro Val Val Gln Leu His
                290                 295                 300

Pro Leu Leu Pro Asp Pro Ser Ala Pro Thr Pro Thr Pro Thr Ser
                305                 310                 315

Pro Leu Leu Asn Thr Ser Tyr Thr His Ser Gln Asn Leu Ser Gln
                320                 325                 330

Glu Gly
    332
```

(2) INFORMATION FOR SEQ ID NO:7:

(i) SEQUENCE CHARACTERISTICS:
(A) LENGTH: 166 amino acids
(B) TYPE: Amino Acid
(D) TOPOLOGY: Linear (xi) SEQUENCE DESCRIPTION: SEQ ID NO:7:

```
Ala Pro Pro Arg Leu Ile Cys Asp Ser Arg Val Leu Glu Arg Tyr
  1               5                  10                  15

Leu Leu Glu Ala Lys Glu Ala Glu Asn Ile Thr Thr Gly Cys Ala
                 20                  25                  30

Glu His Cys Ser Leu Asn Glu Asn Ile Thr Val Pro Asp Thr Lys
                 35                  40                  45

Val Asn Phe Tyr Ala Trp Lys Arg Met Glu Val Gly Gln Gln Ala
                 50                  55                  60

Val Glu Val Trp Gln Gly Leu Ala Leu Leu Ser Glu Ala Val Leu
                 65                  70                  75

Arg Gly Gln Ala Leu Leu Val Asn Ser Ser Gln Pro Trp Glu Pro
                 80                  85                  90

Leu Gln Leu His Val Asp Lys Ala Val Ser Gly Leu Arg Ser Leu
                 95                 100                 105

Thr Thr Leu Leu Arg Ala Leu Gly Ala Gln Lys Glu Ala Ile Ser
                110                 115                 120

Pro Pro Asp Ala Ala Ser Ala Ala Pro Leu Arg Thr Ile Thr Ala
                125                 130                 135

Asp Thr Phe Arg Lys Leu Phe Arg Val Tyr Ser Asn Phe Leu Arg
                140                 145                 150

Gly Lys Leu Lys Leu Tyr Thr Gly Glu Ala Cys Arg Thr Gly Asp
                155                 160                 165

Arg
166
```

(2) INFORMATION FOR SEQ ID NO:8:

(i) SEQUENCE CHARACTERISTICS:
(A) LENGTH: 328 amino acids (B) TYPE: Amino Acid
(D) TOPOLOGY: Linear (xi) SEQUENCE DESCRIPTION: SEQ ID NO:8:

```
Ser Pro Ala Pro Pro Ala Cys Asp Leu Arg Val Leu Ser Lys Leu
  1               5                  10                  15

Leu Arg Asp Ser His Val Leu His Ser Arg Leu Ser Gln Cys Pro
                 20                  25                  30

Glu Val His Pro Leu Pro Thr Pro Val Leu Leu Pro Ala Val Asp
                 35                  40                  45

Phe Ser Leu Gly Glu Trp Lys Thr Gln Met Glu Glu Thr Lys Ala
                 50                  55                  60

Gln Asp Ile Leu Gly Ala Val Thr Leu Leu Leu Glu Gly Val Met
                 65                  70                  75

Ala Ala Arg Gly Gln Leu Gly Pro Thr Cys Leu Ser Ser Leu Leu
                 80                  85                  90

Gly Gln Leu Ser Gly Gln Val Arg Leu Leu Leu Gly Ala Leu Gln
                 95                 100                 105

Ser Leu Leu Gly Thr Gln Gly Arg Thr Thr Ala His Lys Asp Pro
                110                 115                 120

Asn Ala Ile Phe Leu Ser Phe Gln His Leu Leu Arg Gly Lys Val
                125                 130                 135

Arg Phe Leu Met Leu Val Gly Gly Ser Thr Leu Cys Val Arg Arg
                140                 145                 150

Ala Pro Pro Thr Thr Ala Val Pro Ser Arg Thr Ser Leu Val Leu
                155                 160                 165

Thr Leu Asn Glu Leu Pro Asn Arg Thr Ser Gly Leu Leu Glu Thr
                170                 175                 180

Asn Phe Thr Ala Ser Ala Arg Thr Thr Gly Ser Gly Leu Leu Lys
                185                 190                 195

Trp Gln Gln Gly Phe Arg Ala Lys Ile Pro Gly Leu Leu Asn Gln
                200                 205                 210

Thr Ser Arg Ser Leu Asp Gln Ile Pro Gly Tyr Leu Asn Arg Ile
                215                 220                 225

His Glu Leu Leu Asn Gly Thr Arg Gly Leu Phe Pro Gly Pro Ser
                230                 235                 240

Arg Arg Thr Leu Gly Ala Pro Asp Ile Ser Ser Gly Thr Ser Asp
                245                 250                 255

Thr Gly Ser Leu Pro Pro Asn Leu Gln Pro Gly Tyr Ser Pro Ser
                260                 265                 270

Pro Thr His Pro Pro Thr Gly Gln Tyr Thr Leu Phe Pro Leu Pro
                275                 280                 285

Pro Thr Leu Pro Thr Pro Val Val Gln Leu His Pro Leu Leu Pro
                290                 295                 300

Asp Pro Ser Ala Pro Thr Pro Thr Pro Thr Ser Pro Leu Leu Asn
                305                 310                 315

Thr Ser Tyr Thr His Ser Gln Asn Leu Ser Gln Glu Gly
                320                 325         328
```

(2) INFORMATION FOR SEQ ID NO:9:

(i) SEQUENCE CHARACTERISTICS:
(A) LENGTH: 265 amino acids
(B) TYPE: Amino Acid
(D) TOPOLOGY: Linear (xi) SEQUENCE DESCRIPTION: SEQ ID NO:9:

```
Ser Pro Ala Pro Pro Ala Cys Asp Leu Arg Val Leu Ser Lys Leu
  1             5                  10                  15

Leu Arg Asp Ser His Val Leu His Ser Arg Leu Ser Gln Cys Pro
                20                  25                  30

Glu Val His Pro Leu Pro Thr Pro Val Leu Leu Pro Ala Val Asp
                35                  40                  45

Phe Ser Leu Gly Glu Trp Lys Thr Gln Met Glu Glu Thr Lys Ala
                50                  55                  60

Gln Asp Ile Leu Gly Ala Val Thr Leu Leu Leu Glu Gly Val Met
                65                  70                  75

Ala Ala Arg Gly Gln Leu Gly Pro Thr Cys Leu Ser Ser Leu Leu
                80                  85                  90

Gly Gln Leu Ser Gly Gln Val Arg Leu Leu Leu Gly Ala Leu Gln
                95                 100                 105

Ser Leu Leu Gly Thr Gln Leu Pro Pro Gln Gly Arg Thr Thr Ala
               110                 115                 120

His Lys Asp Pro Asn Ala Ile Phe Leu Ser Phe Gln His Leu Leu
               125                 130                 135

Arg Gly Lys Asp Phe Trp Ile Val Gly Asp Lys Leu His Cys Leu
               140                 145                 150

Ser Gln Asn Tyr Trp Leu Trp Ala Ser Glu Val Ala Ala Gly Ile
               155                 160                 165

Gln Ser Gln Asp Ser Trp Ser Ala Glu Pro Asn Leu Gln Val Pro
               170                 175                 180

Gly Pro Asn Pro Arg Ile Pro Glu Gln Asp Thr Arg Thr Leu Glu
               185                 190                 195

Trp Asn Ser Trp Thr Leu Ser Trp Thr Leu Thr Gln Asp Pro Arg
               200                 205                 210

Ser Pro Gly His Phe Leu Arg Asn Ile Arg His Arg Leu Pro Ala
               215                 220                 225

Thr Gln Pro Pro Ala Trp Ile Phe Ser Phe Pro Asn Pro Ser Ser
               230                 235                 240

Tyr Trp Thr Val Tyr Ala Leu Pro Ser Ser Thr His Leu Ala His
               245                 250                 255

Pro Cys Gly Pro Ala Pro Pro Pro Ala Ser
               260                 265
```

(2) INFORMATION FOR SEQ ID NO:10:

(i) SEQUENCE CHARACTERISTICS:
(A) LENGTH: 261 amino acids
(B) TYPE: Amino Acid
(D) TOPOLOGY: Linear (xi) SEQUENCE DESCRIPTION: SEQ ID NO:10:

```
Ser Pro Ala Pro Pro Ala Cys Asp Leu Arg Val Leu Ser Lys Leu
  1             5                  10                  15

Leu Arg Asp Ser His Val Leu His Ser Arg Leu Ser Gln Cys Pro
                20                  25                  30

Glu Val His Pro Leu Pro Thr Pro Val Leu Leu Pro Ala Val Asp
                35                  40                  45

Phe Ser Leu Gly Glu Trp Lys Thr Gln Met Glu Glu Thr Lys Ala
                50                  55                  60

Gln Asp Ile Leu Gly Ala Val Thr Leu Leu Leu Glu Gly Val Met
                65                  70                  75
```

-continued

```
Ala Ala Arg Gly Gln Leu Gly Pro Thr Cys Leu Ser Ser Leu Leu
                80                  85                  90

Gly Gln Leu Ser Gly Gln Val Arg Leu Leu Leu Gly Ala Leu Gln
                95                  100                 105

Ser Leu Leu Gly Thr Gln Gly Arg Thr Thr Ala His Lys Asp Pro
                110                 115                 120

Asn Ala Ile Phe Leu Ser Phe Gln His Leu Leu Arg Gly Lys Asp
                125                 130                 135

Phe Trp Ile Val Gly Asp Lys Leu His Cys Leu Ser Gln Asn Tyr
                140                 145                 150

Trp Leu Trp Ala Ser Glu Val Ala Ala Gly Ile Gln Ser Gln Asp
                155                 160                 165

Ser Trp Ser Ala Glu Pro Asn Leu Gln Val Pro Gly Pro Asn Pro
                170                 175                 180

Arg Ile Pro Glu Gln Asp Thr Arg Thr Leu Glu Trp Asn Ser Trp
                185                 190                 195

Thr Leu Ser Trp Thr Leu Thr Gln Asp Pro Arg Ser Pro Gly His
                200                 205                 210

Phe Leu Arg Asn Ile Arg His Arg Leu Pro Ala Thr Gln Pro Pro
                215                 220                 225

Ala Trp Ile Phe Ser Phe Pro Asn Pro Ser Ser Tyr Trp Thr Val
                230                 235                 240

Tyr Ala Leu Pro Ser Ser Thr His Leu Ala His Pro Cys Gly Pro
                245                 250                 255

Ala Pro Pro Pro Ala Ser
                260 261
```

(2) INFORMATION FOR SEQ ID NO:11:

(i) SEQUENCE CHARACTERISTICS:
(A) LENGTH: 1443 base pairs
(B) TYPE: Nucleic Acid
(C) STRANDEDNESS: Single
(D) TOPOLOGY: Linear (xi) SEQUENCE DESCRIPTION: SEQ ID NO:11:

```
GAGTCCTTGG CCCACCTCTC TCCCACCCGA CTCTGCCGAA AGAAGCACAG    50

AAGCTCAAGC CGCCTCCATG GCCCCAGGAA AGATTCAGGG GAGAGGCCCC   100

ATACAGGGAG CCACTTCAGT TAGACACCCT GGCCAGAATG GAGCTGACTG   150

ATTTGCTCCT GGCGGCCATG CTTCTTGCAG TGGCAAGACT AACTCTGTCC   200

AGCCCCGTAG CTCCTGCCTG TGACCCCAGA CTCCTAAATA AACTGCTGCG   250

TGACTCCCAC CTCCTTCACA GCCGACTGAG TCAGTGTCCC GACGTCGACC   300

CTTTGTCTAT CCCTGTTCTG CTGCCTGCTG TGGACTTTAG CCTGGGAGAA   350

TGGAAAACCC AGACGGAACA GAGCAAGGCA CAGGACATTC TAGGGGCAGT   400

GTCCCTTCTA CTGGAGGGAG TGATGGCAGC ACGAGGACAG TTGGAACCCT   450

CCTGCCTCTC ATCCCTCCTG GGACAGCTTT CTGGGCAGGT TCGCCTCCTC   500

TTGGGGGCCC TGCAGGGCCT CCTAGGAACC CAGGGCAGGA CCACAGCTCA   550

CAAGGACCCC AATGCCCTCT TCTTGAGCTT GCAACAACTG CTTCGGGGAA   600

AGGTGCGCTT CCTGCTTCTG GTAGAAGGTC CCACCCTCTG TGTCAGACGG   650

ACCCTGCCAA CCACAGCTGT CCCAAGCAGT ACTTCTCAAC TCCTCACACT   700

AAACAAGTTC CCAAACAGGA CTTCTGGATT GTTGGAGACG AACTTCAGTG   750
```

-continued

```
TCACAGCCAG AACTGCTGGC CCTGGACTTC TGAGCAGGCT TCAGGGATTC               800

AGAGTCAAGA TTACTCCTGG TCAGCTAAAT CAAACCTCCA GGTCCCCAGT               850

CCAAATCTCT GGATACCTGA ACAGGACACA CGGACCTGTG AATGGAACTC               900

ATGGGCTCTT TGCTGGAACC TCACTTCAGA CCCTGGAAGC CTCAGACATC               950

TCGCCCGGAG CTTTCAACAA AGGCTCCCTG GCATTCAACC TCCAGGGTGG              1000

ACTTCCTCCT TCTCCAAGCC TTGCTCCTGA TGGACACACA CCCTTCCCTC              1050

CTTCACCTGC CTTGCCCACC ACCCATGGAT CTCCACCCCA GCTCCACCCC              1100

CTGTTTCCTG ACCCTTCCAC CACCATGCCT AACTCTACCG CCCCTCATCC              1150

AGTCACAATG TACCCTCATC CCAGGAATTT GTCTCAGGAA ACATAGCGCG              1200

GGCACTGGCC CAGTGAGCGT CTGCAGCTTC TCTCGGGGAC AAGCTTCCCC              1250

AGGAAGGCTG AGAGGCAGCT GCATCTGCTC CAGATGTTCT GCTTTCACCT              1300

AAAAGGCCCT GGGGAAGGGA TACACAGCAC TGGAGATTGT AAAATTTTAG              1350

GAGCTATTTT TTTTTAACCT ATCAGCAATA TTCATCAGAG CAGCTAGCGA              1400

TCTTTGGTCT ATTTTCGGTA TAAATTTGAA AATCACTAAT TCT                     1443
```

(2) INFORMATION FOR SEQ ID NO:12:

(i) SEQUENCE CHARACTERISTICS:
(A) LENGTH: 352 amino acids
(B) TYPE: Amino Acid
(D) TOPOLOGY: Linear (xi) SEQUENCE DESCRIPTION: SEQ ID NO:12:

```
Met Glu Leu Thr Asp Leu Leu Leu Ala Ala Met Leu Leu Ala Val
-21 -20                 -15                 -10

Ala Arg Leu Thr Leu Ser Ser Pro Val Ala Pro Ala Cys Asp Pro
     -5                   1               5

Arg Leu Leu Asn Lys Leu Leu Arg Asp Ser His Leu Leu His Ser
 10                  15                  20

Arg Leu Ser Gln Cys Pro Asp Val Asp Pro Leu Ser Ile Pro Val
 25                  30                  35

Leu Leu Pro Ala Val Asp Phe Ser Leu Gly Glu Trp Lys Thr Gln
 40                  45                  50

Thr Glu Gln Ser Lys Ala Gln Asp Ile Leu Gly Ala Val Ser Leu
 55                  60                  65

Leu Leu Glu Gly Val Met Ala Ala Arg Gly Gln Leu Glu Pro Ser
 70                  75                  80

Cys Leu Ser Ser Leu Leu Gly Gln Leu Ser Gly Gln Val Arg Leu
 85                  90                  95

Leu Leu Gly Ala Leu Gln Gly Leu Leu Gly Thr Gln Gly Arg Thr
100                 105                 110

Thr Ala His Lys Asp Pro Asn Ala Leu Phe Leu Ser Leu Gln Gln
115                 120                 125

Leu Leu Arg Gly Lys Val Arg Phe Leu Leu Leu Val Glu Gly Pro
130                 135                 140

Thr Leu Cys Val Arg Arg Thr Leu Pro Thr Thr Ala Val Pro Ser
145                 150                 155

Ser Thr Ser Gln Leu Leu Thr Leu Asn Lys Phe Pro Asn Arg Thr
160                 165                 170

Ser Gly Leu Leu Glu Thr Asn Phe Ser Val Thr Ala Arg Thr Ala
175                 180                 185
```

```
Gly Pro Gly Leu Leu Ser Arg Leu Gln Gly Phe Arg Val Lys Ile
190                 195                 200

Thr Pro Gly Gln Leu Asn Gln Thr Ser Arg Ser Pro Val Gln Ile
205                 210                 215

Ser Gly Tyr Leu Asn Arg Thr His Gly Pro Val Asn Gly Thr His
220                 225                 230

Gly Leu Phe Ala Gly Thr Ser Leu Gln Thr Leu Glu Ala Ser Asp
235                 240                 245

Ile Ser Pro Gly Ala Phe Asn Lys Gly Ser Leu Ala Phe Asn Leu
250                 255                 260

Gln Gly Gly Leu Pro Pro Ser Pro Ser Leu Ala Pro Asp Gly His
265                 270                 275

Thr Pro Phe Pro Pro Ser Pro Ala Leu Pro Thr Thr His Gly Ser
280                 285                 290

Pro Pro Gln Leu His Pro Leu Phe Pro Asp Pro Ser Thr Thr Met
295                 300                 305

Pro Asn Ser Thr Ala Pro His Pro Val Thr Met Tyr Pro His Pro
310                 315                 320

Arg Asn Leu Ser Gln Glu Thr
325                 330 331
```

(2) INFORMATION FOR SEQ ID NO:13:

(i) SEQUENCE CHARACTERISTICS:
(A) LENGTH: 1536 base pairs
(B) TYPE: Nucleic Acid
(C) STRANDEDNESS: Single
(D) TOPOLOGY: Linear (xi) SEQUENCE DESCRIPTION: SEQ ID NO:13:

```
GAGTCCTTGG CCCACCTCTC TCCCACCCGA CTCTGCCGAA AGAAGCACAG     50

AAGCTCAAGC CGCCTCCATG GCCCCAGGAA AGATTCAGGG GAGAGGCCCC    100

ATACAGGGAG CCACTTCAGT TAGACACCCT GGCCAGAATG GAGCTGACTG    150

ATTTGCTCCT GGCGGCCATG CTTCTTGCAG TGGCAAGACT AACTCTGTCC    200

AGCCCCGTAG CTCCTGCCTG TGACCCCAGA CTCCTAAATA AACTGCTGCG    250

TGACTCCCAC CTCCTTCACA GCCGACTGAG TCAGTGTCCC GACGTCGACC    300

CTTTGTCTAT CCCTGTTCTG CTGCCTGCTG TGGACTTTAG CCTGGGAGAA    350

TGGAAAACCC AGACGGAACA GAGCAAGGCA CAGGACATTC TAGGGGCAGT    400

GTCCCTTCTA CTGGAGGGAG TGATGGCAGC ACGAGGACAG TTGGAACCCT    450

CCTGCCTCTC ATCCCTCCTG GGACAGCTTT CTGGGCAGGT TCGCCTCCTC    500

TTGGGGGCCC TGCAGGGCCT CCTAGGAACC CAGCTTCCTC TACAGGGCAG    550

GACCACAGCT CACAAGGACC CCAATGCCCT CTTCTTGAGC TTGCAACAAC    600

TGCTTCGGGG AAAGGTGCGC TTCCTGCTTC TGGTAGAAGG TCCCACCCTC    650

TGTGTCAGAC GGACCCTGCC AACCACAGCT GTCCCAAGCA GTACTTCTCA    700

ACTCCTCACA CTAAACAAGT TCCCAAACAG GACTTCTGGA TTGTTGGAGA    750

CGAACTTCAG TGTCACAGCC AGAACTGCTG GCCCTGGACT TCTGAGCAGG    800

CTTCAGGGAT TCAGAGTCAA GATTACTCCT GGTCAGCTAA ATCAAACCTC    850

CAGGTCCCCA GTCCAAATCT CTGGATACCT GAACAGGACA CACGGACCTG    900

TGAATGGAAC TCATGGGCTC TTTGCTGGAA CCTCACTTCA GACCCTGGAA    950

GCCTCAGACA TCTCGCCCGG AGCTTTCAAC AAAGGCTCCC TGGCATTCAA   1000
```

```
CCTCCAGGGT GGACTTCCTC CTTCTCCAAG CCTTGCTCCT GATGGACACA    1050

CACCCTTCCC TCCTTCACCT GCCTTGCCCA CCACCCATGG ATCTCCACCC    1100

CAGCTCCACC CCCTGTTTCC TGACCCTTCC ACCACCATGC CTAACTCTAC    1150

CGCCCCTCAT CCAGTCACAA TGTACCCTCA TCCCAGGAAT TTGTCTCAGG    1200

AAACATAGCG CGGGCACTGG CCCAGTGAGC GTCTGCAGCT TCTCTCGGGG    1250

ACAAGCTTCC CCAGGAAGGC TGAGAGGCAG CTGCATCTGC TCCAGATGTT    1300

CTGCTTTCAC CTAAAAGGCC CTGGGGAAGG GATACACAGC ACTGGAGATT    1350

GTAAAATTTT AGGAGCTATT TTTTTTTAAC CTATCAGCAA TATTCATCAG    1400

AGCAGCTAGC GATCTTTGGT CTATTTTCGG TATAAATTTG AAAATCACTA    1450

AAAAAAAAAA AAAAAAAAAA AAAAAAAAAA AAAAAAAAAA AAAAAAAAAA    1500

AAAAAAAAAA AAAAAAAAAA AAAAAAAAAA AAAAAA                   1536
```

(2) INFORMATION FOR SEQ ID NO:14:

(i) SEQUENCE CHARACTERISTICS:
(A) LENGTH: 356 amino acids
(B) TYPE: Amino Acid
(D) TOPOLOGY: Linear (xi) SEQUENCE DESCRIPTION: SEQ ID NO:14:

```
Met Glu Leu Thr Asp Leu Leu Leu Ala Ala Met Leu Leu Ala Val
-21 -20                 -15                 -10

Ala Arg Leu Thr Leu Ser Ser Pro Val Ala Pro Ala Cys Asp Pro
     -5                  1               5

Arg Leu Leu Asn Lys Leu Leu Arg Asp Ser His Leu Leu His Ser
 10                  15                  20

Arg Leu Ser Gln Cys Pro Asp Val Asp Pro Leu Ser Ile Pro Val
 25                  30                  35

Leu Leu Pro Ala Val Asp Phe Ser Leu Gly Glu Trp Lys Thr Gln
 40                  45                  50

Thr Glu Gln Ser Lys Ala Gln Asp Ile Leu Gly Ala Val Ser Leu
 55                  60                  65

Leu Leu Glu Gly Val Met Ala Ala Arg Gly Gln Leu Glu Pro Ser
 70                  75                  80

Cys Leu Ser Ser Leu Leu Gly Gln Leu Ser Gly Gln Val Arg Leu
 85                  90                  95

Leu Leu Gly Ala Leu Gln Gly Leu Leu Gly Thr Gln Leu Pro Leu
100                 105                 110

Gln Gly Arg Thr Thr Ala His Lys Asp Pro Asn Ala Leu Phe Leu
115                 120                 125

Ser Leu Gln Gln Leu Leu Arg Gly Lys Val Arg Phe Leu Leu Leu
130                 135                 140

Val Glu Gly Pro Thr Leu Cys Val Arg Arg Thr Leu Pro Thr Thr
145                 150                 155

Ala Val Pro Ser Ser Thr Ser Gln Leu Leu Thr Leu Asn Lys Phe
160                 165                 170

Pro Asn Arg Thr Ser Gly Leu Leu Glu Thr Asn Phe Ser Val Thr
175                 180                 185

Ala Arg Thr Ala Gly Pro Gly Leu Leu Ser Arg Leu Gln Gly Phe
190                 195                 200

Arg Val Lys Ile Thr Pro Gly Gln Leu Asn Gln Thr Ser Arg Ser
205                 210                 215
```

Pro Val Gln Ile Ser Gly Tyr Leu Asn Arg Thr His Gly Pro Val
220 225 230

Asn Gly Thr His Gly Leu Phe Ala Gly Thr Ser Leu Gln Thr Leu
235 240 245

Glu Ala Ser Asp Ile Ser Pro Gly Ala Phe Asn Lys Gly Ser Leu
250 255 260

Ala Phe Asn Leu Gln Gly Gly Leu Pro Pro Ser Pro Ser Leu Ala
265 270 275

Pro Asp Gly His Thr Pro Phe Pro Pro Ser Pro Ala Leu Pro Thr
280 285 290

Thr His Gly Ser Pro Pro Gln Leu His Pro Leu Phe Pro Asp Pro
295 300 305

Ser Thr Thr Met Pro Asn Ser Thr Ala Pro His Pro Val Thr Met
310 315 320

Tyr Pro His Pro Arg Asn Leu Ser Gln Glu Thr
325 330 335

(2) INFORMATION FOR SEQ ID NO:15:

(i) SEQUENCE CHARACTERISTICS:
(A) LENGTH: 241 amino acids
(B) TYPE: Amino Acid
(D) TOPOLOGY: Linear (xi) SEQUENCE DESCRIPTION: SEQ ID NO:15:

Ser Pro Val Ala Pro Ala Cys Asp Pro Arg Leu Leu Asn Lys Leu
1 5 10 15

Leu Arg Asp Ser His Leu Leu His Ser Arg Leu Ser Gln Cys Pro
20 25 30

Asp Val Asp Pro Leu Ser Ile Pro Val Leu Leu Pro Ala Val Asp
35 40 45

Phe Ser Leu Gly Glu Trp Lys Thr Gln Thr Glu Gln Ser Lys Ala
50 55 60

Gln Asp Ile Leu Gly Ala Val Ser Leu Leu Leu Glu Gly Val Met
65 70 75

Ala Ala Arg Gly Gln Leu Glu Pro Ser Cys Leu Ser Ser Leu Leu
80 85 90

Gly Gln Leu Ser Gly Gln Val Arg Leu Leu Leu Gly Ala Leu Gln
95 100 105

Gly Leu Leu Gly Thr Gln Leu Pro Leu Gln Gly Arg Thr Thr Ala
110 115 120

His Lys Asp Pro Asn Ala Leu Phe Leu Ser Leu Gln Gln Leu Leu
125 130 135

Arg Gly Lys Asp Phe Trp Ile Val Gly Asp Glu Leu Gln Cys His
140 145 150

Ser Gln Asn Cys Trp Pro Trp Thr Ser Glu Gln Ala Ser Gly Ile
155 160 165

Gln Ser Gln Asp Tyr Ser Trp Ser Ala Lys Ser Asn Leu Gln Val
170 175 180

Pro Ser Pro Asn Leu Trp Ile Pro Glu Gln Asp Thr Arg Thr Cys
185 190 195

Glu Trp Asn Ser Trp Ala Leu Cys Trp Asn Leu Thr Ser Asp Pro
200 205 210

Gly Ser Leu Arg His Leu Ala Arg Ser Phe Gln Gln Arg Leu Pro
215 220 225

```
Gly Ile Gln Pro Pro Gly Trp Thr Ser Ser Phe Ser Lys Pro Cys
                230                 235                 240

Ser
241
```

(2) INFORMATION FOR SEQ ID NO:16:

(i) SEQUENCE CHARACTERISTICS:
(A) LENGTH: 335 amino acids
(B) TYPE: Amino Acid
(D) TOPOLOGY: Linear (xi) SEQUENCE DESCRIPTION: SEQ ID NO:16:

```
Ser Pro Val Ala Pro Ala Cys Asp Pro Arg Leu Leu Asn Lys Leu
  1               5                  10                  15

Leu Arg Asp Ser His Leu Leu His Ser Arg Leu Ser Gln Cys Pro
                 20                  25                  30

Asp Val Asp Pro Leu Ser Ile Pro Val Leu Leu Pro Ala Val Asp
                 35                  40                  45

Phe Ser Leu Gly Glu Trp Lys Thr Gln Thr Glu Gln Ser Lys Ala
                 50                  55                  60

Gln Asp Ile Leu Gly Ala Val Ser Leu Leu Leu Glu Gly Val Met
                 65                  70                  75

Ala Ala Arg Gly Gln Leu Glu Pro Ser Cys Leu Ser Ser Leu Leu
                 80                  85                  90

Gly Gln Leu Ser Gly Gln Val Arg Leu Leu Leu Gly Ala Leu Gln
                 95                 100                 105

Gly Leu Leu Gly Thr Gln Leu Pro Leu Gln Gly Arg Thr Thr Ala
                110                 115                 120

His Lys Asp Pro Asn Ala Leu Phe Leu Ser Leu Gln Gln Leu Leu
                125                 130                 135

Arg Gly Lys Val Arg Phe Leu Leu Leu Val Glu Gly Pro Thr Leu
                140                 145                 150

Cys Val Arg Arg Thr Leu Pro Thr Thr Ala Val Pro Ser Ser Thr
                155                 160                 165

Ser Gln Leu Leu Thr Leu Asn Lys Phe Pro Asn Arg Thr Ser Gly
                170                 175                 180

Leu Leu Glu Thr Asn Phe Ser Val Thr Ala Arg Thr Ala Gly Pro
                185                 190                 195

Gly Leu Leu Ser Arg Leu Gln Gly Phe Arg Val Lys Ile Thr Pro
                200                 205                 210

Gly Gln Leu Asn Gln Thr Ser Arg Ser Pro Val Gln Ile Ser Gly
                215                 220                 225

Tyr Leu Asn Arg Thr His Gly Pro Val Asn Gly Thr His Gly Leu
                230                 235                 240

Phe Ala Gly Thr Ser Leu Gln Thr Leu Glu Ala Ser Asp Ile Ser
                245                 250                 255

Pro Gly Ala Phe Asn Lys Gly Ser Leu Ala Phe Asn Leu Gln Gly
                260                 265                 270

Gly Leu Pro Pro Ser Pro Ser Leu Ala Pro Asp Gly His Thr Pro
                275                 280                 285

Phe Pro Pro Ser Pro Ala Leu Pro Thr Thr His Gly Ser Pro Pro
                290                 295                 300

Gln Leu His Pro Leu Phe Pro Asp Pro Ser Thr Thr Met Pro Asn
                305                 310                 315

Ser Thr Ala Pro His Pro Val Thr Met Tyr Pro His Pro Arg Asn
```

320 325 330

Leu Ser Gln Glu Thr
335

(2) INFORMATION FOR SEQ ID NO:17:

(i) SEQUENCE CHARACTERISTICS:
(A) LENGTH: 332 amino acids
(B) TYPE: Amino Acid
(D) TOPOLOGY: Linear (xi) SEQUENCE DESCRIPTION: SEQ ID NO:17:

Ser Pro Ala Pro Pro Ala Cys Asp Pro Arg Leu Leu Asn Lys Leu
1 5 10 15

Leu Arg Asp Ser His Val Leu His Gly Arg Leu Ser Gln Cys Pro
20 25 30

Asp Ile Asn Pro Leu Ser Thr Pro Val Leu Leu Pro Ala Val Asp
35 40 45

Phe Thr Leu Gly Glu Trp Lys Thr Gln Thr Glu Gln Thr Lys Ala
50 55 60

Gln Asp Val Leu Gly Ala Thr Thr Leu Leu Leu Glu Ala Val Met
65 70 75

Thr Ala Arg Gly Gln Val Gly Pro Pro Cys Leu Ser Ser Leu Leu
80 85 90

Val Gln Leu Ser Gly Gln Val Arg Leu Leu Leu Gly Ala Leu Gln
95 100 105

Asp Leu Leu Gly Met Gln Leu Pro Pro Gln Gly Arg Thr Thr Ala
110 115 120

His Lys Asp Pro Ser Ala Ile Phe Leu Asn Phe Gln Gln Leu Leu
125 130 135

Arg Gly Lys Val Arg Phe Leu Leu Leu Val Val Gly Pro Ser Leu
140 145 150

Cys Ala Lys Arg Ala Pro Pro Ala Ile Ala Val Pro Ser Ser Thr
155 160 165

Ser Pro Phe His Thr Leu Asn Lys Leu Pro Asn Arg Thr Ser Gly
170 175 180

Leu Leu Glu Thr Asn Ser Ser Ile Ser Ala Arg Thr Thr Gly Ser
185 190 195

Gly Phe Leu Lys Arg Leu Gln Ala Phe Arg Ala Lys Ile Pro Gly
200 205 210

Leu Leu Asn Gln Thr Ser Arg Ser Leu Asp Gln Ile Pro Gly His
215 220 225

Gln Asn Gly Thr His Gly Pro Leu Ser Gly Ile His Gly Leu Phe
230 235 240

Pro Gly Pro Gln Pro Gly Ala Leu Gly Ala Pro Asp Ile Pro Pro
245 250 255

Ala Thr Ser Gly Met Gly Ser Arg Pro Thr Tyr Leu Gln Pro Gly
260 265 270

Glu Ser Pro Ser Pro Ala His Pro Ser Pro Gly Arg Tyr Thr Leu
275 280 285

Phe Ser Pro Ser Pro Thr Ser Pro Ser Pro Thr Val Gln Leu Gln
290 295 300

Pro Leu Leu Pro Asp Pro Ser Ala Ile Thr Pro Asn Ser Thr Ser
305 310 315

Pro Leu Leu Phe Ala Ala His Pro His Phe Gln Asn Leu Ser Gln
320 325 330

```
Glu Glu
    332
```

(2) INFORMATION FOR SEQ ID NO:18:

(i) SEQUENCE CHARACTERISTICS:
(A) LENGTH: 1026 base pairs
(B) TYPE: Nucleic Acid
(C) STRANDEDNESS: Single
(D) TOPOLOGY: Linear (xi) SEQUENCE DESCRIPTION: SEQ ID NO:18:

```
AGCCCGGCTC CTCCTGCCTG TGACCCCCGA CTCCTAAATA AACTGCTTCG      50

TGACTCCCAT GTCCTTCACG GCAGACTGAG CCAGTGCCCA GACATTAACC     100

CTTTGTCCAC ACCTGTCCTG CTGCCTGCTG TGGACTTCAC CTTGGGAGAA     150

TGGAAAACCC AGACGGAGCA GACAAAGGCA CAGGATGTCC TGGGAGCCAC     200

AACCCTTCTG CTGGAGGCAG TGATGACAGC ACGGGGACAA GTGGGACCCC     250

CTTGCCTCTC ATCCCTGCTG GTGCAGCTTT CTGGACAGGT TCGCCTCCTC     300

CTCGGGGCCC TGCAGGACCT CCTTGGAATG CAGCTTCCTC CACAGGGAAG     350

GACCACAGCT CACAAGGATC CCAGTGCCAT CTTCCTGAAC TTCCAACAAC     400

TGCTCCGAGG AAAGGTGCGT TTCCTGCTCC TTGTAGTGGG GCCCTCCCTC     450

TGTGCCAAGA GGGCCCCACC CGCCATAGCT GTCCCGAGCA GCACCTCTCC     500

ATTCCACACA CTGAACAAGC TCCCAAACAG GACCTCTGGA TTGTTGGAGA     550

CAAACTCCAG TATCTCAGCC AGAACTACTG GCTCTGGATT TCTCAAGAGG     600

CTGCAGGCAT TCAGAGCCAA GATTCCTGGT CTGCTGAACC AAACCTCCAG     650

GTCCCTAGAC CAAATCCCTG GACACCAGAA TGGGACACAC GGACCCTTGA     700

GTGGAATTCA TGGACTCTTT CCTGGACCCC AACCCGGGGC CCTCGGAGCT     750

CCAGACATTC CTCCAGCAAC TTCAGGCATG GCTCCCGGC CAACCTACCT      800

CCAGCCTGGA GAGTCTCCTT CCCCAGCTCA CCCTTCTCCT GGACGATACA     850

CTCTCTTCTC TCCTTCACCC ACCTCGCCCT CCCCCACAGT CCAGCTCCAG     900

CCTCTGCTTC CTGACCCCTC TGCGATCACA CCCAACTCTA CCAGTCCTCT     950

TCTATTTGCA GCTCACCCTC ATTTCCAGAA CCTGTCTCAG GAAGAGTAAG    1000

GTGCTCAGAC CCTGCCAACT TCAGCA                              1026
```

(2) INFORMATION FOR SEQ ID NO:19:

(i) SEQUENCE CHARACTERISTICS:
(A) LENGTH: 1014 base pairs
(B) TYPE: Nucleic Acid
(C) STRANDEDNESS: Single
(D) TOPOLOGY: Linear (xi) SEQUENCE DESCRIPTION: SEQ ID NO:19:

```
AGCCCGGCTC CTCCTGCCTG TGACCCCCGA CTCCTAAATA AACTGCTTCG      50

TGACTCCCAT GTCCTTCACG GCAGACTGAG CCAGTGCCCA GACATTAACC     100

CTTTGTCCAC ACCTGTCCTG CTGCCTGCTG TGGACTTCAC CTTGGGAGAA     150

TGGAAAACCC AGACGGAGCA GACAAAGGCA CAGGATGTCC TGGGAGCCAC     200

AACCCTTCTG CTGGAGGCAG TGATGACAGC ACGGGGACAA GTGGGACCCC     250

CTTGCCTCTC ATCCCTGCTG GTGCAGCTTT CTGGACAGGT TCGCCTCCTC     300
```

-continued

```
CTCGGGGCCC TGCAGGACCT CCTTGGAATG CAGGGAAGGA CCACAGCTCA          350

CAAGGATCCC AGTGCCATCT TCCTGAACTT CCAACAACTG CTCCGAGGAA          400

AGGTGCGTTT CCTGCTCCTT GTAGTGGGGC CCTCCCTCTG TGCCAAGAGG          450

GCCCCACCCG CCATAGCTGT CCCGAGCAGC ACCTCTCCAT TCCACACACT          500

GAACAAGCTC CCAAACAGGA CCTCTGGATT GTTGGAGACA AACTCCAGTA          550

TCTCAGCCAG AACTACTGGC TCTGGATTTC TCAAGAGGCT GCAGGCATTC          600

AGAGCCAAGA TTCCTGGTCT GCTGAACCAA ACCTCCAGGT CCCTAGACCA          650

AATCCCTGGA CACCAGAATG GGACACACGG ACCCTTGAGT GGAATTCATG          700

GACTCTTTCC TGGACCCCAA CCCGGGGCCC TCGGAGCTCC AGACATTCCT          750

CCAGCAACTT CAGGCATGGG CTCCCGGCCA ACCTACCTCC AGCCTGGAGA          800

GTCTCCTTCC CCAGCTCACC CTTCTCCTGG ACGATACACT CTCTTCTCTC          850

CTTCACCCAC CTCGCCCTCC CCCACAGTCC AGCTCCAGCC TCTGCTTCCT          900

GACCCCTCTG CGATCACACC CAACTCTACC AGTCCTCTTC TATTTGCAGC          950

TCACCCTCAT TTCCAGAACC TGTCTCAGGA AGAGTAAGGT GCTCAGACCC         1000

TGCCAACTTC AGCA                                                1014
```

(2) INFORMATION FOR SEQ ID NO:20:

(i) SEQUENCE CHARACTERISTICS:
(A) LENGTH: 328 amino acids
(B) TYPE: Amino Acid
(D) TOPOLOGY: Linear (xi) SEQUENCE DESCRIPTION: SEQ ID NO:20:

```
Ser Pro Ala Pro Pro Ala Cys Asp Pro Arg Leu Leu Asn Lys Leu
  1               5                  10                  15

Leu Arg Asp Ser His Val Leu His Gly Arg Leu Ser Gln Cys Pro
                 20                  25                  30

Asp Ile Asn Pro Leu Ser Thr Pro Val Leu Leu Pro Ala Val Asp
                 35                  40                  45

Phe Thr Leu Gly Glu Trp Lys Thr Gln Thr Glu Gln Thr Lys Ala
                 50                  55                  60

Gln Asp Val Leu Gly Ala Thr Thr Leu Leu Leu Glu Ala Val Met
                 65                  70                  75

Thr Ala Arg Gly Gln Val Gly Pro Pro Cys Leu Ser Ser Leu Leu
                 80                  85                  90

Val Gln Leu Ser Gly Gln Val Arg Leu Leu Leu Gly Ala Leu Gln
                 95                 100                 105

Asp Leu Leu Gly Met Gln Gly Arg Thr Thr Ala His Lys Asp Pro
                110                 115                 120

Ser Ala Ile Phe Leu Asn Phe Gln Gln Leu Leu Arg Gly Lys Val
                125                 130                 135

Arg Phe Leu Leu Leu Val Val Gly Pro Ser Leu Cys Ala Lys Arg
                140                 145                 150

Ala Pro Pro Ala Ile Ala Val Pro Ser Ser Thr Ser Pro Phe His
                155                 160                 165

Thr Leu Asn Lys Leu Pro Asn Arg Thr Ser Gly Leu Leu Glu Thr
                170                 175                 180

Asn Ser Ser Ile Ser Ala Arg Thr Thr Gly Ser Gly Phe Leu Lys
                185                 190                 195

Arg Leu Gln Ala Phe Arg Ala Lys Ile Pro Gly Leu Leu Asn Gln
```

```
                200                 205                 210

Thr Ser Arg Ser Leu Asp Gln Ile Pro Gly His Gln Asn Gly Thr
                215                 220                 225

His Gly Pro Leu Ser Gly Ile His Gly Leu Phe Pro Gly Pro Gln
                230                 235                 240

Pro Gly Ala Leu Gly Ala Pro Asp Ile Pro Pro Ala Thr Ser Gly
                245                 250                 255

Met Gly Ser Arg Pro Thr Tyr Leu Gln Pro Gly Glu Ser Pro Ser
                260                 265                 270

Pro Ala His Pro Ser Pro Gly Arg Tyr Thr Leu Phe Ser Pro Ser
                275                 280                 285

Pro Thr Ser Pro Ser Pro Thr Val Gln Leu Gln Pro Leu Leu Pro
                290                 295                 300

Asp Pro Ser Ala Ile Thr Pro Asn Ser Thr Ser Pro Leu Leu Phe
                305                 310                 315

Ala Ala His Pro His Phe Gln Asn Leu Ser Gln Glu Glu
                320                 325         328
```

(2) INFORMATION FOR SEQ ID NO:21:

(i) SEQUENCE CHARACTERISTICS:
(A) LENGTH: 25 amino acids
(B) TYPE: Amino Acid
(D) TOPOLOGY: Linear (xi) SEQUENCE DESCRIPTION: SEQ ID NO:21:

```
Ser Pro Ala Pro Pro Ala Cys Asp Pro Arg Leu Leu Asn Lys Leu
  1               5                  10                  15

Leu Arg Asp Asp His Val Leu His Gly Arg
                 20                  25
```

(2) INFORMATION FOR SEQ ID NO:22:

(i) SEQUENCE CHARACTERISTICS:
(A) LENGTH: 27 amino acids
(B) TYPE: Amino Acid
(D) TOPOLOGY: Linear (xi) SEQUENCE DESCRIPTION: SEQ ID NO:22:

```
Ser Pro Ala Pro Pro Ala Cys Asp Pro Arg Leu Leu Asn Lys Leu
  1               5                  10                  15

Leu Arg Asp Asp His Ser Val Leu His Gly Arg Leu
                 20                  25      27
```

(2) INFORMATION FOR SEQ ID NO:23:

(i) SEQUENCE CHARACTERISTICS:
(A) LENGTH: 25 amino acids
(B) TYPE: Amino Acid
(D) TOPOLOGY: Linear (xi) SEQUENCE DESCRIPTION: SEQ ID NO:23:

```
Ser Pro Ala Pro Pro Ala Xaa Asp Pro Arg Leu Leu Asn Lys Leu
  1               5                  10                  15

Leu Arg Asp Asp His Val Leu His Gly Arg
                 20                  25
```

(2) INFORMATION FOR SEQ ID NO:24:

(i) SEQUENCE CHARACTERISTICS:
(A) LENGTH: 14 amino acids
(B) TYPE: Amino Acid (D) TOPOLOGY: Linear (xi) SEQUENCE DESCRIPTION: SEQ ID NO:24:

```
Xaa Pro Ala Pro Pro Ala Xaa Asp Pro Arg Leu Xaa Asn Lys
  1               5                   10              14
```

(2) INFORMATION FOR SEQ ID NO:25:

(i) SEQUENCE CHARACTERISTICS:
(A) LENGTH: 9 amino acids
(B) TYPE: Amino Acid
(D) TOPOLOGY: Linear (xi) SEQUENCE DESCRIPTION: SEQ ID NO:25:

```
Pro Arg Leu Leu Asn Lys Leu Leu Arg
  1               5               9
```

(2) INFORMATION FOR SEQ ID NO:26:

(i) SEQUENCE CHARACTERISTICS:
(A) LENGTH: 45 base pairs
(B) TYPE: Nucleic Acid
(C) STRANDEDNESS: Single
(D) TOPOLOGY: Linear (xi) SEQUENCE DESCRIPTION: SEQ ID NO:26:

GCCGTGAAGG ACGTGGTCGT CACGAAGCAG TTTATTTAGG AGTCG 45

(2) INFORMATION FOR SEQ ID NO:27:

(i) SEQUENCE CHARACTERISTICS:
(A) LENGTH: 20 base pairs
(B) TYPE: Nucleic Acid
(C) STRANDEDNESS: Single
(D) TOPOLOGY: Linear (xi) SEQUENCE DESCRIPTION: SEQ ID NO:27:

CCNGCNCCNC CNGCNTGYGA 20

(2) INFORMATION FOR SEQ ID NO:28:

(i) SEQUENCE CHARACTERISTICS:
(A) LENGTH: 21 base pairs
(B) TYPE: Nucleic Acid
(C) STRANDEDNESS: Single
(D) TOPOLOGY: Linear (xi) SEQUENCE DESCRIPTION: SEQ ID NO:28:

NCCRTGNARN ACRTGRTCRT C 21

(2) INFORMATION FOR SEQ ID NO:29:

(i) SEQUENCE CHARACTERISTICS:
(A) LENGTH: 69 base pairs
(B) TYPE: Nucleic Acid
(C) STRANDEDNESS: Single
(D) TOPOLOGY: Linear (xi) SEQUENCE DESCRIPTION: SEQ ID NO:29:

CCAGCGCCGC CAGCCTGTGA CCCCCGACTC CTAAATAAAC TGCCTCGTGA 50

TGACCACGTT CAGCACGGC 69

(2) INFORMATION FOR SEQ ID NO:30:

(i) SEQUENCE CHARACTERISTICS:
(A) LENGTH: 69 base pairs
(B) TYPE: Nucleic Acid

-continued (C) STRANDEDNESS: Single
(D) TOPOLOGY: Linear (xi) SEQUENCE DESCRIPTION: SEQ ID NO:30:

GCCGTGCTGA ACGTGGTCAT CACGAGGCAG TTTATTTAGG AGTCGGGGGT 50

CACAGGCTGG CGGCGCTGG 69

(2) INFORMATION FOR SEQ ID NO:31:

(i) SEQUENCE CHARACTERISTICS:
(A) LENGTH: 69 base pairs
(B) TYPE: Nucleic Acid
(C) STRANDEDNESS: Single
(D) TOPOLOGY: Linear (xi) SEQUENCE DESCRIPTION: SEQ ID NO:31:

CCAGCACCTC CGGCATGTGA CCCCCGACTC CTAAATAAAC TGCTTCGTGA 50

CGACCACGTC CATCACGGC 69

(2) INFORMATION FOR SEQ ID NO:32:

(i) SEQUENCE CHARACTERISTICS:
(A) LENGTH: 69 base pairs
(B) TYPE: Nucleic Acid
(C) STRANDEDNESS: Single
(D) TOPOLOGY: Linear (xi) SEQUENCE DESCRIPTION: SEQ ID NO:32:

GCCGTGATGG ACGTGGTCGT CACGAAGCAG TTTATTTAGG AGTCGGGGGT 50

CACATGCCGG AGGTGCTGG 69

(2) INFORMATION FOR SEQ ID NO:33:

(i) SEQUENCE CHARACTERISTICS:
(A) LENGTH: 69 base pairs
(B) TYPE: Nucleic Acid
(C) STRANDEDNESS: Single
(D) TOPOLOGY: Linear (xi) SEQUENCE DESCRIPTION: SEQ ID NO:33:

CCAGCACCGC CGGCATGTGA CCCCCGACTC CTAAATAAAC TGCTTCGTGA 50

CGATCATGTC TATCACGGT 69

(2) INFORMATION FOR SEQ ID NO:34:

(i) SEQUENCE CHARACTERISTICS:
(A) LENGTH: 69 base pairs
(B) TYPE: Nucleic Acid
(C) STRANDEDNESS: Single
(D) TOPOLOGY: Linear (xi) SEQUENCE DESCRIPTION: SEQ ID NO:34:

ACCGTGATAG ACATGATCGT CACGAAGCAG TTTATTTAGG AGTCGGGGGT 50

CACATGCCGG CGGTGCTGG 69

(2) INFORMATION FOR SEQ ID NO:35:

(i) SEQUENCE CHARACTERISTICS:
(A) LENGTH: 37 base pairs
(B) TYPE: Nucleic Acid
(C) STRANDEDNESS: Single
(D) TOPOLOGY: Linear (xi) SEQUENCE DESCRIPTION: SEQ ID NO:35:

GCTAGCTCTA GAAATTGCTC CTCGTGGTCA TGCTTCT 37

(2) INFORMATION FOR SEQ ID NO:36:

(i) SEQUENCE CHARACTERISTICS:
(A) LENGTH: 22 base pairs
(B) TYPE: Nucleic Acid
(C) STRANDEDNESS: Single
(D) TOPOLOGY: Linear (xi) SEQUENCE DESCRIPTION: SEQ ID NO:36:

CAGTCTGCCG TGAAGGACAT GG 22

(2) INFORMATION FOR SEQ ID NO:37:

(i) SEQUENCE CHARACTERISTICS:
(A) LENGTH: 24 base pairs
(B) TYPE: Nucleic Acid
(C) STRANDEDNESS: Single
(D) TOPOLOGY: Linear (xi) SEQUENCE DESCRIPTION: SEQ ID NO:37:

TGTGGACTTT AGCTTGGGAG AATG 24

(2) INFORMATION FOR SEQ ID NO:38:

(i) SEQUENCE CHARACTERISTICS:
(A) LENGTH: 22 base pairs
(B) TYPE: Nucleic Acid
(C) STRANDEDNESS: Single
(D) TOPOLOGY: Linear (xi) SEQUENCE DESCRIPTION: SEQ ID NO:38:

GGTCCAGGGA CCTGGAGGTT TG 22

(2) INFORMATION FOR SEQ ID NO:39:

(i) SEQUENCE CHARACTERISTICS:
(A) LENGTH: 31 base pairs
(B) TYPE: Nucleic Acid
(C) STRANDEDNESS: Single
(D) TOPOLOGY: Linear (xi) SEQUENCE DESCRIPTION: SEQ ID NO:39:

ATCGATATCG ATAGCCAGAC ACCCCGGCCA G 31

(2) INFORMATION FOR SEQ ID NO:40:

(i) SEQUENCE CHARACTERISTICS:
(A) LENGTH: 36 base pairs
(B) TYPE: Nucleic Acid
(C) STRANDEDNESS: Single
(D) TOPOLOGY: Linear (xi) SEQUENCE DESCRIPTION: SEQ ID NO:40:

GCTAGCTCTA GACAGGGAAG GGAGCTGTAC ATGAGA 36

(2) INFORMATION FOR SEQ ID NO:41:

(i) SEQUENCE CHARACTERISTICS:
(A) LENGTH: 24 base pairs
(B) TYPE: Nucleic Acid
(C) STRANDEDNESS: Single
(D) TOPOLOGY: Linear (xi) SEQUENCE DESCRIPTION: SEQ ID NO:41:

CTCCTTGGAA CCCAGGGCAG GACC 24

(2) INFORMATION FOR SEQ ID NO:42:

(i) SEQUENCE CHARACTERISTICS:
(A) LENGTH: 24 base pairs
(B) TYPE: Nucleic Acid
(C) STRANDEDNESS: Single
(D) TOPOLOGY: Linear (xi) SEQUENCE DESCRIPTION: SEQ ID NO:42:

GGTCCTGCCC TGGGTTCCAA GGAG 24

(2) INFORMATION FOR SEQ ID NO:43:

(i) SEQUENCE CHARACTERISTICS:
(A) LENGTH: 27 base pairs
(B) TYPE: Nucleic Acid
(C) STRANDEDNESS: Single
(D) TOPOLOGY: Linear (xi) SEQUENCE DESCRIPTION: SEQ ID NO:43:

CTGCTCCGAG GAAAGGACTT CTGGATT 27

(2) INFORMATION FOR SEQ ID NO:44:

(i) SEQUENCE CHARACTERISTICS:
(A) LENGTH: 27 base pairs
(B) TYPE: Nucleic Acid
(C) STRANDEDNESS: Single
(D) TOPOLOGY: Linear (xi) SEQUENCE DESCRIPTION: SEQ ID NO:44:

AATCCAGAAG TCCTTTCCTC GGAGCAG 27

(2) INFORMATION FOR SEQ ID NO:45:

(i) SEQUENCE CHARACTERISTICS:
(A) LENGTH: 28 base pairs
(B) TYPE: Nucleic Acid
(C) STRANDEDNESS: Single
(D) TOPOLOGY: Linear (xi) SEQUENCE DESCRIPTION: SEQ ID NO:45:

CCCTCTGCGT CGCGGCGGCC CCACCCAC 28

(2) INFORMATION FOR SEQ ID NO:46:

(i) SEQUENCE CHARACTERISTICS:
(A) LENGTH: 28 base pairs
(B) TYPE: Nucleic Acid
(C) STRANDEDNESS: Single
(D) TOPOLOGY: Linear (xi) SEQUENCE DESCRIPTION: SEQ ID NO:46:

GTGGGTGGGG CCGCCGCGAC GCAGAGGG 28

(2) INFORMATION FOR SEQ ID NO:47:

(i) SEQUENCE CHARACTERISTICS:
(A) LENGTH: 35 base pairs
(B) TYPE: Nucleic Acid
(C) STRANDEDNESS: Single
(D) TOPOLOGY: Linear (xi) SEQUENCE DESCRIPTION: SEQ ID NO:47:

GACTCGAGGA TCCATCGATT TTTTTTTTTT TTTTT 35

(2) INFORMATION FOR SEQ ID NO:48:

(i) SEQUENCE CHARACTERISTICS:
(A) LENGTH: 17 base pairs
(B) TYPE: Nucleic Acid
(C) STRANDEDNESS: Single
(D) TOPOLOGY: Linear (xi) SEQUENCE DESCRIPTION: SEQ ID NO:48:

GACTCGAGGA TCCATCG 17

(2) INFORMATION FOR SEQ ID NO:49:

(i) SEQUENCE CHARACTERISTICS:
(A) LENGTH: 32 base pairs
(B) TYPE: Nucleic Acid
(C) STRANDEDNESS: Single
(D) TOPOLOGY: Linear (xi) SEQUENCE DESCRIPTION: SEQ ID NO:49:

GCTAGCTCTA GAAGCCCGGC TCCTCCTGCC TG 32

(2) INFORMATION FOR SEQ ID NO:50:

(i) SEQUENCE CHARACTERISTICS:
(A) LENGTH: 21 base pairs
(B) TYPE: Nucleic Acid
(C) STRANDEDNESS: Single
(D) TOPOLOGY: Linear (xi) SEQUENCE DESCRIPTION: SEQ ID NO:50:

CGAAATTAAC CCTCACTAAA G 21

(2) INFORMATION FOR SEQ ID NO:51:

(i) SEQUENCE CHARACTERISTICS:
(A) LENGTH: 4 amino acids
(B) TYPE: Amino Acid
(D) TOPOLOGY: Linear (xi) SEQUENCE DESCRIPTION: SEQ ID NO:51:

His Val Leu His
1 4

(2) INFORMATION FOR SEQ ID NO:52:

(i) SEQUENCE CHARACTERISTICS:
(A) LENGTH: 4 amino acids
(B) TYPE: Amino Acid
(D) TOPOLOGY: Linear (xi) SEQUENCE DESCRIPTION: SEQ ID NO:52:

Ser Arg Leu Ser
1 4

(2) INFORMATION FOR SEQ ID NO:53:

(i) SEQUENCE CHARACTERISTICS:
(A) LENGTH: 4 amino acids
(B) TYPE: Amino Acid
(D) TOPOLOGY: Linear (xi) SEQUENCE DESCRIPTION: SEQ ID NO:53:

Ser His Val Leu
1 4

(2) INFORMATION FOR SEQ ID NO:54:

(i) SEQUENCE CHARACTERISTICS:

(A) LENGTH: 4 amino acids
(B) TYPE: Amino Acid
(D) TOPOLOGY: Linear (xi) SEQUENCE DESCRIPTION: SEQ ID NO:54:

His Ser Arg Leu
1 4

(2) INFORMATION FOR SEQ ID NO:55:

(i) SEQUENCE CHARACTERISTICS:
(A) LENGTH: 4 amino acids
(B) TYPE: Amino Acid
(D) TOPOLOGY: Linear (xi) SEQUENCE DESCRIPTION: SEQ ID NO:55:

Ala Val Asp Phe
1 4

(2) INFORMATION FOR SEQ ID NO:56:

(i) SEQUENCE CHARACTERISTICS:
(A) LENGTH: 4 amino acids
(B) TYPE: Amino Acid
(D) TOPOLOGY: Linear (xi) SEQUENCE DESCRIPTION: SEQ ID NO:56:

Ser Leu Gly Glu
1 4

(2) INFORMATION FOR SEQ ID NO:57:

(i) SEQUENCE CHARACTERISTICS:
(A) LENGTH: 4 amino acids
(B) TYPE: Amino Acid
(D) TOPOLOGY: Linear (xi) SEQUENCE DESCRIPTION: SEQ ID NO:57:

Ala Val Thr Leu
1 4

(2) INFORMATION FOR SEQ ID NO:58:

(i) SEQUENCE CHARACTERISTICS:
(A) LENGTH: 4 amino acids
(B) TYPE: Amino Acid
(D) TOPOLOGY: Linear (xi) SEQUENCE DESCRIPTION: SEQ ID NO:58:

Leu Leu Glu Gly
1 4

(2) INFORMATION FOR SEQ ID NO:59:

(i) SEQUENCE CHARACTERISTICS:
(A) LENGTH: 4 amino acids
(B) TYPE: Amino Acid
(D) TOPOLOGY: Linear (xi) SEQUENCE DESCRIPTION: SEQ ID NO:59:

Leu Ser Ser Leu
1 4

(2) INFORMATION FOR SEQ ID NO:60:

(i) SEQUENCE CHARACTERISTICS:
(A) LENGTH: 4 amino acids
(B) TYPE: Amino Acid (D) TOPOLOGY: Linear (xi) SEQUENCE DESCRIPTION: SEQ ID NO:60:

Leu Gly Gln Leu
1 4

(2) INFORMATION FOR SEQ ID NO:61:

(i) SEQUENCE CHARACTERISTICS:
(A) LENGTH: 4 amino acids
(B) TYPE: Amino Acid
(D) TOPOLOGY: Linear (xi) SEQUENCE DESCRIPTION: SEQ ID NO:61:

Cys Leu Ser Ser
1 4

(2) INFORMATION FOR SEQ ID NO:62:

(i) SEQUENCE CHARACTERISTICS:
(A) LENGTH: 4 amino acids
(B) TYPE: Amino Acid
(D) TOPOLOGY: Linear (xi) SEQUENCE DESCRIPTION: SEQ ID NO:62:

Leu Leu Gly Gln
1 4

(2) INFORMATION FOR SEQ ID NO:63:

(i) SEQUENCE CHARACTERISTICS:
(A) LENGTH: 4 amino acids
(B) TYPE: Amino Acid
(D) TOPOLOGY: Linear (xi) SEQUENCE DESCRIPTION: SEQ ID NO:63:

Ser Ser Leu Leu
1 4

(2) INFORMATION FOR SEQ ID NO:64:

(i) SEQUENCE CHARACTERISTICS:
(A) LENGTH: 4 amino acids
(B) TYPE: Amino Acid
(D) TOPOLOGY: Linear (xi) SEQUENCE DESCRIPTION: SEQ ID NO:64:

Gly Gln Leu Ser
1 4

(2) INFORMATION FOR SEQ ID NO:65:

(i) SEQUENCE CHARACTERISTICS:
(A) LENGTH: 4 amino acids
(B) TYPE: Amino Acid
(D) TOPOLOGY: Linear (xi) SEQUENCE DESCRIPTION: SEQ ID NO:65:

Leu Gln Ser Leu
1 4

(2) INFORMATION FOR SEQ ID NO:66:

(i) SEQUENCE CHARACTERISTICS:
(A) LENGTH: 4 amino acids
(B) TYPE: Amino Acid
(D) TOPOLOGY: Linear (xi) SEQUENCE DESCRIPTION: SEQ ID NO:66:

Leu Gly Thr Gln
1 4

(2) INFORMATION FOR SEQ ID NO:67:

(i) SEQUENCE CHARACTERISTICS:
(A) LENGTH: 4 amino acids
(B) TYPE: Amino Acid
(D) TOPOLOGY: Linear (xi) SEQUENCE DESCRIPTION: SEQ ID NO:67:

Ala Leu Gln Ser
1 4

(2) INFORMATION FOR SEQ ID NO:68:

(i) SEQUENCE CHARACTERISTICS:
(A) LENGTH: 4 amino acids
(B) TYPE: Amino Acid
(D) TOPOLOGY: Linear (xi) SEQUENCE DESCRIPTION: SEQ ID NO:68:

Leu Leu Gly Thr
1 4

(2) INFORMATION FOR SEQ ID NO:69:

(i) SEQUENCE CHARACTERISTICS:
(A) LENGTH: 4 amino acids
(B) TYPE: Amino Acid
(D) TOPOLOGY: Linear (xi) SEQUENCE DESCRIPTION: SEQ ID NO:69:

Asn Ala Ile Phe
1 4

(2) INFORMATION FOR SEQ ID NO:70:

(i) SEQUENCE CHARACTERISTICS:
(A) LENGTH: 4 amino acids
(B) TYPE: Amino Acid
(D) TOPOLOGY: Linear (xi) SEQUENCE DESCRIPTION: SEQ ID NO:70:

Leu Ser Phe Gln
1 4

(2) INFORMATION FOR SEQ ID NO:71:

(i) SEQUENCE CHARACTERISTICS:
(A) LENGTH: 22 amino acids
(B) TYPE: Amino Acid
(D) TOPOLOGY: Linear (xi) SEQUENCE DESCRIPTION: SEQ ID NO:71:

Ser Pro Ala Pro Pro Ala Cys Asp Leu Arg Val Leu Ser Lys Leu
1 5 10 15

Leu Arg Asp Ser His Val Leu
20 22

(2) INFORMATION FOR SEQ ID NO:72:

(i) SEQUENCE CHARACTERISTICS:
(A) LENGTH: 24 amino acids
(B) TYPE: Amino Acid
(D) TOPOLOGY: Linear (xi) SEQUENCE DESCRIPTION: SEQ ID NO:72:

His Ser Arg Leu Ser Gln Cys Pro Glu Val His Pro Leu Pro Thr
1 5 10 15

Pro Val Leu Leu Pro Ala Val Asp Phe
20 24

(2) INFORMATION FOR SEQ ID NO:73:

(i) SEQUENCE CHARACTERISTICS:
(A) LENGTH: 23 amino acids
(B) TYPE: Amino Acid
(D) TOPOLOGY: Linear (xi) SEQUENCE DESCRIPTION: SEQ ID NO:73:

Ser Leu Gly Glu Trp Lys Thr Gln Met Glu Glu Thr Lys Ala Gln
1 5 10 15

Asp Ile Leu Gly Ala Val Thr Leu
20 23

(2) INFORMATION FOR SEQ ID NO:74:

(i) SEQUENCE CHARACTERISTICS:
(A) LENGTH: 21 amino acids
(B) TYPE: Amino Acid
(D) TOPOLOGY: Linear (xi) SEQUENCE DESCRIPTION: SEQ ID NO:74:

Leu Leu Glu Gly Val Met Ala Ala Arg Gly Gln Leu Gly Pro Thr
1 5 10 15

Cys Leu Ser Ser Leu Leu
20 21

(2) INFORMATION FOR SEQ ID NO:75:

(i) SEQUENCE CHARACTERISTICS:
(A) LENGTH: 16 amino acids
(B) TYPE: Amino Acid
(D) TOPOLOGY: Linear (xi) SEQUENCE DESCRIPTION: SEQ ID NO:75:

Gly Gln Leu Ser Gly Gln Val Arg Leu Leu Leu Gly Ala Leu Gln
1 5 10 15

Ser
16

(2) INFORMATION FOR SEQ ID NO:76:

(i) SEQUENCE CHARACTERISTICS:
(A) LENGTH: 22 amino acids
(B) TYPE: Amino Acid
(D) TOPOLOGY: Linear (xi) SEQUENCE DESCRIPTION: SEQ ID NO:76:

Leu Leu Gly Thr Gln Leu Pro Pro Gln Gly Arg Thr Thr Ala His
1 5 10 15

Lys Asp Pro Asn Ala Ile Phe
20 22

(2) INFORMATION FOR SEQ ID NO:77:

(i) SEQUENCE CHARACTERISTICS:
(A) LENGTH: 25 amino acids
(B) TYPE: Amino Acid
(D) TOPOLOGY: Linear -continued

```
    (xi) SEQUENCE DESCRIPTION: SEQ ID NO:77:

Leu Ser Phe Gln His Leu Leu Arg Gly Lys Val Arg Phe Leu Met
  1               5                  10                  15

Leu Val Gly Gly Ser Thr Leu Cys Val Arg
                 20                  25
```